(12) United States Patent
Wang et al.

(10) Patent No.: US 10,259,863 B2
(45) Date of Patent: Apr. 16, 2019

(54) BOVINE FUSION ANTIBODIES

(71) Applicant: The California Institute for Biomedical Research, La Jolla, CA (US)

(72) Inventors: Feng Wang, Carlsbad, CA (US); Yong Zhang, Temple City, CA (US); Peter G. Schultz, La Jolla, CA (US)

(73) Assignee: THE CALIFORNIA INSTITUTE FOR BIOMEDICAL RESEARCH, La Jolla, CA (US)

( * ) Notice: Subject to any disclaimer, the term of this patent is extended or adjusted under 35 U.S.C. 154(b) by 45 days.

(21) Appl. No.: 14/760,115

(22) PCT Filed: Jan. 10, 2014

(86) PCT No.: PCT/US2014/011043
§ 371 (c)(1),
(2) Date: Jul. 9, 2015

(87) PCT Pub. No.: WO2014/110368
PCT Pub. Date: Jul. 17, 2014

(65) Prior Publication Data
US 2015/0376264 A1 Dec. 31, 2015

Related U.S. Application Data

(60) Provisional application No. 61/751,598, filed on Jan. 11, 2013.

(51) Int. Cl.
| | |
|---|---|
| C07K 16/28 | (2006.01) |
| C07K 14/575 | (2006.01) |
| C07K 14/64 | (2006.01) |
| A61K 39/00 | (2006.01) |
| A61K 38/16 | (2006.01) |
| C07K 16/00 | (2006.01) |
| C07K 14/605 | (2006.01) |
| C07K 14/61 | (2006.01) |
| C07K 14/635 | (2006.01) |
| C07K 14/81 | (2006.01) |
| C07K 7/08 | (2006.01) |

(52) U.S. Cl.
CPC ............... *C07K 16/00* (2013.01); *C07K 7/08* (2013.01); *C07K 14/575* (2013.01); *C07K 14/5759* (2013.01); *C07K 14/605* (2013.01); *C07K 14/61* (2013.01); *C07K 14/635* (2013.01); *C07K 14/64* (2013.01); *C07K 14/811* (2013.01); *C07K 16/2869* (2013.01); *C07K 2317/565* (2013.01); *C07K 2318/10* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,294,654 B1 | 9/2001 | Bogen et al. | |
| 6,498,020 B1 | 12/2002 | Walker et al. | |
| 6,740,747 B2 | 5/2004 | Kaushik et al. | |
| 7,166,697 B1 | 1/2007 | Galanis et al. | |
| 7,196,185 B2 | 3/2007 | Kaushik et al. | |
| 7,575,893 B2 | 8/2009 | Simmons | |
| 7,592,010 B2 | 9/2009 | Rosen et al. | |
| 7,977,071 B2 | 7/2011 | Nuttal et al. | |
| 9,644,021 B2 * | 5/2017 | Wang ................ | C07K 16/00 |
| 2003/0088074 A1 | 5/2003 | Hamers et al. | |
| 2003/0170646 A1 | 9/2003 | Kaushik et al. | |
| 2003/0232395 A1 | 12/2003 | Hufton | |
| 2006/0160995 A1 | 7/2006 | Baker et al. | |
| 2006/0275254 A1 | 12/2006 | Kim et al. | |
| 2008/0152586 A1 | 6/2008 | Hudson et al. | |

(Continued)

FOREIGN PATENT DOCUMENTS

| | | |
|---|---|---|
| EP | 2194066 A1 | 6/2010 |
| EP | 2322228 A1 | 5/2011 |

(Continued)

OTHER PUBLICATIONS

Li et al., (The FASEB Journal, 2012, 26:1-11).*
Saini et al. (European Journal of Immunology, 1999, 29:2420-2426).*
Almagro & Fransson, Frontiers in Bioscience 2008; 13:1619-33.*
De Genst et al., Developmental and Comparative Immunology, 2006, 30:187-98.*
Ward et al., Nature, 1989, 341:544-546.*
Barthelemy et al. (Journal of Biological Chemistry, 2008, 283:3639-3654).*
Choi et al., 2011, Molecular BioSystems, 2011, 7:3327-334.*
Griffiths et al., The EMBO Journal, 1993, 12:725-734.*

(Continued)

*Primary Examiner* — Julie Wu
(74) *Attorney, Agent, or Firm* — Wilson Sonsini Goodrich & Rosati

(57) ABSTRACT

Disclosed herein are immunoglobulin constructs comprising at least one immunoglobulin domain or fragment thereof; and a therapeutic polypeptide or derivative or variant thereof attached to or inserted into said immunoglobulin domain. Also provided are immunoglobulin constructs comprising a mammalian immunoglobulin heavy chain comprising at least a portion of a knob domain in the complementarity-determining region 3 (CDR3H) or fragment thereof; and a therapeutic polypeptide attached to or inserted into the CDR3H. Also provided are immunoglobulin constructs comprising a mammalian immunoglobulin heavy chain comprising at least a portion of a stalk domain in the complementarity-determining region 3 (CDR3H) or fragment thereof; and a therapeutic polypeptide attached to or inserted into said stalk domain of the CDR3H. Also described herein are methods and compositions comprising the immunoglobulin constructs described herein for treatment and prevention of a disease or condition in a subject.

12 Claims, 8 Drawing Sheets

Specification includes a Sequence Listing.

(56) References Cited

U.S. PATENT DOCUMENTS

| | | | |
|---|---|---|---|
| 2009/0148455 A1* | 6/2009 | Fischer | C07K 16/24 424/139.1 |
| 2009/0286964 A1 | 11/2009 | Gegg et al. | |
| 2009/0304580 A1* | 12/2009 | Goldenberg | A61K 47/48746 424/1.49 |
| 2010/0136032 A1 | 6/2010 | Weinberg et al. | |
| 2010/0311119 A1 | 12/2010 | Hermans et al. | |
| 2011/0039761 A1 | 2/2011 | Eckert et al. | |
| 2011/0172125 A1 | 7/2011 | Ladner | |
| 2011/0189690 A1 | 8/2011 | Shibasaki et al. | |
| 2011/0269938 A1 | 11/2011 | Nuttall et al. | |
| 2011/0293513 A1* | 12/2011 | Govindan | A61K 47/48215 424/1.49 |
| 2012/0128672 A1 | 5/2012 | Keer | |
| 2012/0302737 A1 | 11/2012 | Christensen et al. | |
| 2014/0022767 A1 | 1/2014 | Martinez | |
| 2014/0050720 A1 | 2/2014 | Smider et al. | |
| 2014/0086871 A1* | 3/2014 | Smider | C07K 16/00 424/85.6 |
| 2014/0227267 A1* | 8/2014 | Wang | C07K 16/2869 424/134.1 |
| 2015/0011431 A1 | 1/2015 | Smider et al. | |
| 2015/0192971 A1 | 7/2015 | Shah | |
| 2016/0159920 A1 | 6/2016 | Wang et al. | |
| 2016/0168231 A1 | 6/2016 | De Los Rios et al. | |
| 2016/0237156 A1* | 8/2016 | Wang | C07K 16/2866 |

FOREIGN PATENT DOCUMENTS

| | | | | |
|---|---|---|---|---|
| WO | WO-8907142 A1 | 8/1989 | | |
| WO | WO-9320210 | 10/1993 | | |
| WO | WO-9418221 A1 | 8/1994 | | |
| WO | WO-9622377 A1 | 7/1996 | | |
| WO | WO-0103737 A1 | 1/2001 | | |
| WO | WO-0222809 A2 | 3/2002 | | |
| WO | WO-03030821 A2 | 4/2003 | | |
| WO | WO-03085086 A2 | 10/2003 | | |
| WO | WO-2005007809 A2 | 1/2005 | | |
| WO | WO-2005082353 A3 | 11/2005 | | |
| WO | WO-2009132876 A1 | 11/2009 | | |
| WO | WO-2010028791 | 3/2010 | | |
| WO | WO-2010108048 A2 | 9/2010 | | |
| WO | WO-2011044542 A1 | 4/2011 | | |
| WO | WO-2012007167 A1 | 1/2012 | | |
| WO | WO-2012169822 A2 | 12/2012 | | |
| WO | WO 2012170977 A1 * | 12/2012 | | A61K 48/005 |
| WO | WO-2013106485 | 7/2013 | | |
| WO | WO-2013106489 A1 | 7/2013 | | |
| WO | WO-2015006744 A1 | 1/2015 | | |
| WO | WO-2015017146 A2 | 2/2015 | | |
| WO | WO-2015105741 A1 | 7/2015 | | |

OTHER PUBLICATIONS

Klimka et al., British Journal of Cancer, 2000, 83:252-260.*
Beiboer et al., Journal of Molecular Biology, 2000, 296:833-849.*
Chain H., Crystal Structure of Bovine Antibody Blv5b8 With Ultralong Cdr H3.Accessed PDB: 4K3E-H NCBI Feb. 12, 2016 http://www.ncbi.nlm.nih.gov/protein/4K3E_H.
Co-pending U.S. Appl. No. 14/903,489, filed Jan. 7, 2016.
Immunoglobulin heavy chain variable region, partial [Bos taurus]. Accessed from GenBank: AAC71038.1. NCBI on Feb. 12, 2016 http://ncbi.nlm.nig.gov/protein/AAC71038.1.
Immunoglobulin light chain variable region, partial [Bos taurus] GenBank: AAB81517.1 Accessed via NCBI Feb. 12, 2016 http://ncbi.nlm.nih.gov/protein/2555151.
Immunoglobulin light chain variable region, partial [Bos taurus]. Accessed Feb. 12, 2016 via NCBI GenBank: AAB66580.1 http://ncbi.nlm.nih.gov/protein/2323408.
Nuttall et al. Selection and affinity maturation of IgNAR variable domains targeting Plasmodium falciparum AMA1.Protein: Structure, Function and Bioinformatics. vol. 55, Issue 1 Apr. 2004, pp. 187-197.
Qin W. et al. Fusion protein of CDR mimetic peptide with Fc inhibit TNF-alpha induced cytotoxicity, Molecular Immunology, 43(6); 660-666 (Feb. 1, 2006).
Simmons et al. Shark IgNAR antibody mimotopes target a murine immunoglobulin through extended CDR3 loop structures.Proteins: Structure, Function and Bioinformatics vol. 71, Issue 1 Apr. 2008, pp. 119-130.
Streltsov et al. Crystal Structure of the Amyloid p3 Fragment Provides a Model for Oligomer Formation in Alzheimers Disease The Journal of Neuroscience, Jan. 26, 2011, 31(4):1419-1426, 1419 (with Supplemental Data).
U.S. Appl. No. 14/152,441 Final Office Action dated Nov. 18, 2015.
U.S. Appl. No. 14/152,441 Office Action dated May 18, 2016.
Yang Xi et al. The three complementarity-determining region-like loops in the second extracellular domain of human Fc alpha/mu receptor contribute to its binding of IgA and Igm. Immunobiology,Urban Und Fischer Verlag, DE, 218(5); 798-809 (Oct. 4, 2012).
Conway, S. P. et al. Pharmacokinetics and safety of itraconazole in patients with cystic fibrosis. Journal of Antimicrobial Chemotherapy, Mar. 24, 2004, vol. 53, No. 5, pp. 841-847.
Steltsov, Victor A. et al. Crystal Structure of the Amyloid-p3 Fragment Provides a Model for Oligomer Formation in Alzheimer's Disease. The Journal of Neuroscience 31(4);1419-1426 (Jan. 26, 2011).
U.S. Appl. No. 13/737,910 Office Action dated Aug. 22, 2016.
U.S. Appl. No. 14/152,441 Office Action dated Nov. 30, 2016.
Almagro et al. Characterization of a High-Affinity Human Antibody with a Disulfide bridge in the Third Complementarity-Determining Region of the Heavy Chain. Journal of Molecular Recognition, vol. 25, pp. 125-135 (2012).
Berens, et al. Use of a single VH family and long CDR3s in the variable region of cattle Ig heavy chains. International Immunology, vol. 9, No. 1, pp. 189-199, (1997).
Casset et al. A peptide mimetic of an anti-CD4 monoclonal antibody by rational design. Biochemical and Biophysical Research Communications, vol. 307 pp. 198-205 (2003).
Chen et al. Selection and analysis of an Optimized Anti-VEGF Antibody: Crystal Structure of an Affinity-matured Fab in Complex with Antigen. Journal of Molecular Biology, vol. 293, pp. 865-881(1999).
Collis et al., Analysis of the Antigen Combining Site: Correlations Between Length and Sequence Composition of the Hypervariable Loops and the Nature of the Antigen. Journal of Molecular Biology, vol. 325, pp. 337-354 (2003).
Ekiert et al., Cross-Neutralization of Influenza A viruses mediated by a Single Antibody Loop. Nature, vol. 489, pp. 526-532 (2012).
Elsik et al., The Genome Sequence of Taurine Cattle: A window to ruminant biology and evolution. Science, vol. 324, No. 5926, pp. 522-528 Apr. 24, 2009.
Henderson et al. Structure of an IgNAR-AMA1 Complex: Targeting a Conserved Hydrophobic Cleft Broadens Malarial Strain Recognition. Structure, vol. 15, pp. 1452-1466 (2007).
Hosseini, et al. Duplicated copies of the bovine $J_H$ locus contribute to the Ig repertoire. International Immunology, vol. 16, No. 6, pp. 843-852, May 4, 2004.
Ngo, J. Thomas et al. Computational Complexity, Protein Structure Prediction, and the Levinthal Paradox, Birkhauser, pp. 433-440, 492-495, 1994.
Wells, James A. Additivity of Mutational Effects in Proteins, vol. 29, No. 37, pp. 8509-8517 (Sep. 18, 1990).
Roche, JR et al. Invited review: Body condition score and its association with dairy cow productivity, health, and welfare. Journal of Dairy Science, vol. 92, No. 12, 5769-5801.
Wynne, K. et al. Oxyntomodulin increases energy expenditure in addition to decreasing energy intake in overweight and obese humans: a randomised controlled trial. International Journal of Obesity, vol. 30, 1729-1736, 2006.
Kaushik, et al., Novel Insight into Antibody diversification from Cattle. Veterinary Immunology and Immunopathology, vol. 87, pp. 347-350 (2002).

(56) References Cited

OTHER PUBLICATIONS

Kaushik, et al., Somatic hypermutations and isotype restricted exceptionally long CDR3H contribute to antibody diversification in cattle. Veterinary Immunology and Immunopathology, vol. 127, pp. 106-113 (2009).
Koti, et al. Novel atypical nucleotide insertions specifically at VH-DH junction generate exceptionally long CDR3H in cattle antibodies. Molecular Immunology, vol. 47, No. 11-12, pp. 2119-2128; Jul. 2010.
Koti et al., Organization of $D_H$-Gene Locus is Distinct in Cattle. Developments in biologicals (Basel), vol. 132, pp. 307-313 (2008).
Krause et al, An insertion mutation that distorts antibody binding site architecture enhances function of a human antibody. mBio, vol. 2, No. 1, pp. e00345-10 (2011).
Lopez et al., A single $V_H$ family and long CDR3s are the targets for hypermutation in bovine immunoglobulin heavy chains. Immunological Reviews, vol. 162, pp. 55-66 (1998).
McLellan et al., Structure of HIV-1 gp120 V1/V2 domain with broadly neutralizing antibody PG9. Nature, vol. 480, No. 7377, pp. 336-343 (2011).
NCBI, GenBank Accession No. DM113215.1, Jun. 18, 2009.
NCBI, PDB accession No. 4K3D_H, Jul. 3, 2013.
Nuttall et al, Design and Expression of Soluble CTLA-4 Variable Domain as a Scaffold for the Display of Functional Polypeptides. Proteins: Structure, Function and Genetics, vol. 36, pp. 217-227 (1999).
Paul, W.E. Fv Structure and Diversity in Three Dimensions, Fundamental Immunology, Third Edition (textbook), pp. 292-295; Raven Press, New York (1993).
PCT/US2014/011043 Search Report and Written Opinion dated May 1, 2014.
Pejchal et al., Structure and Function of Broadly Reactive Antibody PG16 Reveal an H3 Subdomain that Mediates Potent Neutralization of HIV-1. PNAS, vol. 107, No. 25, pp. 11483-11488 (2010).
Saini et al., Bovine IgM Antibodies with Exceptionally Long Complementarity-Determining Region 3 of the Heavy Chain Share Unique Structural Property conferring Restricted $V_H$ +$V_\lambda$ pairings. International Immunology, vol. 15, No. 7, pp. 845-853 (2003).
Saini, et al. Exceptionally long CDR3H region with multiple cysteine residues in functional bovine IgM antibodies. European Journal of Immunology vol. 29, No. 8, pp. 2420-2426, (Aug. 1999).
Saini, et al. Extensive CDR3H length heterogeneity exists in bovine Foetal VDJ Rearrangements. Scandinavian Journal of Immunology, vol. 55, No. 2, pp. 140-148, (Feb. 2002).
Saphire et al., Crystal Structure of a Neutralizing Human IgG Against HIV-1: A Template for Vaccine Design. Science, vol. 293, pp. 1155-1159, Aug. 10, 2001.
Shojaei, et al., Unusually long Germline $D_H$ Genes Contribute to Large Sized CDR3H in Bovine Antibodies. Molecular Immunology, vol. 40, pp. 61-67 (2003).

Brumeanu, Teodor, D. et al., Efficient Loading of Identical Viral Peptide onto Class II Molecules by Antigenized Immunoglobulin and Influenza Virus, vol. 178, pp. 1795-1799, (Nov. 1, 1993).
U.S. Appl. No. 13/737,910 Final Office Action dated Jun. 4, 2015.
U.S. Appl. No. 13/737,910 Office Action dated Oct. 16, 2014.
U.S. Appl. No. 14/152,441 Office Action dated Jun. 1, 2015.
Wang, et al. Reshaping Antibody Diversity. Cell, vol. 153, pp. 1379-1393 (Jun. 6, 2013).
Xiao-Qing Qiu et al., Small antibody mimetics comprising two complementarity-determining regions and a framework region for tumor targeting. Nature Biotechnology, vol. 25, No. 8, pp. 921-929 (Aug. 2007).
Zaghouani, et al. Engineered immunoglobulin molecules as vehicles for T cell epitopes. International Reviews of Immunology. vol. 10, No. 2-3, pp. 265-278, (1993).
Zhang, et al. An Antibody CDR3-Erythropoietin Fusion Protein. ACS Chemical Biology, vol. 8, pp. 2117-2121 (2013).
Zhang, et al. An Antibody with a Variable-Region Coiled-Coil "Knob" Domain. Angew. Chem. Int. Ed. vol. 53, pp. 132-135 (2014).
Zhang, et al. Functional Antibody CDR3 Fusion Proteins with Enhanced Pharmacological Properties. Angew. Chem. Int. Ed. vol. 52, pp. 8295-8298 (2013).
Zhao et al. The Bovine Antibody Repertoire. Developmental and Comparative Immunology, vol. 30, No. 1-2, pp. 175-186 (2006).
Zhong et al, Small antibody fusion proteins with complementarity-determining regions and lidamycin for tumor targeting therapy. Oncology Letters, vol. 5, pp. 1183-188 (2013).
Inoue Hidetoshi et al. Affinity transfer to a human protein by CDR3 grafting of camelid VHH, Protein Science: A Publication of the Protein Society. vol. 20, No. 12. Dec. 2011, pp. 1971-1981.
Pistillo MP et al. Molecular Characterization and Applications of Recombinant scFv Antibodies to CD152 Co-Stimulatory Molecule, Tissue Antigens, Munksgaard, Copenhagen, DK, vol. 55, No. 3, Mar. 1, 2000, pp. 229-238.
Ramsland PA et al. Incorporation of long CDR3s into V domains: implications for the structural evolution of the antibody-combining site, Experimental and Clinical Immunogenetics, S. Karger, Basel, CH, vol. 18, No. 4, Jan. 1, 2001, pp. 176-198.
U.S. Appl. No. 13/737,910 Final Office Action dated Feb. 17, 2017.
U.S. Appl. No. 13/737,913 Office Action dated Jan. 27, 2017.
U.S. Appl. No. 13/737,913 Office Action dated Jun. 21, 2016.
Barbas, C.F. et. al. Molecular Profile of an Antibody Response to HIV-1 as Probed by Combinatorial Libraries. Journal of Molecular Biology, 230(3):812-823 (Apr. 5, 1993).
Goldenberg, M. Trastuzumab, a recombinant DNA-derived humanized monoclonal antibody, a novel agent for the treatment of metastatic breast cancer. Clinical Therapeutics, 21(2):309-318 (1999).
U.S. Appl. No. 13/737,910 Non-Final Office Action dated Jan. 18, 2018.
U.S. Appl. No. 14/903,489 Non-Final Office Action dated Jan. 12, 2018.

\* cited by examiner

293-LGR7-Cre

SEQUENCE LISTING

<160> NUMBER OF SEQ ID NOS: 180

<210> SEQ ID NO 1
<211> LENGTH: 648
<212> TYPE: DNA
<213> ORGANISM: Bos sp.

<400> SEQUENCE: 1

```
caggccgtcc tgaaccagcc aagcagcgtc tccgggtctc tggggcagcg ggtctcaatc      60
acctgtagcg ggtcttcctc caatgtcggc aacggctacg tgtcttggta tcagctgatc     120
cctggcagtg ccccacgaac cctgatctac ggcgacacat ccagagcttc tggggtcccc     180
gatcggttct cagggagcag atccggaaac acagctactc tgaccatcag ctccctgcag     240
gctgaggacg aagcagatta tttctgcgca tctgccgagg actctagttc aaatgccgtg     300
tttggaagcg gcaccacact gacagtcctg ggcagcccag agagtccccc ttcagtgact     360
ctgttcccac cctctaccga ggaactgaac ggaaacaagg ccacactggt gtgtctgatc     420
agcgactttt accctggatc cgtcactgtg gtctggaagg cagatggcag cacaattact     480
aggaacgtgg aaactacccg cgcctccaag cagtctaata gtaaatacgc cgccagctcc     540
tatctgagcc tgacctctag tgattggaag tccaaagggt catatagctg cgaagtgacc     600
catgaaggct caaccgtgac taagactgtg aaaccatccg agtgctcc                  648
```

<210> SEQ ID NO 2
<211> LENGTH: 507
<212> TYPE: DNA
<213> ORGANISM: Bos sp.

<400> SEQUENCE: 2

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga gagcagact gtccattacc aaggacaact ctaaaagtca ggtgtcactg     240
agcgtgagct ccgtcaccac agaggatagt gcaacttact attgcaccct gtgtgcaccag     300
gaaactaaga ataccagag ctgtcctgac ggctatcggg agagatctga ttgcagtaat     360
aggccagctt gtggcacatc cgactgctgt cgcgtgtctg tcttcgggaa ctgcctgact     420
accctgcctg tgtcctactc ttatacctac aattatgaat ggcatgtgga tgtctgggga     480
cagggcctgc tggtgacagt ctctagt                                         507
```

<210> SEQ ID NO 3
<211> LENGTH: 1506
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 3

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcaccct gtgtgccagg     300
gaaactaaga ataccagag cggggtggc ggaagcgaat gcatcggtat gttcaaatct      360
tgcgacccgg aaaacgacaa atgctgcaaa ggtcgtacct gctctcgtaa acaccgttgg     420
tgcaaataca aactgggcgg aggtgggagt tcttatacct acaattatga atggcatgtg     480
gatgtctggg gacagggcct gctggtgaca gtctctagtg cttccacaac tgcaccaaag     540
gtgtaccccc tgtcaagctg ctgtggggac aaatcctcta gtaccgtgac actgggatgc     600
ctggtctcaa gctatatgcc cgagcctgtg actgtcacct ggaactcagg agccctgaaa     660
agcggagtgc acaccttccc agctgtgctg cagtcctctg gcctgtatag cctgagttca     720
atggtgacag tccccggcag tacttcaggg cagaccttca cctgtaatgt ggcccatcct     780
gccagctcca ccaaagtgga caaagcagtg aacccaaat cttgcgacaa aactcacaca      840
tgcccaccgt gcccagcacc tgaactcctg ggggaccgt cagtcttcct cttccccca      900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggagt acaagtgcaa ggtctccaac    1140
aaagccctcc cagcccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatcccagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga gagcctctc cctgtctccg    1500
ggtaaa                                                                1506
```

<210> SEQ ID NO 4
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcaccct gtgtgccagg     300
gaaactaaga ataccagag cggggggtggc ggaagcgact gcctgggttt catgcgtaaa    360
```

```
tgcatcccgg acaacgacaa atgctgccgt ccgaacctgg tttgctctcg tacccacaaa    420
tggtgcaaat acgttttcgg cggaggtggg agttcttata cctacaatta tgaatggcat    480
gtggatgtct ggggacaggg cctgctggtg acagtctcta gtgcttccac aactgcacca    540
aaggtgtacc ccctgtcaag ctgctgtggg acaaatcct ctagtaccgt gacactggga    600
tgcctggtct caagctatat gcccgagcct gtgactgtca cctggaactc aggagccctg    660
aaaagcggag tgcacacctt cccagctgtg ctgcagtcct ctggcctgta tagcctgagt    720
tcaatggtga cagtccccgg cagtacttca gggcagacct tcacctgtaa tgtggcccat    780
cctgccagct ccaccaaagt ggacaaagca gtggaaccca atcttgcga caaaactcac     840 acatgcccac cgtgcccagc acctgaactc ctgggggac cgtcagtctt cctcttcccc     900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tcccagcccc catcgagaaa accatctcca aagccaaagg cagccccga    1200 gaaccacagg tgtacaccct gcccccatcc cgggatgagc tgaccaagaa ccaggtcagc   1260
ctgacctgcc tggtcaaagg cttctatccc agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtaaa                                                            1509

<210> SEQ ID NO 5
<211> LENGTH: 1578
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag cggggtggc ggaagcctga atgttacca acatggtaaa      360 gttgtgactt gtcatcgaga tatgaagttt tgctatcata acactggcat gccttttcga    420
aatctcaagc tcatcctaca gggatgttct tcttcgtgca gtgaaacaga aaacaataag    480
tgttgctcaa cagacagatg caacaaaggc ggaggtggga gttcttatac ctacaattat    540
gaatggcatg tggatgtctg gggacagggc ctgctggtga cagtctctag tgcttccaca    600
actgcaccaa aggtgtaccc cctgtcaagc tgctgtgggg acaaatcctc tagtaccgtg    660
acactgggat gcctggtctc aagctatatg cccgagcctg tgactgtcac ctggaactca    720
ggagccctga aaagcggagt gcacaccttc ccagctgtgc tgcagtcctc tggcctgtat    780
agcctgagtt caatggtgac agtccccggc agtacttcag ggcagacctt cacctgtaat    840
```

```
gtggcccatc ctgccagctc caccaaagtg gacaaagcag tggaacccaa atcttgcgac      900
aaaactcaca catgcccacc gtgcccagca cctgaactcc tggggggacc gtcagtcttc      960
ctcttccccc caaaacccaa ggacaccctc atgatctccc ggacccctga ggtcacatgc     1020
gtggtggtgg acgtgagcca cgaagaccct gaggtcaagt tcaactggta cgtggacggc     1080
gtggaggtgc ataatgccaa gacaaagccg cgggaggagc agtacaacag cacgtaccgt     1140
gtggtcagcg tcctcaccgt cctgcaccag gactggctga atggcaagga gtacaagtgc     1200
aaggtctcca acaaagccct cccagccccc atcgagaaaa ccatctccaa agccaaaggg     1260
cagccccgag aaccacaggt gtacaccctg cccccatccc gggatgagct gaccaagaac     1320
caggtcagcc tgacctgcct ggtcaaaggc ttctatccca gcgacatcgc cgtggagtgg     1380
gagagcaatg ggcagccgga gaacaactac aagaccacgc ctcccgtgct ggactccgac     1440
ggctccttct tcctctacag caagctcacc gtggacaaga gcaggtggca gcaggggaac     1500
gtcttctcat gctccgtgat gcatgaggct ctgcacaacc actacacgca gaagagcctc     1560
tccctgtctc cgggtaaa                                                   1578

<210> SEQ ID NO 6
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
caggtccagc tgagagagag cggcccttca ctggtcaagc catcccagac actgagcctg       60
acatgcacag caagcgggtt ttcactgagc gacaaggcag tgggatgggt ccgacaggca      120
ccaggaaaag ccctggaatg gctgggcagc atcgataccg gcgggaacac agggtacaat      180
cccggactga gagcagact gtccattacc aaggacaact ctaaaagtca ggtgtcactg      240
agcgtgagct ccgtcaccac agaggatagt gcaacttact attgcaccte tgtgcaccag      300 gaaactaaga ataccagag cggggtggc ggaagccact ctcagggtac cttcaccect      360 gactactcta ataccctgga ctctcgtcgt gctcaggact tcgttcagtg gctgatgaac      420
accaaacgta accgtaacaa catcgctggc ggaggtggga gttcttatac ctacaattat      480
gaatggcatg tggatgtctg gggacagggc ctgctggtga cagtctctag tgcttccaca      540
actgcaccaa aggtgtaccc cctgtcaagc tgctgtgggg acaaatcctc tagtaccgtg      600
acactgggat gcctggtctc aagctatatg cccgagcctg tgactgtcac ctggaactca      660
ggagccctga aaagcggagt gcacaccttc ccagctgtgc tgcagtcctc tggcctgtat      720
agcctgagtt caatggtgac agtccccggc agtacttcag ggcagacctt cacctgtaat      780
gtggcccatc ctgccagctc caccaaagtg gacaaagcag tggaacccaa atcttgcgac      840
aaaactcaca catgcccacc gtgcccagca cctgaactcc tggggggacc gtcagtcttc      900
ctcttccccc caaaacccaa ggacaccctc atgatctccc ggacccctga ggtcacatgc      960
gtggtggtgg acgtgagcca cgaagaccct gaggtcaagt tcaactggta cgtggacggc     1020
gtggaggtgc ataatgccaa gacaaagccg cgggaggagc agtacaacag cacgtaccgt     1080
gtggtcagcg tcctcaccgt cctgcaccag gactggctga atggcaagga gtacaagtgc     1140
aaggtctcca acaaagccct cccagccccc atcgagaaaa ccatctccaa agccaaaggg     1200
cagccccgag aaccacaggt gtacaccctg cccccatccc gggatgagct gaccaagaac     1260
```

```
caggtcagcc tgacctgcct ggtcaaaggc ttctatccca gcgacatcgc cgtggagtgg    1320
gagagcaatg ggcagccgga gaacaactac aagaccacgc ctcccgtgct ggactccgac    1380
ggctccttct tcctctacag caagctcacc gtggacaaga gcaggtggca gcagggaac    1440 gtcttctcat gctccgtgat gcatgaggct ctgcacaacc actacacgca gaagagcctc    1500
tccctgtctc cgggtaaa                                                  1518
```

<210> SEQ ID NO 7
<211> LENGTH: 1659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180 cccgactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag cggggggtggc ggaagctctg tgagtgaaat acagcttatg    360
cataacctgg gaaaacatct gaactcgatg gagagagtag aatggctgcg taagaagctg    420
caggatgtgc acaattttgt tgcccttgga gctcctctag ctcccagaga tgctggttcc    480
cagaggcccc gaaaaaagga agacaatgtc ttggttgaga gccatgaaaa aagtcttgga    540
gaggcagaca agctgatgt gaatgtatta actaaagcta atcccagggg cggaggtggg    600
agttcttata cctacaatta tgaatggcat gtggatgtct ggggacaggg cctgctggtg    660
acagtctcta gtgcttccac aactgcacca aaggtgtacc ccctgtcaag ctgctgtggg    720
gacaaatcct ctagtaccgt gacactggga tgcctggtct caagctatat gcccgagcct    780
gtgactgtca cctggaactc aggagccctg aaaagcggag tgcacacctt cccagctgtg    840
ctgcagtcct ctggcctgta tagcctgagt tcaatggtga cagtccccgg cagtacttca    900
gggcagacct tcacctgtaa tgtggcccat cctgccagct ccaccaaagt ggacaaagca    960
gtggaaccca atcttgcga caaaactcac acatgcccac cgtgcccagc acctgaactc   1020 ctgggggac cgtcagtctt cctcttcccc ccaaaaccca aggacaccct catgatctcc   1080
cggacccctg aggtcacatg cgtggtggtg gacgtgagcc acgaagaccc tgaggtcaag   1140
ttcaactggt acgtggacgg cgtggaggtg cataatgcca agacaaagcc gcgggaggag   1200
cagtacaaca gcacgtaccg tgtggtcagc gtcctcaccg tcctgcacca ggactggctg   1260
aatggcaagg agtacaagtg caaggtctcc aacaaagccc tcccagcccc catcgagaaa   1320
accatctcca aagccaaagg gcagcccga gaaccacagg tgtacaccct gcccccatcc   1380
cgggatgagc tgaccaagaa ccaggtcagc ctgacctgcc tggtcaaagg cttctatccc   1440
agcgacatcg ccgtggagtg ggagagcaat gggcagccgg agaacaacta caagaccacg   1500
cctcccgtgc tggactccga cggctccttc ttcctctaca gcaagctcac cgtggacaag   1560
agcaggtggc agcaggggaa cgtcttctca tgctccgtga tgcatgaggc tctgcacaac   1620
cactacacgc agaagagcct ctccctgtct ccgggtaaa                          1659
```

```
<210> SEQ ID NO 8
<211> LENGTH: 216
<212> TYPE: PRT
<213> ORGANISM: Bos sp.

<400> SEQUENCE: 8

Gln Ala Val Leu Asn Gln Pro Ser Ser Val Ser Gly Ser Leu Gly Gln
1               5                   10                  15

Arg Val Ser Ile Thr Cys Ser Gly Ser Ser Asn Val Gly Asn Gly
            20                  25                  30

Tyr Val Ser Trp Tyr Gln Leu Ile Pro Gly Ser Ala Pro Arg Thr Leu
            35                  40                  45

Ile Tyr Gly Asp Thr Ser Arg Ala Ser Gly Val Pro Asp Arg Phe Ser
    50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser Asn Ala Val Phe Gly Ser Gly Thr Thr Leu Thr Val Leu Gly Gln
            100                 105                 110

Pro Lys Ser Pro Ser Val Thr Leu Phe Pro Pro Ser Thr Glu Glu
        115                 120                 125

Leu Asn Gly Asn Lys Ala Thr Leu Val Cys Leu Ile Ser Asp Phe Tyr
130                 135                 140

Pro Gly Ser Val Thr Val Val Trp Lys Ala Asp Gly Ser Thr Ile Thr
145                 150                 155                 160

Arg Asn Val Glu Thr Thr Arg Ala Ser Lys Gln Ser Asn Ser Lys Tyr
                165                 170                 175

Ala Ala Ser Ser Tyr Leu Ser Leu Thr Ser Ser Asp Trp Lys Ser Lys
            180                 185                 190

Gly Ser Tyr Ser Cys Glu Val Thr His Glu Gly Ser Thr Val Thr Lys
        195                 200                 205

Thr Val Lys Pro Ser Glu Cys Ser
    210                 215

<210> SEQ ID NO 9
<211> LENGTH: 169
<212> TYPE: PRT
<213> ORGANISM: Bos sp.

<400> SEQUENCE: 9

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
            35                  40                  45

Gly Ser Ile Asp Thr Gly Gly Asn Thr Gly Tyr Asn Pro Gly Leu Lys
        50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Cys Pro Asp Gly Tyr
            100                 105                 110

Arg Glu Arg Ser Asp Cys Ser Asn Arg Pro Ala Cys Gly Thr Ser Asp
```

```
            115                 120                 125
Cys Cys Arg Val Ser Val Phe Gly Asn Cys Leu Thr Thr Leu Pro Val
        130                 135                 140
Ser Tyr Ser Tyr Thr Tyr Asn Tyr Glu Trp His Val Asp Val Trp Gly
145                 150                 155                 160
Gln Gly Leu Leu Val Thr Val Ser Ser
                165

<210> SEQ ID NO 10
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Arg Glu Ser Gly Pro Ser Leu Val Lys Pro Ser Gln
1               5                   10                  15
Thr Leu Ser Leu Thr Cys Thr Ala Ser Gly Phe Ser Leu Ser Asp Lys
            20                  25                  30
Ala Val Gly Trp Val Arg Gln Ala Pro Gly Lys Ala Leu Glu Trp Leu
        35                  40                  45
Gly Ser Ile Asp Thr Gly Gly Asn Thr Gly Tyr Asn Pro Gly Leu Lys
    50                  55                  60
Ser Arg Leu Ser Ile Thr Lys Asp Asn Ser Lys Ser Gln Val Ser Leu
65                  70                  75                  80
Ser Val Ser Ser Val Thr Thr Glu Asp Ser Ala Thr Tyr Tyr Cys Thr
                85                  90                  95
Ser Val His Gln Glu Thr Lys Lys Tyr Gln Ser Gly Gly Gly Gly Ser
            100                 105                 110
Glu Cys Ile Gly Met Phe Lys Ser Cys Asp Pro Glu Asn Asp Lys Cys
        115                 120                 125
Cys Lys Gly Arg Thr Cys Ser Arg Lys His Arg Trp Cys Lys Tyr Lys
    130                 135                 140
Leu Gly Gly Gly Gly Ser Ser Tyr Thr Tyr Asn Tyr Glu Trp His Val
145                 150                 155                 160
Asp Val Trp Gly Gln Gly Leu Leu Val Thr Val Ser Ser Ala Ser Thr
                165                 170                 175
Thr Ala Pro Lys Val Tyr Pro Leu Ser Ser Cys Cys Gly Asp Lys Ser
            180                 185                 190
Ser Ser Thr Val Thr Leu Gly Cys Leu Val Ser Ser Tyr Met Pro Glu
        195                 200                 205
Pro Val Thr Val Thr Trp Asn Ser Gly Ala Leu Lys Ser Gly Val His
    210                 215                 220
Thr Phe Pro Ala Val Leu Gln Ser Ser Gly Leu Tyr Ser Leu Ser Ser
225                 230                 235                 240
Met Val Thr Val Pro Gly Ser Thr Ser Gly Gln Thr Phe Thr Cys Asn
                245                 250                 255
Val Ala His Pro Ala Ser Ser Thr Lys Val Asp Lys Ala Val Glu Pro
            260                 265                 270
Lys Ser Cys Asp Lys Thr His Thr Cys Pro Pro Cys Pro Ala Pro Glu
        275                 280                 285
Leu Leu Gly Gly Pro Ser Val Phe Leu Phe Pro Pro Lys Pro Lys Asp
    290                 295                 300
```

```
Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
            325                 330                 335

Val Glu Val His Asn Ala Lys Thr Lys Pro Arg Glu Glu Gln Tyr Asn
        340                 345                 350

Ser Thr Tyr Arg Val Val Ser Val Leu Thr Val Leu His Gln Asp Trp
    355                 360                 365

Leu Asn Gly Lys Glu Tyr Lys Cys Lys Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
            405                 410                 415

Gln Val Ser Leu Thr Cys Leu Val Lys Gly Phe Tyr Pro Ser Asp Ile
        420                 425                 430

Ala Val Glu Trp Glu Ser Asn Gly Gln Pro Glu Asn Asn Tyr Lys Thr
    435                 440                 445

Thr Pro Pro Val Leu Asp Ser Asp Gly Ser Phe Phe Leu Tyr Ser Lys
450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
            485                 490                 495

Ser Leu Ser Pro Gly Lys
            500

<210> SEQ ID NO 11
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
            85                  90                  95

Ser Val His Gln Glu Thr Lys Lys Tyr Gln Ser Gly Gly Gly Gly Ser
            100                 105                 110

Asp Cys Leu Gly Phe Met Arg Lys Cys Ile Pro Asp Asn Asp Lys Cys
        115                 120                 125

Cys Arg Pro Asn Leu Val Cys Ser Arg Thr His Lys Trp Cys Lys Tyr
    130                 135                 140

Val Phe Gly Gly Gly Gly Ser Ser Tyr Thr Tyr Asn Tyr Glu Trp His
145                 150                 155                 160
```

Val Asp Val Trp Gly Gln Gly Leu Leu Val Thr Val Ser Ser Ala Ser
            165                 170                 175

Thr Thr Ala Pro Lys Val Tyr Pro Leu Ser Ser Cys Cys Gly Asp Lys
            180                 185                 190

Ser Ser Ser Thr Val Thr Leu Gly Cys Leu Val Ser Ser Tyr Met Pro
            195                 200                 205

Glu Pro Val Thr Val Thr Trp Asn Ser Gly Ala Leu Lys Ser Gly Val
            210                 215                 220

His Thr Phe Pro Ala Val Leu Gln Ser Ser Gly Leu Tyr Ser Leu Ser
225                 230                 235                 240

Ser Met Val Thr Val Pro Gly Ser Thr Ser Gly Gln Thr Phe Thr Cys
            245                 250                 255

Asn Val Ala His Pro Ala Ser Ser Thr Lys Val Asp Lys Ala Val Glu
            260                 265                 270

Pro Lys Ser Cys Asp Lys Thr His Thr Cys Pro Pro Cys Pro Ala Pro
            275                 280                 285

Glu Leu Leu Gly Gly Pro Ser Val Phe Leu Phe Pro Pro Lys Pro Lys
            290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
            325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Lys Val Ser Asn Lys Ala Leu
            370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
            405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
            485                 490                 495

Leu Ser Leu Ser Pro Gly Lys
            500

<210> SEQ ID NO 12
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Arg Glu Ser Gly Pro Ser Leu Val Lys Pro Ser Gln

-continued

```
1               5                   10                  15
Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
            35                  40              45

Gly Ser Ile Asp Thr Gly Gly Asn Thr Gly Tyr Asn Pro Gly Leu Lys
 50                  55                  60

Ser Arg Leu Ser Ile Thr Lys Asp Asn Ser Lys Ser Gln Val Ser Leu
 65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Leu Lys Cys Tyr Gln His Gly Lys Val Val Thr Cys His Arg Asp Met
            115                 120                 125

Lys Phe Cys Tyr His Asn Thr Gly Met Pro Phe Arg Asn Leu Lys Leu
            130                 135                 140

Ile Leu Gln Gly Cys Ser Ser Cys Ser Glu Thr Glu Asn Asn Lys
145                 150                 155                 160

Cys Cys Ser Thr Asp Arg Cys Asn Lys Gly Gly Gly Ser Ser Tyr
                165                 170                 175

Thr Tyr Asn Tyr Glu Trp His Val Asp Val Trp Gly Gln Gly Leu Leu
                180                 185                 190

Val Thr Val Ser Ser Ala Ser Thr Thr Ala Pro Lys Val Tyr Pro Leu
            195                 200                 205

Ser Ser Cys Cys Gly Asp Lys Ser Ser Ser Thr Val Thr Leu Gly Cys
 210                 215                 220

Leu Val Ser Ser Tyr Met Pro Glu Pro Val Thr Val Thr Trp Asn Ser
225                 230                 235                 240

Gly Ala Leu Lys Ser Gly Val His Thr Phe Pro Ala Val Leu Gln Ser
                245                 250                 255

Ser Gly Leu Tyr Ser Leu Ser Ser Met Val Thr Val Pro Gly Ser Thr
            260                 265                 270

Ser Gly Gln Thr Phe Thr Cys Asn Val Ala His Pro Ala Ser Ser Thr
            275                 280                 285

Lys Val Asp Lys Ala Val Glu Pro Lys Ser Cys Asp Lys Thr His Thr
            290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
            355                 360                 365

Lys Pro Arg Glu Glu Gln Tyr Asn Ser Thr Tyr Arg Val Val Ser Val
            370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
            420                 425                 430
```

```
Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
            485                 490                 495

Gln Gln Gly Asn Val Phe Ser Cys Ser Val Met His Glu Ala Leu His
                500                 505                 510

Asn His Tyr Thr Gln Lys Ser Leu Ser Leu Ser Pro Gly Lys
            515                 520                 525

<210> SEQ ID NO 13
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

His Ser Gln Gly Thr Phe Thr Ser Asp Tyr Ser Lys Tyr Leu Asp Ser
        115                 120                 125

Arg Arg Ala Gln Asp Phe Val Gln Trp Leu Met Asn Thr Lys Arg Asn
    130                 135                 140

Arg Asn Asn Ile Ala Gly Gly Gly Ser Ser Tyr Thr Tyr Asn Tyr
145                 150                 155                 160

Glu Trp His Val Asp Val Trp Gly Gln Gly Leu Leu Val Thr Val Ser
                165                 170                 175

Ser Ala Ser Thr Thr Ala Pro Lys Val Tyr Pro Leu Ser Ser Cys Cys
            180                 185                 190

Gly Asp Lys Ser Ser Ser Thr Val Thr Leu Gly Cys Leu Val Ser Ser
        195                 200                 205

Tyr Met Pro Glu Pro Val Thr Val Thr Trp Asn Ser Gly Ala Leu Lys
    210                 215                 220

Ser Gly Val His Thr Phe Pro Ala Val Leu Gln Ser Ser Gly Leu Tyr
225                 230                 235                 240

Ser Leu Ser Ser Met Val Thr Val Pro Gly Ser Thr Ser Gly Gln Thr
                245                 250                 255

Phe Thr Cys Asn Val Ala His Pro Ala Ser Ser Thr Lys Val Asp Lys
```

```
                260                 265                 270
Ala Val Glu Pro Lys Ser Cys Asp Lys Thr His Thr Cys Pro Pro Cys
            275                 280                 285

Pro Ala Pro Glu Leu Leu Gly Gly Pro Ser Val Phe Leu Phe Pro Pro
        290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505

<210> SEQ ID NO 14
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110
```

Ser Val Ser Glu Ile Gln Leu Met His Asn Leu Gly Lys His Leu Asn
            115                 120                 125

Ser Met Glu Arg Val Glu Trp Leu Arg Lys Lys Leu Gln Asp Val His
        130                 135                 140

Asn Phe Val Ala Leu Gly Ala Pro Leu Ala Pro Arg Asp Ala Gly Ser
145                 150                 155                 160

Gln Arg Pro Arg Lys Lys Glu Asp Asn Val Leu Val Glu Ser His Glu
                165                 170                 175

Lys Ser Leu Gly Glu Ala Asp Lys Ala Asp Val Asn Val Leu Thr Lys
                180                 185                 190

Ala Lys Ser Gln Gly Gly Gly Ser Ser Tyr Thr Tyr Asn Tyr Glu
            195                 200                 205

Trp His Val Asp Val Trp Gly Gln Gly Leu Leu Val Thr Val Ser Ser
        210                 215                 220

Ala Ser Thr Thr Ala Pro Lys Val Tyr Pro Leu Ser Ser Cys Cys Gly
225                 230                 235                 240

Asp Lys Ser Ser Ser Thr Val Thr Leu Gly Cys Leu Val Ser Ser Tyr
                245                 250                 255

Met Pro Glu Pro Val Thr Val Thr Trp Asn Ser Gly Ala Leu Lys Ser
            260                 265                 270

Gly Val His Thr Phe Pro Ala Val Leu Gln Ser Ser Gly Leu Tyr Ser
        275                 280                 285

Leu Ser Ser Met Val Thr Val Pro Gly Ser Thr Ser Gly Gln Thr Phe
        290                 295                 300

Thr Cys Asn Val Ala His Pro Ala Ser Ser Thr Lys Val Asp Lys Ala
305                 310                 315                 320

Val Glu Pro Lys Ser Cys Asp Lys Thr His Thr Cys Pro Pro Cys Pro
                325                 330                 335

Ala Pro Glu Leu Leu Gly Gly Pro Ser Val Phe Leu Phe Pro Pro Lys
            340                 345                 350

Pro Lys Asp Thr Leu Met Ile Ser Arg Thr Pro Glu Val Thr Cys Val
        355                 360                 365

Val Val Asp Val Ser His Glu Asp Pro Glu Val Lys Phe Asn Trp Tyr
370                 375                 380

Val Asp Gly Val Glu Val His Asn Ala Lys Thr Lys Pro Arg Glu Glu
385                 390                 395                 400

Gln Tyr Asn Ser Thr Tyr Arg Val Val Ser Val Leu Thr Val Leu His
                405                 410                 415

Gln Asp Trp Leu Asn Gly Lys Glu Tyr Lys Cys Lys Val Ser Asn Lys
            420                 425                 430

Ala Leu Pro Ala Pro Ile Glu Lys Thr Ile Ser Lys Ala Lys Gly Gln
        435                 440                 445

Pro Arg Glu Pro Gln Val Tyr Thr Leu Pro Pro Ser Arg Asp Glu Leu
        450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
                485                 490                 495

Tyr Lys Thr Thr Pro Pro Val Leu Asp Ser Asp Gly Ser Phe Phe Leu
            500                 505                 510

Tyr Ser Lys Leu Thr Val Asp Lys Ser Arg Trp Gln Gln Gly Asn Val
        515                 520                 525

Phe Ser Cys Ser Val Met His Glu Ala Leu His Asn His Tyr Thr Gln

```
              530                 535                 540
Lys Ser Leu Ser Leu Ser Pro Gly Lys
545                 550

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Ser Gly Gly Gly Gly Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Ser Gly Gly Gly Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser
1               5

<210> SEQ ID NO 18
<211> LENGTH: 11
<212> TYPE: PRT
<213> ORGANISM: Bos sp.

<400> SEQUENCE: 18

Thr Ser Val His Gln Glu Thr Lys Lys Tyr Gln
1               5                   10

<210> SEQ ID NO 19
<211> LENGTH: 9
<212> TYPE: PRT
<213> ORGANISM: Bos sp.

<400> SEQUENCE: 19

Val His Gln Glu Thr Lys Lys Tyr Gln
1               5

<210> SEQ ID NO 20
<211> LENGTH: 5
<212> TYPE: PRT
<213> ORGANISM: Bos sp.

<400> SEQUENCE: 20

Thr Thr Val His Gln
1               5
```

```
<210> SEQ ID NO 21
<211> LENGTH: 5
<212> TYPE: PRT
<213> ORGANISM: Bos sp.

<400> SEQUENCE: 21

Thr Ser Val His Gln
1               5

<210> SEQ ID NO 22
<211> LENGTH: 3
<212> TYPE: PRT
<213> ORGANISM: Bos sp.

<400> SEQUENCE: 22

Val His Gln
1

<210> SEQ ID NO 23
<211> LENGTH: 3
<212> TYPE: PRT
<213> ORGANISM: Bos sp.

<400> SEQUENCE: 23

Lys Lys Gln
1

<210> SEQ ID NO 24
<211> LENGTH: 3
<212> TYPE: PRT
<213> ORGANISM: Bos sp.

<400> SEQUENCE: 24

Val Tyr Gln
1

<210> SEQ ID NO 25
<211> LENGTH: 7
<212> TYPE: PRT
<213> ORGANISM: Bos sp.
<220> FEATURE:
<221> NAME/KEY: MOD_RES
<222> LOCATION: (7)..(7)
<223> OTHER INFORMATION: Any amino acid

<400> SEQUENCE: 25

Cys Thr Thr Val His Gln Xaa
1               5

<210> SEQ ID NO 26
<211> LENGTH: 7
<212> TYPE: PRT
<213> ORGANISM: Bos sp.
<220> FEATURE:
<221> NAME/KEY: MOD_RES
<222> LOCATION: (7)..(7)
<223> OTHER INFORMATION: Any amino acid

<400> SEQUENCE: 26

Cys Thr Ser Val His Gln Xaa
1               5

<210> SEQ ID NO 27
<211> LENGTH: 6
<212> TYPE: PRT
```

```
<213> ORGANISM: Bos sp.
<220> FEATURE:
<221> NAME/KEY: MOD_RES
<222> LOCATION: (2)..(5)
<223> OTHER INFORMATION: Any amino acid

<400> SEQUENCE: 27

Cys Xaa Xaa Xaa Xaa Gln
1               5

<210> SEQ ID NO 28
<211> LENGTH: 5
<212> TYPE: PRT
<213> ORGANISM: Bos sp.
<220> FEATURE:
<221> NAME/KEY: MOD_RES
<222> LOCATION: (1)..(2)
<223> OTHER INFORMATION: Any amino acid

<400> SEQUENCE: 28

Xaa Xaa Val His Gln
1               5

<210> SEQ ID NO 29
<211> LENGTH: 6
<212> TYPE: PRT
<213> ORGANISM: Bos sp.
<220> FEATURE:
<221> NAME/KEY: MOD_RES
<222> LOCATION: (2)..(3)
<223> OTHER INFORMATION: Any amino acid

<400> SEQUENCE: 29

Cys Xaa Xaa Val His Gln
1               5

<210> SEQ ID NO 30
<211> LENGTH: 5
<212> TYPE: PRT
<213> ORGANISM: Bos sp.
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 30

Xaa Xaa Val Xaa Gln
1               5

<210> SEQ ID NO 31
<211> LENGTH: 6
<212> TYPE: PRT
<213> ORGANISM: Bos sp.
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 31

Cys Xaa Xaa Val Xaa Gln
1               5
```

```
<210> SEQ ID NO 32
<211> LENGTH: 5
<212> TYPE: PRT
<213> ORGANISM: Bos sp.
<220> FEATURE:
<221> NAME/KEY: MOD_RES
<222> LOCATION: (1)..(2)
<223> OTHER INFORMATION: Any amino acid

<400> SEQUENCE: 32

Xaa Xaa Lys Lys Gln
1               5

<210> SEQ ID NO 33
<211> LENGTH: 6
<212> TYPE: PRT
<213> ORGANISM: Bos sp.
<220> FEATURE:
<221> NAME/KEY: MOD_RES
<222> LOCATION: (2)..(3)
<223> OTHER INFORMATION: Any amino acid

<400> SEQUENCE: 33

Cys Xaa Xaa Lys Lys Gln
1               5

<210> SEQ ID NO 34
<211> LENGTH: 7
<212> TYPE: PRT
<213> ORGANISM: Bos sp.

<400> SEQUENCE: 34

Tyr Thr Tyr Asn Tyr Glu Trp
1               5

<210> SEQ ID NO 35
<211> LENGTH: 6
<212> TYPE: PRT
<213> ORGANISM: Bos sp.

<400> SEQUENCE: 35

Tyr Thr Tyr Asn Tyr Glu
1               5

<210> SEQ ID NO 36
<211> LENGTH: 7
<212> TYPE: PRT
<213> ORGANISM: Bos sp.

<400> SEQUENCE: 36

Tyr Leu Tyr Thr Tyr Glu His
1               5

<210> SEQ ID NO 37
<211> LENGTH: 6
<212> TYPE: PRT
<213> ORGANISM: Bos sp.

<400> SEQUENCE: 37

Tyr Leu Tyr Thr Tyr Glu
1               5

<210> SEQ ID NO 38
<211> LENGTH: 4
<212> TYPE: PRT
<213> ORGANISM: Bos sp.
```

```
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 38

Tyr Xaa Tyr Xaa
1

<210> SEQ ID NO 39
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 39

Tyr Xaa Tyr Xaa Tyr
1               5

<210> SEQ ID NO 40
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 40

Tyr Xaa Tyr Xaa Tyr Xaa
1               5

<210> SEQ ID NO 41
<211> LENGTH: 7
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 41

Tyr Xaa Tyr Xaa Tyr Xaa Xaa
1               5
```

<210> SEQ ID NO 42
<211> LENGTH: 3
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Any amino acid

<400> SEQUENCE: 42

Tyr Glu Xaa
1

<210> SEQ ID NO 43
<211> LENGTH: 3
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Any amino acid

<400> SEQUENCE: 43

Tyr Asp Xaa
1

<210> SEQ ID NO 44
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Any amino acid

<400> SEQUENCE: 44

Xaa Tyr Glu
1

<210> SEQ ID NO 45
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Any amino acid

<400> SEQUENCE: 45

Xaa Tyr Asp
1

<210> SEQ ID NO 46
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(4)
<223> OTHER INFORMATION: Any amino acid

<400> SEQUENCE: 46

Tyr Xaa Xaa Xaa Trp
1               5

```
<210> SEQ ID NO 47
<211> LENGTH: 8
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(7)
<223> OTHER INFORMATION: Any amino acid

<400> SEQUENCE: 47

Tyr Xaa Xaa Xaa Xaa Xaa Xaa Trp
1               5

<210> SEQ ID NO 48
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(33)
<223> OTHER INFORMATION: Any amino acid

<400> SEQUENCE: 48

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa Xaa
            20                  25                  30

Xaa Cys

<210> SEQ ID NO 49
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
```

```
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(42)
<223> OTHER INFORMATION: Any amino acid

<400> SEQUENCE: 49

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Xaa Xaa Xaa Xaa Xaa Xaa Xaa Cys
        35                  40

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(20)
<223> OTHER INFORMATION: Any amino acid

<400> SEQUENCE: 50

Cys Xaa Xaa Xaa Xaa Xaa Xaa Xaa Xaa Xaa Xaa Xaa Cys Xaa Cys Xaa
1               5                   10                  15

Xaa Xaa Xaa Xaa Cys
            20

<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 51
```

Cys Xaa Xaa Xaa Xaa Xaa Xaa Xaa Xaa Xaa Cys Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25              30

Xaa Xaa Cys
        35

<210> SEQ ID NO 52
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(40)
<223> OTHER INFORMATION: Any amino acid

<400> SEQUENCE: 52

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25              30

Xaa Xaa Xaa Xaa Xaa Xaa Xaa Xaa Cys
        35                  40

<210> SEQ ID NO 53
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid

<400> SEQUENCE: 53

Cys Xaa Xaa Xaa Xaa Xaa Xaa Xaa Xaa Xaa Cys Xaa Xaa Xaa Xaa
1               5                   10                  15

Xaa Cys Xaa Cys Xaa Xaa Xaa Xaa Cys Xaa Xaa Xaa Xaa Xaa Xaa
            20                  25                  30

Xaa Cys

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(35)
<223> OTHER INFORMATION: Any amino acid

<400> SEQUENCE: 54

Cys Xaa Xaa Xaa Xaa Xaa Xaa Xaa Xaa Xaa Xaa Cys Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Cys
        35

<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(35)
<223> OTHER INFORMATION: Any amino acid

<400> SEQUENCE: 55

Cys Xaa Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Cys Xaa Cys Xaa Xaa Xaa Xaa
                20                  25                  30

Xaa Xaa Xaa Cys
        35

<210> SEQ ID NO 56
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 56

Cys Xaa Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Cys Xaa Cys Xaa Xaa Xaa Xaa
                20                  25                  30

Xaa Xaa Cys
        35

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(14)
<223> OTHER INFORMATION: Any amino acid
<220> FEATURE:
<221> NAME/KEY: MOD_RES
<222> LOCATION: (16)..(23)
<223> OTHER INFORMATION: Any amino acid
<220> FEATURE:
<221> NAME/KEY: MOD_RES
<222> LOCATION: (25)..(32)
<223> OTHER INFORMATION: Any amino acid

<400> SEQUENCE: 57

Cys Xaa Xaa Xaa Xaa Xaa Xaa Xaa Xaa Xaa Xaa Xaa Xaa Xaa Cys Xaa
1               5                   10                  15

Xaa Xaa Xaa Xaa Xaa Xaa Xaa Cys Xaa Xaa Xaa Xaa Xaa Xaa Xaa Xaa
                20                  25                  30

Cys

```
<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 58

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Cys
        35

<210> SEQ ID NO 59
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid

<400> SEQUENCE: 59

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys
            20

<210> SEQ ID NO 60
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 60

Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Xaa Cys Xaa Cys Xaa Xaa Xaa Xaa
            20                  25                  30

Xaa Xaa Cys
        35

<210> SEQ ID NO 61
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(32)
<223> OTHER INFORMATION: Any amino acid
<220> FEATURE:
<221> NAME/KEY: MOD_RES
<222> LOCATION: (34)..(42)
<223> OTHER INFORMATION: Any amino acid

<400> SEQUENCE: 61

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Cys Xaa Xaa Xaa Xaa Xaa Xaa Xaa Xaa Xaa Cys
        35                  40

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
```

```
            polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 62

Cys Xaa Xaa Xaa Xaa Xaa Xaa Xaa Xaa Cys Xaa Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Cys
        35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(36)
<223> OTHER INFORMATION: Any amino acid

<400> SEQUENCE: 63

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Xaa Cys
        35

<210> SEQ ID NO 64
<211> LENGTH: 37
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(36)
<223> OTHER INFORMATION: Any amino acid

<400> SEQUENCE: 64

Cys Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Xaa Xaa Xaa Cys
        35

<210> SEQ ID NO 65
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (35)..(44)
<223> OTHER INFORMATION: Any amino acid

<400> SEQUENCE: 65

Cys Xaa Xaa Xaa Xaa Xaa Xaa Xaa Cys Xaa Xaa Xaa Cys Xaa Xaa
1               5                   10                  15

Xaa Xaa Xaa Xaa Cys Xaa Xaa Xaa Xaa Xaa Cys Xaa Cys Xaa Xaa
            20                  25                  30
```

Xaa Cys Xaa Xaa Xaa Xaa Xaa Xaa Xaa Xaa Xaa Cys
         35                  40                  45

<210> SEQ ID NO 66
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(33)
<223> OTHER INFORMATION: Any amino acid

<400> SEQUENCE: 66

Cys Xaa Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Xaa Cys Xaa Cys Xaa Xaa Cys Xaa Xaa
            20                  25                  30

Xaa Cys

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid

<400> SEQUENCE: 67

Cys Xaa Xaa Xaa Xaa Xaa Xaa Xaa Xaa Xaa Xaa Xaa Xaa Xaa Xaa Xaa
1               5                   10                  15

Xaa Cys Xaa Xaa Xaa Xaa Xaa Cys Xaa Cys
            20                  25

```
<210> SEQ ID NO 68
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid

<400> SEQUENCE: 68

Cys Xaa Xaa Xaa Xaa Xaa Xaa Cys Xaa Xaa Xaa Xaa Cys Xaa Cys Xaa
1               5                   10                  15

Xaa Xaa Xaa Cys Xaa Xaa Xaa Xaa Xaa Cys
            20                  25

<210> SEQ ID NO 69
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid

<400> SEQUENCE: 69

Cys Xaa Xaa Xaa Xaa Xaa Xaa Xaa Xaa Xaa Xaa Xaa Cys Xaa Xaa Xaa
1               5                   10                  15

Xaa Cys Xaa Xaa Xaa Xaa Xaa Cys Xaa Xaa Xaa Xaa Xaa Xaa Cys Xaa
            20                  25                  30

Xaa Xaa Cys
        35

<210> SEQ ID NO 70
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid

<400> SEQUENCE: 70

Cys Xaa Xaa Xaa Xaa Xaa Xaa Xaa Xaa Cys Xaa Xaa Cys Xaa Xaa Xaa
1               5                   10                  15

Xaa Xaa Xaa Cys Xaa Xaa Xaa Xaa Xaa Cys
            20                  25

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(36)
<223> OTHER INFORMATION: Any amino acid

<400> SEQUENCE: 71

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa Xaa
            20                  25                  30

Xaa Xaa Xaa Xaa Cys
        35

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(20)
<223> OTHER INFORMATION: Any amino acid
<220> FEATURE:
<221> NAME/KEY: MOD_RES
<222> LOCATION: (22)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 72

Cys Xaa Xaa Xaa Xaa Xaa Xaa Xaa Xaa Xaa Cys Xaa Cys Xaa Xaa
 1               5                  10                  15

Xaa Xaa Xaa Xaa Cys Xaa Xaa Xaa Xaa Cys Xaa Cys
                20                  25

<210> SEQ ID NO 73
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid

<400> SEQUENCE: 73

Cys Xaa Xaa Xaa Xaa Xaa Xaa Xaa Xaa Xaa Xaa Cys Xaa Xaa Xaa Xaa
 1               5                  10                  15

Xaa Cys Xaa Xaa Xaa Xaa Xaa Cys Xaa Cys Xaa Xaa Cys
                20                  25

<210> SEQ ID NO 74
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(15)
<223> OTHER INFORMATION: Any amino acid
<220> FEATURE:
```

```
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid

<400> SEQUENCE: 74

Cys Xaa Xaa Xaa Xaa Xaa Xaa Xaa Xaa Xaa Xaa Xaa Xaa Xaa Cys
1               5                   10                  15

Xaa Xaa Cys Xaa Xaa Xaa Cys Xaa Cys Xaa Cys
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(16)
<223> OTHER INFORMATION: Any amino acid
<220> FEATURE:
<221> NAME/KEY: MOD_RES
<222> LOCATION: (18)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid

<400> SEQUENCE: 75

Cys Xaa Xaa Xaa Xaa Xaa Xaa Xaa Xaa Xaa Xaa Xaa Xaa Xaa Xaa
1               5                   10                  15

Cys Xaa Xaa Xaa Xaa Xaa Cys Xaa Cys
            20                  25

<210> SEQ ID NO 76
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(12)
<223> OTHER INFORMATION: Any amino acid
<220> FEATURE:
<221> NAME/KEY: MOD_RES
<222> LOCATION: (14)..(22)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
```

<222> LOCATION: (27)..(37)
<223> OTHER INFORMATION: Any amino acid

<400> SEQUENCE: 76

Cys Xaa Xaa Xaa Xaa Cys Xaa Xaa Xaa Xaa Xaa Cys Xaa Xaa Xaa
1               5                   10                  15

Xaa Xaa Xaa Xaa Xaa Cys Xaa Xaa Cys Xaa Xaa Xaa Xaa Xaa
            20                  25                  30

Xaa Xaa Xaa Xaa Xaa Cys
        35

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(37)
<223> OTHER INFORMATION: Any amino acid

<400> SEQUENCE: 77

Cys Xaa Xaa Xaa Xaa Xaa Xaa Cys Xaa Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Xaa Xaa Xaa Xaa Cys
        35

<210> SEQ ID NO 78
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:

```
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (23)..(27)
<223> OTHER INFORMATION: Any amino acid
<220> FEATURE:
<221> NAME/KEY: MOD_RES
<222> LOCATION: (29)..(37)
<223> OTHER INFORMATION: Any amino acid

<400> SEQUENCE: 78

Cys Xaa Xaa Xaa Xaa Xaa Xaa Cys Xaa Xaa Xaa Cys Xaa Cys Xaa
1               5                   10                  15

Cys Xaa Xaa Xaa Xaa Cys Xaa Xaa Xaa Xaa Cys Xaa Xaa Xaa Xaa
                20                  25                  30

Xaa Xaa Xaa Xaa Xaa Cys
        35

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid

<400> SEQUENCE: 79

Cys Xaa Xaa Xaa Xaa Xaa Xaa Xaa Xaa Xaa Xaa Cys Xaa Xaa Xaa
1               5                   10                  15

Xaa Xaa Cys Xaa Xaa Xaa Xaa Xaa Cys
                20                  25

<210> SEQ ID NO 80
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(34)
```

<223> OTHER INFORMATION: Any amino acid

<400> SEQUENCE: 80

Cys Xaa Xaa Xaa Xaa Xaa Xaa Xaa Cys Xaa Xaa Xaa Cys Xaa Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Xaa Cys
        35

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid

<400> SEQUENCE: 81

Cys Xaa Xaa Xaa Xaa Xaa Xaa Xaa Cys Xaa Xaa Xaa Xaa Xaa Cys Xaa
1               5                   10                  15

Cys Xaa Xaa Cys
            20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(20)
<223> OTHER INFORMATION: Any amino acid

<400> SEQUENCE: 82

Cys Xaa Xaa Xaa Xaa Xaa Xaa Xaa Xaa Xaa Xaa Cys Xaa Cys Xaa Xaa
1               5                   10                  15

Xaa Xaa Xaa Xaa Cys
                20

<210> SEQ ID NO 83
<211> LENGTH: 43
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (37)..(42)
<223> OTHER INFORMATION: Any amino acid

<400> SEQUENCE: 83

Cys Xaa Xaa Xaa Xaa Xaa Xaa Xaa Xaa Xaa Cys Xaa Xaa Xaa Cys
1               5                   10                  15

Xaa Xaa Xaa Cys Xaa Xaa Xaa Xaa Xaa Cys Xaa Xaa Xaa Xaa Xaa
            20                  25                  30

Xaa Cys Xaa Cys Xaa Xaa Xaa Xaa Xaa Xaa Cys
        35                  40

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(22)
<223> OTHER INFORMATION: Any amino acid
<220> FEATURE:
<221> NAME/KEY: MOD_RES
<222> LOCATION: (24)..(35)
<223> OTHER INFORMATION: Any amino acid
<220> FEATURE:
<221> NAME/KEY: MOD_RES
<222> LOCATION: (37)..(38)
<223> OTHER INFORMATION: Any amino acid

<400> SEQUENCE: 84

Cys Xaa Xaa Xaa Xaa Xaa Xaa Xaa Xaa Xaa Xaa Cys Xaa Xaa Xaa Xaa
1               5                   10                  15

Cys Xaa Xaa Xaa Xaa Xaa Cys Xaa Xaa Xaa Xaa Xaa Xaa Xaa Xaa
```

```
            20                  25                  30

Xaa Xaa Xaa Cys Xaa Xaa Cys
        35

<210> SEQ ID NO 85
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(38)
<223> OTHER INFORMATION: Any amino acid
<220> FEATURE:
<221> NAME/KEY: MOD_RES
<222> LOCATION: (40)..(42)
<223> OTHER INFORMATION: Any amino acid

<400> SEQUENCE: 85

Cys Xaa Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Cys Xaa Cys Xaa Xaa Xaa
            20                  25                  30

Xaa Xaa Xaa Xaa Xaa Xaa Cys Xaa Xaa Xaa Cys
        35                  40

<210> SEQ ID NO 86
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(37)
<223> OTHER INFORMATION: Any amino acid
<220> FEATURE:
<221> NAME/KEY: MOD_RES
```

<222> LOCATION: (39)..(40)
<223> OTHER INFORMATION: Any amino acid

<400> SEQUENCE: 86

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Xaa Xaa Xaa Xaa Cys Xaa Xaa Cys
        35                  40

<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(38)
<223> OTHER INFORMATION: Any amino acid

<400> SEQUENCE: 87

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Xaa Xaa Xaa Xaa Cys
        35

<210> SEQ ID NO 88
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:

```
<221> NAME/KEY: MOD_RES
<222> LOCATION: (29)..(42)
<223> OTHER INFORMATION: Any amino acid

<400> SEQUENCE: 88

Cys Xaa Xaa Xaa Xaa Xaa Xaa Xaa Xaa Xaa Xaa Xaa Xaa Xaa Xaa
 1               5                  10                  15

Xaa Cys Xaa Xaa Xaa Xaa Xaa Cys Xaa Cys Xaa Cys Xaa Xaa Xaa
             20                  25                  30

Xaa Xaa Xaa Xaa Xaa Xaa Xaa Xaa Xaa Xaa Cys
         35                  40

<210> SEQ ID NO 89
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(28)
<223> OTHER INFORMATION: Any amino acid
<220> FEATURE:
<221> NAME/KEY: MOD_RES
<222> LOCATION: (30)..(35)
<223> OTHER INFORMATION: Any amino acid

<400> SEQUENCE: 89

Cys Xaa Xaa Xaa Xaa Xaa Xaa Xaa Xaa Xaa Xaa Cys Xaa Xaa Xaa
 1               5                  10                  15

Xaa Cys Xaa Cys Xaa Xaa Xaa Xaa Xaa Xaa Xaa Cys Xaa Xaa Xaa
             20                  25                  30

Xaa Xaa Xaa Cys
         35

<210> SEQ ID NO 90
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid
```

```
<220> FEATURE:
<221> NAME/KEY: MOD_RES
<222> LOCATION: (35)..(36)
<223> OTHER INFORMATION: Any amino acid

<400> SEQUENCE: 90

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Cys Xaa Xaa Xaa Xaa Xaa Xaa
            20                  25                  30

Xaa Cys Xaa Xaa Cys
        35

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(36)
<223> OTHER INFORMATION: Any amino acid

<400> SEQUENCE: 91

Cys Xaa Xaa Xaa Xaa Xaa Xaa Xaa Xaa Xaa Xaa Xaa Xaa Cys Xaa Xaa
1               5                   10                  15

Xaa Xaa Xaa Cys Xaa Xaa Xaa Xaa Xaa Cys Xaa Cys Xaa Xaa Xaa
            20                  25                  30

Xaa Xaa Xaa Xaa Cys
        35

<210> SEQ ID NO 92
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
```

<223> OTHER INFORMATION: Any amino acid
<220> FEATURE:
<221> NAME/KEY: MOD_RES
<222> LOCATION: (28)..(31)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (35)..(43)
<223> OTHER INFORMATION: Any amino acid

<400> SEQUENCE: 92

Cys Xaa Xaa Xaa Xaa Xaa Xaa Xaa Xaa Xaa Cys Xaa Xaa Xaa Xaa
 1               5                  10                  15

Xaa Xaa Cys Xaa Xaa Xaa Xaa Xaa Cys Xaa Cys Xaa Xaa Xaa Cys
             20                  25                  30

Xaa Cys Xaa Xaa Xaa Xaa Xaa Xaa Xaa Xaa Cys
         35                  40

<210> SEQ ID NO 93
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(32)
<223> OTHER INFORMATION: Any amino acid
<220> FEATURE:
<221> NAME/KEY: MOD_RES
<222> LOCATION: (34)..(35)
<223> OTHER INFORMATION: Any amino acid

<400> SEQUENCE: 93

Cys Xaa Xaa Xaa Xaa Xaa Xaa Xaa Xaa Xaa Xaa Xaa Cys Xaa Xaa
 1               5                  10                  15

Xaa Xaa Cys Xaa Xaa Xaa Xaa Xaa Cys Xaa Xaa Xaa Xaa Xaa Xaa
             20                  25                  30

Cys Xaa Xaa Cys
 35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES

```
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid

<400> SEQUENCE: 94

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Cys Xaa Xaa Cys
        35

<210> SEQ ID NO 95
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(35)
<223> OTHER INFORMATION: Any amino acid

<400> SEQUENCE: 95

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Cys
        35

<210> SEQ ID NO 96
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
```

```
<221> NAME/KEY: MOD_RES
<222> LOCATION: (13)..(18)
<223> OTHER INFORMATION: Any amino acid
<220> FEATURE:
<221> NAME/KEY

```
Xaa Xaa Xaa Xaa Cys Xaa Xaa Xaa Xaa Xaa Cys
        35                  40
```

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(28)
<223> OTHER INFORMATION: Any amino acid
<220> FEATURE:
<221> NAME/KEY: MOD_RES
<222> LOCATION: (30)..(37)
<223> OTHER INFORMATION: Any amino acid

<400> SEQUENCE: 98

```
Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Cys Xaa Xaa Xaa
            20                  25                  30

Xaa Xaa Xaa Xaa Xaa Cys
        35
```

<210> SEQ ID NO 99
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(15)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (25)..(33)
<223> OTHER INFORMATION: Any amino acid

<400> SEQUENCE: 99

```
Cys Xaa Xaa Xaa Xaa Xaa Xaa Xaa Cys Xaa Xaa Xaa Xaa Xaa Xaa Cys
1               5                   10                  15

Xaa Xaa Xaa Cys Xaa Xaa Xaa Cys Xaa Xaa Xaa Xaa Xaa Xaa Xaa Xaa
```

20                  25                  30

Xaa Cys

<210> SEQ ID NO 100
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(32)
<223> OTHER INFORMATION: Any amino acid
<220> FEATURE:
<221> NAME/KEY: MOD_RES
<222> LOCATION: (34)..(38)
<223> OTHER INFORMATION: Any amino acid

<400> SEQUENCE: 100

Cys Xaa Xaa Xaa Xaa Xaa Xaa Xaa Xaa Xaa Cys Xaa Xaa Xaa Xaa Xaa
1               5                   10                  15

Xaa Xaa Xaa Cys Xaa Xaa Xaa Xaa Xaa Cys Xaa Xaa Xaa Xaa Xaa Xaa
                20                  25                  30

Cys Xaa Xaa Xaa Xaa Xaa Cys
        35

<210> SEQ ID NO 101
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (19)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(39)
<223> OTHER INFORMATION: Any amino acid
<220> FEATURE:
<221> NAME/KEY: MOD_RES
<222> LOCATION: (41)..(45)

<223> OTHER INFORMATION: Any amino acid

<400> SEQUENCE: 101

Cys Xaa Xaa Xaa Xaa Xaa Xaa Xaa Xaa Xaa Cys Xaa Xaa Cys Xaa
1               5                   10                  15

Xaa Cys Xaa Xaa Xaa Xaa Xaa Xaa Xaa Cys Xaa Cys Xaa Xaa Xaa Xaa
        20                  25                  30

Xaa Xaa Xaa Xaa Xaa Xaa Xaa Cys Xaa Xaa Xaa Xaa Xaa Cys
        35                  40                  45

<210> SEQ ID NO 102
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(38)
<223> OTHER INFORMATION: Any amino acid
<220> FEATURE:
<221> NAME/KEY: MOD_RES
<222> LOCATION: (40)..(43)
<223> OTHER INFORMATION: Any amino acid

<400> SEQUENCE: 102

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Cys Xaa Xaa
            20                  25                  30

Xaa Xaa Xaa Xaa Xaa Cys Xaa Xaa Xaa Xaa Cys
        35                  40

<210> SEQ ID NO 103
<211> LENGTH: 1971
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac aggtacaat     180 cccggactga agagcagact gtccattacc aaggacaact ctaaaagtca ggtgtcactg    240

```
agcgtgagct ccgtcaccac agaggatagt gcaacttact attgcacctc tgtgcaccag      300
gaaactaaga ataccagag cggggtggc ggaagcgggg gtggcggaag cgctcctctg      360
ggcggtcctg aaccagcaca gtacgaggaa ctgacactgt tgttccatgg agccttgcag      420
ctgggccagg ccctcaacgg cgtgtaccgc gccacagagg cacgtttgac cgaggccgga      480
cacagcctgg gtttgtacga cagagccctg gagtttctgg gtaccgaagt gcgtcagggc      540
caggacgcaa ctcaggagct gagaacctcc ctctctgaga tccaggtgga ggaggacgcc      600
ctgcacctgc gcgccgaggc gacagcacgc tctttgggag aagttgctcg cgctcagcag      660
gccctgcgtg ataccgtgcg gagactccaa gttcagctca gaggcgcttg gctcggacag      720
gcgcatcagg agttcgagac cctgaaagct cgtgccgaca acagtccca cctgctgtgg      780 gcgctcaccg gtcacgtcca cgccagcaa cgcgaaatgg ccgagcagca gcaatggctg      840
cgccaaatcc agcagcgcct gcataccgcg gccctgccag cgtaaggcgg aggtgggagt      900
ggcggaggtg ggagttctta tacctacaat tatgaatggc atgtggatgt ctggggacag      960
ggcctgctgg tgacagtctc tagtgcttcc acaactgcac caaaggtgta ccccctgtca     1020
agctgctgtg gggacaaatc tctagtacc gtgacactgg gatgcctggt ctcaagctat     1080
atgcccgagc ctgtgactgt cacctggaac tcaggagccc tgaaaagcgg agtgcacacc     1140
ttcccagctg tgctgcagtc ctctggcctg tatagcctga gttcaatggt gacagtcccc     1200
ggcagtactt cagggcagac cttcacctgt aatgtggccc atcctgccag ctccaccaaa     1260
gtggacaaag cagtggaacc caaatcttgc gacaaaactc acacatgccc accgtgccca     1320
gcacctgaac tcctgggggg accgtcagtc ttcctcttcc ccccaaaacc caaggacacc     1380
ctcatgatct cccggacccc tgaggtcaca tgcgtggtgg tggacgtgag ccacgaagac     1440
cctgaggtca gttcaactgg tacgtggac ggcgtggagg tgcataatgc caagacaaag     1500 ccgcggagg agcagtacaa cagcacgtac cgtgtggtca gcgtcctcac cgtcctgcac     1560
caggactggc tgaatggcaa ggagtacaag tgcaaggtct ccaacaaagc cctcccagcc     1620
cccatcgaga aaaccatctc caaagccaaa gggcagcccc gagaaccaca ggtgtacacc     1680
ctgcccccat cccgggatga gctgaccaag aaccaggtca gcctgacctg cctggtcaaa     1740
ggcttctatc ccagcgacat cgccgtggag tgggagagca atgggcagcc ggagaacaac     1800
tacaagacca cgcctcccgt gctggactcc gacggctcct tcttcctcta cagcaagctc     1860
accgtggaca agagcaggtg gcagcagggg aacgtcttct catgctccgt gatgcatgag     1920
gctctgcaca accactacac gcagaagagc ctctccctgt ctccgggtaa a              1971
```

<210> SEQ ID NO 104  
<211> LENGTH: 1941  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 104

```
caggtccagc tgagagagag cggccccttca ctggtcaagc catcccagac actgagcctg       60
acatgcacag caagcgggtt ttcactgagc gacaaggcag tgggatgggt ccgacaggca      120
ccaggaaaag ccctggaatg gctgggcagc atcgataccg gcgggaacac agggtacaat      180 cccgactga agagcagact gtccattacc aaggacaact ctaaaagtca ggtgtcactg      240
agcgtgagct ccgtcaccac agaggatagt gcaacttact attgcacctc tgtgcaccag      300
```

```
gaaactaaga aataccagag cgggggtggc ggaagcgctc ctctgggcgg tcctgaacca    360
gcacagtacg aggaactgac actgttgttc catggagcct tgcagctggg ccaggccctc    420
aacggcgtgt accgcgccac agaggcacgt ttgaccgagg ccggacacag cctgggtttg    480
tacgacagag ccctggagtt tctgggtacc gaagtgcgtc agggccagga cgcaactcag    540
gagctgagaa cctccctctc tgagatccag gtggaggagg acgccctgca cctgcgcgcc    600
gaggcgacag cacgctcttt gggagaagtt gctcgcgctc agcaggccct gcgtgatacc    660
gtgcggagac tccaagttca gctcagaggc gcttggctcg acaggcgca tcaggagttc    720 gagaccctga agctcgtgc cgacaaacag tcccacctgc tgtgggcgct caccggtcac    780
gtccagcgcc agcaacgcga atggccgagc agcagcaat ggctgcgcca atccagcag    840 cgcctgcata ccgcggccct gccagcgtaa ggcggaggtg ggagttctta tacctacaat    900
tatgaatggc atgtggatgt ctggggacag ggcctgctgg tgacagtctc tagtgcttcc    960
acaactgcac caaaggtgta ccccctgtca agctgctgtg gggacaaatc tctagtacc   1020 gtgacactgg gatgcctggt ctcaagctat atgcccgagc ctgtgactgt cacctggaac   1080
tcaggagccc tgaaaagcgg agtgcacacc ttcccagctg tgctgcagtc ctctggcctg   1140
tatagcctga gttcaatggt gacagtcccc ggcagtactt cagggcagac cttcacctgt   1200
aatgtggccc atcctgccag ctccaccaaa gtggacaaag cagtggaacc caaatcttgc   1260
gacaaaactc acacatgccc accgtgccca gcacctgaac tcctgggggg accgtcagtc   1320
ttcctcttcc ccccaaaacc caaggacacc ctcatgatct cccggacccc tgaggtcaca   1380
tgcgtggtgg tggacgtgag ccacgaagac cctgaggtca agttcaactg gtacgtggac   1440
ggcgtggagg tgcataatgc caagacaaag ccgcgggagg agcagtacaa cagcacgtac   1500
cgtgtggtca gcgtcctcac cgtcctgcac caggactggc tgaatggcaa ggagtacaag   1560
tgcaaggtct ccaacaaagc cctcccagcc cccatcgaga aaaccatctc caaagccaaa   1620
gggcagcccc gagaaccaca ggtgtacacc ctgcccccat cccgggatga gctgaccaag   1680
aaccaggtca gcctgacctg cctggtcaaa ggcttctatc ccagcgacat cgccgtggag   1740
tgggagagca atgggcagcc ggagaacaac tacaagacca cgcctcccgt gctggactcc   1800
gacggctcct tcttcctcta cagcaagctc accgtggaca agagcaggtg gcagcagggg   1860
aacgtcttct catgctccgt gatgcatgag gctctgcaca accactacac gcagaagagc   1920
ctctccctgt ctccgggtaa a                                             1941
```

<210> SEQ ID NO 105
<211> LENGTH: 1980
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga aataccagag cgggggtggc ggaagcttcc caaccattcc cttatccagg    360
```

```
cttttttgaca acgctatgct ccgcgcccat cgtctgcacc agctggcctt tgacacctac      420
caggagtttg aagaagccta tatcccaaag gaacagaagt attcattcct gcagaacccc      480
cagacctccc tctgtttctc agagtctatt ccgacaccct ccaacaggga ggaaacacaa      540
cagaaatcca acctagagct gctccgcatc tccctgctgc tcatccagtc gtggctggag      600
cccgtgcagt tcctcaggag tgtcttcgcc aacagcctgg tgtacggcgc ctctgacagc      660
aacgtctatg acctcctaaa ggacctagag gaaggcatcc aaacgctgat ggggaggctg      720
gaagatggca gccccggac tgggcagatc ttcaagcaga cctacagcaa gttcgacaca      780
aactcacaca acgatgacgc actactcaag aactacgggc tgctctactg cttcaggaag      840
gacatggaca aggtcgagac attcctgcgc atcgtgcagt gccgctctgt ggagggcagc      900
tgtggcttcg gcggaggtgg gagttcttat acctacaatt atgaatggca gtgggatgtc      960
tggggacagg gcctgctggt gacagtctct agtgcttcca caactgcacc aaaggtgtac     1020
cccctgtcaa gctgctgtgg ggacaaatcc tctagtaccg tgacactggg atgcctggtc     1080
tcaagctata tgcccgagcc tgtgactgtc acctggaact caggagccct gaaaagcgga     1140
gtgcacacct tcccagctgt gctgcagtcc tctggcctgt atagcctgag ttcaatggtg     1200
acagtccccg gcagtacttc agggcagacc ttcacctgta atgtggccca tcctgccagc     1260
tccaccaaag tggacaaagc agtggaaccc aaatcttgcg acaaaactca cacatgccca     1320
ccgtgcccag cacctgaact cctgggggga ccgtcagtct tcctcttccc cccaaaaccc     1380
aaggacaccc tcatgatctc ccggacccct gaggtcacat gcgtggtggt ggacgtgagc     1440
cacgaagacc ctgaggtcaa gttcaactgg tacgtggacg gcgtggaggt gcataatgcc     1500
aagacaaagc cgcggggagga gcagtacaac agcacgtacc gtgtggtcag cgtcctcacc     1560
gtcctgcacc aggactggct gaatggcaag gagtacaagt gcaaggtctc caacaaagcc     1620
ctcccagccc ccatcgagaa aaccatctcc aaagccaaag gcagccccg agaaccacag     1680 gtgtacaccc tgcccccatc ccgggatgag ctgaccaaga accaggtcag cctgacctgc     1740
ctggtcaaag gcttctatcc cagcgacatc gccgtggagt gggagagcaa tgggcagccg     1800
gagaacaact acaagaccac gcctcccgtg ctggactccg acggctcctt cttcctctac     1860
agcaagctca ccgtggacaa gagcaggtgg cagcagggga acgtcttctc atgctccgtg     1920
atgcatgagg ctctgcacaa ccactacacg cagaagagcc tctccctgtc tccgggtaaa     1980
```

<210> SEQ ID NO 106
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
caggtccagc tgagagagag cggcccttca ctggtcaagc catcccagac actgagcctg       60
acatgcacag caagcgggtt ttcactgagc gacaaggcag tgggatgggt ccgacaggca      120
ccaggaaaag ccctggaatg gctgggcagc atcgataccg gcgggaacac aggtacaat      180 cccggactga agagcagact gtccattacc aaggacaact ctaaaagtca ggtgtcactg      240
agcgtgagct ccgtcaccac agaggatagt gcaacttact attgcacctc tgtgcaccag      300
gaaactaaga ataccagag cgggggtggc ggaagcatga gctacaactt gcttggattc      360
ctacaaagaa gcagcaattt tcagtgtcag aagctcctgt ggcaattgaa tgggaggctt      420
```

```
gaatactgcc tcaaggacag gatgaacttt gacatccctg aggagattaa gcagctgcag    480
cagttccaga aggaggacgc cgcattgacc atctatgaga tgctccagaa catctttgct    540
attttcagac aagattcatc tagcactggc tggaatgaga ctattgttga aacctcctg     600 gctaatgtct atcatcagat aaaccatctg aagacagtcc tggaagaaaa actggagaaa    660
gaagatttca ccaggggaaa actcatgagc agtctgcacc tgaaaagata ttatgggagg    720
attctgcatt acctgaaggc caaggagtac agtcactgtg cctggaccat agtcagagtg    780
gaaatcctaa ggaacttta cttcattaac agacttacag gttacctccg aaacggcgga    840
ggtgggagtt cttataccta caattatgaa tggcatgtgg atgtctgggg acagggcctg    900
ctggtgacag tctctagtgc ttccacaact gcaccaaagg tgtacccct gtcaagctgc      960 tgtggggaca atcctctag taccgtgaca ctgggatgcc tggtctcaag ctatatgccc    1020
gagcctgtga ctgtcacctg aactcagga gccctgaaaa gcggagtgca caccttccca    1080
gctgtgctgc agtcctctgg cctgtatagc ctgagttcaa tggtgacagt ccccggcagt    1140
acttcagggc agaccttcac ctgtaatgtg gcccatcctg ccagctccac caaagtggac    1200
aaagcagtgg aacccaaatc ttgcgacaaa actcacacat gcccaccgtg cccagcacct    1260
gaactcctgg ggggaccgtc agtcttcctc ttccccccaa acccaagga caccctcatg    1320 atctcccgga cccctgaggt cacatgcgtg gtggtggacg tgagccacga agaccctgag    1380
gtcaagttca actggtacgt ggacggcgtg gaggtgcata atgccaagac aaagccgcgg    1440
gaggagcagt acaacagcac gtaccgtgtg gtcagcgtcc tcaccgtcct gcaccaggac    1500
tggctgaatg gcaaggagta caagtgcaag gtctccaaca aagccctccc agcccccatc    1560
gagaaaacca tctccaaagc caaagggcag ccccgagaac cacaggtgta caccctgccc    1620
ccatcccggg atgagctgac caagaaccag gtcagcctga cctgcctggt caaaggcttc    1680
tatcccagcg acatcgccgt ggagtgggag agcaatgggc agccggagaa caactacaag    1740
accacgcctc ccgtgctgga ctccgacggc tccttcttcc tctacagcaa gctcaccgtg    1800
gacaagagca ggtggcagca ggggaacgtc ttctcatgct ccgtgatgca tgaggctctg    1860
cacaaccact acacgcagaa gagcctctcc ctgtctccgg gtaaa                   1905
```

<210> SEQ ID NO 107
<211> LENGTH: 1845
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg cgggaacac agggtacaat     180 cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga aataccagag cggtggcgga ggatctgttc aattcaaaa ggttcaagat    360 gataccaaaa ctctgattaa aactattgtc acgcgtataa acgacatcag ccatacccag    420
tcggttagct caaagcaaaa agttaccggt ttggactttta ttccgggact gcacccgatc    480 ctgacccctta gtaaaatgga ccagacactg gccgtctacc agcaaatcct gacatcgatg    540
```

```
ccatccagaa atgtgataca aattagcaac gatttggaaa accttcgcga tctgctgcac    600
gtgctggcct tcagtaagtc ctgtcatctg ccgtgggcgt cgggactgga gactcttgac    660
tcgctgggtg gagtgttaga ggcctctggc tattctactg aagtcgttgc gctgtcacgc    720
ctccagggga gcctgcagga catgctgtgg cagctggacc tgtcacctgg ctgcggaggt    780
ggtggttcat cttatacccta caattatgaa tggcatgtgg atgtctgggg acagggcctg    840
ctggtgacag tctctagtgc ttccacaact gcaccaaagg tgtacccccct gtcaagctgc    900 tgtggggaca atcctctag taccgtgaca ctgggatgcc tggtctcaag ctatatgccc    960
gagcctgtga ctgtcacctg gaactcagga gccctgaaaa gcggagtgca caccttccca   1020
gctgtgctgc agtcctctgg cctgtatagc ctgagttcaa tggtgacagt ccccggcagt   1080
acttcagggc agaccttcac ctgtaatgtg cccatcctg ccagctccac caaagtggac    1140
aaagcagtgg aacccaaatc ttgcgacaaa actcacacat gcccaccgtg cccagcacct   1200
gaactcctgg ggggaccgtc agtcttcctc ttccccccaa acccaaggga cacccctcatg   1260 atctcccgga cccctgaggt cacatgcgtg gtggtggacg tgagccacga agaccctgag   1320
gtcaagttca actggtacgt ggacggcgtg gaggtgcata atgccaagac aaagccgcgg   1380
gaggagcagt acaacagcac gtaccgtgtg gtcagcgtcc tcaccgtcct gcaccaggac   1440
tggctgaatg gcaaggagta caagtgcaag gtctccaaca aagccctccc agcccccatc   1500
gagaaaacca tctccaaagc caagggcag ccccgagaac acaggtgta caccctgccc    1560 ccatcccggg atgagctgac caagaaccag gtcagcctga cctgcctggt caaaggcttc   1620
tatcccagcg acatcgccgt ggagtgggag agcaatgggc agccggagaa caactacaag   1680
accacgcctc ccgtgctgga ctccgacggc tccttcttcc tctacagcaa gctcaccgtg   1740
gacaagagca ggtggcagca ggggaacgtc ttctcatgct ccgtgatgca tgaggctctg   1800
cacaaccact acacgcagaa gagcctctcc ctgtctccgg gtaaa              1845
```

<210> SEQ ID NO 108
<211> LENGTH: 656
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Gly Gly Gly Gly Ser Ala Pro Leu Gly Gly Pro Glu Pro Ala Gln Tyr
        115                 120                 125
```

```
Glu Glu Leu Thr Leu Leu Phe His Gly Ala Leu Gln Leu Gly Gln Ala
        130                 135                 140

Leu Asn Gly Val Tyr Arg Ala Thr Glu Ala Arg Leu Thr Glu Ala Gly
145                 150                 155                 160

His Ser Leu Gly Leu Tyr Asp Arg Ala Leu Glu Phe Leu Gly Thr Glu
                165                 170                 175

Val Arg Gln Gly Gln Asp Ala Thr Gln Glu Leu Arg Thr Ser Leu Ser
                180                 185                 190

Glu Ile Gln Val Glu Glu Asp Ala Leu His Leu Arg Ala Glu Ala Thr
        195                 200                 205

Ala Arg Ser Leu Gly Glu Val Ala Arg Ala Gln Gln Ala Leu Arg Asp
210                 215                 220

Thr Val Arg Arg Leu Gln Val Gln Leu Arg Gly Ala Trp Leu Gly Gln
225                 230                 235                 240

Ala His Gln Glu Phe Glu Thr Leu Lys Ala Arg Ala Asp Lys Gln Ser
                245                 250                 255

His Leu Leu Trp Ala Leu Thr Gly His Val Gln Arg Gln Arg Glu
                260                 265                 270

Met Ala Glu Gln Gln Gln Trp Leu Arg Gln Ile Gln Gln Arg Leu His
        275                 280                 285

Thr Ala Ala Leu Pro Ala Gly Gly Gly Ser Gly Gly Gly Gly Ser
290                 295                 300

Ser Tyr Thr Tyr Asn Tyr Glu Trp His Val Asp Val Trp Gly Gln Gly
305                 310                 315                 320

Leu Leu Val Thr Val Ser Ser Ala Ser Thr Thr Ala Pro Lys Val Tyr
                325                 330                 335

Pro Leu Ser Ser Cys Cys Gly Asp Lys Ser Ser Ser Thr Val Thr Leu
                340                 345                 350

Gly Cys Leu Val Ser Ser Tyr Met Pro Glu Pro Val Thr Val Thr Trp
        355                 360                 365

Asn Ser Gly Ala Leu Lys Ser Gly Val His Thr Phe Pro Ala Val Leu
370                 375                 380

Gln Ser Ser Gly Leu Tyr Ser Leu Ser Ser Met Val Thr Val Pro Gly
385                 390                 395                 400

Ser Thr Ser Gly Gln Thr Phe Thr Cys Asn Val Ala His Pro Ala Ser
                405                 410                 415

Ser Thr Lys Val Asp Lys Ala Val Glu Pro Lys Ser Cys Asp Lys Thr
                420                 425                 430

His Thr Cys Pro Pro Cys Pro Ala Pro Glu Leu Leu Gly Gly Pro Ser
        435                 440                 445

Val Phe Leu Phe Pro Pro Lys Pro Lys Asp Thr Leu Met Ile Ser Arg
450                 455                 460

Thr Pro Glu Val Thr Cys Val Val Val Asp Val Ser His Glu Asp Pro
465                 470                 475                 480

Glu Val Lys Phe Asn Trp Tyr Val Asp Gly Val Glu Val His Asn Ala
                485                 490                 495

Lys Thr Lys Pro Arg Glu Glu Gln Tyr Asn Ser Thr Tyr Arg Val Val
                500                 505                 510

Ser Val Leu Thr Val Leu His Gln Asp Trp Leu Asn Gly Lys Glu Tyr
            515                 520                 525

Lys Cys Lys Val Ser Asn Lys Ala Leu Pro Ala Pro Ile Glu Lys Thr
530                 535                 540
```

```
Ile Ser Lys Ala Lys Gly Gln Pro Arg Glu Pro Gln Val Tyr Thr Leu
545                 550                 555                 560

Pro Pro Ser Arg Asp Glu Leu Thr Lys Asn Gln Val Ser Leu Thr Cys
            565                 570                 575

Leu Val Lys Gly Phe Tyr Pro Ser Asp Ile Ala Val Glu Trp Glu Ser
        580                 585                 590

Asn Gly Gln Pro Glu Asn Asn Tyr Lys Thr Thr Pro Pro Val Leu Asp
    595                 600                 605

Ser Asp Gly Ser Phe Phe Leu Tyr Ser Lys Leu Thr Val Asp Lys Ser
610                 615                 620

Arg Trp Gln Gln Gly Asn Val Phe Ser Cys Ser Val Met His Glu Ala
625                 630                 635                 640

Leu His Asn His Tyr Thr Gln Lys Ser Leu Ser Leu Ser Pro Gly Lys
                645                 650                 655

<210> SEQ ID NO 109
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
                100                 105                 110

Ala Pro Leu Gly Gly Pro Glu Pro Ala Gln Tyr Glu Glu Leu Thr Leu
            115                 120                 125

Leu Phe His Gly Ala Leu Gln Leu Gly Gln Ala Leu Asn Gly Val Tyr
        130                 135                 140

Arg Ala Thr Glu Ala Arg Leu Thr Glu Ala Gly His Ser Leu Gly Leu
145                 150                 155                 160

Tyr Asp Arg Ala Leu Glu Phe Leu Gly Thr Glu Val Arg Gln Gly Gln
                165                 170                 175

Asp Ala Thr Gln Glu Leu Arg Thr Ser Leu Ser Glu Ile Gln Val Glu
            180                 185                 190

Glu Asp Ala Leu His Leu Arg Ala Glu Ala Thr Ala Arg Ser Leu Gly
        195                 200                 205

Glu Val Ala Arg Ala Gln Ala Leu Arg Asp Thr Val Arg Arg Leu
    210                 215                 220

Gln Val Gln Leu Arg Gly Ala Trp Leu Gly Gln Ala His Gln Glu Phe
225                 230                 235                 240

Glu Thr Leu Lys Ala Arg Ala Asp Lys Gln Ser His Leu Leu Trp Ala
                245                 250                 255
```

Leu Thr Gly His Val Gln Arg Gln Gln Arg Glu Met Ala Glu Gln Gln
                260                 265                 270

Gln Trp Leu Arg Gln Ile Gln Gln Arg Leu His Thr Ala Ala Leu Pro
        275                 280                 285

Ala Gly Gly Gly Ser Ser Tyr Thr Tyr Asn Tyr Glu Trp His Val
290                 295                 300

Asp Val Trp Gly Gln Gly Leu Leu Val Thr Val Ser Ser Ala Ser Thr
305                 310                 315                 320

Thr Ala Pro Lys Val Tyr Pro Leu Ser Ser Cys Cys Gly Asp Lys Ser
                325                 330                 335

Ser Ser Thr Val Thr Leu Gly Cys Leu Val Ser Ser Tyr Met Pro Glu
            340                 345                 350

Pro Val Thr Val Thr Trp Asn Ser Gly Ala Leu Lys Ser Gly Val His
            355                 360                 365

Thr Phe Pro Ala Val Leu Gln Ser Ser Gly Leu Tyr Ser Leu Ser Ser
370                 375                 380

Met Val Thr Val Pro Gly Ser Thr Ser Gly Gln Thr Phe Thr Cys Asn
385                 390                 395                 400

Val Ala His Pro Ala Ser Ser Thr Lys Val Asp Lys Ala Val Glu Pro
                405                 410                 415

Lys Ser Cys Asp Lys Thr His Thr Cys Pro Pro Cys Pro Ala Pro Glu
            420                 425                 430

Leu Leu Gly Gly Pro Ser Val Phe Leu Phe Pro Pro Lys Pro Lys Asp
            435                 440                 445

Thr Leu Met Ile Ser Arg Thr Pro Glu Val Thr Cys Val Val Val Asp
450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
            500                 505                 510

Leu Asn Gly Lys Glu Tyr Lys Cys Lys Val Ser Asn Lys Ala Leu Pro
            515                 520                 525

Ala Pro Ile Glu Lys Thr Ile Ser Lys Ala Lys Gly Gln Pro Arg Glu
530                 535                 540

Pro Gln Val Tyr Thr Leu Pro Pro Ser Arg Asp Glu Leu Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
            595                 600                 605

Leu Thr Val Asp Lys Ser Arg Trp Gln Gln Gly Asn Val Phe Ser Cys
            610                 615                 620

Ser Val Met His Glu Ala Leu His Asn His Tyr Thr Gln Lys Ser Leu
625                 630                 635                 640

Ser Leu Ser Pro Gly Lys
                645

<210> SEQ ID NO 110
<211> LENGTH: 660

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Phe Pro Thr Ile Pro Leu Ser Arg Leu Phe Asp Asn Ala Met Leu Arg
        115                 120                 125

Ala His Arg Leu His Gln Leu Ala Phe Asp Thr Tyr Gln Glu Phe Glu
    130                 135                 140

Glu Ala Tyr Ile Pro Lys Glu Gln Lys Tyr Ser Phe Leu Gln Asn Pro
145                 150                 155                 160

Gln Thr Ser Leu Cys Phe Ser Glu Ser Ile Pro Thr Pro Ser Asn Arg
                165                 170                 175

Glu Glu Thr Gln Gln Lys Ser Asn Leu Glu Leu Leu Arg Ile Ser Leu
            180                 185                 190

Leu Leu Ile Gln Ser Trp Leu Glu Pro Val Gln Phe Leu Arg Ser Val
        195                 200                 205

Phe Ala Asn Ser Leu Val Tyr Gly Ala Ser Asp Ser Asn Val Tyr Asp
    210                 215                 220

Leu Leu Lys Asp Leu Glu Glu Gly Ile Gln Thr Leu Met Gly Arg Leu
225                 230                 235                 240

Glu Asp Gly Ser Pro Arg Thr Gly Gln Ile Phe Lys Gln Thr Tyr Ser
                245                 250                 255

Lys Phe Asp Thr Asn Ser His Asn Asp Asp Ala Leu Leu Lys Asn Tyr
            260                 265                 270

Gly Leu Leu Tyr Cys Phe Arg Lys Asp Met Asp Lys Val Glu Thr Phe
        275                 280                 285

Leu Arg Ile Val Gln Cys Arg Ser Val Glu Gly Ser Cys Gly Phe Gly
    290                 295                 300

Gly Gly Gly Ser Ser Tyr Thr Tyr Asn Tyr Glu Trp His Val Asp Val
305                 310                 315                 320

Trp Gly Gln Gly Leu Leu Val Thr Val Ser Ser Ala Ser Thr Thr Ala
                325                 330                 335

Pro Lys Val Tyr Pro Leu Ser Ser Cys Cys Gly Asp Lys Ser Ser Ser
            340                 345                 350

Thr Val Thr Leu Gly Cys Leu Val Ser Ser Tyr Met Pro Glu Pro Val
        355                 360                 365

Thr Val Thr Trp Asn Ser Gly Ala Leu Lys Ser Gly Val His Thr Phe
    370                 375                 380
```

Pro Ala Val Leu Gln Ser Ser Gly Leu Tyr Ser Leu Ser Ser Met Val
385                 390                 395                 400

Thr Val Pro Gly Ser Thr Ser Gly Gln Thr Phe Thr Cys Asn Val Ala
            405                 410                 415

His Pro Ala Ser Ser Thr Lys Val Asp Lys Ala Val Glu Pro Lys Ser
        420                 425                 430

Cys Asp Lys Thr His Thr Cys Pro Pro Cys Pro Ala Pro Glu Leu Leu
    435                 440                 445

Gly Gly Pro Ser Val Phe Leu Phe Pro Pro Lys Pro Lys Asp Thr Leu
    450                 455                 460

Met Ile Ser Arg Thr Pro Glu Val Thr Cys Val Val Val Asp Val Ser
465                 470                 475                 480

His Glu Asp Pro Glu Val Lys Phe Asn Trp Tyr Val Asp Gly Val Glu
            485                 490                 495

Val His Asn Ala Lys Thr Lys Pro Arg Glu Glu Gln Tyr Asn Ser Thr
        500                 505                 510

Tyr Arg Val Val Ser Val Leu Thr Val Leu His Gln Asp Trp Leu Asn
    515                 520                 525

Gly Lys Glu Tyr Lys Cys Lys Val Ser Asn Lys Ala Leu Pro Ala Pro
    530                 535                 540

Ile Glu Lys Thr Ile Ser Lys Ala Lys Gly Gln Pro Arg Glu Pro Gln
545                 550                 555                 560

Val Tyr Thr Leu Pro Pro Ser Arg Asp Glu Leu Thr Lys Asn Gln Val
            565                 570                 575

Ser Leu Thr Cys Leu Val Lys Gly Phe Tyr Pro Ser Asp Ile Ala Val
        580                 585                 590

Glu Trp Glu Ser Asn Gly Gln Pro Glu Asn Asn Tyr Lys Thr Thr Pro
    595                 600                 605

Pro Val Leu Asp Ser Asp Gly Ser Phe Phe Leu Tyr Ser Lys Leu Thr
    610                 615                 620

Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
            645                 650                 655

Ser Pro Gly Lys
            660

<210> SEQ ID NO 111
<211> LENGTH: 635
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu

-continued

```
            65                  70                  75                  80
        Ser Val Ser Ser Val Thr Thr Glu Asp Ser Ala Thr Tyr Tyr Cys Thr
                        85                  90                  95

Ser Val His Gln Glu Thr Lys Lys Tyr Gln Ser Gly Gly Gly Gly Ser
                        100                 105                 110

Met Ser Tyr Asn Leu Leu Gly Phe Leu Gln Arg Ser Asn Phe Gln
                        115                 120                 125

Cys Gln Lys Leu Leu Trp Gln Leu Asn Gly Arg Leu Glu Tyr Cys Leu
                        130                 135                 140

Lys Asp Arg Met Asn Phe Asp Ile Pro Glu Glu Ile Lys Gln Leu Gln
        145                 150                 155                 160

Gln Phe Gln Lys Glu Asp Ala Ala Leu Thr Ile Tyr Glu Met Leu Gln
                        165                 170                 175

Asn Ile Phe Ala Ile Phe Arg Gln Asp Ser Ser Thr Gly Trp Asn
                        180                 185                 190

Glu Thr Ile Val Glu Asn Leu Leu Ala Asn Val Tyr His Gln Ile Asn
                        195                 200                 205

His Leu Lys Thr Val Leu Glu Glu Lys Leu Glu Lys Glu Asp Phe Thr
                        210                 215                 220

Arg Gly Lys Leu Met Ser Ser Leu His Leu Lys Arg Tyr Tyr Gly Arg
        225                 230                 235                 240

Ile Leu His Tyr Leu Lys Ala Lys Glu Tyr Ser His Cys Ala Trp Thr
                        245                 250                 255

Ile Val Arg Val Glu Ile Leu Arg Asn Phe Tyr Phe Ile Asn Arg Leu
                        260                 265                 270

Thr Gly Tyr Leu Arg Asn Gly Gly Gly Ser Ser Tyr Thr Tyr Asn
                        275                 280                 285

Tyr Glu Trp His Val Asp Val Trp Gly Gln Gly Leu Leu Val Thr Val
                        290                 295                 300

Ser Ser Ala Ser Thr Thr Ala Pro Lys Val Tyr Pro Leu Ser Ser Cys
        305                 310                 315                 320

Cys Gly Asp Lys Ser Ser Thr Val Thr Leu Gly Cys Leu Val Ser
                        325                 330                 335

Ser Tyr Met Pro Glu Pro Val Thr Val Thr Trp Asn Ser Gly Ala Leu
                        340                 345                 350

Lys Ser Gly Val His Thr Phe Pro Ala Val Leu Gln Ser Ser Gly Leu
                        355                 360                 365

Tyr Ser Leu Ser Ser Met Val Thr Val Pro Gly Ser Thr Ser Gly Gln
                        370                 375                 380

Thr Phe Thr Cys Asn Val Ala His Pro Ala Ser Ser Thr Lys Val Asp
        385                 390                 395                 400

Lys Ala Val Glu Pro Lys Ser Cys Asp Lys Thr His Thr Cys Pro Pro
                        405                 410                 415

Cys Pro Ala Pro Glu Leu Leu Gly Gly Pro Ser Val Phe Leu Phe Pro
                        420                 425                 430

Pro Lys Pro Lys Asp Thr Leu Met Ile Ser Arg Thr Pro Glu Val Thr
                        435                 440                 445

Cys Val Val Val Asp Val Ser His Glu Asp Pro Glu Val Lys Phe Asn
        450                 455                 460

Trp Tyr Val Asp Gly Val Glu Val His Asn Ala Lys Thr Lys Pro Arg
        465                 470                 475                 480

Glu Glu Gln Tyr Asn Ser Thr Tyr Arg Val Val Ser Val Leu Thr Val
                        485                 490                 495
```

```
Leu His Gln Asp Trp Leu Asn Gly Lys Glu Tyr Lys Cys Lys Val Ser
                500                 505                 510

Asn Lys Ala Leu Pro Ala Pro Ile Glu Lys Thr Ile Ser Lys Ala Lys
            515                 520                 525

Gly Gln Pro Arg Glu Pro Gln Val Tyr Thr Leu Pro Pro Ser Arg Asp
    530                 535                 540

Glu Leu Thr Lys Asn Gln Val Ser Leu Thr Cys Leu Val Lys Gly Phe
545                 550                 555                 560

Tyr Pro Ser Asp Ile Ala Val Glu Trp Glu Ser Asn Gly Gln Pro Glu
                565                 570                 575

Asn Asn Tyr Lys Thr Thr Pro Pro Val Leu Asp Ser Asp Gly Ser Phe
            580                 585                 590

Phe Leu Tyr Ser Lys Leu Thr Val Asp Lys Ser Arg Trp Gln Gln Gly
        595                 600                 605

Asn Val Phe Ser Cys Ser Val Met His Glu Ala Leu His Asn His Tyr
    610                 615                 620

Thr Gln Lys Ser Leu Ser Leu Ser Pro Gly Lys
625                 630                 635

<210> SEQ ID NO 112
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Asp Ser Trp Met Glu Glu Val Ile Lys Leu Cys Gly Arg Glu Leu Val
        115                 120                 125

Arg Ala Gln Ile Ala Ile Cys Gly Met Ser Thr Trp Ser Ile Glu Gly
    130                 135                 140

Arg Ser Leu Ser Gln Glu Asp Ala Pro Gln Thr Pro Arg Pro Val Ala
145                 150                 155                 160

Glu Ile Val Pro Ser Phe Ile Asn Lys Asp Thr Glu Thr Ile Asn Met
                165                 170                 175

Met Ser Glu Phe Val Ala Asn Leu Pro Gln Glu Leu Lys Leu Thr Leu
            180                 185                 190

Ser Glu Met Gln Pro Ala Leu Pro Gln Leu Gln Gln His Val Pro Val
        195                 200                 205

Leu Lys Asp Ser Ser Leu Leu Phe Glu Glu Phe Lys Lys Leu Ile Arg
```

```
            210                 215                 220
Asn Arg Gln Ser Glu Ala Ala Asp Ser Ser Pro Ser Glu Leu Lys Tyr
225                 230                 235                 240

Leu Gly Leu Asp Thr His Ser Ile Glu Gly Arg Gln Leu Tyr Ser Ala
            245                 250                 255

Leu Ala Asn Lys Cys Cys His Val Gly Cys Thr Lys Arg Ser Leu Ala
                260                 265                 270

Arg Phe Cys Gly Gly Gly Ser Ser Tyr Thr Tyr Asn Tyr Glu Trp
            275                 280                 285

His Val Asp Val Trp Gly Gln Gly Leu Leu Val Thr Val Ser Ser Ala
        290                 295                 300

Ser Thr Thr Ala Pro Lys Val Tyr Pro Leu Ser Ser Cys Cys Gly Asp
305                 310                 315                 320

Lys Ser Ser Ser Thr Val Thr Leu Gly Cys Leu Val Ser Ser Tyr Met
                325                 330                 335

Pro Glu Pro Val Thr Val Thr Trp Asn Ser Gly Ala Leu Lys Ser Gly
            340                 345                 350

Val His Thr Phe Pro Ala Val Leu Gln Ser Ser Gly Leu Tyr Ser Leu
        355                 360                 365

Ser Ser Met Val Thr Val Pro Gly Ser Thr Ser Gly Gln Thr Phe Thr
    370                 375                 380

Cys Asn Val Ala His Pro Ala Ser Ser Thr Lys Val Asp Lys Ala Val
385                 390                 395                 400

Glu Pro Lys Ser Cys Asp Lys Thr His Thr Cys Pro Pro Cys Pro Ala
                405                 410                 415

Pro Glu Leu Leu Gly Gly Pro Ser Val Phe Leu Phe Pro Pro Lys Pro
            420                 425                 430

Lys Asp Thr Leu Met Ile Ser Arg Thr Pro Glu Val Thr Cys Val Val
        435                 440                 445

Val Asp Val Ser His Glu Asp Pro Glu Val Lys Phe Asn Trp Tyr Val
    450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Ala
            500                 505                 510

Leu Pro Ala Pro Ile Glu Lys Thr Ile Ser Lys Ala Lys Gly Gln Pro
        515                 520                 525

Arg Glu Pro Gln Val Tyr Thr Leu Pro Pro Ser Arg Asp Glu Leu Thr
    530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
        595                 600                 605

Ser Cys Ser Val Met His Glu Ala Leu His Asn His Tyr Thr Gln Lys
    610                 615                 620

Ser Leu Ser Leu Ser Pro Gly Lys
625                 630
```

<210> SEQ ID NO 113
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Val Pro Ile Gln Lys Val Gln Asp Thr Lys Thr Leu Ile Lys Thr
        115                 120                 125

Ile Val Thr Arg Ile Asn Asp Ile Ser His Thr Gln Ser Val Ser Ser
130                 135                 140

Lys Gln Lys Val Thr Gly Leu Asp Phe Ile Pro Gly Leu His Pro Ile
145                 150                 155                 160

Leu Thr Leu Ser Lys Met Asp Gln Thr Leu Ala Val Tyr Gln Gln Ile
                165                 170                 175

Leu Thr Ser Met Pro Ser Arg Asn Val Ile Gln Ile Ser Asn Asp Leu
            180                 185                 190

Glu Asn Leu Arg Asp Leu Leu His Val Leu Ala Phe Ser Lys Ser Cys
        195                 200                 205

His Leu Pro Trp Ala Ser Gly Leu Glu Thr Leu Asp Ser Leu Gly Gly
    210                 215                 220

Val Leu Glu Ala Ser Gly Tyr Ser Thr Glu Val Val Ala Leu Ser Arg
225                 230                 235                 240

Leu Gln Gly Ser Leu Gln Asp Met Leu Trp Gln Leu Asp Leu Ser Pro
                245                 250                 255

Gly Cys Gly Gly Gly Gly Ser Ser Tyr Thr Tyr Asn Tyr Glu Trp His
            260                 265                 270

Val Asp Val Trp Gly Gln Gly Leu Leu Val Thr Val Ser Ser Ala Ser
        275                 280                 285

Thr Thr Ala Pro Lys Val Tyr Pro Leu Ser Ser Cys Cys Gly Asp Lys
    290                 295                 300

Ser Ser Ser Thr Val Thr Leu Gly Cys Leu Val Ser Ser Tyr Met Pro
305                 310                 315                 320

Glu Pro Val Thr Val Thr Trp Asn Ser Gly Ala Leu Lys Ser Gly Val
                325                 330                 335

His Thr Phe Pro Ala Val Leu Gln Ser Ser Gly Leu Tyr Ser Leu Ser
            340                 345                 350

Ser Met Val Thr Val Pro Gly Ser Thr Ser Gly Gln Thr Phe Thr Cys

```
                355                 360                 365
Asn Val Ala His Pro Ala Ser Ser Thr Lys Val Asp Lys Ala Val Glu
    370                 375                 380

Pro Lys Ser Cys Asp Lys Thr His Thr Cys Pro Pro Cys Pro Ala Pro
385                 390                 395                 400

Glu Leu Leu Gly Gly Pro Ser Val Phe Leu Phe Pro Pro Lys Pro Lys
                405                 410                 415

Asp Thr Leu Met Ile Ser Arg Thr Pro Glu Val Thr Cys Val Val Val
            420                 425                 430

Asp Val Ser His Glu Asp Pro Glu Val Lys Phe Asn Trp Tyr Val Asp
        435                 440                 445

Gly Val Glu Val His Asn Ala Lys Thr Lys Pro Arg Glu Glu Gln Tyr
    450                 455                 460

Asn Ser Thr Tyr Arg Val Val Ser Val Leu Thr Val Leu His Gln Asp
465                 470                 475                 480

Trp Leu Asn Gly Lys Glu Tyr Lys Cys Lys Val Ser Asn Lys Ala Leu
                485                 490                 495

Pro Ala Pro Ile Glu Lys Thr Ile Ser Lys Ala Lys Gly Gln Pro Arg
            500                 505                 510

Glu Pro Gln Val Tyr Thr Leu Pro Pro Ser Arg Asp Glu Leu Thr Lys
        515                 520                 525

Asn Gln Val Ser Leu Thr Cys Leu Val Lys Gly Phe Tyr Pro Ser Asp
    530                 535                 540

Ile Ala Val Glu Trp Glu Ser Asn Gly Gln Pro Glu Asn Asn Tyr Lys
545                 550                 555                 560

Thr Thr Pro Pro Val Leu Asp Ser Asp Gly Ser Phe Phe Leu Tyr Ser
                565                 570                 575

Lys Leu Thr Val Asp Lys Ser Arg Trp Gln Gln Gly Asn Val Phe Ser
            580                 585                 590

Cys Ser Val Met His Glu Ala Leu His Asn His Tyr Thr Gln Lys Ser
        595                 600                 605

Leu Ser Leu Ser Pro Gly Lys
    610                 615

<210> SEQ ID NO 114
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
aacctgggtc tggactgcga cgaacactct tctgaatctc gttgctgccg ttacccgctg      60
accgttgact tcgaggcgtt cggttgggac tggatcatcg ctccgaaacg ttacaaagct     120
aactactgct ctggtcagtg cgaatacatg ttcatgcaga ataccccgca cccacctg      180 gttcagcagg ctaacccgcg tggttctgct ggtccgtgct gcaccccgac caaaatgtct     240
ccgatcaaca tgctgtactt caacgacaaa cagcagatca tctacggtaa aatcccgggt     300
atggttgttg accgttgcgg ttgctcttaa                                      330

<210> SEQ ID NO 115
<211> LENGTH: 1162
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 115

```
ggatccggtg gtttcaccat caaactgctg ctgttcatcg ttccgctggt tatctcttct      60
cgtatcgacc aggacaactc ttctttcgac tctctgtctc cggaaccgaa atctcgtttc     120
gctatgctgg acgacgttaa aatcctggct aacggtctgc tgcagctggg tcacggtctg     180
aaagacttcg ttcacaaaac caaaggtcag atcaacgaca tcttccagaa actgaacatc     240
ttcgaccagt ctttctacga cctgtctctg cagacctctg aaatcaaaga agaagaaaaa     300
gaactgcgtc gtaccaccta caaactgcag gttaaaaacg aagaagttaa aaacatgtct     360
ctggaactga actctaaact ggaatctctg ctggaagaaa aatcctgct gcagcagaaa      420
gttaaatacc tggaagaaca gctgaccaac ctgatccaga accagccgga aaccccggaa     480
cacccggaag ttacctctct gaaaaccttc gttgaaaaac aggacaactc tatcaaagac     540
ctgctgcaga ccgttgaaga ccagtacaaa cagctgaacc agcagcactc tcagatcaaa     600
gaaatcgaaa accagctgcg tcgtacctct atccaggaac cgaccgaaat ctctctgtct     660
tctaaaccgc gtgctccgcg taccaccccg ttcctgcagc tgaacgaaat ccgtaacgtt     720
aaacacgacg gtatcccggc tgaatgcacc accatctaca ccgtggtga acacacctct      780
ggtatgtacg ctatccgtcc gtctaactct caggttttcc acgtttactg cgacgttatc     840
tctggttctc cgtggaccct gatccagcac cgtatcgacg ttctcagaa cttcaacgaa      900
acctgggaaa actacaaata cggtttcggt cgtctggacg gtgaattctg gctgggtctg     960
gaaaaaatct actctatcgt taaacagtct aactacgttc tgcgtatcga actggaagac    1020
tggaaagaca caaaacacta catcgaatac tctttctacc tgggtaacca cgaaaccaac    1080
tacaccctgc acctggttgc tatcaccggt aacgttccga acgctatccc gaagaagaag    1140
aagaaaaaaa agaagaagaa at                                             1162
```

<210> SEQ ID NO 116
<211> LENGTH: 573
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 116

```
ttcccaacca ttcccttatc caggcttttt gacaacgcta tgctccgcgc ccatcgtctg      60
caccagctgg cctttgacac ctaccaggag tttgaagaag cctatatccc aaaggaacag     120
aagtattcat tcctgcagaa cccccagacc tccctctgtt tctcagagtc tattccgaca     180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaggaccct agaggaaggc     360
atccaaacgc tgatggggag gctggaagat ggcagccccc ggactgggca gatcttcaag     420
cagacctaca gcaagttcga cacaaactca cacaacgatg acgcactact caagaactac     480
gggctgctct actgcttcag gaaggacatg gacaaggtcg acattcct gcgcatcgtg      540
cagtgccgct ctgtggaggg cagctgtggc ttc                                  573
```

<210> SEQ ID NO 117
<211> LENGTH: 495

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
tgtgatctgc ctcaaaccca cagcctgggt agcaggagga ccttgatgct cctggcacag      60
atgaggagaa tctctctttt ctcctgcttg aaggacagac atgactttgg atttccccag     120
gaggagtttg gcaaccagtt ccaaaaggct gaaaccatcc ctgtcctcca tgagatgatc     180
cagcagatct tcaatctctt cagcacaaag gactcatctg ctgcttggga tgagaccctc     240
ctagacaaat tctacactga actctaccag cagctgaatg acctggaagc ctgtgtgata     300 caggggtgg gggtgacaga gactcccctg atgaaggagg actccattct ggctgtgagg     360
aaatacttcc aaagaatcac tctctatctg aaagagaaga atacagccc ttgtgcctgg     420 gaggttgtca gagcagaaat catgagatct ttttctttgt caacaaactt gcaagaaagt     480
ttaagaagta aggaa                                                      495

<210> SEQ ID NO 118
<211> LENGTH: 170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
ctgaaatgtt accaacatgg taaagttgtg acttgtcatc gagatatgaa gttttgctat      60
cataacactg gcatgccttt tcgaaatctc aagctcatcc tacagggatg ttcttcttcg     120
tgcagtgaaa cagaaaacaa taagtgttgc tcaacagaca gatgcaacaa                170

<210> SEQ ID NO 119
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
cgaatgcatc ggtatgttca aatcttgcga cccggaaaac gacaaatgct gcaaaggtcg      60
tacctgctct cgtaaacacc gttggtgcaa atacaaactg                           100

<210> SEQ ID NO 120
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gactgcctgg gtttcatgcg taaatgcatc ccggacaacg acaaatgctg ccgtccgaac      60
ctggtttgct ctcgtaccca caatggtgc aaatacgttt tc                         102

<210> SEQ ID NO 121
<211> LENGTH: 252
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 121

```
tctgtgagtg aaatacagct tatgcataac ctgggaaaac atctgaactc gatggagaga        60
gtagaatggc tgcgtaagaa gctgcaggat gtgcacaatt ttgttgccct tggagctcct       120
ctagctccca gagatgctgg ttcccagagg ccccgaaaaa aggaagacaa tgtcttggtt       180
gagagccatg aaaaaagtct tggagaggca gacaaagctg atgtgaatgt attaactaaa       240
gctaaatccc ag                                                           252
```

<210> SEQ ID NO 122
<211> LENGTH: 597
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
atgaactgcg tgtgccgcct ggtgctggtg gtgctgagcc tgtggccgga taccgcggtg        60
gcgccgggcc cgccgccggg cccgccgcgc gtgagcccgg atccgcgcgc ggaactggat       120
agcaccgtgc tgctgacccg cagcctgctg gcggataccc gccagctggc ggcgcagctg       180
cgcgataaat ttccggcgga tggcgatcat aacctggata gcctgccgac cctggcgatg       240
agcgcgggcg cgctgggcgc gctgcagctg ccgggcgtgc tgacccgcct gcgcgcggat       300
ctgctgagct atctgcgcca tgtgcagtgg ctgcgccgcg cgggcggcag cagcctgaaa       360
accctggaac cggaactggg caccctgcag gcgcgcctgg atcgcctgct gcgccgcctg       420
cagctgctga tgagccgcct ggcgctgccg cagccgccgc cggatccgcc ggcgccgccg       480
ctggcgccgc cgagcagcgc gtggggcggc attcgcgcgg cgctggcgat tctgggcggc       540
ctgcatctga ccctggattg ggcggtgcgc ggcctgctgc tgctgaaaac cgcctg          597
```

<210> SEQ ID NO 123
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
gatagctgga tggaagaagt gattaaactg tgcggccgcg aactggtgcg cgcgcagatt        60
gcgatttgcg gcatgagcac ctggagcatt gaaggccgca gcctgagcca ggaagatgcg       120
ccgcagaccc cgcgcccggt ggcggaaatt gtgccgagct ttattaacaa agataccgaa       180
accattaaca tgatgagcga atttgtggcg aacctgccgc aggaactgaa actgaccctg       240
agcgaaatgc agccggcgct gccgcagctg cagcagcatg tgccggtgct gaaagatagc       300
agcctgctgt ttgaagaatt taaaaaactg attcgcaacc gccagagcga agcggcggat       360
agcagcccga gcgaactgaa atatctgggc ctggataccc atagcattga aggccgccag       420
ctgtatagcg cgctggcgaa caaatgctgc catgtgggct gcaccaaacg cagcctggcg       480
cgcttttgc                                                               489
```

<210> SEQ ID NO 124
<211> LENGTH: 306
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 124
agcctgagcc aggaagatgc gccgcagacc ccgcgcccgg tggcggaaat tgtgccgagc    60
tttattaaca aagataccga aaccattaac atgatgagcg aatttgtggc gaacctgccg   120
caggaactga aactgaccct gagcgaaatg cagccggcgc tgccgcagct gcagcagcat   180
gtgccggtgc tgaaagatag cagcctgctg tttgaagaat ttaaaaaact gattcgcaac   240
cgccagagcg aagcggcgga tagcagcccg agcgaactga aatatctggg cctggatacc   300
catagc                                                              306

<210> SEQ ID NO 125
<211> LENGTH: 222
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
ccgcgcagcg cgaaagaact gcgctgccag tgcattaaaa cctatagcaa accgtttcat    60
ccgaaattta ttaagaact gcgcgtgatt gaaagcggcc gcattgcgc gaacaccgaa     120 attattgtga aactgagcga tggccgcgaa ctgtgcctgg atccgaaaga aaactgggtg   180
cagcgcgtgg tggaaaaatt tctgaaacgc gcggaaaaca gc                      222

<210> SEQ ID NO 126
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tgcaaaggca aggcgcgaa atgcagccgc ctgatgtatg attgctgcac cggcagctgc     60
cgcagcggca aatgc                                                    75

<210> SEQ ID NO 127
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gcgggctgca aaacttttt ttggaaaacc tttaccagct gcggc                    45

<210> SEQ ID NO 128
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
atgtgcatgc cgtgctttac caccgatcat cagatggcgc gcaaatgcga tgattgctgc    60
```

```
ggcggcaaag gccgcggcaa atgctatggc ccgcagtgcc tg                              102
```

<210> SEQ ID NO 129
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
aaaccggtga gcctgagcta tcgctgcccg tgccgctttt ttgaaagcca tgtggcgcgc         60
gcgaacgtga aacatctgaa aattctgaac accccgaact gcgcgctgca gattgtggcg        120
cgcctgaaaa acaacaaccg ccaggtgtgc attgatccga aactgaaatg gattcaggaa        180
tatctggaaa aagcgctgaa caaa                                               204
```

<210> SEQ ID NO 130
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
cagggccagg atcgccatat gattcgcatg cgccagctga ttgatattgt ggatcagctg         60
aaaaactatg tgaacgatct ggtgccggaa tttctgccgg cgccggaaga tgtggaaacc        120
aactgcgaat ggagcgcgtt tagctgcttt cagaaagcgc agctgaaaag cgcgaacacc        180
ggcaacaacg aacgcattat taacgtgagc attaaaaaac tgaaacgcaa accgccgagc        240
accaacgcgg gccgccgcca gaaacatcgc ctgacctgcc cgagctgcga tagctatgaa        300
aaaaaaccgc cgaaagaatt tctggaacgc tttaaaagcc tgctgcagaa aatgattcat        360
cagcatctga gcagccgcac ccatggcagc gaagatagc                               399
```

<210> SEQ ID NO 131
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
gcgcaagagc cagtcaaagg tccagtctcc actaagcctg gctcctgccc cattatcttg         60
atccggtgcg ccatgttgaa tcccctaac cgctgcttga agatactga ctgcccagga         120
atcaagaagt gctgtgaagg ctcttgcggg atggcctgtt tcgttcccca g                 171
```

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132

```
tatcgcaaat gtagaggagg ccgaaggtgg tgctaccaaa ag                             42
```

<210> SEQ ID NO 133
<211> LENGTH: 109

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 134
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Ser Gly Gly Phe Thr Ile Lys Leu Leu Leu Phe Ile Val Pro Leu
1               5                   10                  15

Val Ile Ser Ser Arg Ile Asp Gln Asp Asn Ser Ser Phe Asp Ser Leu
            20                  25                  30

Ser Pro Glu Pro Lys Ser Arg Phe Ala Met Leu Asp Asp Val Lys Ile
        35                  40                  45

Leu Ala Asn Gly Leu Leu Gln Leu Gly His Gly Leu Lys Asp Phe Val
50                  55                  60

His Lys Thr Lys Gly Gln Ile Asn Asp Ile Phe Gln Lys Leu Asn Ile
65                  70                  75                  80

Phe Asp Gln Ser Phe Tyr Asp Leu Ser Leu Gln Thr Ser Glu Ile Lys
                85                  90                  95

Glu Glu Glu Lys Glu Leu Arg Arg Thr Thr Tyr Lys Leu Gln Val Lys
            100                 105                 110

Asn Glu Glu Val Lys Asn Met Ser Leu Glu Leu Asn Ser Lys Leu Glu
        115                 120                 125

Ser Leu Leu Glu Glu Lys Ile Leu Leu Gln Gln Lys Val Lys Tyr Leu
130                 135                 140

Glu Glu Gln Leu Thr Asn Leu Ile Gln Asn Gln Pro Glu Thr Pro Glu
145                 150                 155                 160

His Pro Glu Val Thr Ser Leu Lys Thr Phe Val Glu Lys Gln Asp Asn
                165                 170                 175

Ser Ile Lys Asp Leu Leu Gln Thr Val Glu Asp Gln Tyr Lys Gln Leu
            180                 185                 190

Asn Gln Gln His Ser Gln Ile Lys Glu Ile Glu Asn Gln Leu Arg Arg
        195                 200                 205
```

```
Thr Ser Ile Gln Glu Pro Thr Glu Ile Ser Leu Ser Ser Lys Pro Arg
    210                 215                 220

Ala Pro Arg Thr Thr Pro Phe Leu Gln Leu Asn Glu Ile Arg Asn Val
225                 230                 235                 240

Lys His Asp Gly Ile Pro Ala Glu Cys Thr Thr Ile Tyr Asn Arg Gly
                245                 250                 255

Glu His Thr Ser Gly Met Tyr Ala Ile Arg Pro Ser Asn Ser Gln Val
                260                 265                 270

Phe His Val Tyr Cys Asp Val Ile Ser Gly Ser Pro Trp Thr Leu Ile
                275                 280                 285

Gln His Arg Ile Asp Gly Ser Gln Asn Phe Asn Glu Thr Trp Glu Asn
    290                 295                 300

Tyr Lys Tyr Gly Phe Gly Arg Leu Asp Gly Glu Phe Trp Leu Gly Leu
305                 310                 315                 320

Glu Lys Ile Tyr Ser Ile Val Lys Gln Ser Asn Tyr Val Leu Arg Ile
                325                 330                 335

Glu Leu Glu Asp Trp Lys Asp Asn Lys His Tyr Ile Glu Tyr Ser Phe
                340                 345                 350

Tyr Leu Gly Asn His Glu Thr Asn Tyr Thr Leu His Leu Val Ala Ile
                355                 360                 365

Thr Gly Asn Val Pro Asn Ala Ile Pro Lys Lys Lys Lys Lys Lys Lys
    370                 375                 380

Lys Lys Lys
385

<210> SEQ ID NO 135
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175
```

```
Leu Arg Ile Val Gln Cys Arg Ser Val Glu Gly Ser Cys Gly Phe
            180                 185                 190
```

```
<210> SEQ ID NO 136
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136
```

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

```
<210> SEQ ID NO 137
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137
```

```
Leu Lys Cys Tyr Gln His Gly Lys Val Val Thr Cys His Arg Asp Met
1               5                   10                  15

Lys Phe Cys Tyr His Asn Thr Gly Met Pro Phe Arg Asn Leu Lys Leu
            20                  25                  30

Ile Leu Gln Gly Cys Ser Ser Ser Cys Ser Glu Thr Glu Asn Asn Lys
        35                  40                  45

Cys Cys Ser Thr Asp Arg Cys Asn
    50                  55
```

```
<210> SEQ ID NO 138
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 138

Glu Cys Ile Gly Met Phe Lys Ser Cys Asp Pro Glu Asn Asp Lys Cys
1               5                   10                  15

Cys Lys Gly Arg Thr Cys Ser Arg Lys His Arg Trp Cys Lys Tyr Lys
            20                  25                  30

Leu

<210> SEQ ID NO 139
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Cys Leu Gly Phe Met Arg Lys Cys Ile Pro Asp Asn Asp Lys Cys
1               5                   10                  15

Cys Arg Pro Asn Leu Val Cys Ser Arg Thr His Lys Trp Cys Lys Tyr
            20                  25                  30

Val Phe

<210> SEQ ID NO 140
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 141
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe

```
                 50                  55                  60
Pro Ala Asp Gly Asp His Asn Leu Asp Ser Leu Pro Thr Leu Ala Met
 65                  70                  75                  80

Ser Ala Gly Ala Leu Gly Ala Leu Gln Leu Pro Gly Val Leu Thr Arg
                 85                  90                  95

Leu Arg Ala Asp Leu Leu Ser Tyr Leu Arg His Val Gln Trp Leu Arg
                100                 105                 110

Arg Ala Gly Gly Ser Ser Leu Lys Thr Leu Glu Pro Glu Leu Gly Thr
                115                 120                 125

Leu Gln Ala Arg Leu Asp Arg Leu Leu Arg Arg Leu Gln Leu Leu Met
            130                 135                 140

Ser Arg Leu Ala Leu Pro Gln Pro Pro Pro Asp Pro Pro Ala Pro Pro
145                 150                 155                 160

Leu Ala Pro Pro Ser Ser Ala Trp Gly Gly Ile Arg Ala Ala Leu Ala
                165                 170                 175

Ile Leu Gly Gly Leu His Leu Thr Leu Asp Trp Ala Val Arg Gly Leu
                180                 185                 190

Leu Leu Leu Lys Thr Arg Leu
                195

<210> SEQ ID NO 142
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ser Trp Met Glu Glu Val Ile Lys Leu Cys Gly Arg Glu Leu Val
 1               5                  10                  15

Arg Ala Gln Ile Ala Ile Cys Gly Met Ser Thr Trp Ser Ile Glu Gly
                20                  25                  30

Arg Ser Leu Ser Gln Glu Asp Ala Pro Gln Thr Pro Arg Pro Val Ala
            35                  40                  45

Glu Ile Val Pro Ser Phe Ile Asn Lys Asp Thr Glu Thr Ile Asn Met
 50                  55                  60

Met Ser Glu Phe Val Ala Asn Leu Pro Gln Glu Leu Lys Leu Thr Leu
 65                  70                  75                  80

Ser Glu Met Gln Pro Ala Leu Pro Gln Leu Gln Gln His Val Pro Val
                 85                  90                  95

Leu Lys Asp Ser Ser Leu Leu Phe Glu Phe Lys Lys Leu Ile Arg
                100                 105                 110

Asn Arg Gln Ser Glu Ala Ala Asp Ser Ser Pro Ser Glu Leu Lys Tyr
            115                 120                 125

Leu Gly Leu Asp Thr His Ser Ile Glu Gly Arg Gln Leu Tyr Ser Ala
        130                 135                 140

Leu Ala Asn Lys Cys Cys His Val Gly Cys Thr Lys Arg Ser Leu Ala
145                 150                 155                 160

Arg Phe Cys

<210> SEQ ID NO 143
<211> LENGTH: 102
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 143

Ser Leu Ser Gln Glu Asp Ala Pro Gln Thr Pro Arg Pro Val Ala Glu
1               5                   10                  15

Ile Val Pro Ser Phe Ile Asn Lys Asp Thr Glu Thr Ile Asn Met Met
            20                  25                  30

Ser Glu Phe Val Ala Asn Leu Pro Gln Glu Leu Lys Leu Thr Leu Ser
        35                  40                  45

Glu Met Gln Pro Ala Leu Pro Gln Leu Gln Gln His Val Pro Val Leu
    50                  55                  60

Lys Asp Ser Ser Leu Leu Phe Glu Glu Phe Lys Lys Leu Ile Arg Asn
65                  70                  75                  80

Arg Gln Ser Glu Ala Ala Asp Ser Ser Pro Ser Glu Leu Lys Tyr Leu
                85                  90                  95

Gly Leu Asp Thr His Ser
            100

<210> SEQ ID NO 144
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Pro Arg Ser Ala Lys Glu Leu Arg Cys Gln Cys Ile Lys Thr Tyr Ser
1               5                   10                  15

Lys Pro Phe His Pro Lys Phe Ile Lys Glu Leu Arg Val Ile Glu Ser
            20                  25                  30

Gly Pro His Cys Ala Asn Thr Glu Ile Ile Val Lys Leu Ser Asp Gly
        35                  40                  45

Arg Glu Leu Cys Leu Asp Pro Lys Glu Asn Trp Val Gln Arg Val Val
    50                  55                  60

Glu Lys Phe Leu Lys Arg Ala Glu Asn Ser
65                  70

<210> SEQ ID NO 145
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Ala Gly Cys Lys Asn Phe Phe Trp Lys Thr Phe Thr Ser Cys Gly
1               5                   10                  15
```

<210> SEQ ID NO 147
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu
```

<210> SEQ ID NO 148
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 149
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110
```

```
Ser Leu Leu Gln Lys Met Ile His Gln His Leu Ser Ser Arg Thr His
        115                 120                 125

Gly Ser Glu Asp Ser
    130

<210> SEQ ID NO 150
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ala Gln Glu Pro Val Lys Gly Pro Val Ser Thr Lys Pro Gly Ser Cys
1               5                   10                  15

Pro Ile Ile Leu Ile Arg Cys Ala Met Leu Asn Pro Pro Asn Arg Cys
            20                  25                  30

Leu Lys Asp Thr Asp Cys Pro Gly Ile Lys Lys Cys Cys Glu Gly Ser
        35                  40                  45

Cys Gly Met Ala Cys Phe Val Pro Gln
    50                  55

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Tyr Arg Lys Cys Arg Gly Gly Arg Arg Trp Cys Tyr Gln Lys
1               5                   10

<210> SEQ ID NO 152
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 1-5 "Gly Gly Gly
      Gly Ser" repeating units wherein some positions may be absent

<400> SEQUENCE: 152

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 153
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Glu Gly Arg
1
```

```
<210> SEQ ID NO 154
<211> LENGTH: 6
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Thr or Ser

<400> SEQUENCE: 154

Cys Thr Xaa Val His Gln
1               5

<210> SEQ ID NO 155
<211> LENGTH: 14
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (7)..(14)
<223> OTHER INFORMATION: Any amino acid and this region may encompass
     1-8 residues

<400> SEQUENCE: 155

Cys Thr Xaa Val His Gln Xaa Xaa Xaa Xaa Xaa Xaa Xaa Xaa
1               5                   10

<210> SEQ ID NO 156
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile
<220> FEATURE:
<221> NAME/KEY: MOD_RES
<222> LOCATION: (4)..(4)
<223> OTHER INFORMATION: Val or Lys
<220> FEATURE:
<221> NAME/KEY: MOD_RES
<222> LOCATION: (5)..(5)
<223> OTHER INFORMATION: His, Lys or Tyr

<400> SEQUENCE: 156

Cys Xaa Xaa Xaa Xaa Gln
1               5

<210> SEQ ID NO 157
<211> LENGTH: 5
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile

<400> SEQUENCE: 157
```

```
Xaa Xaa Val His Gln
1               5

<210> SEQ ID NO 158
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile

<400> SEQUENCE: 158

Cys Xaa Xaa Val His Gln
1               5

<210> SEQ ID NO 159
<211> LENGTH: 5
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile
<220> FEATURE:
<221> NAME/KEY: MOD_RES
<222> LOCATION: (4)..(4)
<223> OTHER INFORMATION: His, Tyr or Lys

<400> SEQUENCE: 159

Xaa Xaa Val Xaa Gln
1               5

<210> SEQ ID NO 160
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile
<220> FEATURE:
<221> NAME/KEY: MOD_RES
<222> LOCATION: (5)..(5)
<223> OTHER INFORMATION: His, Tyr or Lys

<400> SEQUENCE: 160

Cys Xaa Xaa Val Xaa Gln
1               5

<210> SEQ ID NO 161
<211> LENGTH: 5
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
```

```
<222> LOCATION: (2)..(2)
<223> OTHER INFORMATION: Thr, Ser, Ala, Pro or Ile

<400> SEQUENCE: 161

Xaa Xaa Lys Lys Gln
1               5

<210> SEQ ID NO 162
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile

<400> SEQUENCE: 162

Cys Xaa Xaa Lys Lys Gln
1               5

<210> SEQ ID NO 163
<211> LENGTH: 4
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Asn or Ile
<220> FEATURE:
<221> NAME/KEY: MOD_RES
<222> LOCATION: (4)..(4)
<223> OTHER INFORMATION: Glu or Asp

<400> SEQUENCE: 163

Tyr Xaa Tyr Xaa
1

<210> SEQ ID NO 164
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile

<400> SEQUENCE: 164

Tyr Xaa Tyr Xaa Tyr
1               5

<210> SEQ ID NO 165
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile
<220> FEATURE:
```

```
<221> NAME/KEY: MOD_RES
<222> LOCATION: (6)..(6)
<223> OTHER INFORMATION: Glu or Asp

<400> SEQUENCE: 165

Tyr Xaa Tyr Xaa Tyr Xaa
1               5

<210> SEQ ID NO 166
<211> LENGTH: 7
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile
<220> FEATURE:
<221> NAME/KEY: MOD_RES
<222> LOCATION: (6)..(6)
<223> OTHER INFORMATION: Glu or Asp
<220> FEATURE:
<221> NAME/KEY: MOD_RES
<222> LOCATION: (7)..(7)
<223> OTHER INFORMATION: His, Trp, Asn, Phe, Ile or Tyr

<400> SEQUENCE: 166

Tyr Xaa Tyr Xaa Tyr Xaa Xaa
1               5

<210> SEQ ID NO 167
<211> LENGTH: 3
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr

<400> SEQUENCE: 167

Tyr Xaa Xaa
1

<210> SEQ ID NO 168
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Asn or Ile
<220> FEATURE:
<221> NAME/KEY: MOD_RES
<222> LOCATION: (3)..(3)
<223> OTHER INFORMATION: Glu or Asp

<400> SEQUENCE: 168

Xaa Tyr Xaa
1

<210> SEQ ID NO 169
<211> LENGTH: 8
<212> TYPE: PRT
<213> ORGANISM: Bos sp.
```

```
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(7)
<223> OTHER INFORMATION: Any amino acid and this region may encompass
     1-4 residues

<400> SEQUENCE: 169

Tyr Xaa Xaa Xaa Xaa Xaa Xaa Trp
1               5

<210> SEQ ID NO 170
<211> LENGTH: 8
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(4)
<223> OTHER INFORMATION: Tyr, His, Gly or Asn
<220> FEATURE:
<221> NAME/KEY: MOD_RES
<222> LOCATION: (5)..(5)
<223> OTHER INFORMATION: Val, Ile or Ala
<220> FEATURE:
<221> NAME/KEY: MOD_RES
<222> LOCATION: (6)..(6)
<223> OTHER INFORMATION: Asp, Asn, Thr or Glu
<220> FEATURE:
<221> NAME/KEY: MOD_RES
<222> LOCATION: (7)..(7)
<223> OTHER INFORMATION: Ala, Val, Ser or Thr

<400> SEQUENCE: 170

Tyr Xaa Xaa Xaa Xaa Xaa Xaa Trp
1               5

<210> SEQ ID NO 171
<211> LENGTH: 7
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (7)..(7)
<223> OTHER INFORMATION: Any amino acid

<400> SEQUENCE: 171

Cys Thr Xaa Val His Gln Xaa
1               5

<210> SEQ ID NO 172
<211> LENGTH: 3
<212> TYPE: PRT
<213> ORGANISM: Bos sp.
<220> FEATURE:
```

```
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: Any amino acid

<400> SEQUENCE: 172

Tyr Xaa Xaa
1

<210> SEQ ID NO 173
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Glu or Asp

<400> SEQUENCE: 173

Xaa Tyr Xaa
1

<210> SEQ ID NO 174
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(4)
<223> OTHER INFORMATION: Any amino acid

<400> SEQUENCE: 174

Tyr Xaa Xaa Xaa Trp
1               5

<210> SEQ ID NO 175
<211> LENGTH: 8
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(7)
<223> OTHER INFORMATION: Any amino acid

<400> SEQUENCE: 175

Tyr Xaa Xaa Xaa Xaa Xaa Xaa Trp
1               5

<210> SEQ ID NO 176
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Pro or Ser

<400> SEQUENCE: 176

Cys Xaa Asp Gly
1

<210> SEQ ID NO 177
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Ser or Thr

<400> SEQUENCE: 177

Thr Xaa Val His Gln
1               5

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: See specification as filed for detailed
      description of substitutions and preferred embodiments

<400> SEQUENCE: 178

Gly Gly Gly Gly Ser
1               5

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Gly Gly Gly Ser Gly Gly Gly Gly Ser
1               5                   10

<210> SEQ ID NO 180
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Lys Lys Arg
1
```

BOVINE FUSION ANTIBODIES

CROSS-REFERENCE TO RELATED APPLICATIONS

This application is a U.S. National Stage entry of International Application No. PCT/US14/11043, filed Jan. 10, 2014, which claims the benefit of priority from U.S. Provisional Application No. 61/751,598, filed Jan. 11, 2013, all of which are incorporated by reference herein in their entirety.

In compliance with 37 C.F.R. § 1.71(g)(1), disclosure is herein made that according to 35 U.S.C. 102(c) the claimed invention was made pursuant to a Joint Research Agreement that was in effect on or before the effective filing date of claimed invention, and as a result of activities undertaken within the scope of the Joint Research Agreement by or on behalf of The California Institute for Biomedical Research and The Scripps Research Institute.

SEQUENCE LISTING

The instant application contains a Sequence Listing, which has been submitted electronically in ASCII format and is hereby incorporated by reference in its entirety. Said ASCII copy, created on Aug. 26, 2015, is named 41135-703-831_ST25.txt and is 175,620 bytes in size.

BACKGROUND

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (e.g., polyclonal antibodies) made from an ensemble of individual antibody producing cells.

Some bovine antibodies have unusually long VH CDR3 sequences compared to other vertebrates. For example, about 10% of IgM contains "ultralong" CDR3 sequences, which can be up to 61 amino acids long. These unusual CDR3s often have multiple cysteines. Functional VH genes form through a process called V(D)J recombination, wherein the D-region encodes a significant proportion of CDR3. A unique D-region encoding an ultralong sequence has been identified in cattle. Ultralong CDR3s are partially encoded in the cattle genome, and provide a unique characteristic of their antibody repertoire in comparison to humans. Kaushik et al. (U.S. Pat. Nos. 6,740,747 and 7,196,185) disclose several bovine germline D-gene sequences unique to cattle stated to be useful as probes and a bovine VDJ cassette stated to be useful as a vaccine vector.

SUMMARY OF THE INVENTION

In some embodiments is a recombinant antibody or fragment thereof, wherein at least a portion of the recombinant antibody or fragment thereof is based on or derived from at least a portion of an ultralong CDR3.

In some embodiments is an antibody or fragment thereof comprising: (a) a first antibody sequence, wherein at least a portion of the first antibody sequence is derived from at least a portion of an ultralong CDR3; (b) a non-antibody sequence; and (c) optionally, a second antibody sequence, wherein at least a portion of the second antibody sequence is derived from at least a portion of an ultralong CDR3.

The antibodies disclosed herein may be a chimeric, human engineered, or humanized antibody. The antibodies disclosed herein may be a bovinized or fully bovine antibody. The antibodies disclosed herein may comprise a Fab, a scFv, dsFv, diabody, $(dsFv)_2$, minibody, flex minibody or bi-specific fragment. The antibodies disclosed herein may be an isolated antibody.

The antibodies disclosed herein may further comprise a non-antibody sequence. The non-antibody sequence may be derived from a mammal. The mammal may be a bovine, human, or non-bovine mammal. The antibodies disclosed herein may comprise a non-antibody sequence derived from a non-bovine animal. The non-bovine animal may be a scorpion. The non-bovine animal may be a lizard. The lizard may be a gila monster. The non-antibody sequence may be a derived from a growth factor. The growth factor may be a GCSF, GMCSF or FGF21. The GCSF may be a bovine GCSF. Alternatively, the GCSF may be a human GCSF. The GMCSF and/or the FGF21 may be from a human. The non-antibody sequence may be a derived from a cytokine. The cytokine may be a beta-interferon. The non-antibody sequence may be a derived from a hormone. The hormone may be an exendin-4, GLP-1, parathyroid hormone or erythropoietin. The GLP-1 and/or erythropoietin may be from a human. The non-antibody sequence may be a derived from a toxin. The toxin may be Moka1, Mamba1, Amgen1, 550 peptide or VM-24. The non-antibody sequence may be derived from or based on a synthetic peptide. The synthetic peptide may be oxyntomodulin. The non-antibody region may comprise elafin or a fragment thereof. The non-antibody region may comprise BCCX2 or a fragment thereof. The non-antibody sequences disclosed herein may replace at least a portion of the ultralong CDR3. The non-antibody sequences disclosed herein may be inserted into the sequence of the ultralong CDR3.

The antibodies disclosed herein may comprise an ultralong CDR3 based on or derived from a cow ultralong CDR3. At least a portion of the antibodies disclosed herein may be from a mammal. At least a portion of the first antibody sequence and/or at least a portion of the second antibody sequence of the antibodies disclosed herein may be from a mammal. The mammal may be a bovine, human or non-bovine mammal.

The antibodies disclosed herein may comprise 3 or more amino acids in length. The antibodies disclosed herein may comprise a sequence that is based on or derived from an ultralong CDR3 disclosed herein. The antibodies disclosed herein may comprise 1 or more amino acid residues based on or derived from a stalk domain of the ultralong CDR3. The antibodies disclosed herein may comprise 1 or more amino acid residues based on or derived from a knob domain of the ultralong CDR3.

At least a portion of the antibodies disclosed herein may be based on or derived from at least a portion of an ultralong CDR3 disclosed herein. The portion of the antibody based on or derived from at least a portion of the ultralong CDR3 may be 20 or fewer amino acids in length. The portion of the antibody based on or derived from at least a portion of the ultralong CDR3 may be 3 or more amino acids in length The antibodies disclosed herein may comprise 1 or more conserved motifs derived from a stalk domain of the ultralong CDR3. The one or more conserved motifs derived from the stalk. The 1 or more conserved motifs derived from the stalk domain of the ultralong CDR3 may comprise any of the stalk domain conserved motifs disclosed herein. The 1 or more conserved motifs derived from the stalk domain of the ultralong CDR3 may comprise any of the stalk domain conserved motifs disclosed in Table 4 (SEQ ID NOS: 18-47).

The portion of the ultralong CDR3s disclosed herein may comprise at least a portion of a stalk domain of the ultralong CDR3, at least a portion of the knob domain of the ultralong CDR3, or a combination thereof.

The antibodies disclosed herein may comprise a sequence selected from any one of SEQ ID NOS: 18-47. The antibodies disclosed herein may comprise a sequence that is 50% or more homologous to a sequence selected from any one of SEQ ID NOS: 18-24 and 34-37.

A portion of any of the antibodies disclosed herein may be based on or derived from at least a portion of a single ultralong CDR3 sequence. A portion of the antibodies disclosed herein may be based on or derived from at least a portion of two or more different ultralong CDR3 sequences.

In any of the embodiments disclosed herein, the portion of the ultralong CDR3 is based on or derived from a BLV1H12 ultralong CDR3 sequence. The portion of the ultralong CDR3 may be based on or derived from a sequence that is 50% or more homologous to a BLV1H12 ultralong CDR3 sequence. The portion of the ultralong CDR3 may be based on or derived from a BLV5B8, BLVCV1, BLV5D3, BLV8C11, BF1H1, or F18 ultralong CDR3 sequence. The portion of the ultralong CDR3 may be based on or derived from a sequence that is 50% or more homologous to a BLV5B8, BLVCV1, BLV5D3, BLV8C11, BF1H1, or F18 ultralong CDR3 sequence.

The antibodies disclosed herein may comprise a first and/or second antibody sequence that is 3 or more amino acids in length. A portion of the first antibody sequence derived from at least a portion of the ultralong CDR3 and/or the portion of the second antibody sequence derived from at least a portion of the ultralong CDR3 may be 20 or fewer amino acids in length. A portion of the first antibody sequence derived from at least a portion of the ultralong CDR3 and/or the portion of the second antibody sequence derived from at least a portion of the ultralong CDR3 may be 3 or more amino acids in length.

In any of the embodiments disclosed herein, the first and/or second antibody sequences comprise 1 or more amino acid residues based on or derived from a stalk domain of the ultralong CDR3. The first and/or second antibody sequences comprise 1 or more amino acid residues based on or derived from a knob domain of the ultralong CDR3. The 1 or more amino acid residues derived from the knob domain of the ultralong CDR3 may be a serine and/or cysteine residue. The first and/or second antibody sequences comprise 1 or more conserved motifs derived from a stalk domain of the ultralong CDR3. The one or more conserved motifs derived from the stalk domain of the ultralong CDR3 may comprise a sequence selected from any one of SEQ ID NOS: 18-47.

In any of the embodiments disclosed herein, the portion of the first antibody sequence derived from at least a portion of the ultralong CDR3 and/or the portion of the second antibody sequence derived from at least a portion of the ultralong CDR3 comprises a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 18-24 and 34-37. The portion of the first antibody sequence derived from at least a portion of the ultralong CDR3 may comprise a sequence selected from any one of SEQ ID NOS: 18-33. The portion of the first antibody sequence derived from at least a portion of the ultralong CDR3 may comprise a sequence that is 50% or more homologous to a sequence selected from any one of SEQ ID NOS: 18-24.

In any of the embodiments disclosed herein, the portion of the second antibody sequence derived from at least a portion of the ultralong CDR3 comprises a sequence selected from any one of SEQ ID NOS: 34-47. The portion of the second antibody sequence derived from at least a portion of the ultralong CDR3 may comprise a sequence that is 50% or more homologous to a sequence selected from any one of SEQ ID NOS: 34-37. The portion of the first antibody sequence derived from at least a portion of the ultralong CDR3 and the portion of the second antibody sequence derived from at least a portion of the ultralong CDR3 may be derived from the same ultralong CDR3 sequence.

In any of the embodiments disclosed herein, the portion of the first antibody sequence derived from at least a portion of the ultralong CDR3 and the portion of the second antibody sequence derived from at least a portion of the ultralong CDR3 are derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a sequence that is 50% or more homologous to a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The portions of the ultralong CDR3 of the first and/or second antibody sequences may be based on or derived from a sequence that is 50% or more homologous to a BLV5B8, BLVCV1, BLV5D3, BLV8C11, BF1H1, or F18 ultralong CDR3 sequence.

In any of the embodiments disclosed herein, the ultralong CDR3 is based on or derived from an ultralong CDR3 that is 35 or more amino acids in length. The ultralong CDR3 may be based on or derived from an ultralong CDR3 comprising 3 or more cysteine residues.

In any of the embodiments disclosed herein, the ultralong CDR3 is based on or derived from an ultralong CDR3 comprises one or more cysteine motifs. The one or more cysteine motifs may be selected from the group consisting of SEQ ID NOS: 48-102. The one or more cysteine motifs may selected from a cysteine motif disclosed in Table 5.

The antibodies disclosed herein may be based on or derived from an ultralong CDR3 that is 35 or more amino acids in length. The antibodies disclosed herein may be based on or derived from an ultralong CDR3 comprising 3 or more cysteine residues. The antibodies disclosed herein may be based on or derived from an ultralong CDR3 comprising 1 or more cysteine motifs.

The antibodies disclosed herein may comprise an ultralong CDR3 that is 35 or more amino acids in length. The antibodies disclosed herein may comprise an ultralong CDR3 comprising 3 or more cysteine residues. The antibodies disclosed herein may comprise an ultralong CDR3 comprising 1 or more cysteine motifs.

In any of the embodiments disclosed herein, the ultralong CDR3 is a heavy chain CDR3. The ultralong CDR3 comprises an amino acid sequence derived from or based on a non-human DH sequence. The ultralong CDR3 may comprise an amino acid sequence derived from or based on a JH sequence. The ultralong CDR3 may comprise an amino acid sequence derived from or based on a non-human VH sequence; an amino acid sequence derived from or based on a non-human DH sequence; and/or an amino acid sequence derived from or based on a JH sequence. The ultralong CDR3 may comprise an additional amino acid sequence comprising at least about two amino acid residues positioned between the VH derived amino acid sequence and the DH derived amino acid sequence.

Any of the antibodies disclosed herein may comprise a sequence based on or derived from a sequence selected from SEQ ID NOs: 9-14 or 108-113, the antibody or binding fragment thereof encoded by the DNA sequence based on or derived from any of SEQ ID NOs: 2-7 or 103-107. Any of the antibodies disclosed herein may comprise a sequence based on or derived from a sequence selected from SEQ ID NO:8, the antibody or binding fragment thereof encoded by the DNA sequence based on or derived from SEQ ID NO:1.

Any of the ultralong CDR3s disclosed herein may comprise a sequence based on or derived from a sequence selected from SEQ ID NOs: 9-14 or 108-113. Any of the antibodies disclosed herein may comprise a sequence based on or derived from a sequence selected from SEQ ID NO:8. Any of the ultralong CDR3s disclosed herein may be encoded by a DNA sequence that is derived from or based on SEQ ID NOs: 2-7 or 103-107. Any of the antibodies disclosed herein may comprise a portion encoded by a DNA sequence that is derived from or based on SEQ ID NO: 1.

Any of the antibodies disclosed herein may comprise one or more linkers. The one or more linkers may comprise a sequence disclosed in Table 3. Any of the antibodies disclosed herein may comprise first linker sequence. Any of the antibodies disclosed herein may comprise second linker sequence. The first and second linker sequences comprise the same sequence. The first and second linker sequences comprise different sequences. The first and/or second linker sequences may be the same length. The first and/or second linker sequences may be different lengths. The first and/or second linker sequences may be 3 or more amino acids in length.

The first and/or second linker sequence may attach the non-antibody sequence to the portion based on or derived from the portion of the ultralong CDR3. The first and/or second linker sequences may attach the non-antibody sequence to the first antibody sequence. The first and/or second linker sequences may attach the non-antibody sequence to the second antibody sequence. The first and/or second linker sequences may be adjacent to a non-antibody sequence, a portion of an ultralong CDR3 sequence, a cleavage site sequence, an antibody sequence, or a combination thereof.

The first and/or second linker sequences comprise one or more glycine residues. The first and/or second linker sequences comprise two or more consecutive glycine residues. The first and/or second linker sequences comprise one or more serine residues. The first and/or second linker sequence comprise one or more polar amino acid residues. The one or more polar amino acid residues may be selected from serine, threonine, asparagine, or glutamine. The polar amino acid residues comprise uncharged side chains. The first and/or second linker sequences comprise the sequence (GGGGS)$_n$ (SEQ ID NO: 152), wherein n=1 to 5; the sequence GGGSGGGGS (SEQ ID NO: 15); the sequence GGGGSGGGS (SEQ ID NO: 16); or a combination thereof.

Any of the antibodies disclosed herein may comprise one or more cleavage sites. The one or more cleavage sites comprise a recognition site for a protease. The protease may be a Factor Xa or thrombin. The one or more cleavage sites comprise an amino acid sequence of IEGR (SEQ ID NO: 153).

The one or more cleavage site may be between a first antibody sequence and the non-antibody sequence. The one or more cleavage sites may be between a second antibody sequence and the non-antibody sequence. The one or more cleavage sites may be between the one or more linkers and the non-antibody sequence. The one or more cleavage sites may be between a first antibody sequence and the one or more linkers. The one or more cleavage sites may be between a second antibody sequence and the one or more linkers. The one or more cleavage sites may be adjacent to a non-antibody sequence, a portion of an ultralong CDR3 sequence, a linker sequence, an antibody sequence, or a combination thereof.

In some embodiments is a library of antibodies or binding fragments thereof, wherein the antibodies or binding fragments thereof comprise an ultralong CDR3.

In some embodiments is a library of antibodies or binding fragments thereof, wherein the antibodies or binding fragments thereof comprise any of the antibodies disclosed herein.

In some embodiments is a nucleic acid library comprising a plurality of polynucleotides comprising sequences coding for antibodies or binding fragments thereof, wherein the antibodies or binding fragments thereof comprise an ultralong CDR3.

In some embodiments is a nucleic acid library comprising a plurality of polynucleotides comprising sequences coding for antibodies or binding fragments thereof, wherein the antibodies or binding fragments thereof comprise any of the antibodies disclosed herein.

In some embodiments is a polynucleotide comprising a nucleic acid sequence that encodes a variable region, wherein the variable region comprises an ultralong CDR3.

In some embodiments is a vector comprising a polynucleotide, wherein the polynucleotide comprises a nucleic acid sequence that encodes a variable region, wherein the variable region comprises an ultralong CDR3.

In some embodiments is a host cell comprising a polynucleotide, wherein the polynucleotide comprises a nucleic acid sequence that encodes a variable region, wherein the variable region comprises an ultralong CDR3.

In some embodiments is a polynucleotide comprising a nucleic acid sequence that encodes the antibody or binding fragment thereof of any of the antibodies disclosed herein.

In some embodiments is a vector comprising a polynucleotide, wherein the polynucleotide comprises a nucleic acid sequence that encodes the antibody or binding fragment thereof of any of the antibodies disclosed herein.

In some embodiments is a host cell comprising a polynucleotide, wherein the polynucleotide comprises a nucleic acid sequence that encodes the antibody or binding fragment thereof of any of the antibodies disclosed herein.

In some embodiments is a method of producing an antibody or binding fragment thereof comprising an ultralong CDR3 or fragment thereof comprising culturing a host cell comprising a polynucleotide, wherein the polynucleotide comprises a nucleic acid sequence that encodes the antibody or binding fragment thereof of any of the antibodies disclosed herein under conditions wherein the polynucleotide sequence is expressed and the antibody or binding fragment thereof comprising an ultralong CDR3 or fragment thereof is produced. The method may further comprise recovering the antibody or binding fragment thereof comprising the ultralong CDR3 or fragment thereof from the host cell culture.

In some embodiments is a pharmaceutical composition comprising any of the antibodies disclosed herein.

In some embodiments is a pharmaceutical composition comprising (a) an antibody or fragment thereof comprising sequence based on or derived from at least a portion of an ultralong CDR3; and (b) a pharmaceutically acceptable excipient.

In some embodiments is a method of treating a disease or condition in a subject in need thereof comprising administering to the mammal a therapeutically effective amount of any of the antibodies disclosed herein. In some instances, the antibodies disclosed herein comprise an ultralong CDR3 sequence and a non-antibody sequence. In some instances, the non-antibody sequence is selected from the group comprising Moka1, Vm24, human GLP-1, Exendin-4, beta-interferon, human EPO, human FGF21, human GMCSF, human interferon-beta, bovine GCSF, human GCSF and a derivative or variant thereof.

The disease or condition may be selected from the group comprising autoimmune disease, heteroimmune disease or condition, inflammatory disease, pathogenic infection, thromboembolic disorder, respiratory disease or condition, metabolic disease, central nervous system (CNS) disorder, bone disease, cancer, blood disorder, obesity, diabetes, osteoporosis, anemia, or pain.

The disease or condition would benefit from the modulation of an ion channel. The ion channel may be selected from the group comprising a potassium ion channel, sodium ion channel, or acid sensing ion channel. The ion channel may be selected from the group comprising Kv1.3 ion channel, Nav1.7 ion channel and acid sensing ion channel (ASIC).

The disease or condition would benefit from the modulation of a receptor. The receptor may be selected from the group comprising GLP1R, GCGR, EPO receptor, FGFR, FGF21R, CSFR, GMCSFR, and GCSFR.

The disease or condition may be mastitis.

The subject may be a mammal. The mammal may be a bovine or human.

In any or all of the above or below disclosure (e.g., antibodies, uses, or methods) or embodiments utilizing an antibody comprising an ultralong CDR3, any antibody comprising an ultralong CDR3 may be used including, for example, any of the above mentioned antibodies comprising an ultralong CDR3.

BRIEF DESCRIPTION OF THE DRAWINGS

The foregoing summary, as well as the following detailed description of the disclosure, may be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

Figure 1:
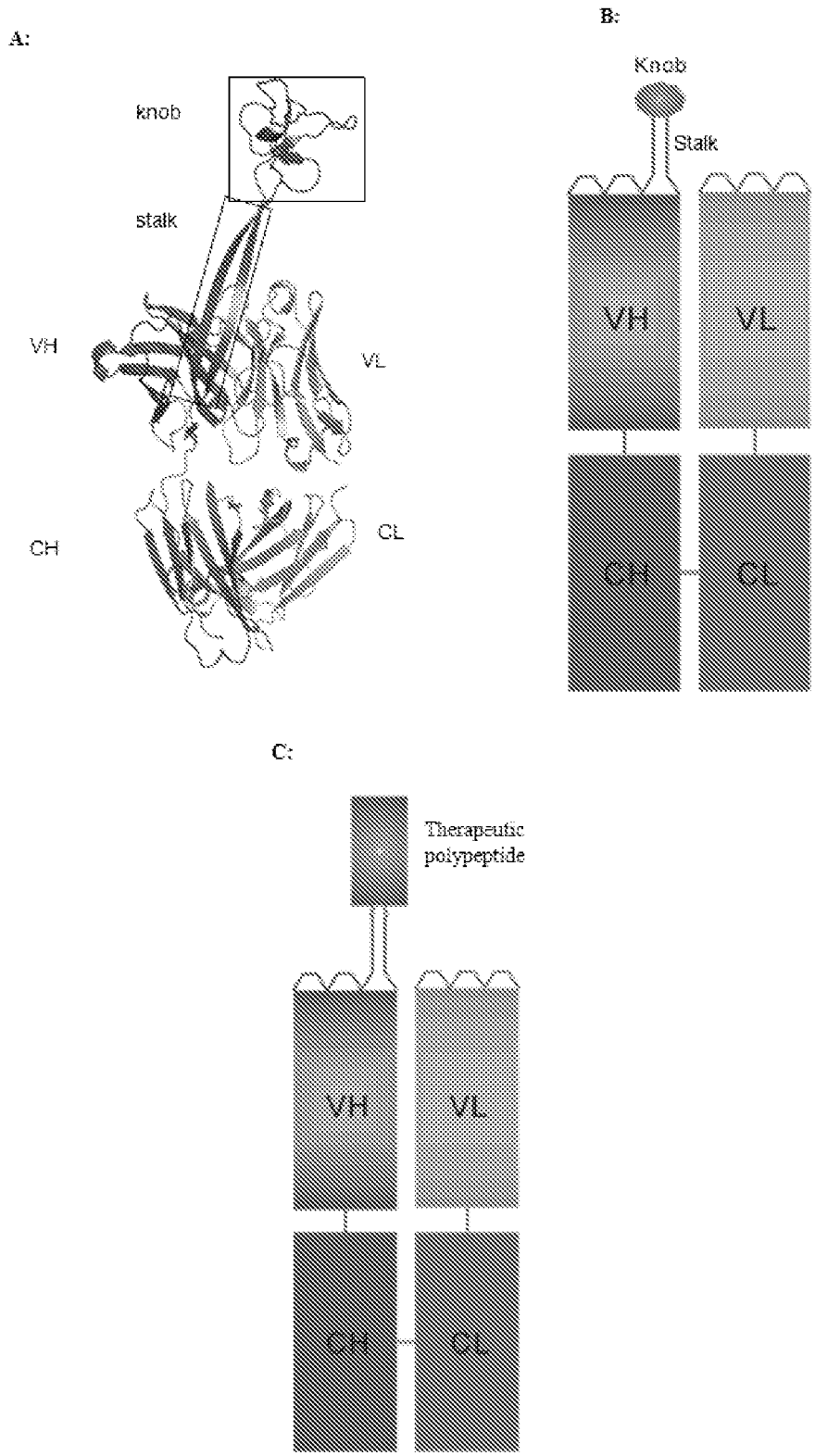
FIG. 1A-1C depict schemes showing insertion of therapeutic polypeptide into the ultralong CDR3 region of a heavy chain region of bovine BLV1H12 antibody to design an immunoglobulin construct described herein. FIG. 1A shows a ribbon diagram of bovine G-CSF attached to the knob domain of a heavy chain region of bovine BLV1H12 antibody. FIG. 1B shows a cartoon depicting the BLV1H12 antibody. FIG. 1C shows a cartoon depicting a therapeutic polypeptide inserted into the ultralong CDR3 region of an immunoglobulin heavy chain region, said insertion can be with or without a linker of sequence.

FIG. 2A-2B depict Western blots and SDS-PAGE of BLV1H12 fusion antibodies disclosed herein. FIG. 2A shows a Western blot of harvest supernatant of BLV1H12 fusion with 550 peptide, Amgen1 and Mamba1. FIG. 2B shows an SDS PAGE of purified BLV1H12 fusion with 550, Amgen1 and Mamba.

FIG. 3 shows an SDS-PAGE of a BLV1H12-betatrophin fusion protein with a single GGGGS (SEQ ID NO: 17) linker (L1) or double GGGGS (SEQ ID NO: 17) linker (L2).

FIG. 4A shows an SDS-PAGE of a BLV1H12-relaxin-2 fusion protein.

FIG. 4B shows a graph of the in vitro activity of a relaxin-2 protein and a BLV1H12-relaxin-2 fusion protein in a relaxin receptor (LGR7) overexpressing cell line.

FIG. 5A shows an SDS-PAGE of a BLV1H12-hGH fusion protein.

FIG. 5B shows a graph of the in vitro activity of a BLV1H12-hGH fusion protein in human IM9 cells. In vitro activity of bIg-beta-hGH was determined by STAT5 phosphorylation.

FIG. 6A shows an SDS-PAGE of a BLV1H12-human interferon-beta fusion protein.

FIG. 6B shows a graph of the in vitro activity of a BLV1H12-human interferon-beta fusion protein in HEK-Blue IFN-a/b cells.

FIG. 7A shows an SDS-PAGE of a BLV1H12 hLeptin based fusion protein.

FIG. 7B shows a graph of the in vitro activities of a hLeptin protein and a BLV1H12 hLeptin based fusion protein in a Leptin receptor overexpressing cell line.

FIG. 8A shows an SDS-PAGE of a BLV1H12 hrelaxin2 based fusion protein.

FIG. 8B shows a graph of the in vitro activities of a relaxin-2 protein and BLV1H12-hrelaxin2 based fusion protein in a relaxin receptor (LGR7) overexpressing cell line.

DETAILED DESCRIPTION OF THE INVENTION

Disclosed herein are methods of improving one or more pharmacodynamic properties of a polypeptide and fusion proteins thereof.

In an embodiment, the present disclosure provides an antibody comprising at least a portion of an ultralong CDR3. The portion of the ultralong CDR3 may be derived from or based on an ultralong CDR3 that is 35 amino acids in length or more (e.g., 40 or more, 45 or more, 50 or more, 55 or more, 60 or more).

The portion of the ultralong CDR3 may comprise at least a portion of a knob domain of an ultralong CDR3, at least a portion of a stalk domain of an ultralong CDR3, or a combination thereof. The portion of the knob domain of the ultralong CDR3 may comprise one or more conserved motifs derived from the knob domain of the ultralong CDR3. The one or more conserved motifs derived from the knob domain of the ultralong CDR3 may comprise one or more cysteine motifs disclosed herein.

The portion of the stalk domain of the ultralong CDR3 may comprise one or more conserved motifs derived from the stalk domain of the ultralong CDR3.

The portion of the ultralong CDR3 may comprise at least 3 cysteine residues or more. The portion of the ultralong CDR3 may comprise 4 or more, 6 or more, 8 or more, 9 or more, 10 or more, 11 or more, 12 or more, 13 or more, 14 or more, or 15 or more cysteine residues. The antibody may comprise one or more cysteine motifs.

The CDR3 may be 35 amino acids in length or more. The ultralong CDR3 may comprise at least a portion of a knob domain of a CDR3, at least a portion of a stalk domain of a CDR3, or a combination thereof. The portion of the knob domain of the CDR3 may comprise one or more conserved motifs derived from the knob domain of the ultralong CDR3. The portion of the stalk domain of the CDR3 may comprise one or more conserved motifs derived from the stalk domain of the ultralong CDR3. Alternatively, or additionally, the antibody comprises at least 3 cysteine residues or more. The antibody may comprise one or more cysteine motifs.

In another embodiment, the present disclosure provides an antibody comprising an ultralong CDR3, wherein the CDR3 is 35 amino acids in length or more and comprises at least 3 cysteine residues or more, including, for example, 4 or more, 6 or more, and 8 or more.

In some instances, the antibodies disclosed herein further comprise a non-ultralong CDR3 antibody sequence. The non-ultralong CDR3 antibody sequence typically does not comprise an ultralong CDR3 sequence. The non-ultralong CDR3 antibody sequence may comprise at least a portion of a heavy chain, a portion of a light chain, or a combination thereof. The amino acid sequence identity of the non-ultralong CDR3 antibody peptide sequence to the ultralong CDR3 peptide sequence is about 40% or less, about 35% or less, about 30% or less, about 25% or less, about 20% or less, about 15% or less, 10% or less, about 5% or less, about 3% or less, or about 1% or less.

A portion of the antibodies disclosed herein may be derived from or based on a mammalian antibody. Alternatively, or additionally, a portion of the antibodies disclosed herein may be derived from or based on a non-mammalian antibody. For example, a portion of the antibodies disclosed herein may be derived from or based on a bovine antibody. The antibody may comprise at least a portion of a BLV1H12 and/or BLVCV1 antibody. Alternatively, or additionally, the antibody comprises at least a portion of a BLV5D3, BLV8C11, BF1H1, BLV5B8 and/or F18 antibody. The antibody may comprise at least a portion of a human antibody. The antibody may be a chimeric, recombinant, engineered, synthetic, humanized, fully human, or human engineered antibody. Alternatively, or additionally, the antibody may be a bovinized, bovine engineered or fully bovine antibody.

The portion of the ultralong CDR3 may be derived from or based on a bovine ultralong CDR3 sequence. Alternatively, the portion of the ultralong CDR3 sequence may be derived from or based on a camelid or shark CDR3 sequence.

The antibodies disclosed herein may comprise antibody sequences from two or more different antibodies. The two or more different antibodies may be from the same species. For example, the specie may be a bovine specie, human specie, or murine specie. The two or more different antibodies may be from the same type of animal. For example the two or more different antibodies may be from a cow. The two or more different antibodies may be from a human. Alternatively, the two or more different antibodies are from different species. For example, the two or more different antibodies are from a human specie and bovine specie. In another example, the two or more different antibodies are from a bovine specie and a non-bovine specie. In another example, the two or more different antibodies are from a human specie and a non-human specie.

In some instances, the antibodies disclosed herein further comprise a non-antibody sequence. In some embodiments, the antibodies disclosed herein comprise a portion of an ultralong CDR3 and a non-antibody sequence. The portion of the ultralong CDR3 can comprise any of the ultralong CDR3s or portions thereof disclosed herein. The non-antibody sequence may be inserted into the portion of the ultralong CDR3. The non-antibody sequence may be adjacent to a portion of the ultralong CDR3, non-bovine sequence, linker, cleavage site, or any combination thereof. Alternatively, the non-antibody sequence is conjugated or attached to the portion of the ultralong CDR3.

In another embodiment, the antibodies disclosed herein comprise an ultralong CDR3, wherein the ultralong CDR3 comprises a non-antibody sequence.

The non-antibody sequence may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be derived from a therapeutic polypeptide. As used herein, the terms "non-antibody sequence", "non-antibody peptide" and "therapeutic polypeptide" may be used interchangeably. The non-antibody sequence may be of human. For example, the non-antibody sequence may be derived from or based on a parathyroid hormone. Alternatively, the non-antibody sequence may be of non-human origin. The non-human origin may be a bovine, rodent, snake, lizard, bird, fish, turtle, etc. The non-antibody sequence may be based on or derived from a snake peptide. For example, the non-antibody sequence may comprise Mamba1. The non-antibody sequence may comprise a synthetic sequence. For example, the non-antibody sequence may comprise oxyntomodulin, 550 peptide, or Amgen1.

The non-antibody sequence may comprise a portion of a non-antibody protein such as a peptide or domain. The non-antibody sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the antibody.

In some instances, the antibodies disclosed herein may comprise a portion based on or derived from a non-bovine sequence. The portion based on or derived from the non-bovine sequence may be inserted into the portion of the ultralong CDR3. Alternatively, the portion based on or derived from the non-bovine sequence may be conjugated or attached to the portion of the ultralong CDR3. The portion based on or derived from the non-bovine sequence may be adjacent the portion of the ultralong CDR3.

In some instances, the antibodies disclosed herein further comprise a non-bovine sequence. In some embodiments, the antibodies disclosed herein comprise a portion of an ultralong CDR3 and a non-bovine sequence. The portion of the ultralong CDR3 can comprise any of the ultralong CDR3s or portions thereof disclosed herein. The non-bovine sequence may be inserted into the portion of the ultralong CDR3. The non-bovine sequence may be adjacent to a portion of the ultralong CDR3, non-antibody sequence, linker, cleavage site, or any combination thereof. Alternatively, the non-bovine sequence is conjugated or attached to the ultralong CDR3 sequence.

The non-bovine sequence can be derived from or based on at least a portion of an antibody sequence. The antibody sequence can encode at least a portion of a variable region, at least a portion of a constant region or a combination thereof.

In some instances, the antibodies disclosed herein further comprise one or more linkers. The one or more linkers may be inserted into the portion of the ultralong CDR3. The one or more linkers may be adjacent to an ultralong CDR3, non-antibody sequence, non-ultralong antibody sequence, cleavage site, or a combination thereof. The one or more linkers may comprise an amino acid sequence of (GGGGS)$_n$ (SEQ ID NO: 152) wherein n=1 to 5. Alternatively, or additionally, the one or more linker comprise an amino acids sequence of GGGSGGGGS (SEQ ID NO: 15) or GGGGSGGGS (SEQ ID NO: 16).

In some instances, the antibodies disclosed herein bind to one or more targets. The non-antibody sequence of the antibody may bind to the one or more target. Alternatively, or additionally, a variable region of the antibody may bind to the one or more targets. The target may be a protein target. The protein target may be a transmembrane protein target. Such transmembrane targets may include, but are not limited to, GPCRs, ion channels, transporters, and cell surface receptors.

Provided herein is an immunoglobulin construct comprising a mammalian immunoglobulin heavy chain comprising at least a portion of complementarity determining region 3 (CDR3H); and a therapeutic polypeptide, wherein the therapeutic polypeptide is inserted into or replaces at least a portion of the CDR3H. The immunoglobulin construct may comprise one or more linkers. The one or more linkers can connect the therapeutic polypeptide to the heavy chain. In some embodiments, the linker comprises an amino acid sequence of (GGGGS)$_n$ (SEQ ID NO: 152) wherein n=1 to 5. Alternatively, or additionally, the linker comprises an amino acid sequence of GGGSGGGGS (SEQ ID NO: 15) or GGGGSGGGS (SEQ ID NO: 16). The therapeutic polypeptide may be a synthetic peptide. The therapeutic polypeptide may modulate a receptor. The therapeutic polypeptide may be a receptor agonist. Alternatively, the therapeutic polypeptide is a receptor antagonist. The therapeutic polypeptide may be a hormone. In some instances, the therapeutic polypeptide is selected from the group comprising oxyntomodulin, 550 peptide, Amgen1, Mamba1, and parathyroid hormone. Provided herein are immunoglobulin constructs comprising a mammalian immunoglobulin heavy chain comprising a knob domain in the complementarity determining region 3 (CDR3H) or fragment thereof; and a therapeutic polypeptide attached to said knob domain of the CDR3H, wherein said mammalian immunoglobulin is a bovine immunoglobulin. In some embodiments, the bovine immunoglobulin is a BLV1H12 antibody. In some embodiments of the immunoglobulin constructs described herein, at least a portion of the knob domain is replaced by the therapeutic polypeptide. The knob domain of the CDR3H may comprise one or more conserved motifs derived from the knob domain of the ultralong CDR3H. The immunoglobulin construct may further comprise at least a portion of a stalk domain in the CDR3H. The portion of the stalk domain of the CDR3H may comprise one or more conserved motifs derived from the stalk domain of the ultralong CDR33H.

Further provided herein are antibodies or fragments thereof comprising a stalk domain in the complementarity determining region 3 (CDR3H) or fragment thereof; and a therapeutic polypeptide. In some instances, the complementarity determining region 3 (CDR3H) is derived from a bovine ultralong CDR3H. The therapeutic polypeptide can be any of the therapeutic polypeptides disclosed herein. For example, the therapeutic polypeptide is Moka1. In another example, the therapeutic polypeptide is relaxin. The therapeutic polypeptide may be human relaxin. The therapeutic polypeptide may be human relaxin2. The therapeutic polypeptide may be leptin. The therapeutic polypeptide may be human leptin. The therapeutic polypeptide may be Vm24. The therapeutic polypeptide may be GLP-1. The therapeutic polypeptide may be Exendin-4. The therapeutic polypeptide may be erythropoietin (EPO). The EPO may be human EPO. The therapeutic polypeptide may be may be FGF21. The FGF21 may be human FGF21. The therapeutic polypeptide may be GMCSF. The GMCSF may be human GMCSF. The therapeutic polypeptide may be interferon. The interferon may be interferon-alpha. The interferon may be a human interferon. The interferon may be interferon-beta. The interferon-beta may be human interferon-beta. The therapeutic polypeptide may be growth hormone (GH). The growth hormone may be a human growth hormone (hGH). The therapeutic polypeptide may be betatrophin. The therapeutic polypeptide may be synthetically produced. The therapeutic polypeptide may be a recombinant polypeptide. The therapeutic polypeptide can be attached to the stalk domain. In some instances, the antibody or fragment thereof further comprises a linker. The linker can attach the therapeutic polypeptide to the stalk domain. Alternatively, or additionally, the antibody or fragment thereof further comprises at least a portion of a knob domain in the CDR3H. In some instances, the linker attaches the therapeutic polypeptide to the knob domain. In some instances, the knob domain is attached to the stalk domain. The portion of the knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

In some instances, an antibody or fragment thereof is provided herein. The antibody or fragment thereof can comprise at least one immunoglobulin domain or fragment thereof; and a therapeutic polypeptide or derivative or variant thereof. The therapeutic polypeptide, or derivative or variant thereof can be attached to the immunoglobulin domain. In some instances, the therapeutic polypeptide is Moka1, Vm24, GLP-1, Exendin-4, human EPO, human FGF21, human GMCSF, human interferon-beta, or derivative or variant thereof. In some embodiments, the immunoglobulin domain is an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. In some instances, the immunoglobulin domain is from an engineered antibody or recombinant antibody. In other instances, the immunoglobulin domain is from a humanized, human engineered or fully human antibody. In certain embodiments, the mammalian antibody is a bovine antibody. In other instances, the mammalian antibody is a human antibody. In other instances, the mammalian antibody is a murine antibody. In some instances, the immunoglobulin domain is a heavy chain region comprising a knob domain in the complementarity determining region 3 (CDR3H) or fragment thereof. The therapeutic polypeptide can be attached to the knob domain. Alternatively, or additionally, the immunoglobulin domain is a heavy chain region comprising a stalk domain in the complementarity-determining region 3 (CDR3H) or fragment thereof. In some instances, the therapeutic polypeptide is attached to the stalk domain. In some instances, the antibody or fragment thereof further comprises a linker. The linker can attach the therapeutic polypeptide to the immunoglobulin domain or fragment thereof. The knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

Provided herein is an immunoglobulin construct comprising at least one immunoglobulin domain or fragment thereof; and a G-CSF polypeptide or derivative or variant thereof attached to said immunoglobulin domain. In some embodiments, the immunoglobulin domain is an immunoglobulin A, an immunoglobulin D, an immunoglobulin E, an immunoglobulin G, or an immunoglobulin M. In some embodiments, the immunoglobulin domain is an immunoglobulin heavy chain region or fragment thereof. In an embodiment, the immunoglobulin domain is from a mammalian or chimeric antibody. In other instances, the immunoglobulin domain is from a humanized, human engineered or fully human antibody. In certain embodiments, the mammalian antibody is a bovine antibody. In some instances, the mammalian antibody is a human antibody. In other instances, the mammalian antibody is a murine antibody. In an embodiment, the immunoglobulin domain is a heavy chain region comprising a knob domain in the complementarity determining region 3 (CDR3H) or fragment thereof. In an embodiment, the G-CSF polypeptide is attached to the knob domain. The immunoglobulin domain may be a heavy chain region comprising a stalk domain in the complementarity determining region 3 (CDR3H) or fragment thereof. The G-CSF polypeptide may be attached to the stalk domain. The knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

In certain embodiments, provided is an immunoglobulin construct comprising at least one immunoglobulin domain or fragment thereof; and a G-CSF polypeptide or derivative or variant thereof attached to said immunoglobulin domain, wherein said G-CSF polypeptide is a bovine G-CSF polypeptide or derivative or variant thereof. In certain embodiments provided herein is a pharmaceutical composition comprising an immunoglobulin construct provided herein, and a pharmaceutically acceptable carrier. In certain embodiments is provided a method of preventing or treating a disease in a mammal in need thereof comprising administering a pharmaceutical composition described herein to said mammal. The immunoglobulin domain may be a heavy chain region comprising a knob domain in the complementarity determining region 3 (CDR3H) or fragment thereof. The G-CSF polypeptide may be attached to the knob domain. The immunoglobulin domain may be a heavy chain region comprising a stalk domain in the complementarity determining region 3 (CDR3H) or fragment thereof. The G-CSF polypeptide may be attached to the stalk domain. The knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

In some embodiments is an antibody or fragment thereof comprising: (a) a first antibody sequence, wherein at least a portion of the first antibody sequence is derived from at least a portion of an ultralong CDR3; and (b) a non-antibody sequence. The antibody or fragment thereof may further comprise a second antibody sequence, wherein at least a portion of the second antibody sequence is derived from at least a portion of an ultralong CDR3. The ultralong CDR3 from which the first antibody sequence and/or second antibody sequence may be derived from a ruminant. The ruminant can be a cow. At least a portion of the first antibody sequence and/or at least a portion of the second antibody sequence can be derived from a mammal. The mammal may be a bovine. Alternatively, the mammal is a non-bovine mammal, such as a human. The first and/or second antibody sequences may be 3 or more amino acids in length. The amino acids may be consecutive amino acids. Alternatively, the amino acids are non-consecutive amino acids. The first and/or second antibody sequences may comprise a bovine antibody sequence comprising 3 or more amino acids in length. The bovine antibody may be a BLVH12, BLV5B8, BLVCV1, BLV5D3, BLV8C11, BF1H1, or F18 antibody. The first and/or second antibody sequences may comprise a human antibody sequence comprising 3 or more amino acids in length. The portion of the first antibody sequence derived from at least a portion of the ultralong CDR3 and/or the portion of the second antibody sequence derived from at least a portion of the ultralong CDR3 can be 20 or fewer amino acids in length. The portion of the first antibody sequence derived from at least a portion of the ultralong CDR3 and/or the portion of the second antibody sequence derived from at least a portion of the ultralong CDR3 may be 3 or more amino acids in length. The first and/or second antibody sequences can comprise 1 or more, 2 or more, 3 or more, 4 or more, 5 or more, 6 or more, 7 or more, 8 or more, 9 or more, 10 or more, 15 or more, 20 or more, 30 or more, or 40 or more amino acid residues derived from a knob domain of the ultralong CDR3. The 1 or more amino acid residues derived from the knob domain of the ultralong CDR3 may be a serine and/or cysteine residue. The first and/or second antibody sequences may comprise 1 or more, 2 or more, 3 or more, 4 or more, 5 or more, 6 or more, 7 or more, 8 or more, 9 or more, or 10 or more amino acid residues derived from a stalk domain of the ultralong CDR3. The first and/or second antibody sequences may comprise 1 or more, 2 or more, 3 or more, 4 or more, or 5 or more conserved motifs derived from a stalk domain of the ultralong CDR3. The one or more conserved motifs derived from the stalk domain of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 18-24 and 34-37. The portion of the first antibody sequence derived from at least a portion of the ultralong CDR3 may comprise a sequence selected from any one of SEQ ID NOS: 18-33. The portion of the first antibody sequence derived from at least a portion of the ultralong CDR3 may comprise a sequence that is 50% or more homologous to a sequence selected from any one of SEQ ID NOS: 18-24. The portion of the first antibody sequence derived from at least a portion of the ultralong CDR3 may comprise a sequence that is 50% or more homologous to a sequence selected from any one of SEQ ID NOS: 22-24. The portion of the second antibody sequence derived from at least a portion of the ultralong CDR3 may comprise a sequence selected from any one of SEQ ID NOS: 34-47. The portion of the second antibody sequence derived from at least a portion of the ultralong CDR3 may comprise a sequence that may be 50% or more homologous to a sequence selected from any one of SEQ ID NOS: 34-37. The portion of the first antibody sequence derived from at least a portion of the ultralong CDR3 and the portion of the second antibody sequence derived from at least a portion of the ultralong CDR3 may be derived from the same ultralong CDR3 sequence. The portion of the first antibody sequence derived from at least a portion of the ultralong CDR3 and the portion of the second antibody sequence derived from at least a portion of the ultralong CDR3 may be derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The antibody may further comprise one or more linker sequences.

The present disclosure also provides antibodies that comprise a heavy chain polypeptide, wherein the heavy chain polypeptide comprises at least a portion of an ultralong CDR3 sequence. The heavy chain polypeptide may comprise a polypeptide sequence of any one of SEQ ID NOs: 9-14 or 108-113. The heavy chain polypeptide may comprise a polypeptide sequence encoded by the DNA of any one of SEQ ID NOs: 2-7 or 103-107. Also provided are antibodies comprising a heavy chain polypeptide, wherein the heavy chain polypeptide comprises an ultralong CDR3 sequence and the heavy chain polypeptide sequences are substantially similar to those polypeptide sequences provided by any one of SEQ ID NOs: 9-14 or 108-113. A heavy chain polypeptide sequence may be considered substantially similar to a polypeptide sequence provided by any one of SEQ ID NOs: 9-14 or 108-113 where the heavy chain polypeptide sequence shares 60%, 70%, 80%, 90%, 95%, 99%, or more nucleic acid identity to a nucleotide sequence provided by any one of SEQ ID NOs: 9-14 or 108-113. The antibodies may further comprise a light chain polypeptide. The light chain polypeptide may comprise a polypeptide sequence of SEQ ID NO: 8. The light chain polypeptide may comprise a polypeptide sequence encoded by the DNA sequence based on or derived from SEQ ID NO:1. Also provided are antibodies further comprising a light chain polypeptide, wherein the light chain polypeptide comprises an ultralong CDR3 sequence and the light chain polypeptide sequences are substantially similar to those polypeptide sequences provided by SEQ ID NO: 8. A light chain polypeptide sequence may be considered substantially similar to a polypeptide sequence provided by SEQ ID NO: 1 where the light chain polypeptide sequence shares 60%, 70%, 80%, 90%, 95%, 99%, or more nucleic acid identity to a nucleotide sequence provided by any one of SEQ ID NO: 1. The antibody may have therapeutic activity in an animal. The antibody can have therapeutic activity in infectious disease in a subject. The antibody may comprise a monoclonal antibody, polyclonal antibody, chimeric antibody, recombinant antibody, engineered antibody, or synthetic antibody. The antibody may comprise a mammalian antibody. The antibody may comprise a bovine antibody. The antibody may comprise a G-CSF polypeptide, or derivative or variant thereof. The antibody may comprise a mammalian G-CSF polypeptide, or derivative or variant thereof. The antibody may comprise a bovine G-CSF, or derivative or variant thereof. In some embodiments, a pharmaceutical composition of therapeutic formulation comprises an antibody described herein and a pharmaceutically acceptable carrier. In certain embodiments, the antibody is used in a method of treating a subject in need thereof, with a therapeutically effective amount of the antibody or a pharmaceutical composition described herein. In some embodiments, a nucleic acid molecule or a complement thereof encodes a therapeutic immunoglobulin described herein.

Genetic Sequences

The present disclosure provides genetic sequences (e.g., genes, nucleic acids, polynucleotides) encoding antibodies comprising ultralong CDR3 sequences or portions thereof. The present disclosure provides genetic sequences (e.g., genes, nucleic acids, polynucleotides) encoding antibodies comprising the knob domain and/or knob domain of ultralong CDR3 sequences. In another embodiment, the present disclosure provides genetic sequences encoding an antibody or immunoglobulin construct described herein.

The present disclosure also provides genetic sequences (e.g., genes, nucleic acids, polynucleotides) encoding an ultralong CDR3 or portion thereof. The present disclosure also provides genetic sequences (e.g., genes, nucleic acids, polynucleotides) encoding the knob domain and/or knob domain of an ultralong CDR3.

In an embodiment, the present disclosure provides genetic sequences encoding an antibody comprising an ultralong CDR3. The ultralong CDR3 may be 35 amino acids in length or more (e.g., 40 or more, 45 or more, 50 or more, 55 or more, 60 or more). The ultralong CDR3 may comprise at least a portion of a knob domain of a CDR3, at least a portion of a stalk domain of a CDR3, or a combination thereof. Such an antibody may comprise at least 3 cysteine residues or more (e.g., 4 or more, 6 or more, 8 or more) within the ultralong CDR3. The antibody may comprise one or more cysteine motifs. The antibody may comprise a non-antibody sequence within the ultralong CDR3. Alternatively, or additionally, the antibody comprises a non-bovine sequence. The antibody may further comprise an antibody sequence. The antibody may comprise a cytotoxic agent or therapeutic polypeptide. The cytotoxic agent or therapeutic polypeptide may be conjugated to the ultralong CDR3. The antibody may bind to a target. The target may be a protein target, such as a transmembrane protein target.

In another embodiment, the present disclosure provides genetic sequences encoding an antibody comprising an ultralong CDR3, wherein the CDR3 is 35 amino acids in length or more and is derived from or based on a non-human sequence. The genetic sequences encoding the ultralong CDR3 may be derived from any species that naturally produces ultralong CDR3 antibodies, including ruminants such as cattle (Bos taurus). Alternatively, the ultralong CDR3 sequence may be derived from a camelid or shark CDR3 sequence.

In another embodiment, the present disclosure provides genetic sequences encoding an antibody comprising an ultralong CDR3, wherein the CDR3 comprises a non-antibody protein sequence. The genetic sequences encoding the non-antibody protein sequences may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be derived from a therapeutic polypeptide. The non-antibody protein sequence may be of human or non-human origin. The non-antibody sequence may comprise a synthetic sequence. The non-antibody sequence may comprise a portion of a non-antibody protein such as a peptide or domain. The non-antibody protein sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the antibody. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody comprising an ultralong CDR3 and a non-bovine sequence. The ultralong CDR3 can be derived from a ruminant. The ruminant can be a bovine. The non-bovine sequence can be derived from or based on a non-bovine mammal sequence. For example, the non-bovine sequence can be derived from or based on a human, mouse, rat, sheep, dog, and/or goat sequence. The non-bovine sequence can be within the ultralong CDR3. Alternatively, the non-bovine sequence is linked or attached to the ultralong CDR3 sequence. The non-bovine sequence can be derived from or based on at least a portion of an antibody sequence. The antibody sequence can encode a variable region, constant region or a combination thereof. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides genetic sequences encoding an antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides genetic sequences encoding an antibody comprising an ultralong CDR3, wherein the CDR3 is 35 amino acids in length or more and comprises at least 3 cysteine residues or more, wherein the ultralong CDR3 is a component of an immunoconjugate.

In another embodiment, the present disclosure provides genetic sequences encoding an antibody comprising an ultralong CDR3 wherein the CDR3 is 35 amino acids in length or more and comprises at least 3 cysteine residues or more and wherein the antibody comprising an ultralong CDR3 binds to a transmembrane protein target. Such transmembrane targets may include, but are not limited to, GPCRs, ion channels, transporters, and cell surface receptors.

In another embodiment, the present disclosure provides genetic sequences encoding an antibody comprising an ultralong CDR3, wherein the antibody comprising an ultralong CDR3 binds to a transmembrane protein target. Such transmembrane targets may include, but are not limited to, GPCRs, ion channels, transporters, and cell surface receptors. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody or fragment thereof comprising: (a) a first antibody sequence, wherein at least a portion of the first antibody sequence is derived from at least a portion of an ultralong CDR3; and (b) a non-antibody sequence. The antibody or fragment thereof may further comprise a second antibody sequence, wherein at least a portion of the second antibody sequence is derived from at least a portion of an ultralong CDR3. The ultralong CDR3 from which the first antibody sequence and/or second antibody sequence may be derived from a ruminant. The ruminant can be a cow. At least a portion of the first antibody sequence and/or at least a portion of the second antibody sequence can be derived from a mammal. The mammal may be a bovine. Alternatively, the mammal is a non-bovine mammal, such as a human. The first and/or second antibody sequences may be 3 or more amino acids in length. The amino acids may be consecutive amino acids. Alternatively, the amino acids are non-consecutive amino acids. The first and/or second antibody sequences may comprise a bovine antibody sequence comprising 3 or more amino acids in length. The bovine antibody may be a BLVH12, BLV5B8, BLVCV1, BLV5D3, BLV8C11, BF1H1, or F18 antibody. The first and/or second antibody sequences may comprise a human antibody sequence comprising 3 or more, 4 or more, 5 or more, 6 or more, 7 or more, 8 or more, 9 or more, 10 or more, 15 or more, 20 or more, 30 or more, 40 or more, 50 or more, 60 or more, or 70 or more amino acids in length. The portion of the first antibody sequence derived from at least a portion of the ultralong CDR3 and/or the portion of the second antibody sequence derived from at least a portion of the ultralong CDR3 can be 20 or fewer amino acids in length. The portion of the first antibody sequence derived from at least a portion of the ultralong CDR3 and/or the portion of the second antibody sequence derived from at least a portion of the ultralong CDR3 may be 3 or more amino, 4 or more, 5 or more, 6 or more, 7 or more, 8 or more, 9 or more, 10 or more, 15 or more, or 20 or more acids in length. The first and/or second antibody sequences can comprise 1 or more, 2 or more, 3 or more, 4 or more, 5 or more, 6 or more, 7 or more, 8 or more, 9 or more, 10 or more, 15 or more, 20 or more, 30 or more, or 40 or more amino acid residues derived from a knob domain of the ultralong CDR3. The 1 or more amino acid residues derived from the knob domain of the ultralong CDR3 may be a serine and/or cysteine residue. The first and/or second antibody sequences may comprise 1 or more, 2 or more, 3 or more, 4 or more, 5 or more, 6 or more, 7 or more, 8 or more, 9 or more, or 10 or more amino acid residues derived from a stalk domain of the ultralong CDR3. The first and/or second antibody sequences may comprise 1 or more, 2 or more, 3 or more, 4 or more, or 5 or more conserved motifs derived from a stalk domain of the ultralong CDR3. The one or more conserved motifs derived from the stalk domain of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 18-24 and 34-37. The portion of the first antibody sequence derived from at least a portion of the ultralong CDR3 may comprise a sequence selected from any one of SEQ ID NOS: 18-33. The portion of the first antibody sequence derived from at least a portion of the ultralong CDR3 may comprise a sequence that is 50% or more homologous to a sequence selected from any one of SEQ ID NOS: 18-24. The portion of the first antibody sequence derived from at least a portion of the ultralong CDR3 may comprise a sequence that is 50% or more homologous to a sequence selected from any one of SEQ ID NOS: 22-24. The portion of the second antibody sequence derived from at least a portion of the ultralong CDR3 may comprise a sequence selected from any one of SEQ ID NOS: 34-47. The portion of the second antibody sequence derived from at least a portion of the ultralong CDR3 may comprise a sequence that may be 50% or more homologous to a sequence selected from any one of SEQ ID NOS: 34-37. The portion of the first antibody sequence derived from at least a portion of the ultralong CDR3 and the portion of the second antibody sequence derived from at least a portion of the ultralong CDR3 may be derived from the same ultralong CDR3 sequence. The portion of the first antibody sequence derived from at least a portion of the ultralong CDR3 and the portion of the second antibody sequence derived from at least a portion of the ultralong CDR3 may be derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The antibody may further comprise one or more linker sequences.

The present disclosure also provides isolated genetic sequences (e.g., genes, nucleic acids, polynucleotides, oligonucleotides) such as genetic sequences encoding antibodies that comprise a heavy chain polypeptide, wherein the heavy chain polypeptide comprises at least a portion of an ultralong CDR3 sequence. The heavy chain polypeptide may comprise a polypeptide sequence of any one of SEQ ID NOs: 9-14 or 108-113. The heavy chain polypeptide may comprise a polypeptide sequence encoded by the DNA of any one of SEQ ID NOs: 2-7 or 103-107. Also provided are isolated genetic sequences (e.g., genes, nucleic acids, polynucleotides, oligonucleotides) such as genetic sequences encoding antibodies comprising a heavy chain polypeptide, wherein the heavy chain polypeptide comprises an ultralong CDR3 sequence and the heavy chain polypeptide sequences are substantially similar to those polypeptide sequences provided by any one of SEQ ID NOs: 9-14 or 108-113. A heavy chain polypeptide sequence may be considered substantially similar to a polypeptide sequence provided by any one of SEQ ID NOs: 9-14 or 108-113 where the heavy chain polypeptide sequence shares 60%, 70%, 80%, 90%, 95%, 99%, or more nucleic acid identity to a nucleotide sequence provided by any one of SEQ ID NOs: 9-14 or 108-113 or hybridizes to any one of SEQ ID NOs: 9-14 or 108-113 under stringent hybridization conditions. The isolated genetic sequences (e.g., genes, nucleic acids, polynucleotides, oligonucleotides) such as genetic sequences encoding antibodies may further comprise a light chain polypeptide. The light chain polypeptide may comprise a polypeptide sequence of SEQ ID NO: 8. The light chain polypeptide may comprise a polypeptide sequence encoded by the DNA sequence based on or derived from SEQ ID NO:1. Also provided are isolated genetic sequences (e.g., genes, nucleic acids, polynucleotides, oligonucleotides) such as genetic sequences encoding antibodies further comprising a light chain polypeptide, wherein the light chain polypeptide comprises an ultralong CDR3 sequence and the light chain polypeptide sequences are substantially similar to those polypeptide sequences provided by SEQ ID NO: 8. A light chain polypeptide sequence may be considered substantially similar to a polypeptide sequence provided by SEQ ID NO: 1 where the light chain polypeptide sequence shares 60%, 70%, 80%, 90%, 95%, 99%, or more nucleic acid identity to a nucleotide sequence provided by any one of SEQ ID NO: 1 or hybridizes to SEQ ID NOS: 1 under stringent hybridization conditions.

Cells

The present disclosure provides cells comprising genetic sequences encoding antibodies comprising ultralong CDR3 sequences or portions thereof. The present disclosure provides cells comprising genetic sequences encoding antibodies comprising at least a portion of a knob domain or at least a portion of a knob domain of an ultralong CDR3 sequence.

The present disclosure provides cells comprising genetic sequences (e.g., genes, nucleic acids, polynucleotides) encoding an ultralong CDR3 or portion thereof. The present disclosure also provides cells comprising genetic sequences (e.g., genes, nucleic acids, polynucleotides) encoding the knob domain and/or knob domain of an ultralong CDR3.

In an embodiment, the present disclosure provides cells expressing an antibody comprising an ultralong CDR3. The cells may be prokaryotic or eukaryotic, and an antibody comprising an ultralong CDR3 may be expressed on the cell surface or secreted into the media. When displayed on the cell surface an antibody preferentially contains a motif for insertion into the plasmid membrane such as a membrane spanning domain at the C-terminus or a lipid attachment site. For bacterial cells, an antibody comprising an ultralong CDR3 may be secreted into the periplasm. When the cells are eukaryotic, they may be transiently transfected with genetic sequences encoding an antibody comprising an ultralong CDR3. Alternatively, a stable cell line or stable pools may be created by transfecting or transducing genetic sequences encoding an antibody comprising an ultralong CDR3 by methods well known to those of skill in the art. Cells can be selected by fluorescence activated cell sorting (FACS) or through selection for a gene encoding drug resistance. Cells useful for producing antibodies comprising ultralong CDR3 sequences include prokaryotic cells like *E. coli*, eukaryotic cells like the yeasts *Saccharomyces cerevisiae* and *Pichia pastoris*, insect cells (e.g., Sf9, Hi5), chinese hamster ovary (CHO) cells, monkey cells like COS-1, or human cells like HEK-293, HeLa, SP-1.

Library Methods

The present disclosure provides methods for making libraries comprising antibodies comprising ultralong CDR3 sequences. Methods for making libraries of spatially addressed libraries are described in WO 2010/054007. Methods of making libraries in yeast, phage, *E. coli*, or mammalian cells are well known in the art.

The present disclosure also provides methods of screening libraries of antibodies comprising ultralong CDR3 sequences.

General Techniques

The present disclosure relies on routine techniques in the field of recombinant genetics. Basic texts disclosing the general methods of use in this present disclosure include Sambrook and Russell, Molecular Cloning: A Laboratory Manual 3d ed. (2001); Kriegler, Gene Transfer and Expression: A Laboratory Manual (1990); and Ausubel et al., Current Protocols in Molecular Biology (1994).

For nucleic acids, sizes are given in either kilobases (Kb) or base pairs (bp). These are estimates derived from agarose or polyacrylamide gel electrophoresis, from sequenced nucleic acids, or from published DNA sequences. For proteins, sizes are given in kilo-Daltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage and Caruthers, Tetrahedron Letters, 22:1859-1862 (1981), using an automated synthesizer, as described in Van Devanter et al., Nucleic Acids Res., 12:6159-6168 (1984). Purification of oligonucleotides is by either native polyacrylamide gel electrophoresis or by anion-exchange chromatography as described in Pearson & Reanier, J. Chrom., 255:137-149 (1983). The sequence of the cloned genes and synthetic oligonucleotides can be verified after cloning using, e.g., the chain termination method for sequencing double-stranded templates of Wallace et al., Gene, 16:21-26 (1981).

The nucleic acids encoding recombinant polypeptides of the present disclosure may be cloned into an intermediate vector before transformation into prokaryotic or eukaryotic cells for replication and/or expression. The intermediate vector may be a prokaryote vector such as a plasmid or shuttle vector.

Antibodies with UltraLong CDR3 Sequences

In an embodiment, bovine antibodies are identified and/or produced. Multiple techniques exist to identify and/or produce antibodies.

Antibodies of the present disclosure may be isolated by screening including, high-throughput screening, of combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N. J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N. J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). Such screening may be iterative until a hit is obtained.

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Phage display libraries of bovine antibodies may be a source of bovine antibody gene sequences, including ultralong CDR3 sequences.

Typically, a non-human antibody is humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005); Klimka et al., Br. J. Cancer, 83:252-260 (2000) (describing the "guided selection" approach to FR shuffling); and Studnicka et al., U.S. Pat. No. 5,766,886.

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., Biol. Chem. 272:10678-10684 (1997) and Rosok et al., J. Biol. Chem. 271:22611-22618 (1996)).

Antibodies with ultralong CDR3 sequences may also include non-antibody sequences, such as cytokines, therapeutic polypeptides or growth factors, into the CDR3 region. The resultant antibody can be effective in treating or preventing a disease or condition. For example, an antibody comprising an ultralong CDR3 inhibits tumor metastasis. In some embodiments, the cytokine, therapeutic polypeptide or growth factor may be shown to have an antiproliferative effect on at least one cell population. Alternatively, or additionally, the resultant antibody modulates the expression or activity of a target (e.g., protein target, transmembrane protein target). For example, an antibody comprising an ultralong CDR3 inhibits or blocks an ion channel. The non-antibody sequence may be a hormone, lymphokine, interleukin, chemokine, cytokine, peptide toxin, growth factor, and combinations thereof. The growth factor may be GCSF. The GCSF may be a bovine GCSF. The GCSF may be a human GCSF. The growth factor may be GMCSF. The GMCSF may be a bovine GMCSF. The GMCSF may be human GMCSF. The growth factor may be GDF11. The growth factor may be FGF21. The cytokine may be an interferon, interleukin or stromal cell-derived factor 1 (SDF-1). The interferon may be interferon-beta. The interferon may be interferon-alpha. The interferon may be λ-interferon. The interleukin may be interleukin 8 (IL-8). The interleukin may be interleukin 10 (IL-10). The interleukin may be interleukin 11 (IL-11). The interleukin may be interleukin 21 (IL-21). The hormone may be exendin-4. The hormone may be GLP-1. The hormone may be relaxin. The relaxin may be a human relaxin. The hormone may be oxyntomodulin. The hormone may be glucagon-like peptide 1 (GLP-1). The hormone may be exendin-4. The hormone may be leptin. The leptin may be a human leptin. The hormone may be betatrophin. The hormone may be bovine growth hormone (bGH). The hormone may be human growth hormone (hGH). The hormone may be parathyroid hormone. The hormone may be erythropoietin. The hormone may be somatostatin. The hormone may be exenatide. The toxin may be Moka1. The toxin may be VM-24. The toxin may be Mamba1. The toxin may be Amgen1. The toxin may be 550 peptide. The toxin may be protoxin2. The toxin may be ziconotide. The toxin may be chlorotoxin. The protein may be angiopoeitin-like 3 (ANGPTL3). The non-antibody region may comprise elafin or a fragment thereof. The non-antibody region may comprise BCCX2 or a fragment thereof.

The antibody fusions disclosed herein may comprise a non-antibody sequence based on or derived from one or more sequences disclosed in Table 13. The non-antibody sequence may be based on or derived from one or more sequences selected from SEQ ID NOs: 114-132. The non-antibody sequence may be based on or derived from a sequence that is at least about 50% homologous to a sequence selected from a group consisting of SEQ ID NOs: 114-132. The non-antibody sequence may be based on or derived from a sequence that is at least about 60% homologous to a sequence selected from a group consisting of SEQ ID NOs: 114-132. The non-antibody sequence may be based on or derived from a sequence that is at least about 70% homologous to a sequence selected from a group consisting of SEQ ID NOs: 114-132. The non-antibody sequence may be based on or derived from a sequence that is at least about 80% homologous to a sequence selected from a group consisting of SEQ ID NOs: 114-132. The non-antibody sequence may be based on or derived from a sequence that is at least about 90% homologous to a sequence selected from a group consisting of SEQ ID NOs: 114-132. The non-antibody sequence may be based on or derived from a sequence that is at least about 95% homologous to a sequence selected from a group consisting of SEQ ID NOs: 114-132.

The non-antibody sequence may be based on or derived from a sequence that comprises 10 or more nucleotides selected from a sequence selected from a group consisting of SEQ ID NOs: 114-132. The non-antibody sequence may be based on or derived from a sequence that comprises 20 or more nucleotides selected from a sequence selected from a group consisting of SEQ ID NOs: 114-132. The non-antibody sequence may be based on or derived from a sequence that comprises 50 or more nucleotides selected from a sequence selected from a group consisting of SEQ ID NOs: 114-132. The non-antibody sequence may be based on or derived from a sequence that comprises 70 or more nucleotides selected from a sequence selected from a group consisting of SEQ ID NOs: 114-132. The non-antibody sequence may be based on or derived from a sequence that comprises 100 or more nucleotides selected from a sequence selected from a group consisting of SEQ ID NOs: 114-132. The nucleotides may be consecutive. Alternatively, the nucleotides are non-consecutive.

The antibody fusions disclosed herein may comprise a non-antibody sequence based on or derived from one or more sequences disclosed in Table 14. The non-antibody sequence may be based on or derived from one or more sequences selected from SEQ ID NOs: 133-151. The non-antibody sequence may be based on or derived from a sequence that is at least about 50% homologous to a sequence selected from a group consisting of SEQ ID NOs: 133-151. The non-antibody sequence may be based on or derived from a sequence that is at least about 60% homologous to a sequence selected from a group consisting of SEQ ID NOs: 133-151. The non-antibody sequence may be based on or derived from a sequence that is at least about 70% homologous to a sequence selected from a group consisting of SEQ ID NOs: 133-151. The non-antibody sequence may be based on or derived from a sequence that is at least about 80% homologous to a sequence selected from a group consisting of SEQ ID NOs: 133-151. The non-antibody sequence may be based on or derived from a sequence that is at least about 90% homologous to a sequence selected from a group consisting of SEQ ID NOs: 133-151. The non-antibody sequence may be based on or derived from a sequence that is at least about 95% homologous to a sequence selected from a group consisting of SEQ ID NOs: 133-151.

The non-antibody sequence may be based on or derived from a sequence that comprises 10 or more amino acids selected from a sequence selected from a group consisting of SEQ ID NOs: 133-151. The non-antibody sequence may be based on or derived from a sequence that comprises 20 or more amino acids selected from a sequence selected from a group consisting of SEQ ID NOs: 133-151. The non-antibody sequence may be based on or derived from a sequence that comprises 50 or more amino acids selected from a sequence selected from a group consisting of SEQ ID NOs: 133-151. The non-antibody sequence may be based on or derived from a sequence that comprises 70 or more amino acids selected from a sequence selected from a group consisting of SEQ ID NOs: 133-151. The non-antibody sequence may be based on or derived from a sequence that comprises 100 or more amino acids selected from a sequence selected from a group consisting of SEQ ID NOs: 133-151. The amino acids may be consecutive. Alternatively, the amino acids are non-consecutive.

The antibodies disclosed herein may comprise one or more sequences based on or derived from a mammalian, avian, reptilian, amphibian, fish, insect, bug, or arachnid sequence. Mammals include, but are not limited to, cows, bison, buffalo, humans, mice, dogs, cats, sheep, goats, or rabbits. Avians include, but are not limited to, chicken, geese, doves, eagles, sparrows, and pigeons. Reptiles include, but are not limited to, lizards, gators, snakes, and turtles. Amphibians include, but are not limited to, frogs, salamanders, toads, and newts. Fish include, but are not limited to, tuna, salmon, whales, and sharks. Insects, bugs, and arachnids include, but are not limited to, flies, mosquitoes, spiders, and scorpions. The non-antibody sequence may be based on or derived from a bovine or human sequence. Alternatively, the non-antibody sequence is based on or derived from a lizard or scorpion sequence. The lizard may be a gila monster.

In some embodiments, the non-antibody sequence is linked to an end of an ultralong CDR3 sequence. For example, the non-antibody sequence can be linked to the 5' end or 3' end of the ultralong CDR3 nucleotide sequence. In another example, the non-antibody sequence can be linked to the N-terminus or C-terminus of the ultralong CDR3 peptide sequence.

In another embodiment, the non-antibody sequence is inserted within an ultralong CDR3 sequence. For example, the non-antibody sequence is inserted between the stalk domain of an ultralong CDR3 sequence. The non-antibody sequence can be inserted within the stalk domain of an ultralong CDR3 sequence. In another example, the non-antibody sequence is inserted between the stalk domain and the knob domain of an ultralong CDR3 sequence. Alternatively, the non-antibody sequence is inserted within the knob domain of an ultralong CDR3 sequence.

Insertion of the non-antibody sequence into the antibody region may comprise replacing of at least a portion of an antibody or fragment thereof from which the antibody region comprises. The non-antibody region may replace at least a portion of a heavy chain. The non-antibody region may replace at least a portion of a light chain. The non-antibody region may replace at least a portion of a variable domain. The non-antibody region may replace at least a portion of a constant domain. The non-antibody region may replace at least a portion of a complementarity determining region (CDR). The non-antibody region may replace at least a portion of a CDR1. The non-antibody region may replace at least a portion of a CDR2. The non-antibody region may replace at least a portion of a CDR3. The CDR may be an ultralong CDR3.

The non-antibody sequence may replace at least a portion of an ultralong CDR3 sequence. The non-antibody sequence can replace about 1 or more, 2 or more, 3 or more, 4 or more, 5 or more, 10 or more, 15 or more, 20 or more, 25 or more, 30 or more, 35 or more, 40 or more, 45 or more, 50 or more, 55 or more amino acids of the ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the ultralong CDR3 peptide sequence. The non-antibody sequence can replace at least a portion of a knob domain of an ultralong CDR3. The non-antibody sequence can replace about 5 or more, 10 or more, 15 or more, 20 or more, 25 or more, 30 or more, 35 or more, 40 or more, 45 or more amino acids of the knob domain of an ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the knob domain of the ultralong CDR3 peptide sequence. The non-antibody sequence can replace at least a portion of a stalk domain of an ultralong CDR3. The non-antibody sequence can replace about 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more amino acids of the stalk domain of an ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the stalk domain of the ultralong CDR3 peptide sequence. The amino acids may be consecutive amino acids. Alternatively, the amino acids are non-consecutive amino acids. The ultralong CDR3 may comprise one or more conserved motifs. The conserved motifs may be stalk domain conserved motifs as disclosed herein. Alternatively, the conserved motifs may be knob domain conserved motifs as disclosed herein.

In some embodiments, the non-antibody sequence replaces at least a portion of an ultralong CDR3 sequence. The non-antibody sequence can replace about 5 or more, 10 or more, 15 or more, 20 or more, 25 or more, 30 or more, 40 or more, 50 or more, 55 or more, 60 or more, 70 or more, 80 or more, 90 or more, 100 or more, 110 or more, 120 or more, 130 or more, 140 or more, 150 or more, 160 or more, 170 or more nucleotides of the ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the ultralong CDR3 nucleotide sequence. The non-antibody sequence can replace at least a portion of a knob domain of an ultralong CDR3. The non-antibody sequence can replace about 5 or more, 10 or more, 15 or more, 20 or more, 25 or more, 30 or more, 40 or more, 50 or more, 55 or more, 60 or more, 70 or more, 80 or more, 90 or more, 100 or more, 110 or more, 120 or more, 130 or more, 140 or more nucleotides of the knob domain of an ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the knob domain of the ultralong CDR3 nucleotide sequence. The non-antibody sequence can replace at least a portion of a stalk domain of an ultralong CDR3. The non-antibody sequence can replace about 5 or more, 10 or more, 15 or more, 20 or more, 25 or more, 30 or more, 35 or more, 40 or more, 45 or more, 50 or more, 55 or more, 60 or more, 65 or more, 70 or more nucleotides of the stalk domain of an ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the stalk domain of the ultralong CDR3 nucleotide sequence. The nucleotides may be consecutive nucleotides. Alternatively, the nucleotides are non-consecutive nucleotides. The ultralong CDR3 may comprise one or more conserved motifs. The conserved motifs may be stalk domain conserved motifs as disclosed herein. Alternatively, the conserved motifs may be knob domain conserved motifs as disclosed herein.

An antibody comprising an ultralong CDR3 sequence and a non-antibody sequence may further comprise one or more cleavage sites between the ultralong CDR3 sequence and the non-antibody sequence. The one or more cleavage sites may be in front of the N-terminus of the non-antibody peptide sequence. For example, a cleavage site is inserted at the N-terminus of the non-antibody peptide sequence and at the C-terminus of the ultralong CDR3 peptide sequence. Alternatively, the one or more cleave sites are behind the C-terminus of the non-antibody peptide sequence. For example the cleavage site is inserted at the C-terminus of the non-antibody peptide sequence and at the N-terminus of the ultralong CDR3 peptide sequence. The one or more cleavage sites may flank both the N-terminus and the C-terminus of the non-antibody peptide sequence. The one or more cleavage sites may be upstream of the non-antibody nucleotide sequence. For example, the one or more cleavage sites may be at the 5' end of the non-antibody nucleotide sequence and at the 3' end of the ultralong CDR3 nucleotide sequence. The one or more cleavage sites may be downstream of the non-antibody nucleotide sequence. For example, the one or more cleavage sites may be at the 3' end of the non-antibody nucleotide sequence and at the 5' end of the ultralong CDR3 nucleotide sequence. The one or more cleavage sites may flank both the 5' end and the 3' end of the non-antibody nucleotide sequence. The one or more cleavage sites may directly flank the non-antibody sequence. For example, there are zero nucleotides or amino acids between the cleavage site sequence and the non-antibody sequence. Alternatively, the one or more cleavage sites may indirectly flank the non-antibody sequence. For example, there are one or more nucleotides between the cleavage site nucleotide sequence and the non-antibody nucleotide sequence. There may be 2 or more, 3 or more, 4 or more, 5 or more, 6 or more, 7 or more, 8 or more, 9 or more, 10 or more, 12 or more, 15 or more, 20 or more nucleotides between the cleavage site nucleotide sequence and the non-antibody nucleotide sequence. In another example, there are one or more amino acids between the cleavage site peptide sequence and the non-antibody peptide sequence. There may be 2 or more, 3 or more, 4 or more, 5 or more, 6 or more, 7 or more, 8 or more, 9 or more, 10 or more, 12 or more, 15 or more, 20 or more amino acids between the cleavage site peptide sequence and the non-antibody peptide sequence. The cleavage site may be adjacent to the sequence based on or derived from the ultralong CDR3 sequence, linker sequence, non-antibody sequence, non-bovine sequence, or a combination thereof. The cleavage site may be between the sequence based on or derived from the ultralong CDR3 sequence and the linker sequence. The cleavage site may be between the sequence based on or derived from the ultralong CDR3 sequence and the non-antibody sequence. The cleavage site may be between the linker sequence and the non-antibody sequence. The cleavage site may be for a protease. The protease may be a serine protease, threonine protease, cysteine protease, aspartate protease, or metalloprotease. The protease may include, but is not limited to, Factor Xa protease, chymotrypsin-like protease, trypsin-like protease, elastase-like protease, subtilisin-like protease, actinidain, bromelain, calpains, caspases, cathepsins, Mir1-CP, papain, HIV-1 protease, chymosin, renin, cathepsin D, pepsin, plasmepsin, nepenthesin, metalloexopeptidases, and metalloendopeptidases. The cleavage site may be a cleavage site for Factor Xa or thrombin. For example, the cleavage site may comprise the amino acid sequence of IEGR (SEQ ID NO: 153). Alternatively, the cleavage site is for a nuclease. The antibody comprising the ultralong CDR3 sequence and non-antibody sequence may be cleaved by one or more proteases. Cleavage of the antibody by the one or more protease can result in release of one or more ends of the non-antibody peptide from the ultralong CDR3 region of the antibody. For example, cleavage of the antibody results in release of the N-terminus of the non-antibody peptide from the ultralong CDR3 region. Alternatively, cleavage of the antibody results in release of the C-terminus of the non-antibody peptide from the ultralong CDR3 region.

The non-antibody sequence may be linked to the ultralong CDR3 sequence via one or more linkers. The non-antibody sequence may be inserted with an ultralong CDR3 sequence. In some instances, two or more linkers are used to link the non-antibody sequence to the ultralong CDR3 sequence. The two or more linkers may comprise the same sequence. Alternatively, the two or more linkers comprise different sequences. The one or more linker sequences may be the same length. The one or more linker sequences may be different lengths. The one or more linker sequences may be 3 or more, 4 or more, 5 or more, 6 or more, 7 or more, 8 or more, 9 or more or 10 or more amino acids in length. The one or more linker sequences may comprise 1 or more, 2 or more, 3 or more, 4 or more, 5 or more, 6 or more, 7 or more, 8 or more, 9 or more, or 10 or more glycine residues. The one or more linker sequences may comprise 2 or more, 3 or more, 4 or more, or 5 or more consecutive glycine residues. The one or more linker sequences may comprise 1 or more serine residues. The one or more linker sequences may comprise 1 or more, 2 or more, 3 or more, 4 or more, or 5 or more polar amino acid residues. The polar amino acid residues may be selected from serine, threonine, asparagine, or glutamine. The polar amino acid residues may comprise uncharged side chains. The linkers may be attached to the N-terminal, C-terminal, or both N-and C-termini of the non-antibody peptide sequence. The linkers may be attached to the 5'-end, 3'-end, or both the 5'- and 3' ends of the non-antibody nucleotide sequence. In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Alternatively, the linker comprises an amino acid sequence of (GGGGS)$_n$ (SEQ ID NO: 152), wherein n=1 to 5. The linker may comprise an amino acid sequence of GGGSGGGGS (SEQ ID NO: 15) or GGGGSGGGS (SEQ ID NO: 16). Amino acid residues which comprise an amino acid linker component include those occurring naturally, as well as minor amino acids and non-naturally occurring amino acids including analogs, such as citrulline. Amino acid linker components can be designed and optimized in their selectivity for enzymatic cleavage by a particular enzymes, for example, a tumor-associated protease, cathepsin B, C and D, or a plasmin protease.

The ultralong CDR3 may be based on or derived from a single ultralong CDR3 sequence. Alternatively, the ultralong CDR3 is based on or derived from two or more ultralong CDR3 sequences. The two or more ultralong CDR3 sequences may be from the same animal. Alternatively, the two or more ultralong CDR3 sequences are from two or more different animals.

The ultralong CDR3 may comprise at least a portion of a stalk domain of an ultralong CDR3. The antibodies disclosed herein may comprise 1 or more, 2 or more, 3 or more, 4 or more, 5 or more, 6 or more 7 or more, 8 or more, 9 or more, or 10 or more amino acids derived from or based on the stalk domain of the ultralong CDR3. The antibodies disclosed herein may comprise 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, or 2 or fewer amino acids derived from or based the stalk domain of the ultralong CDR3. The amino acids may be consecutive amino acids. Alternatively, the amino acids are non-consecutive amino acids. The antibodies disclosed herein may comprise a sequence that is 50% or more, 60% or more, 70% or more, 80% or more, 85% or more, 90% or more, 95% or more, 97% or more, 99% or more, or 100% homologous the sequence of the stalk domain of the ultralong CDR3. The ultralong CDR3 may comprise one or more conserved motifs derived from or based on a stalk domain of the ultralong CDR3. The antibodies disclosed herein may comprise 1 or more, 2 or more, 3 or more, 4 or more, or 5 or more conserved motifs derived from or based on the stalk domain of the ultralong CDR3. The one or more conserved motifs derived from or based on the stalk domain of the ultralong CDR3 may comprise a sequence selected from any one of SEQ ID NOS: 18-47. The antibodies disclosed herein may comprise a sequence that is 50% or more, 60% or more, 70% or more, 80% or more, 85% or more, 90% or more, 95% or more, 97% or more, 99% or more, or 100% homologous to a sequence selected from any one of SEQ ID NOS: 18-24 and 34-37. The antibodies disclosed herein may comprise a sequence that is 50% or more, 60% or more, 70% or more, 80% or more, 85% or more, 90% or more, 95% or more, 97% or more, 99% or more, or 100% homologous to a sequence selected from any one of SEQ ID NOS: 22-24.

The one or more conserved motifs derived from or based on the stalk domain of the ultralong CDR3 may comprise a CT(T/S)VHQ motif (SEQ ID NO: 154). Alternatively, the one or more conserved motifs derived from or based on the stalk domain of the ultralong CDR3 comprise a CT(T/S)VHQ$X_n$ motif (SEQ ID NO: 155). N may be between 1 to 8, between 1 to 7, between 1 to 6, between 1 to 5, between 1 to 4, or between 1 to 3. The one or more conserved motifs derived from or based on the stalk domain of the ultralong CDR3 may comprise a CX$^1$ X$^2$ X$^3$ X$^4$Q motif (SEQ ID NO: 156). X$^1$ may be a T, S, A, or G residue. X$^2$ may be a T, S, A, P, or I residue. X$^3$ may be a V or K residue. X$^4$ may be an H, K, or Y residue. The one or more conserved motifs derived from or based on the stalk domain of the ultralong CDR3 may comprise an X$^1$ X$^2$VHQ motif (SEQ ID NO: 157). X$^1$ may be a T, S, A, or G residue. X$^2$ may be a T, S, A, P or I residue. The one or more conserved motifs derived from or based on the stalk domain of the ultralong CDR3 may comprise a CX$^1$ X$^2$VHQ motif (SEQ ID NO: 158). X$^1$ may be a T, S, A, or G residue. X$^2$ may be a T, S, A, P or I residue. The one or more conserved motifs derived from or based on the stalk domain of the ultralong CDR3 may comprise an X$^1$ X$^2$VX$^3$Q motif (SEQ ID NO: 159). X$^1$ may be a T, S, A, or G residue. X$^2$ may be a T, S, A, P or I residue. X$^3$ may be an H, Y or K residue. The one or more conserved motifs derived from or based on the stalk domain of the ultralong CDR3 may comprise a CX$^1$ X$^2$VX$^3$Q motif (SEQ ID NO: 160). X$^1$ may be a T, S, A, or G residue. X$^2$ may be a T, S, A, P or I residue. X$^3$ may be an H, Y or K residue. The one or more conserved motifs derived from or based on the stalk domain of the ultralong CDR3 may comprise an X$^1$ X$^2$KKQ motif (SEQ ID NO: 161). X$^1$ may be a T, S, A, or G residue. X$^2$ may be a T, S, A, P or I residue. The one or more conserved motifs derived from or based on the stalk domain of the ultralong CDR3 may comprise a CX$^1$ X$^2$KKQ motif (SEQ ID NO: 162). X$^1$ may be a T, S, A, or G residue. X$^2$ may be a T, S, A, P or I residue.

The one or more conserved motifs derived from or based on the stalk domain of the ultralong CDR3 may comprise an YX$^1$YX$^2$ motif (SEQ ID NO: 163). X$^1$ may be a T, S, N, or I residue. X$^2$ may be an E or D residue. The one or more conserved motifs derived from or based on the stalk domain of the ultralong CDR3 may comprise an YX$^1$YX$^2$Y motif (SEQ ID NO: 164). X$^1$ may be an L, S, T, or R residue. X$^2$ may be a T, S, N or I residue. The one or more conserved motifs derived from or based on the stalk domain of the ultralong CDR3 may comprise an YX$^1$YX$^2$YX$^3$ motif (SEQ ID NO: 165). X$^1$ may be an L, S, T, or R residue. X$^2$ may be a T, S, N or I residue. X$^3$ may be an E or D residue. The one or more conserved motifs derived from or based on the stalk domain of the ultralong CDR3 may comprise an YX$^1$YX$^2$YX$^3$X$^4$ motif (SEQ ID NO: 166). X$^1$ may be an L, S, T, or R residue. X$^2$ may be a T, S, N or I residue. X$^3$ may be an E or D residue. X$^4$ may be an H, W, N, F, I or Y residue. The one or more conserved motifs derived from or based on the stalk domain of the ultralong CDR3 may comprise an Y(E/D)X motif (SEQ ID NO: 167). X may be an H, W, N, F, I or Y residue. The one or more conserved motifs derived from or based on the stalk domain of the ultralong CDR3 may comprise an XY(E/D) motif (SEQ ID NO: 168). X may be a T, S, N or I residue. The one or more conserved motifs derived from or based on the stalk domain of the ultralong CDR3 may comprise an Y(E/D)X$^1$X$_n$W motif (SEQ ID NO: 169). X$^1$ may be an H, W, N, F, I or Y residue. N is between 1 to 4, between 1 to 3 or between 1 to 2. The one or more conserved motifs derived from or based on the stalk domain of the ultralong CDR3 may comprise an Y(E/D)X$^1$X$^2$ X$^3$X$^4$X$^5$W motif (SEQ ID NO: 170). X$^1$ may be an H, W, N, F, I or Y residue. X$^2$ may be an Y, H, G, or N residue. X3 may be a V, I, or A residue. X$^4$ may be a D, N, T, or E residue. X$^5$ may be an A, V, S, or T residue.

The antibodies disclosed herein may comprise a first conserved motif derived from or based on the stalk domain of the ultralong CDR3 selected from any of SEQ ID NOS: 18-33 and a second conserved motif derived from or based on the stalk domain of the ultralong CDR3 selected from any of SEQ ID NOS: 34-47. The antibodies disclosed herein may comprise a first conserved motif derived from or based on the stalk domain of the ultralong CDR3 selected from a group comprising CT(T/S)VHQX$_n$ (SEQ ID NO: 171), CX$^1$X$^2$ X$^3$X$^4$Q (SEQ ID NO: 27), X$^1$X$^2$VHQ (SEQ ID NO: 28), CX$^1$X$^2$ VHQ (SEQ ID NO: 29), X$^1$X$^2$VX$^3$Q (SEQ ID NO: 30), CX$^1$X$^2$VX$^3$Q (SEQ ID NO: 31), X$^1$X$^2$KKQ (SEQ ID NO: 32), and CX$^1$X$^2$KKQ (SEQ ID NO: 33) and a second conserved motif derived from or based on the stalk domain of the ultralong CDR3 selected from the group comprising YX$^1$YX$^2$ (SEQ ID NO: 38), YX$^1$YX$^2$Y (SEQ ID NO: 39), YX$^1$YX$^2$YX$^3$ (SEQ ID NO: 40), YX$^1$YX$^2$YX$^3$X$^4$ (SEQ ID NO: 41), Y(E/D)X (SEQ ID NO: 172), XY(E/D) (SEQ ID NO: 173), Y(E/D)X$^1$X$_n$W (SEQ ID NO: 174), and Y(E/D)X$^1$X$^2$ X$^3$X$^4$X$^5$W (SEQ ID NO: 175).

The ultralong CDR3 may comprise at least a portion of a knob domain of an ultralong CDR3. The antibodies disclosed herein may comprise 1 or more, 2 or more, 3 or more, 4 or more, 5 or more, 6 or more 7 or more, 8 or more, 9 or more, or 10 or more amino acids derived from or based on the knob domain of the ultralong CDR3. The antibodies disclosed herein may comprise 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, or 2 or fewer amino acids derived from or based the knob domain of the ultralong CDR3. The amino acids may be consecutive amino acids. Alternatively, the amino acids are non-consecutive amino acids. The antibodies disclosed herein may comprise a sequence that is 50% or more, 60% or more, 70% or more, 80% or more, 85% or more, 90% or more, 95% or more, 97% or more, 99% or more, or 100% homologous the sequence of the knob domain of the ultralong CDR3. The ultralong CDR3 may comprise one or more conserved motifs derived from or based on a knob domain of the ultralong CDR3. The antibodies disclosed herein may comprise 1 or more, 2 or more, 3 or more, 4 or more, or 5 or more conserved motifs derived from or based on the knob domain of the ultralong CDR3. The one or more conserved motifs derived from or based on the knob domain may comprise a cysteine motif as disclosed herein. Alternatively, or additionally, one or more conserved motifs derived from or based on the knob domain comprises a C(P/S)DG motif (SEQ ID NO: 176).

The antibodies disclosed herein may comprise a sequence based on or derived from a mammal. The mammal may be a bovine. Alternatively, the mammal is a non-bovine mammal, such as a human. The antibody sequences may be 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The amino acids may be consecutive amino acids. Alternatively, the amino acids are non-consecutive amino acids.

The antibody sequences may comprise a bovine antibody sequence comprising 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The bovine antibody may be a BLVH12, BLV5B8, BLVCV1, BLV5D3, BLV8C11, BF1H1, or F18 antibody. The antibody sequences may comprise a human antibody sequence comprising 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The amino acids may be consecutive amino acids. Alternatively, the amino acids are non-consecutive amino acids.

The antibody sequence based on or derived from at least a portion of the ultralong CDR3 can be 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, or 5 or fewer amino acids in length. The antibody sequence based on or derived from at least a portion of the ultralong CDR3 may be 3 or more, 4 or more, 5 or more, 6 or more, 7 or more, 8 or more, 9 or more, 10 or more, 11 or more, 12 or more, 13 or more, 14 or more, or 15 or more amino acids in length. The amino acids may be consecutive amino acids. Alternatively, the amino acids are non-consecutive amino acids.

The antibody sequence based on or derived from at least a portion of the ultralong CDR3 can contain 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 50 or more, 60 or more, 70 or more, 80 or more, 90 or more, or 100 or more nucleic acid modifications or alterations in the nucleotide sequence of the ultralong CDR3 from which it is based on or derived from. The modifications and/or alterations may comprise substitutions, deletions, and/or insertions. Substitutions may comprise replacing one nucleic acid with another nucleic acid. The nucleic acid may be a natural nucleic acid or a non-natural nucleic acid.

The antibody sequence based on or derived from at least a portion of the ultralong CDR3 can contain 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 50 or more, or 60 or more amino acid modifications or alterations in the peptide sequence of the ultralong CDR3 from which it is based on or derived from. The modifications and/or alterations may comprise substitutions, deletions, and/or insertions. Substitutions may comprise replacing one amino acid with another amino acid. The amino acids to be substituted may contain one or more similar features to the amino acid by which it is replaced. The features may include, but are not limited to, size, polarity, hydrophobicity, acidity, side chain, and bond formations. The amino acid may be a natural amino acid or a non-natural amino acid.

Bispecific Antibodies

Bispecific antibodies may be monoclonal, preferably human or humanized, antibodies that have binding specificities for at least two different antigens. For example, one of the binding specificities may be for a first antigen and the other may be for any other antigen. Exemplary bispecific antibodies may bind to two different epitopes of the same protein. Bispecific antibodies may also be used to localize cytotoxic agents to cells which express a particular protein. These antibodies possess a binding arm specific for the particular protein and an arm which binds the cytotoxic agent (e.g., saporin, anti-interferon-α, vinca alkaloid, ricin A chain, methotrexate or radioactive isotope hapten). Bispecific antibodies may be prepared as full length antibodies or antibody fragments (e.g., $F(ab')_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, and in Traunecker et al., EMBO J., 10: 3655 (1991).

Multivalent Antibodies

A multivalent antibody may be internalized (and/or catabolized) faster than a bivalent antibody by a cell expressing an antigen to which the antibodies bind. The antibodies of the present disclosure may be multivalent antibodies (which are other than of the IgM class) with three or more antigen binding sites (e.g., tetravalent antibodies), which may be produced by recombinant expression of nucleic acid encoding the polypeptide chains of the antibody. The multivalent antibody may comprise a dimerization domain and three or more antigen binding sites. A preferred dimerization domain may comprise (or consist of) an Fc region or a hinge region. In this scenario, the antibody will comprise an Fc region and three or more antigen binding sites amino-terminal to the Fe region. A preferred multivalent antibody may comprise (or consist of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. A multivalent antibody may preferably further comprises at least two (and preferably four) light chain variable domain polypeptides. A multivalent antibody may, for instance, comprise from about two to about eight light chain variable domain polypeptides. The light chain variable domain polypeptides may comprise a light chain variable domain and, optionally, further comprise a CL domain.

Antibody Variants

In some embodiments, amino acid sequence modification(s) of the antibodies comprising an ultralong CDR3 as described herein are contemplated. For example, it may be desirable to improve the binding affinity and/or other biological properties of the antibody. Amino acid sequence variants including, for example, conservatively modified variants, of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

Antibody Derivatives

The antibodies comprising an ultralong CDR3 as disclosed herein may be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Vectors, Host Cells and Recombinant Methods

For recombinant production of an antibody or fragment thereof as disclosed herein, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). In an exemplary embodiment, nucleic acid encoding an antibody comprising an ultralong CDR3, a variable region comprising an ultralong CDR3, or an ultralong CDR3, is isolated and inserted into a replicable vector for further cloning (amplification of the DNA) or for expression. Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a partially human ultralong CDR3 antibody chain under the direction of the polyhedrin promoter or other strong baculovirus promoters.

Engineered Hybridomas

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed. Hybridomas. Including bovine hybridomas, may be a source of bovine antibody gene sequences, including ultralong CDR3 sequences.

Transgenic Mammals

A nucleic acid sequence encoding a germline antibody polypeptide of the present disclosure can be introduced into a non-human mammal to generate a transgenic animal that expresses the germline antibody polypeptide. Unlike the transgenic animal models more commonly seen, the transgene expressed by the transgenic mammals of the present disclosure need not replace at least one allele of the endogenous coding sequence responsible for the variable regions of antibody chains following somatic recombination. Due to allelic exclusion, the presence of an exogenous, post-somatic rearrangement version of the germline V region DNA will inhibit the endogenous alleles of pre-somatic rearrangement V minigenes from undergoing somatic rearrangement and contributing to the makeup of antibody chains this mammal may produce. Thus, when exposed to a particular antigen, the mammal will generate heterologous antibodies comprising one endogenously rearranged antibody chain, and one transgenic gene which was rearranged a priori. Such heterologous antibodies are invaluable in research and in treating certain conditions in live subjects. On the other hand, a method that directs the integration of the transgene to the locus of an endogenous allele will fully serve the purpose of practicing the present disclosure as well.

The general methods of generating transgenic animals have been well established and frequently practiced. For reviews and protocols for generating transgenic animals and related methods for genetic manipulations, see, e.g., Mansour et al., Nature 336:348-352 (1988); Capecchi et al., Trends Genet. 5:70-76 (1989); Capecchi, Science 244:1288-1292 (1989); Capecchi et al., Current Communications in Molecular Biology, pp 45-52, Capecchi, M. R. (ed.), Cold Spring Harbor Press, Cold Spring Harbor, N.Y. (1989); Frohman et al., Cell 56: 145-147 (1989); Brinster et al., Proc. Natl. Acad. Sci. USA 82:4438-4442 (1985); Evans et. al., Nature 292:154-156 (1981); Bradley et al., Nature 309:255-258 (1984); Gossler et al., Proc. Natl. Acad. Sci. USA 83:9065-9069 (1986); Robertson et al., Nature 322: 445-448 (1986); Jaenisch Science 240:1468-1474 (1988); and Siedel, G. E., Jr., "Critical review of embryo transfer procedures with cattle" in Fertilization and Embryonic Development in Vitro, page 323, L. Mastroianni, Jr. and J. D. Biggers, ed., Plenum Press, New York, N.Y. (1981).

An exemplary transgenic animal of the present disclosure is mouse, whereas a number of other transgenic animals can also be produced using the same general method. These animals include, but are not limited to: rabbits, sheep, cattle, and pigs (Jaenisch Science 240:1468-1474 (1988); Hammer et al., J. Animal. Sci. 63:269 (1986); Hammer et al. Nature 315:680 (1985); Wagner et al., Theriogenology 21:29 (1984)).

Pharmaceutical Compositions

Antibodies comprising an ultralong CDR3, antibody fragments, nucleic acids, or vectors disclosed herein can be formulated in compositions, especially pharmaceutical compositions. Such compositions with antibodies comprising an ultralong CDR3 comprise a therapeutically or prophylactically effective amount of antibodies comprising an ultralong CDR3, antibody fragment, nucleic acid, or vector disclosed herein in admixture with a suitable carrier, e.g., a pharmaceutically acceptable agent. Typically, antibodies comprising an ultralong CDR3, antibody fragments, nucleic acids, or vectors disclosed herein are sufficiently purified for administration before formulation in a pharmaceutical composition.

Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol)phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™. series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of antibodies comprising an ultralong CDR3, antibody fragments, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141). Exemplary hyaluronic acid containing compositions of the present disclosure comprise a hyaluronic acid ester polymer in an amount of approximately 0.1% to about 40% (w/w) of an antibody comprising an ultralong CDR3 to hyaluronic acid polymer.

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which an antibody comprising an ultralong CDR3, antibody fragment, nucleic acid, or vector disclosed herein has been absorbed or encapsulated. Where an implantation device is used, the device may be implanted into any suitable tissue or organ, and delivery of an antibody comprising an ultralong CDR3 antibody fragment, nucleic acid, or vector disclosed herein can be directly through the device via bolus, or via continuous administration, or via catheter using continuous infusion.

A pharmaceutical composition comprising an antibody comprising an ultralong CDR3, antibody fragment, nucleic acid, or vector disclosed herein may be formulated for inhalation, such as for example, as a dry powder Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 μm to 5 μm; however, larger particles may be used, for example, if each particle is fairly porous.

Certain formulations containing antibodies comprising an ultralong CDR3, antibody fragments, nucleic acids, or vectors disclosed herein may be administered orally. Formulations administered in this fashion may be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also can be employed.

Another preparation may involve an effective quantity of an antibody comprising an ultralong CDR3, antibody fragment, nucleic acid, or vector disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size.

Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

In some embodiments, antibodies comprising an ultralong CDR3 or fragments thereof are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., IgG1, IgG2, IgG3, or IgG4) that is responsible for increasing the in vivo serum half-life of the IgG molecule.

A salvage receptor binding epitope may include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also WO 97/34631 and WO 96/32478 which describe Fc variants and their interaction with the salvage receptor.

Mutation of residues within Fc receptor binding sites may result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g., replacing an IgG1 residue with a corresponding IgG2 residue at that position). For example, it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., Mol. Immunol. 30:105-8, 1993).

In some embodiments is a pharmaceutical composition comprising an antibody comprising an ultralong CDR3; and a pharmaceutically acceptable carrier. The antibody may comprise a therapeutic polypeptide, or derivative or variant thereof. The therapeutic polypeptide may be a non-antibody sequence. The therapeutic polypeptide, or derivative or variant thereof can be within the ultralong CDR3. In some instances, the therapeutic polypeptide is Moka1, Vm24, GLP-1, Exendin-4, human EPO, human FGF21, 550 peptide human GMCSF, human interferon-beta, human GCSF, bovine GCSF or derivative or variant thereof. Alternatively, the antibody is an immunoconjugate as described herein. The antibody can comprise one or more immunoglobulin domains. In some embodiments, the immunoglobulin domain is an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. In some instances, the immunoglobulin domain is from an engineered antibody or recombinant antibody. In other instances, the immunoglobulin domain is from a humanized, human engineered or fully human antibody. The mammalian antibody may be a bovine antibody. The mammalian antibody may be a human antibody. In other instances, the mammalian antibody is a murine antibody. The ultralong CDR3 can comprise at least a portion of a knob domain in the CDR3. The therapeutic polypeptide can be attached to the knob domain. Alternatively, or additionally, the ultralong CDR3 comprises at least a portion of a stalk domain in the CDR3. The therapeutic polypeptide may be attached to the stalk domain. In some instances, the antibody further comprises a linker. The linker can be within the ultralong CDR3. The linker can attach the therapeutic polypeptide to the immunoglobulin domain or fragment thereof. In other instances, the linker attaches the therapeutic polypeptide to the knob domain or stalk domain. In certain embodiments is a method of preventing or treating a disease in a subject in need thereof comprising administering this pharmaceutical composition to the subject. In some embodiments, the pharmaceutical composition comprising an immunoglobulin construct comprising a heavy chain polypeptide comprising a sequence selected from any one of SEQ ID NOs: 9-14 or 108-113 and the polypeptide sequence encoded by the DNA any one of SEQ ID NOs: 2-7 or 103-107; and a light chain polypeptide comprising a sequence selected from SEQ ID NO: 8 and a polypeptide sequence encoded by the DNA of SEQ ID NO: 1; and a pharmaceutically acceptable carrier. In certain embodiments is a method of preventing or treating a disease in a mammal in need thereof comprising administering this pharmaceutical composition to the mammal. In some embodiments, the disease is an infectious disease such as mastitis. In certain embodiments, the mammal in need is a dairy animal selected from a list comprising cow, camel, donkey, goat, horse, reindeer, sheep, water buffalo, moose and yak. In some embodiments, the mammal in need is bovine.

In some embodiments, the pharmaceutical compositions disclosed herein may be useful for providing prognostic or providing diagnostic information.

Kits/Articles of Manufacture

As an additional aspect, the present disclosure includes kits which comprise one or more compounds or compositions packaged in a manner which facilitates their use to practice methods of the present disclosure. In one embodiment, such a kit includes a compound or composition described herein (e.g., a composition comprising an antibody comprising an ultralong CDR3 alone or in combination with a second agent), packaged in a container with a label affixed to the container or a package insert that describes use of the compound or composition in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The article of manufacture may comprise (a) a first container with a composition contained therein, wherein the composition comprises an antibody comprising an ultralong CDR3 as disclosed herein; and (b) a second container with a composition contained therein, wherein the composition comprises a further therapeutic agent. The article of manufacture in this embodiment disclosed herein may further comprise a package insert indicating that the first and second compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. Preferably, the compound or composition is packaged in a unit dosage form. The kit may further include a device suitable for administering the composition according to a specific route of administration or for practicing a screening assay. Preferably, the kit contains a label that describes use of the antibody comprising an ultralong CDR3 composition.

In certain embodiments, the composition comprising the antibody is formulated in accordance with routine procedures as a pharmaceutical composition adapted for intravenous administration to mammals, such as humans, bovines, felines, canines, and murines. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the composition described herein which will be effective in the treatment, inhibition and prevention of a disease or disorder associated with aberrant expression and/or activity of a Therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

The following are examples of the methods and compositions of the disclosure. It is understood that various other embodiments may be practiced, given the general description provided above.

Pharmacological Properties

Further disclosed herein are methods of improving one or more pharmacological properties of a therapeutic peptide. The method may comprise producing an antibody disclosed herein. Examples of pharmacological properties may include, but are not limited to, half-life, stability, solubility, immunogenicity, toxicity, bioavailability, absorption, liberation, distribution, metabolization, and excretion. Liberation may refer to the process of releasing of a therapeutic peptide from the pharmaceutical formulation. Absorption may refer to the process of a substance entering the blood circulation. Distribution may refer to the dispersion or dissemination of substances throughout the fluids and tissues of the body. Metabolization (or biotransformation, or inactivation) may refer to the recognition by an organism that a foreign substance is present and the irreversible transformation of parent compounds into daughter metabolites. Excretion may refer to the removal of the substances from the body.

The half-life of a therapeutic peptide may greater than the half-life of the non-conjugated therapeutic peptide. The half-life of the therapeutic peptide may be greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. The half-life of the therapeutic peptide may be greater than 4 hours when administered to a subject. The half-life of the therapeutic peptide may be greater than 6 hours when administered to a subject.

The half-life of the therapeutic peptide may increase by at least about 2, 4, 6, 8, 10, 12, 14, 16, 18, or 20 or more hours. The half-life of the therapeutic peptide may increase by at least about 2 hours. The half-life of the therapeutic peptide may increase by at least about 4 hours. The half-life of the therapeutic peptide may increase by at least about 6 hours. The half-life of the therapeutic peptide may increase by at least about 8 hours.

The half-life of a therapeutic peptide an antibody described herein may be at least about 1.5, 2, 2.5, 3, 3.5, 4, 4.5, 5, 5.5, 6, 6.5, 7, 7.5, 8, 8.5, 9, 9.5, or 10-fold greater than the half-life of the non-conjugated therapeutic peptide. The half-life of a therapeutic peptide an antibody described herein may be at least about 15, 16, 17, 18, 19, 20, 25, 30, 35, 40, 45, or 50-fold greater than the half-life of the non-conjugated therapeutic peptide. The half-life of a therapeutic peptide an antibody described herein may be at least about 2-fold greater than the half-life of the non-conjugated therapeutic peptide. The half-life of a therapeutic peptide an antibody described herein may be at least about 5-fold greater than the half-life of the non-conjugated therapeutic peptide. The half-life of a therapeutic peptide an antibody described herein may be at least about 10-fold greater than the half-life of the non-conjugated therapeutic peptide.

The half-life of a therapeutic peptide an antibody described herein may be at least about 5%, 10%, 15%, 20%, 25%, 30%, 35%, 40%, 45%, 55%, 60%, 65%, 70%, 75%, 80%, 85%, 90%, 95%, or 97% greater than the half-life of the non-conjugated therapeutic peptide. The half-life of a therapeutic peptide an antibody described herein may be at least about 10% greater than the half-life of the non-conjugated therapeutic peptide. The half-life of a therapeutic peptide an antibody described herein may be at least about 20% greater than the half-life of the non-conjugated therapeutic peptide. The half-life of a therapeutic peptide an antibody described herein may be at least about 30% greater than the half-life of the non-conjugated therapeutic peptide. The half-life of a therapeutic peptide an antibody described herein may be at least about 40% greater than the half-life of the non-conjugated therapeutic peptide. The half-life of a therapeutic peptide an antibody described herein may be at least about 50% greater than the half-life of the non-conjugated therapeutic peptide.

The antibodies may be modified or altered to reduce immunogenicity. For example, the sequence of a partially bovine or non-bovine antibody may be modified or altered to reduce immunogenicity to humans. A non-human antibody may be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Methods of Treatment

Further disclosed herein are methods of preventing or treating a disease or condition in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is oxyntomodulin, 550 peptide, Amgen1, Mamba1, parathyroid hormone, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 can comprise at least a portion of a knob domain. The knob domain may comprise a conserved motif within the knob domain of an ultralong CDR3. For example, the knob domain may comprise a cysteine motif disclosed herein. The therapeutic polypeptide can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide can be attached to the stalk domain. In some instances, the antibody, antibody fragment or immunoglobulin construct further comprises a linker. The linker can attach the therapeutic polypeptide to the immunoglobulin domain or fragment thereof. In other instances, the linker attaches the therapeutic polypeptide to the knob domain or stalk domain. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

In some embodiments is a method of preventing or treating a disease or condition in a subject in need thereof comprising administering to the subject a composition comprising: an immunoglobulin construct comprising a heavy chain polypeptide comprising a sequence that is substantially similar to a sequence selected from SEQ ID NOs: 9-14 or 108-113; and a light chain polypeptide comprising the sequence that is substantially similar to a sequence of SEQ ID NO: 8. The heavy chain polypeptide sequence may share 50%, 60%, 70%, 80%, 85%, 90%, 95%, 97%, 99%, or more amino acid sequence identity to a heavy chain sequence provided by any one of SEQ ID NOs: 9-14 or 108-113. The light chain polypeptide sequence may share 50%, 60%, 70%, 80%, 85%, 90%, 95%, 97%, 99%, or more amino acid sequence identity to a light chain sequence provided by SEQ ID NO: 8. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

In an embodiment is provided a method of preventing or treating a disease or condition in a subject in need thereof comprising administering to the subject a composition comprising: an immunoglobulin construct comprising a heavy chain polypeptide comprising a polypeptide sequence encoded by a DNA sequence that is substantially similar to a sequence selected from SEQ ID NOs: 2-7 or 103-107; and a light chain polypeptide comprising a polypeptide sequence encoded by a DNA sequence that is substantially similar to a sequence of SEQ ID NO: 1. The heavy chain nucleotide sequence may share 50%, 60%, 70%, 80%, 85%, 90%, 95%, 97%, 99%, or more homology to a heavy chain sequence provided by any one of SEQ ID NOs: 2-7 or 103-107. The light chain nucleotide sequence may share 50%, 60%, 70%, 80%, 85%, 90%, 95%, 97%, 99%, or more homology to a light chain sequence provided by SEQ ID NO: 1. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

Disclosed herein in some embodiments is a method of preventing or treating an autoimmune disease in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is Moka1, VM-24 or beta-interferon or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The Moka1, VM-24, beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The Moka1, VM-24, beta-interferon, or a derivative or variant thereof can be attached to the stalk domain. In some instances, the antibody, antibody fragment or immunoglobulin construct further comprises a linker. The linker can attach Moka1, VM-24, beta-interferon, or a derivative or variant thereof to the immunoglobulin domain or fragment thereof. In other instances, the linker attaches Moka1, VM-24, beta-interferon, or a derivative or variant thereof to the knob domain or stalk domain. In some instances, the autoimmune disease is a T-cell mediated autoimmune disease. T-cell mediated autoimmune diseases include, but are not limited to, multiple sclerosis, type-1 diabetes, and psoriasis. In other instances, the autoimmune disease lupus, Sjogren's syndrome, scleroderma, rheumatoid arthritis, dermatomyositis, Hasmimoto's thyroiditis, Addison's disease, celiac disease, Crohn's disease, pernicious anemia, pemphigus vulgaris, vitiligo, autoimmune hemolytic anemia, idiopathic thrombocytopenic purpura, myasthenia gravis, Ord's thyroiditis, Graves' disease, Guillain-Barre syndrome, acute disseminated encephalomyelitis, opsoclonus-myoclonus syndrome, ankylosing spondylitisis, antiphospholipid antibody syndrome, aplastic anemia, autoimmune hepatitis, Goodpasture's syndrome, Reiter's syndrome, Takayasu's arteritis, temporal arteritis, Wegener's granulomatosis, alopecia universalis, Behcet's disease, chronic fatigue, dysautonomia, endometriosis, interstitial cystitis, neuromyotonia, scleroderma, and vulvodynia. Lupus can include, but is not limited to, acute cutaneous lupus erythematosus, subacute cutaneous lupus erythematosus, chronic cutaneous lupus erythematosus, discoid lupus erythematosus, childhood discoid lupus erythematosus, generalized discoid lupus erythematosus, localized discoid lupus erythematosus, chilblain lupus erythematosus (hutchinson), lupus erythematosus-lichen planus overlap syndrome, lupus erythematosus panniculitis (lupus erythematosus profundus), tumid lupus erythematosus, verrucous lupus erythematosus (hypertrophic lupus erythematosus), complement deficiency syndromes, drug-induced lupus erythematosus, neonatal lupus erythematosus, and systemic lupus erythematosus.

Further disclosed herein is a method of preventing or treating a disease or condition which would benefit from the modulation of a potassium voltage-gated channel in a subject in need thereof comprising administering a composition comprising one or more antibodies comprising an ultralong CDR3 as disclosed herein to said subject. The composition can further comprise a pharmaceutically acceptable carrier. In some instances, the potassium voltage-gated channel is a KCNA3 or $K_v1.3$ channel. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is Moka1, VM-24, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The Moka1, VM-24, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The Moka1, VM-24, or a derivative or variant thereof can be attached to the stalk domain. In some instances, the antibody, antibody fragment or immunoglobulin construct further comprises a linker. The linker can attach Moka1, VM-24, or a derivative or variant thereof to the immunoglobulin domain or fragment thereof. In other instances, the linker attaches Moka1, VM-24, beta-interferon, or a derivative or variant thereof to the knob domain or stalk domain. In some instances, the disease or condition is an autoimmune disease. The autoimmune disease can be a T-cell mediated autoimmune disease. In some instances, modulating a potassium voltage-gated channel comprises inhibiting or blocking a potassium voltage-gated channel. In some instances, the disease or condition is episodic ataxia, seizure, or neuromyotonia.

Provided herein is a method of preventing or treating a metabolic disease or condition in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, FGF21, oxyntomodulin or derivative or variant thereof. The GLP-1 may be a human GLP-1. In some instances, the FGF21 is a human FGF21. The therapeutic polypeptide may be beta-trophin. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, FGF21, oxyntomodulin or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The GLP-1, Exendin-4, FGF21, oxyntomodulin or a derivative or variant thereof can be attached to the stalk domain. In some instances, the antibody, antibody fragment or immunoglobulin construct further comprises a linker. The linker can attach GLP-1, Exendin-4, FGF21, oxyntomodulin, or a derivative or variant thereof to the immunoglobulin domain or fragment thereof. In other instances, the linker attaches GLP-1, Exendin-4, FGF21, oxyntomodulin, or a derivative or variant thereof to the knob domain or stalk domain. Metabolic diseases and/or conditions can include disorders of carbohydrate metabolism, amino acid metabolism, organic acid metabolism (organic acidurias), fatty acid oxidation and mitochondrial metabolism, porphyrin metabolism, purine or pyrimidine metabolism, steroid metabolism, mitochondrial function, peroxisomal function, urea cycle disorder, urea cycle defects or lysosomal storage disorders. In some instances, the metabolic disease or condition is diabetes. In other instances, the metabolic disease or condition is glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a central nervous system (CNS) disorder in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, or derivative or variant thereof. The GLP-1 may be a human GLP-1. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The GLP-1, Exendin-4, or a derivative or variant thereof can be attached to the stalk domain. In some instances, the antibody, antibody fragment or immunoglobulin construct further comprises a linker. The linker can attach GLP-1, Exendin-4, or a derivative or variant thereof to the immunoglobulin domain or fragment thereof. In other instances, the linker attaches GLP-1, Exendin-4, or a derivative or variant thereof to the knob domain or stalk domain. In some instances, the CNS disorder is Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a disease or condition which benefits from a GLP-1R and/or glucagon receptor (GCGR) agonist in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, oxyntomodulin, or derivative or variant thereof. The GLP-1 may be a human GLP-1. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, oxyntomodulin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The GLP-1, Exendin-4, oxyntomodulin, or a derivative or variant thereof can be attached to the stalk domain. In some instances, the antibody, antibody fragment or immunoglobulin construct further comprises a linker. The linker can attach GLP-1, Exendin-4, oxyntomodulin, or a derivative or variant thereof to the immunoglobulin domain or fragment thereof. In other instances, the linker attaches GLP-1, Exendin-4, oxyntomodulin, or a derivative or variant thereof to the knob domain or stalk domain. The disease or condition can be a metabolic disease or disorder. In some instances, the disease or condition is diabetes. In other instances, the disease or condition is obesity. Additional diseases and/or conditions which benefit from a GLP-1R and/or GCGR agonist include, but are not limited to, dyslipidemia, cardiovascular and fatty liver diseases.

Provided herein is a method of preventing or treating a blood disorder in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is erythropoietin, GMCSF, or derivative or variant thereof. The erythropoietin may be a human erythropoietin. The GMCSF may be a human GMCSF. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The erythropoietin, GMCSF, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The erythropoietin, GMCSF, or a derivative or variant thereof can be attached to the stalk domain. In some instances, the antibody, antibody fragment or immunoglobulin construct further comprises a linker. The linker can attach erythropoietin, GMCSF, or a derivative or variant thereof to the immunoglobulin domain or fragment thereof. In other instances, the linker attaches erythropoietin, GMCSF, or a derivative or variant thereof to the knob domain or stalk domain. In some instances, the blood disorder is anemia. Examples of anemia include, but are not limited to, herditary xerocytosis, congenital dyserythropoietic anemia, Rh null disease, infectious mononucleosis related anemia, drugs-related anemia, aplastic anemia, microcytic anemia, macrocytic anemia, normocytic anemia, hemolytic anemia, poikilocytic anemia, spherocytic anemia, drepanocytic anemia, normochromic anemia, hyperchromic anemia, hypochromic anemia, macrocytic-normochromic anemia, microcytic-hypochromic anemia, normocytic-normochromic anemia, iron-deficiency anemia, pernicious anemia, folate-deficiency anemia, thalassemia, sideroblastic anemia, posthemorrhagic anemia, sickle cell anemia, chronic anemia, achrestic anemia, autoimmune haemolytic anemia, Cooley's anemia, drug-induced immune haemolytic anemia, erythroblastic anemia, hypoplastic anemia, Diamond-Blackfan anemia, Pearson's anemia, transient anemia, Fanconi's anemia, Lederer's anemia, myelpathic anemia, nutritional anemia, spur-cell anemia, Von Jaksh's anemia, sideroblatic anemia, sideropenic anemia, alpha thalassemia, beta thalassemia, hemoglobin h disease, acute acquired hemolytic anemia, warm autoimmune hemolytic anemia, cold autoimmune hemolytic anemia, primary cold autoimmune hemolytic anemia, secondary cold autoimmune hemolytic anemia, secondary autoimmune hemolytic anemia, primary autoimmune hemolytic anemia, x-linked sideroblastic anemia, pyridoxine-responsive anemia, nutritional sideroblastic anemia, pyridoxine deficiency-induced sideroblastic anemia, copper deficiency-induced sideroblastic anemia, cycloserine-induced sideroblastic anemia, chloramphenicol-induced sideroblastic anemia, ethanol-induced sideroblastic anemia, isoniazid-induced sideroblastic anemia, drug-induced sideroblastic anemia, toxin-induced sideroblastic anemia, microcytic hyperchromic anemia, macrocytic hyperchromic anemia, megalocytic-normochromic anemia, drug-induced immune hemolytic anemia, non-hereditary spherocytic anemia, inherited spherocytic anemia, and congenital spherocytic anemia. In other instances, the blood disorder is malaria. Alternatively, the blood disorder is lymphoma, leukemia, multiple myeloma, or myelodysplastic syndrome. In some instances, the blood disorder is neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefit is from stimulating or increasing white blood cell production in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GMCSF, or derivative or variant thereof. The GMCSF may be a human GMCSF. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GMCSF, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The GMCSF, or a derivative or variant thereof can be attached to the stalk domain. In some instances, the antibody, antibody fragment or immunoglobulin construct further comprises a linker. The linker can attach GMCSF, or a derivative or variant thereof to the immunoglobulin domain or fragment thereof. In other instances, the linker attaches GMCSF, or a derivative or variant thereof to the knob domain or stalk domain. In some instances, the disease or disorder is neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefit is from stimulating or increasing red blood cell production in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is erythropoietin, or derivative or variant thereof. The erythropoietin may be a human erythropoietin. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The erythropoietin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The erythropoietin, or a derivative or variant thereof can be attached to the stalk domain. In some instances, the antibody, antibody fragment or immunoglobulin construct further comprises a linker. The linker can attach erythropoietin, or a derivative or variant thereof to the immunoglobulin domain or fragment thereof. In other instances, the linker attaches erythropoietin, or a derivative or variant thereof to the knob domain or stalk domain. In some instances, the disease or disorder is anemia.

Provided herein is a method of preventing or treating obesity in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, FGF21, oxyntomodulin, or derivative or variant thereof. The GLP-1 may be a human GLP-1. In some instances, the FGF21 is a human FGF21. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, FGF21, oxyntomodulin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The GLP-1, Exendin-4, FGF21, oxyntomodulin, or a derivative or variant thereof can be attached to the stalk domain. In some instances, the antibody, antibody fragment or immunoglobulin construct further comprises a linker. The linker can attach GLP-1, Exendin-4, FGF21, oxyntomodulin, or a derivative or variant thereof to the immunoglobulin domain or fragment thereof. In other instances, the linker attaches GLP-1, Exendin-4, FGF21, oxyntomodulin, or a derivative or variant thereof to the knob domain or stalk domain.

Provided herein is a method of preventing or treating a pain in a subject in need thereof comprising a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is protoxin2, 550 peptide, Amgen1, Mamba1 or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The protoxin2, 550 peptide, Amgen1, Mamba1 or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The protoxin2, 550 peptide, Amgen1, Mamba1 or a derivative or variant thereof can be attached to the stalk domain. In some instances, the antibody, antibody fragment or immunoglobulin construct further comprises a linker. The linker can attach protoxin2, 550 peptide, Amgen1, Mamba1 or a derivative or variant thereof to the immunoglobulin domain or fragment thereof. In other instances, the linker attaches protoxin2, 550 peptide, Amgen1, Mamba1 or a derivative or variant thereof to the knob domain or stalk domain. In some instances, pain is chronic pain. Alternatively, pain is acute pain.

Provided herein is a method of preventing or treating a disease or condition which benefits from modulating a sodium ion channel in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is protoxin2, 550 peptide, Amgen1, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The protoxin2, 550 peptide, Amgen1, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The protoxin2, 550 peptide, Amgen1, or a derivative or variant thereof can be attached to the stalk domain. In some instances, the antibody, antibody fragment or immunoglobulin construct further comprises a linker. The linker can attach protoxin2, 550 peptide, Amgen1, or a derivative or variant thereof to the immunoglobulin domain or fragment thereof. In other instances, the linker attaches protoxin2, 550 peptide, Amgen1, or a derivative or variant thereof to the knob domain or stalk domain. In some instances, the sodium ion channel is a $Na_v$ channel. In some instances, the $Na_v$ channel is a $Na_v1.7$ channel. In some instances, modulating a sodium ion channel comprises inhibiting or blocking a sodium ion channel. In some instances, the disease or condition is Dravet Syndrome, generalized epilepsy with febrile seizures plus (GEFS+), paramyotonia congenital or erythromelalgia. In some instances, the disease or condition is pain.

Provided herein is a method of preventing or treating a disease or condition which benefits from modulating an acid sensing ion channel (ASIC) in a subject in need thereof comprising a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is protoxin2, Mamba1, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The protoxin2, Mamba1, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The protoxin2, Mamba1, or a derivative or variant thereof can be attached to the stalk domain. In some instances, the antibody, antibody fragment or immunoglobulin construct further comprises a linker. The linker can attach protoxin2, Mamba1, or a derivative or variant thereof to the immunoglobulin domain or fragment thereof. In other instances, the linker attaches protoxin2, Mamba1, or a derivative or variant thereof to the knob domain or stalk domain. In some instances, modulating an ASIC comprises inhibiting or blocking the ASIC. In some instances, the disease or condition is a central nervous system disorder. In other instances, the disease or condition is pain.

Provided herein is a method of preventing or treating a pathogenic infection in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is beta-interferon, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The beta-interferon, or a derivative or variant thereof can be attached to the stalk domain. In some instances, the antibody, antibody fragment or immunoglobulin construct further comprises a linker. The linker can attach beta-interferon, or a derivative or variant thereof to the immunoglobulin domain or fragment thereof. In other instances, the linker attaches beta-interferon, or a derivative or variant thereof to the knob domain or stalk domain. In some instances, the pathogenic infection is a viral, bacterial, fungal, or parasitic infection. In some instances, the viral infection is a herpes virus.

Provided herein is a method of preventing or treating a cancer in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is beta-interferon, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The beta-interferon, or a derivative or variant thereof can be attached to the stalk domain. In some instances, the antibody, antibody fragment or immunoglobulin construct further comprises a linker. The linker can attach beta-interferon, or a derivative or variant thereof to the immunoglobulin domain or fragment thereof. In other instances, the linker attaches beta-interferon, or a derivative or variant thereof to the knob domain or stalk domain. In some instances, the cancer is a hematological malignancy. The hematological malignancy can be a leukemia or lymphoma. In some instances, the hematological malignancy is a B-cell lymphoma, T-cell lymphoma, follicular lymphoma, marginal zone lymphoma, hairy cell leukemia, chronic myeloid leukemia, mantle cell lymphoma, nodular lymphoma, Burkitt's lymphoma, cutaneous T-cell lymphoma, chronic lymphocytic leukemia, or small lymphocytic leukemia.

Provided herein is a method of preventing or treating a bone disease in a subject in need thereof comprising administering a composition comprising one or more antibodies, antibody fragments, or immunoglobulin constructs described herein to said subject. In some instances, the subject is a mammal. In certain instances, the mammal is a human. Alternatively, the mammal is a bovine. In some instances, the one or more antibodies, antibody fragments, or immunoglobulin constructs comprise a parathyroid hormone. Alternatively, or additionally, the one or more antibodies, antibody fragments, or immunoglobulin constructs comprise at least a portion of a CDR3H. The portion of the CDR3H can be a stalk domain or knob domain in the CDR3H. In some instances, the one or more antibodies, antibody fragments, or immunoglobulin constructs further comprise a linker. The linker can attach the parathyroid hormone to the portion of the CDR3H. In some instances, the bone disease is osteoporosis. Additional bone diseases include, but are not limited to, low bone density, osteogenesis imperfecta, osteitis condensans ilii, osteochondritis dissecans, osteochondroma (bone tumor), osteomalacia, osteomyelitis, osteopenia, osteopetrosis, osteosarcoma (bone tumor), osteonecrosis, osteoarthritis, osteitis pubis, and Paget's disease of bone.

Provided herein is a method of preventing or treating a disease or condition in a subject in need thereof, the method comprising administering a composition comprising one or more antibodies comprising an ultralong CDR3 as disclosed herein to said subject. The composition may further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is relaxin, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The relaxin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The relaxin, or a derivative or variant thereof can be attached to the stalk domain. In some instances, the antibody, antibody fragment or immunoglobulin construct further comprises a linker. The linker can attach relaxin, or a derivative or variant thereof to the immunoglobulin domain or fragment thereof. In other instances, the linker attaches relaxin, or a derivative or variant thereof to the knob domain or stalk domain. The disease or condition may be a cardiovascular disease. The cardiovascular disease may be acute heart failure. Additional cardiovascular diseases include, but are not limited to, congestive heart failure, compensated heart failure or decompensated heart failure. The disease or condition may be an autoimmune disorder. The autoimmune disorder may be scleroderma, diffuse scleroderma or systemic scleroderma. The disease or condition may be an inflammatory disease. The inflammatory disease may be fibromyalgia. The disease or condition may be fibrosis. Alternatively, the disease or condition is pregnancy. The antibody fusion protein may be used to treat preeclampsia or induce labor.

Provided herein is a method of preventing or treating a disease in a mammal in need thereof comprising administering a pharmaceutical composition described herein to said mammal. In some embodiments, the disease is an infectious disease. In certain embodiments, the infectious disease is mastitis. In some embodiments, the infectious disease is a respiratory disease. In certain embodiments, the respiratory disease is bovine respiratory disease of shipping fever. In certain embodiments, the mammal in need is a dairy animal selected from a list comprising cow, camel, donkey, goat, horse, reindeer, sheep, water buffalo, moose and yak. In some embodiments, the mammal in need is bovine.

Provided are methods of treatment, inhibition and prevention by administration to a subject of an effective amount of an antibody or pharmaceutical composition described herein. The antibody may be substantially purified (e.g., substantially free from substances that limit its effect or produce undesired side-effects). The subject can be an animal, including but not limited to animals such as cows, pigs, sheep, goats, rabbits, horses, chickens, cats, dogs, mice, etc. The subject can be a mammal. In some instances, the subject is a human. Alternatively, the subject is a bovine.

Further disclosed herein are uses of an antibody fusion protein in the manufacture of a medicament for the treatment of a disease or condition. Disclosed herein is the use of an antibody fusion protein in the manufacture of a medicament for the treatment of a disease or condition, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may comprise GCSF. The GCSF may be a human GCSF. The therapeutic polypeptide may be Moka1. The therapeutic polypeptide may be VM24. The therapeutic polypeptide may be Exendin-4. The therapeutic polypeptide may be erythropoietin. The erythropoietin may be a human erythropoietin. The therapeutic polypeptide may be leptin. The therapeutic polypeptide may be a growth hormone (GH). The growth hormone may be a human growth hormone (hGH). The therapeutic polypeptide may be interferon-alpha. The therapeutic polypeptide may be interferon-beta. The therapeutic polypeptide may be GLP-1. The therapeutic polypeptide may be relaxin. The therapeutic polypeptide may be a 550 peptide. The therapeutic polypeptide may be Mamba1. The therapeutic polypeptide may be BCCX2. The therapeutic polypeptide may be elem. The therapeutic polypeptide may be betatrophin. The therapeutic polypeptide may be GDF11. The therapeutic polypeptide may be GMCSF. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. The disease or condition may be a growth disorder.

Disclosed herein is the use of an antibody fusion protein in the manufacture of a medicament for the treatment of a cell proliferative disorder, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The cell proliferative disorder may be cancer. The therapeutic polypeptide may be BCCX2.

Disclosed herein is the use of an antibody fusion protein in the manufacture of a medicament for the treatment of a metabolic disorder, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The metabolic disorder may be diabetes. Diabetes may be type I diabetes. Diabetes may be type II diabetes. The therapeutic polypeptide may be Exendin-4. The therapeutic polypeptide may be GLP-1. The therapeutic polypeptide may be leptin. The therapeutic polypeptide may be betatrophin.

Disclosed herein is the use of an antibody fusion protein in the manufacture of a medicament for the treatment of an autoimmune disease or condition, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be Moka1. The therapeutic polypeptide may be VM24.

Disclosed herein is the use of an antibody fusion protein in the manufacture of a medicament for the treatment of an inflammatory disease or condition, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be elafin. The therapeutic polypeptide may be interferon-beta.

Disclosed herein is the use of an antibody fusion protein in the manufacture of a medicament for the treatment of a disease or condition of the central nervous system, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be a 550 peptide. The therapeutic polypeptide may be Mamba1.

Disclosed herein is the use of an antibody fusion protein in the manufacture of a medicament for the treatment of a cardiovascular disease or condition, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be relaxin. The therapeutic polypeptide may be GDF11.

Disclosed herein is the use of an antibody fusion protein in the manufacture of a medicament for the treatment of a hematological disease or condition, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be GCSF. The GCSF may be a human GCSF. The therapeutic polypeptide may be erythropoietin. The erythropoietin may be a human erythropoietin. The therapeutic polypeptide may be GMCSF.

Disclosed herein is the use of an antibody fusion protein in the manufacture of a medicament for the treatment of a pathogenic infection, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be interferon-alpha.

Disclosed herein is the use of an antibody fusion protein in the manufacture of a medicament for the treatment of a growth disorder, the antibody fusion protein comprising comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be a growth hormone. The growth hormone may be a human growth hormone (hGH).

Further disclosed herein are uses of an antibody fusion protein for the treatment of a disease or condition. Disclosed herein is the use of an antibody fusion protein for the treatment of a disease or condition in a subject in need thereof, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may comprise GCSF. The GCSF may be a human GCSF. The therapeutic polypeptide may be Moka1. The therapeutic polypeptide may be VM24. The therapeutic polypeptide may be Exendin-4. The therapeutic polypeptide may be erythropoietin. The erythropoietin may be a human erythropoietin. The therapeutic polypeptide may be leptin. The therapeutic polypeptide may be a growth hormone (GH). The growth hormone may be a human growth hormone (hGH). The therapeutic polypeptide may be interferon-alpha. The therapeutic polypeptide may be interferon-beta. The therapeutic polypeptide may be GLP-1. The therapeutic polypeptide may be relaxin. The therapeutic polypeptide may be a 550 peptide. The therapeutic polypeptide may be Mamba1. The therapeutic polypeptide may be BCCX2. The therapeutic polypeptide may be elafin. The therapeutic polypeptide may be betatrophin. The therapeutic polypeptide may be GDF11. The therapeutic polypeptide may be GMCSF. The disease or condition may be an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain. The disease or condition may be a growth disorder.

Disclosed herein is the use of an antibody fusion protein for the treatment of a cell proliferative disorder in a subject in need thereof, the antibody fusion protein comprising comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be BCCX2.

Disclosed herein is the use of an antibody fusion protein for the treatment of a metabolic disorder in a subject in need thereof, the antibody fusion protein comprising comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be Exendin-4. The therapeutic polypeptide may be GLP-1. The therapeutic polypeptide may be leptin. The therapeutic polypeptide may be betatrophin.

Disclosed herein is the use of an antibody fusion protein for the treatment of an autoimmune disease or condition in a subject in need thereof, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be Moka1. The therapeutic polypeptide may be VM24.

Disclosed herein is the use of an antibody fusion protein for the treatment of an inflammatory disease or condition in a subject in need thereof, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be elafin. The therapeutic polypeptide may be interferon-beta.

Disclosed herein is the use of an antibody fusion protein for the treatment of a disease or condition of the central nervous system in a subject in need thereof, the antibody fusion protein comprising (a) at least a portion of an ultralong CDR3; and (b) a therapeutic polypeptide. The antibody may be an immunoconjugate as described herein. The antibody can comprise one or more immunoglobulin domains.

The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be a 550 peptide. The therapeutic polypeptide may be Mamba1.

Disclosed herein is the use of an antibody fusion protein for the treatment of a cardiovascular disease or condition in a subject in need thereof, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be relaxin. The therapeutic polypeptide may be GDF11.

Disclosed herein is the use of an antibody fusion protein for the treatment of a hematological disease or condition in a subject in need thereof, the antibody fusion protein comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be GCSF. The GCSF may be a human GCSF. The GCSF may be a bovine GCSF. The therapeutic polypeptide may be erythropoietin. The erythropoietin may be a human erythropoietin. The therapeutic polypeptide may be GMCSF.

Disclosed herein is the use of an antibody fusion protein for the treatment of a pathogenic infection in a subject in need thereof, the antibody fusion protein comprising comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. The therapeutic polypeptide may be interferon-alpha.

Disclosed herein is the use of an antibody fusion protein for the treatment of a growth disorder in a subject in need thereof, the antibody fusion protein comprising comprising (a) at least a portion of an ultralong CDR3; and (b) a therapeutic polypeptide. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The therapeutic polypeptide, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ motif (SEQ ID NO: 177). The therapeutic polypeptide, or a derivative or variant thereof can be attached to the stalk domain. In some instances, the antibody, antibody fragment or immunoglobulin construct further comprises a linker. The linker can attach therapeutic polypeptide, or a derivative or variant thereof to the immunoglobulin domain or fragment thereof. In other instances, the linker attaches therapeutic polypeptide, or a derivative or variant thereof to the knob domain or stalk domain. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. Examples of growth disorders included, but are not limited to, achondroplasia, achondroplasia in children, acromegaly, adiposogenital dystrophy, dwarfism, gigantism, Brooke Greenberg, hemihypertrophy, hypochondroplasia, Jansen's metaphyseal chondrodysplasia, Kowarski syndrome, Léri-Weill dyschondrosteosis, local gigantism, macrodystrophia lipomatosa, Majewski's polydactyly syndrome, microcephalic osteodysplastic primordial dwarfism type II, midget, overgrowth syndrome, parastremmatic dwarfism, primordial dwarfism, pseudoachondroplasia, psychosocial short stature, Seckel syndrome, short rib—polydactyly syndrome and Silver-Russell syndrome. The therapeutic polypeptide may be a growth hormone. The growth hormone may be a human growth hormone (hGH).

Various delivery systems are known and can be used to administer an antibody formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the heteromultimer compositions described herein into the central nervous system by any suitable route, including intraventricular and intrathecal injection; intraventricular injection may be facilitated by an intraventricular catheter, for example, attached to a reservoir, such as an Ommaya reservoir.

In a specific embodiment, it is desirable to administer the antibody, or compositions described herein locally to the area in need of treatment; this may be achieved by, for example, and not by way of limitation, local infusion, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the antibody or pharmaceutical composition is delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the heteromultimers or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In a specific embodiment comprising a nucleic acid encoding an antibody described herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

In certain embodiments, the half-life of a therapeutic polypeptide in an antibody fusion protein disclosed herein is greater than the half-life of a free therapeutic polypeptide. The half-life of a therapeutic polypeptide in antibody fusion protein disclosed herein may be at least about 1.5, 2, 2.5, 3, 3.5, 4, 4.5, 5, 5.5, 6, 6.5, 7, 7.5, 8, 8.5, 9, 9.5, or 10-fold greater than the half-life of the free therapeutic polypeptide. The half-life of a therapeutic polypeptide in antibody fusion protein disclosed herein may be at least about 2-fold greater than the half-life of the free therapeutic polypeptide. The half-life of a therapeutic polypeptide in antibody fusion protein disclosed herein may be at least about 3-fold greater than the half-life of the free therapeutic polypeptide. The half-life of a therapeutic polypeptide in antibody fusion protein disclosed herein may be at least about 5-fold greater than the half-life of the free therapeutic polypeptide. The half-life of a therapeutic polypeptide in antibody fusion protein disclosed herein may be at least about 5%, 10%, 15%, 20%, 25%, 30%, 35%, 40%, 45%, 50%, 55%, 60%, 65%, 70%, 75%, 80%, 85%, 90%, or 95% greater than the half-life of the free therapeutic polypeptide. The half-life of a therapeutic polypeptide in antibody fusion protein disclosed herein may be at least about 10% greater than the half-life of the free therapeutic polypeptide. The half-life of a therapeutic polypeptide in antibody fusion protein disclosed herein may be at least about 15% greater than the half-life of the free therapeutic polypeptide. The half-life of a therapeutic polypeptide in antibody fusion protein disclosed herein may be at least about 20% greater than the half-life of the free therapeutic polypeptide. The half-life of a therapeutic polypeptide in antibody fusion protein disclosed herein may be at least about 30% greater than the half-life of the free therapeutic polypeptide. In some embodiments, the half-life of an immunoglobulin construct provided herein is greater than 4 hours when administered to a subject. In certain embodiments, the half-life of an immunoglobulin construct provided herein is greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. In some instances, the subject is a mammal. In some embodiments, the subject is a mouse or a bovine. In other instances, the subject is a human. In certain embodiments, a pharmaceutical composition comprising the immunoglobulin construct is administered to the subject once a day, every two days, every three days, every 4 days, every 7 days, every 10 days, every 14 days, every 21 days, every 28 days, every 2 months, or every three months.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure

Example 1

Constructing Vectors of BLV1H12-Oxyntomodulin Fusion Proteins for Expression in Mammalian Cells A gene encoding oxyntomodulin was synthesized by Genscript or IDT, and amplified by polymerase chain reaction (PCR). To optimize the folding and stability of fusion proteins, flexible linkers of (GGGGS) (SEQ ID NO: 17) were added on both ends of oxyntomodulin fragments. Subsequently, PCR fragments of oxyntomodulin were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-oxyntomodulin fusion proteins were generated by in-frame ligation of the amplified BLV1H12-oxyntomodulin fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 2

Expression and Purification of BLV1H12-Oxyntomodulin Fusion Antibodies

BLV1H12-oxyntomodulin fusion antibodies were expressed through transient transfections of free style HEK 293 cells with vectors encoding BLV1H12-protoxin2 fusion heavy chain and the BLV1H12 light chain. Expressed BLV1H12-oxyntomodulin fusion antibodies were secreted into the culture medium and harvested at 48 hours and 96 hours after transfection. The BLV1H12-oxyntomodulin fusion proteins can be purified by Protein A/G chromatography (Thermo Fisher Scientific, IL), and analyzed by SDS-PAGE gel.

Example 3

Constructing Vectors of BLV1H12-550 Fusion Proteins for Expression in Mammalian Cells A gene encoding 550 was synthesized by Genscript or IDT, and amplified by polymerase chain reaction (PCR). To optimize the folding and stability of fusion proteins, flexible linkers of GGGGS (SEQ ID NO: 17) were added on both ends of 550 fragments. Subsequently, PCR fragments of 550 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-550 fusion proteins were generated by in-frame ligation of the amplified BLV1H12-550 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 4

Expression and Purification of BLV1H12-550 Fusion Antibodies

Figure 2A:
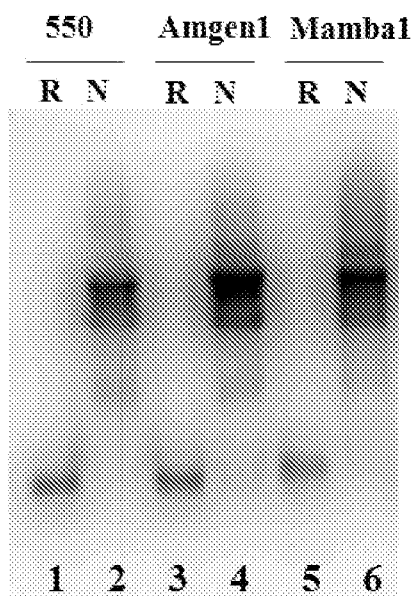
Figure 2B:
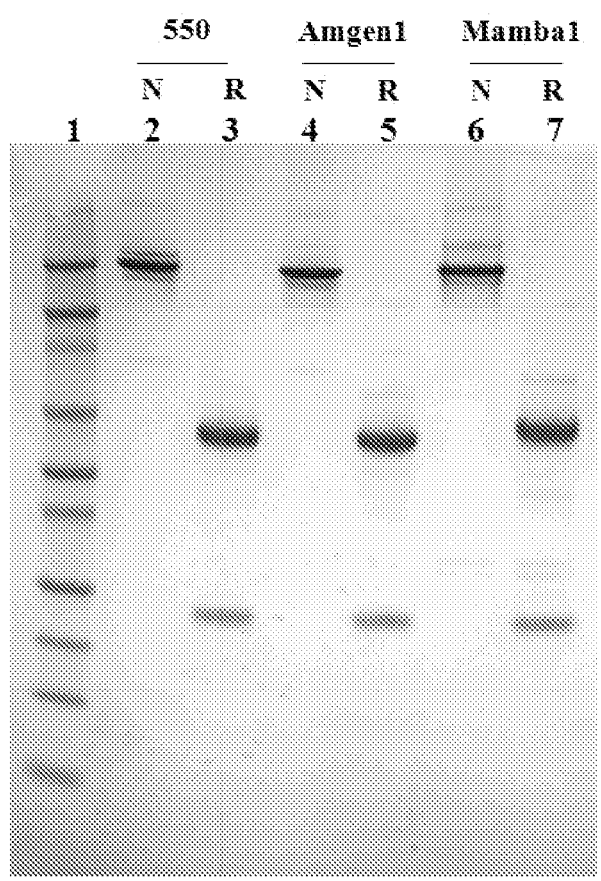

BLV1H12-550 fusion antibodies were expressed through transient transfections of free style HEK 293 cells with vectors encoding BLV1H12-fusion heavy chain and the BLV1H12 light chain. Expressed BLV1H12-550 fusion antibodies were secreted into the culture medium and harvested every 48 hours for twice after transfection. The BLV1H12-550 fusion antibodies were purified by Protein A/G chromatography (Thermo Fisher Scientific, IL), and analyzed by SDS PAGE gel. FIG. 2A show a Western blot of the 550 peptide (Lane 1=550 peptide reduced conditions; Lane 2=550 peptide non-reduced conditions). FIG. 2B shows the SDS PAGE of the 550 peptide (Lane 1=protein standard; Lane 2=550 peptide non-reduced conditions; Lane 3=550 peptide reduced conditions).

Example 5

Constructing Vectors of BLV1H12-Amgen1 Fusion Proteins for Expression in Mammalian Cells A gene encoding Amgen1 was synthesized by Genscript or IDT, and amplified by polymerase chain reaction (PCR). To optimize the folding and stability of fusion proteins, flexible linkers of GGGGS (SEQ ID NO: 17) were added on both ends of Amgen1 fragments. Subsequently, PCR fragments of Amgen1 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-Amgen1 fusion proteins were generated by in-frame ligation of the amplified BLV1H12-Amgen1 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 6

Expression and Purification of BLV1H12-Amgen1 Fusion Antibodies

BLV1H12-Amgen1 fusion antibodies were expressed through transient transfections of free style HEK 293 cells with vectors encoding BLV1H12-Amgen1 fusion heavy chain and the BLV1H12 light chain. Expressed BLV1H12-Amgen1 fusion antibodies were secreted into the culture medium and harvested at 48 hours and 96 hours after transfection. The BLV1H12-Amgen1 fusion antibodies were purified by Protein A/G chromatography (Thermo Fisher Scientific, IL), and analyzed by SDS-PAGE gel. FIG. 2A shows a Western blot of Amgen1 (Lane 3=Amgen1 reduced conditions; Lane 4=Amgen1 non-reduced conditions). FIG. 2B shows the SDS PAGE of Amgen1 (Lane 1=protein standard; Lane 4=Amgen1 non-reduced conditions; Lane 5=Amgen1 reduced conditions).

Example 7

Constructing Vectors of BLV1H12-Mamba1 Fusion Proteins for Expression in Mammalian Cells A gene encoding Mamba1 was synthesized by Genscript or IDT, and amplified by polymerase chain reaction (PCR).

To optimize the folding and stability of fusion proteins, flexible linkers of GGGGS (SEQ ID NO: 17) were added on both ends of Mamba1 fragments. Subsequently, PCR fragments of Mamba1 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-Mamba1 fusion proteins were generated by in-frame ligation of the amplified BLV1H12-Mamba1 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 8

Expression and Purification of BLV1H12-Mamba1 Fusion Antibodies

BLV1H12-Mamba1 fusion antibodies were expressed through transient transfections of free style HEK 293 cells with vectors encoding BLV1H12-Mamba1 fusion heavy chain and the BLV1H12 light chain. Expressed BLV1H12-Mamba1 fusion antibodies were secreted into the culture medium and harvested every 48 hours for twice after transfection. The BLV1H12-Mamba1 fusion antibodies were purified by Protein A/G chromatography (Thermo Fisher Scientific, IL), and analyzed by SDS-PAGE gel. FIG. 2A shows the Western blot of Mamba1 (Lane 5=Mamba1 non-reduced conditions; Lane 6=Mamba1 reduced conditions). FIG. 2B shows the SDS PAGE of the Mamba1 (Lane 1=protein standard; Lane 6=Mamba1 non-reduced conditions; Lane 7=Mamba1 reduced conditions).

Example 9

Constructing Vectors of BLV1H12-Parathyroid Hormone Fusion Proteins for Expression in Mammalian Cells A gene encoding human parathyroid hormone (hPTH) was synthesized by Genscript or IDT, and amplified by polymerase chain reaction (PCR). To optimize the folding and stability of fusion proteins, flexible linkers of GGGGS (SEQ ID NO: 17) were added on both ends of human parathyroid hormone (hPTH) fragments. Subsequently, PCR fragments of human parathyroid hormone (hPTH) were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-hPTH fusion proteins were generated by in-frame ligation of the amplified BLV1H12-hPTH fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 10

Expression and Purification of BLV1H12-Parathyroid Fusion Antibodies

BLV1H12-parathyroid (PTH) fusion antibodies are expressed through transient transfections of free style HEK 293 cells with vectors encoding BLV1H12-hPTH fusion heavy chain and the BLV1H12 light chain. Expressed BLV1H12-parathyroid (PTH) fusion antibodies are secreted into the culture medium and harvested every 48 hours for twice after transfection. The BLV1H12-parathyroid (PTH) fusion antibodies are purified by Protein A/G chromatography (Thermo Fisher Scientific, IL), and analyzed by SDS-PAGE gel.

Example 11

Constructing Vectors of BLV1H12-Therapeutic Polypeptide Fusion Proteins for Expression in Mammalian Cells Genes encoding various therapeutic polypeptides were synthesized by Genscript (NJ, USA) and amplified by polymerase chain reaction (PCR). To optimize the folding and stability of the immunoglobulin constructs, one or more flexible linkers of (GGGGS)n (n=0, 1) (SEQ ID NO: 178), GGGSGGGGS (SEQ ID NO: 15), and/or GGGGSGGGS (SEQ ID NO: 16) were added on both ends of the gene fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12-bGCSF fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Nucleic acid sequences of the BLV1H12-fusion proteins are displayed in Tables 1 and 6. Peptide sequences of the BLVH12-fusion proteins are displayed in Tables 2 and 7. As shown in the tables, the bovine heavy chain sequence is in bold font; the human heavy chain sequence is highlighted with a dashed underline; the non-antibody sequence is in italicized font; the stalk domain is in bold font and underlined; the knob domain is in bold font and double underlined; the linker sequence is in italicized font and squiggly underlined.

Example 12

Expression and Purification of BLV1H12-Therapeutic Polypeptide Fusion Antibodies BLV1H12-therapeutic polypeptide fusion antibodies can be expressed through transient transfections of free style HEK 293 cells with vectors encoding BLV1H12-fusion protein heavy chain and the BLV1H12 light chain. Expressed BLV1H12-protein fusion antibodies are secreted into the culture medium and harvested at 48 hours and 96 hours after transfection. The BLV1H12-therapeutic polypeptide fusion antibodies are purified by Protein A/G chromatography (Thermo Fisher Scientific, IL), and analyzed by SDS-PAGE gel. BLV1H12-therapeutic polypeptide fusion antibodies comprising a cleavage site can be further treated with protease to release the N-terminus and/or C-terminus of the fused therapeutic polypeptides. After treatment, BLV1H12-therapeutic polypeptide fusion antibody can be re-purified by Protein A/G affinity column to remove protease and analyzed by SDS-PAGE gel.

Example 13

Construction of BLV1H12 Betatrophin Based Fusion Protein Vectors for Expression in Mammalian Cells A gene encoding betatrophin was synthesized by Genscript or IDT, and amplified by polymerase chain reaction (PCR). To optimize the folding and stability of fusion proteins, flexible linkers of GGGGS (SEQ ID NO: 17) OR GGGGSGGGGS (SEQ ID NO: 179) were added on both ends of the betatrophin fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12-betatrophin fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 14

Expression and Purification of BLV1H12 Betatrophin Based Fusion Proteins

Figure 3:
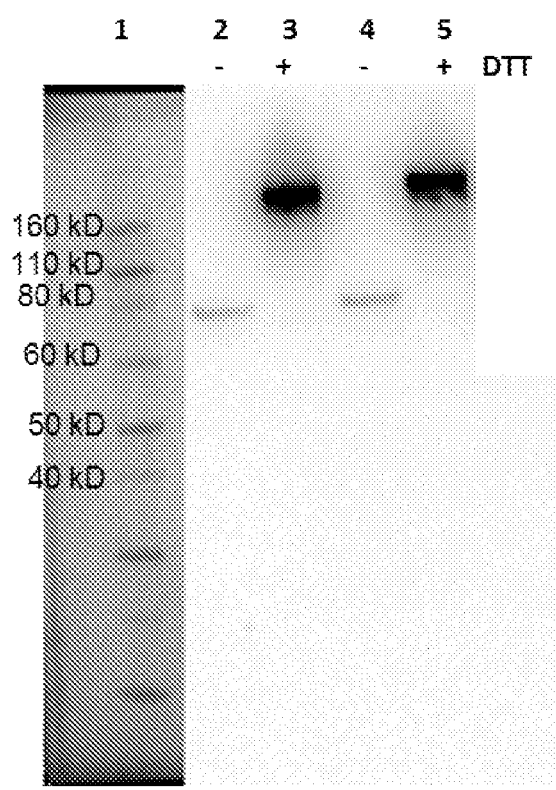

BLV1H12 betatrophin based fusion proteins were expressed through transient transfections of free style HEK293 cells with vectors encoding BLV1H12 betatrophin fusion protein heavy chain and the bovine antibody light chain. Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel (FIG. 3). As shown in FIG. 3, Lane 1 contains the protein ladder; Lane 2 contains BLV1H12-L1 betatrophin fusion protein; Lane 3 contains BLV1H12-L1 betatrophin fusion protein treated with DTT; Lane 4 contains BLV1H12-L2 betatrophin fusion protein; and Lane 5 contains BLV1H12-L2 betatrophin fusion protein treated with DTT.

Example 15

Construction of BLV1H12 Relaxin Based Fusion Protein Vectors for Expression in Mammalian Cells A gene encoding relaxin was synthesized by Genscript or IDT, and amplified by polymerase chain reaction (PCR). To optimize the folding and stability of fusion proteins, GGGGS (SEQ ID NO: 17) linkers were added to each end of the relaxin fragment. In addition, the two native cleavage sites (KR between B chain and connecting peptide, RKKR (SEQ ID NO: 180) between connecting peptide and A chain) were engineered to IEGR (SEQ ID NO: 153) for Factor Xa process. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12-relaxin fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 16

Expression and Purification of BLV1H12 Relaxin Based Fusion Proteins

Figure 4A:
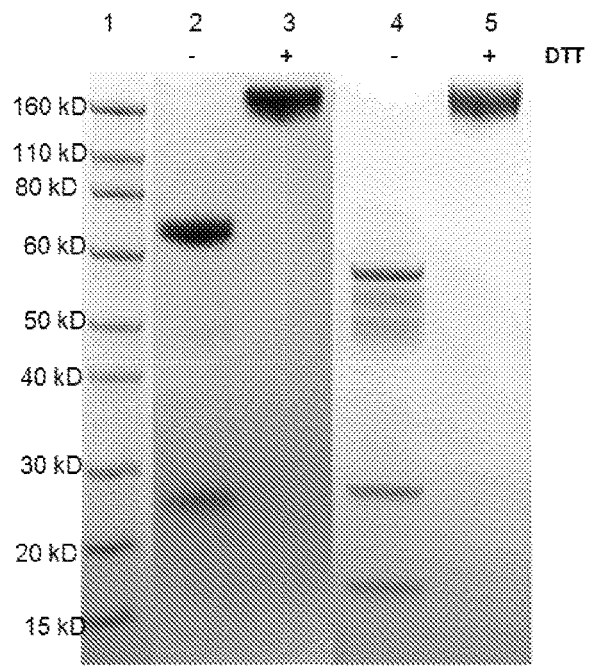

BLV1H12 relaxin based fusion proteins were expressed through transient transfections of free style HEK293 cells with vectors encoding BLV1H12 relaxin fusion protein heavy chain and the bovine antibody light chain. Expressed fusion proteins were secreted into the culture medium and harvested at 48 and 96 hours after transfection. The fusion proteins were purified by Protein A/G chromatography (Thermo Fisher Scientific, IL). Purified BLV1H12 relaxin fusion protein was processed by Factor Xa (GE Healthcare, 1 ug Factor Xa~100 ug fusion protein, 20 mM Tris-HCl, 100 mM NaCl, 2 mM $CaCl_2$, pH 8.0) room temperature for 14 hours. Processed fusion protein was purified by Protein G resin again (3,4: +/−DTT), PBS buffer exchanged and analyzed by SDS-PAGE gel (FIG. 4A). As shown in FIG. 4A, Lane 1 contains the protein ladder; Lane 2 contains BLV1H12-relaxin fusion processed with Factor Xa protein; Lane 3 contains BLV1H12-relaxin fusion protein processed with Factor Xa and treated with DTT; Lane 4 contains BLV1H12-relaxin fusion processed with Factor Xa protein and purified twice; and Lane 5 contains BLV1H12-relaxin fusion protein processed with Factor Xa, purified twice and treated with DTT.

Example 17

Figure 4B:
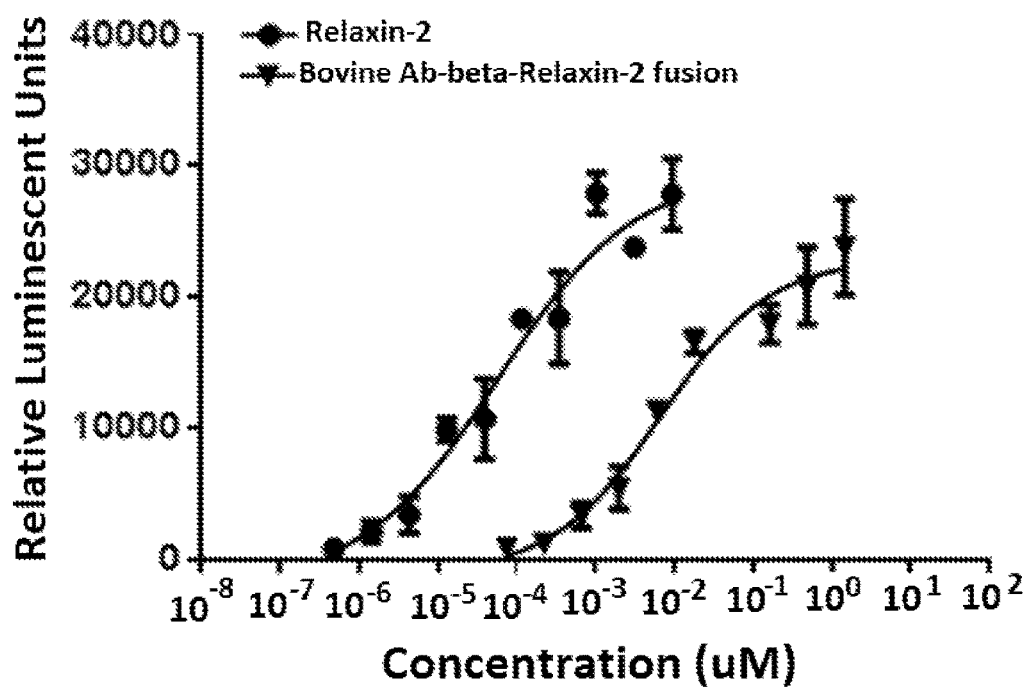
Figure 5A:
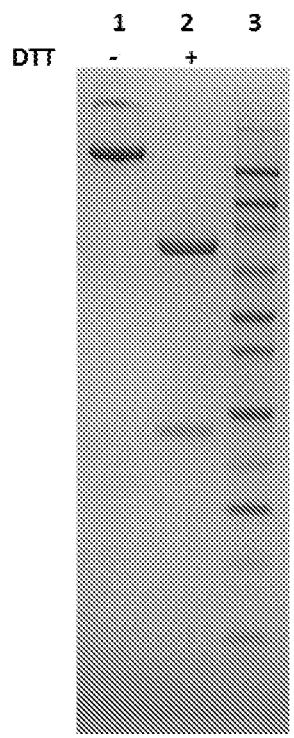
Figure 5B:
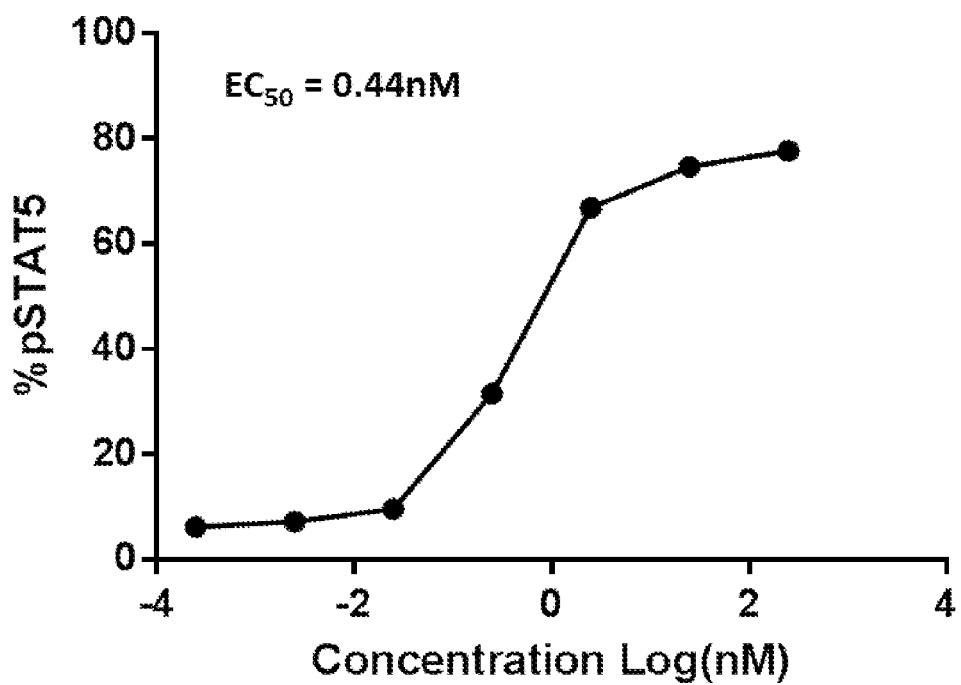

In Vitro Activity of BLV1H12 hRelaxin Fusion 293 stable cells overexpressing relaxin receptor (LGR7) and CRE-responsive luciferase were seeded in a 384-well plate for 24 hours. Cells were subsequently treated with different doses of relaxin-2 or antibody fused Relaxin-2 proteins for 24 hours. Luciferase assays were conducted and data were analyzed using GraphPad Prism 6. Results for the luciferase assays are shown in Table 8 and FIG. 4B. As shown in FIG. 4B, circles represent Relaxin-2 and upside-down triangles represent BLV1H12 hRelaxin fusion proteins that have been cleaved by Factor Xa and purified.

TABLE 8

| Relaxin-2 | | | | Antibody-Relaxin-2-cleaved and purified | | | |
|---|---|---|---|---|---|---|---|
| Conc. (uM) | Fluorescence reading | | | Conc. (uM) | Fluorescence reading | | |
| 0.00946 | 30160 | 24880 | 28480 | 1.47 | 23520 | 27600 | 20320 |
| 0.003153 | 24480 | 23280 | 23680 | 0.49 | 23200 | 21840 | 17600 |
| 0.001051 | 29040 | 26800 | | 0.163333 | 16320 | 18480 | 19120 |

TABLE 8-continued

| Relaxin-2 | | | | Antibody-Relaxin-2-cleaved and purified | | | |
|---|---|---|---|---|---|---|---|
| Conc. (uM) | Fluorescence reading | | | Conc. (uM) | Fluorescence reading | | |
| 0.00035 | 21520 | 14560 | 19120 | 0.018148 | 17200 | | 16000 |
| 0.000117 | 18480 | | 18240 | 0.006049 | 11320 | 10800 | 11840 |
| 0.0000389 | 12080 | 7120 | 12800 | 0.002016 | 6720 | 5920 | 3600 |
| 0.000013 | 10800 | 8960 | 9840 | 0.000672 | 2640 | 4400 | 2960 |
| 0.00000433 | 4400 | 2400 | | 0.000224 | 1280 | 1200 | 1040 |
| 0.00000144 | 2880 | 2160 | 1280 | 0.0000747 | 320 | 1440 | 720 |
| 0.000000481 | 1440 | 480 | 560 | | | | |

Example 18

Figure 6A:
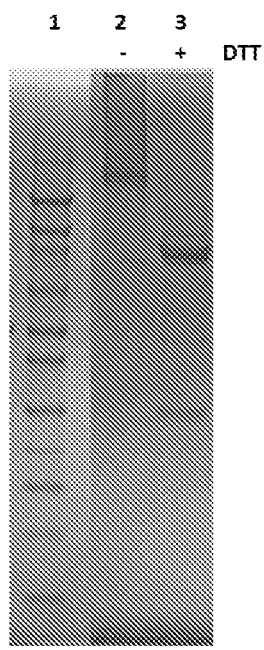

Construction of BLV1H12 Human Growth Hormone (hGH) Based Fusion Protein Vectors for Expression in Mammalian Cells A gene encoding human growth hormone (hGH) was synthesized by Genscript or IDT, and amplified by polymerase chain reaction (PCR). To optimize the folding and stability of fusion proteins, flexible linkers of GGGGS (SEQ ID NO: 17) were added on both ends of the hGH fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12-hGH fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 19

Expression and Purification of BLV1H12 hGH Based Fusion Proteins

BLV1H12 hGH based fusion proteins were expressed through transient transfections of free style HEK293 cells with vectors encoding BLV1H12 hGH fusion protein heavy chain and the bovine antibody light chain. Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel (FIG. 5A). As shown in FIG. 5A, Lane 1 contains BLV1H12-hGH single linker fusion protein; Lane 2 contains BLV1H12-hGH single linker fusion protein treated with DTT; and Lane 3 contains the protein ladder.

Example 20

In Vitro Activity of BLV1H12 hGH Fusion Proteins in IM9 Cells

Human IM9 cells (from ATCC) were starved overnight in assay medium (1% charcoal stripped FBS in RPMI) before stimulation with various concentration of hGH fusion protein for 10 min at 37° C. Stimulated cells were fixed, permeabilized and stained for pSTAT5 followed manufacturer's instruction (Cell Signaling Technology, #3939). Percentage of phosphorylation was analyzed using Flowjo software (Tree Star Inc.) after performing FACS. Percentage of pSTAT5 phosphorylation is shown in Table 9 and FIG. 5B. The $EC_{50}$ of BLV1H12 hGH was 0.44 nM.

TABLE 9

| bAb-hGH-Fc (nM) | pSTAT5 (%) |
|---|---|
| 0.00025 | 6.18 |
| 0.0025 | 7.17 |
| 0.025 | 9.6 |
| 0.25 | 31.5 |
| 2.5 | 66.9 |
| 25 | 74.7 |
| 250 | 77.7 |

Example 21

Construction of BLV1H12 Human Interferon Beta (IFN-Beta) Based Fusion Protein Vectors for Expression in Mammalian Cells A gene encoding human interferon beta (IFN-beta) was synthesized by Genscript or IDT, and amplified by polymerase chain reaction (PCR). To optimize the folding and stability of fusion proteins, flexible linkers of GGGGS (SEQ ID NO: 17) were added on both ends of the IFN-beta fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12-IFN-beta fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 22

Expression and purification of BLV1H12 IFN-beta based Fusion Proteins

BLV1H12 IFN-beta based fusion proteins were expressed through transient transfections of free style HEK293 cells with vectors encoding BLV1H12 IFN-beta fusion protein heavy chain and the bovine antibody light chain. Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel (FIG. 6A). As shown in FIG. 6A, Lane 1 contains the protein ladder; Lane 2 contains BLV1H12-IFN-beta single linker fusion protein; Lane 3 contains BLV1H12-IFN-beta single fusion protein treated with DTT.

Example 23

Figure 6B:
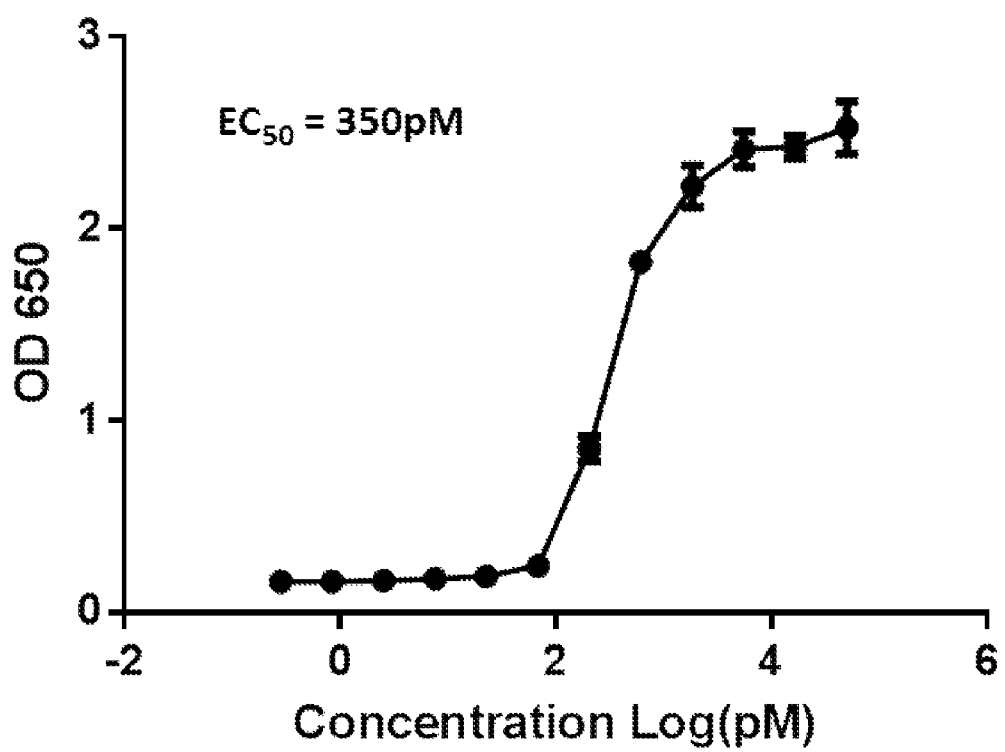

Activity of BLV1H12 IFN-Beta Fusion Proteins in HEK-Blue IFN-a/b Cells hIFN-beta activity was assessed by HEK-Blue IFN-a/b Cells (from invivoGen) following manufacturer suggested protocol. Briefly, cells were detached by tryspin, washed with PBS, and resuspended in HEK-Blue Detection medium. Cells were plated with increasing concentration of BLV1H12 hIFNb fusion protein in 96 well plate and incubate overnight at 37° C. SEAP activities were assessed by reading the at 650 nm with a microplate reader. Table 10 and FIG. 6B show the SEAP activities of BLV1H12 IFN-beta. The $EC_{50}$ of BLV1H12 IFN-beta was 350 pM.

TABLE 10

| bAb-hIFNb-Fc (pM) | OD650 Reading | SD |
|---|---|---|
| 0.282251 | 0.161667 | 0.002494 |
| 0.846754 | 0.161333 | 0.002867 |
| 2.540263 | 0.167333 | 0.0033 |
| 7.62079 | 0.177 | 0.001414 |
| 22.86237 | 0.189 | 0.003742 |
| 68.58711 | 0.243667 | 0.012037 |
| 205.7613 | 0.854667 | 0.065219 |
| 617.284 | 1.825 | 0.042708 |
| 1851.852 | 2.220333 | 0.109302 |
| 5555.556 | 2.413333 | 0.092737 |
| 16666.67 | 2.426333 | 0.06078 |
| 50000 | 2.526667 | 0.13679 |

Example 24

Construction of BLV1H12 Human Leptin Based Fusion Protein Vectors for Expression in Mammalian Cells A gene encoding human leptin (hLeptin) was synthesized by Genscript or IDT, and amplified by polymerase chain reaction (PCR). To optimize the folding and stability of fusion proteins, flexible linkers of GGGGS (SEQ ID NO: 17) were added on both ends of the hLeptin fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12-hLeptin fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 25

Expression and Purification of BLV1H12 hLeptin Based Fusion Proteins

Figure 7A:
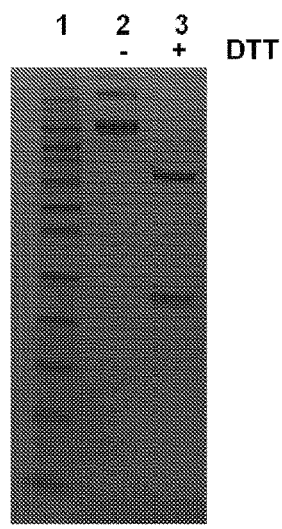

BLV1H12 hLeptin based fusion proteins were expressed through transient transfections of free style HEK293 cells with vectors encoding BLV1H12 hLeptin fusion protein heavy chain and the bovine antibody light chain. Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel (FIG. 7A). As shown in FIG. 7A, Lane 1 contains the protein ladder; Lane 2 contains BLV1H12 hLeptin fusion protein, Lane 3 contains BLV1H12 hLeptin fusion protein treated with DTT.

Example 26

Figure 7B:
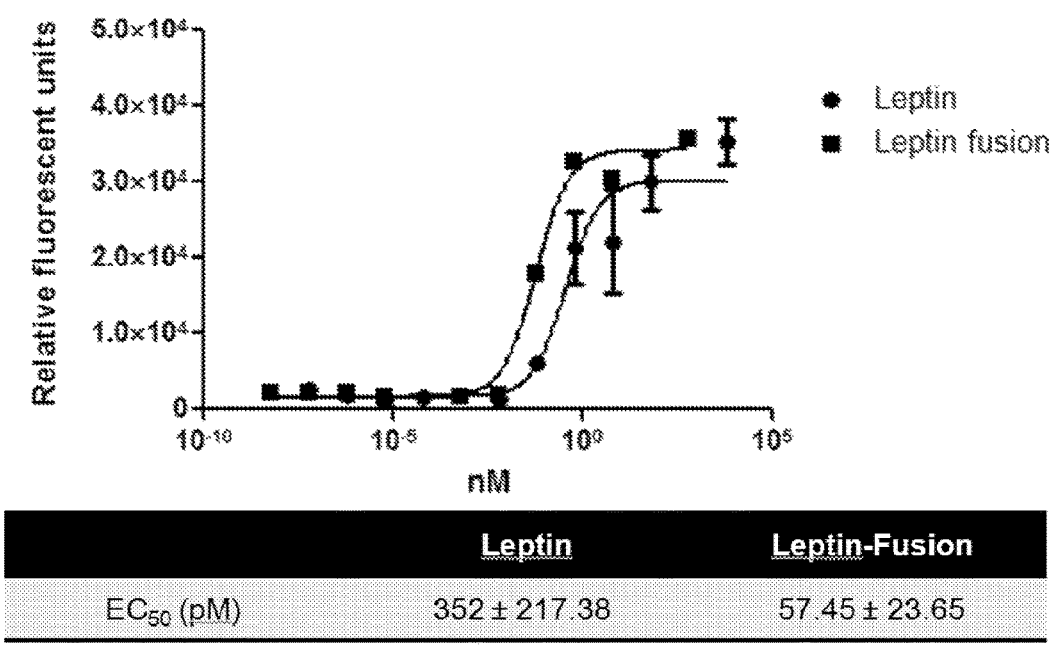

In Vitro Activity of BLV1H12 hLeptin in Leptin Receptor Overexpressing Cell Line Baf3-LepR stable cell line was washed three times by PBS to remove hLeptin and seeded to 96-well plate as 5000 cells/well (in RPMI1640+2% FBS, 100 ul/well). BLV hLeptin fusion protein or human leptin (R&D, used as control) were added into each well from 0.01 pg/ml to 100 ug/ml (10 times concentrated in dose) duplicated in parallel. Multiwell plates were incubated at 37° C. for 72 hrs. AlamarBlue regent (life technologies) was added into each well (10 ul/well) and incubated at 37° C. for 4 hrs. Emission was detected at 590 nm under excitation at 560 nm. Data was analyzed by GraphpadPrizm. Table 11 shows displays the fluorescence intensity of Leptin and BLV1H12 hLeptin IgG. FIG. 7B shows a graphical representation of the data in Table 11. As shown in FIG. 7B, Leptin is represented by a circle and Leptin fusion is represented by a square. The $EC_{50}$ of Leptin was 352±217.38 pM and the $EC_{50}$ of Leptin fusion was 57.45±23.65 pM.

TABLE 11

| Concentration | hLeptin | | Her2 Ab-Leptin fusion | |
|---|---|---|---|---|
| (pg/ml) | nM | Fluorescent reading | nM | Fluorescent Reading |
| 10000000 | 6250 | 38295.18 | 32378.82 | 555.5555 | 43213.7 | 28582.49 |
| 1000000 | 62.5 | 33529.8 | 26397.22 | 5.555555 | 28754.25 | 32516.39 |
| 100000 | 6.25 | 28976.38 | 15315.51 | 0.555556 | 38770.45 | 26796.44 |
| 10000 | 0.625 | 25986.69 | 16493.59 | 0.055556 | 16460.37 | 19492.49 |
| 1000 | 0.0625 | 6998.362 | 5190.263 | 0.005556 | 2293.709 | 2020.082 |
| 100 | 6.25E−03 | 725.125 | 1739.12 | 0.000556 | 1816.013 | 1854.177 |
| 10 | 6.25E−05 | 924.247 | 2110.954 | 5.56E−06 | 1680.684 | 2041.523 |
| 1 | 6.25E−06 | 2188.549 | 237.864 | 5.56E−07 | 2400.505 | 2124.939 |
| 0.1 | 6.25E−07 | 1703.089 | 2010.094 | 5.56E−08 | 2271.716 | 2182.896 |
| 0.01 | 6.25E−08 | 2496.955 | 2518.867 | 5.56E−09 | 2304.249 | 2215.647 |

Example 27

Construction of BLV1H12 Human Relaxin 2 Based Fusion Protein Vectors for Expression in Mammalian Cells A gene encoding human relaxin 2 (hRelaxin2) was synthesized by Genscript or IDT, and amplified by polymerase chain reaction (PCR). To optimize the folding and stability of fusion proteins, flexible linkers of GGGGS (SEQ ID NO: 17) were added on both ends of the hRelaxin2 fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12 hRelaxin2 fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 28

Expression and Purification of BLV1H12 hRelaxin2 Based Fusion Proteins

Figure 8A:
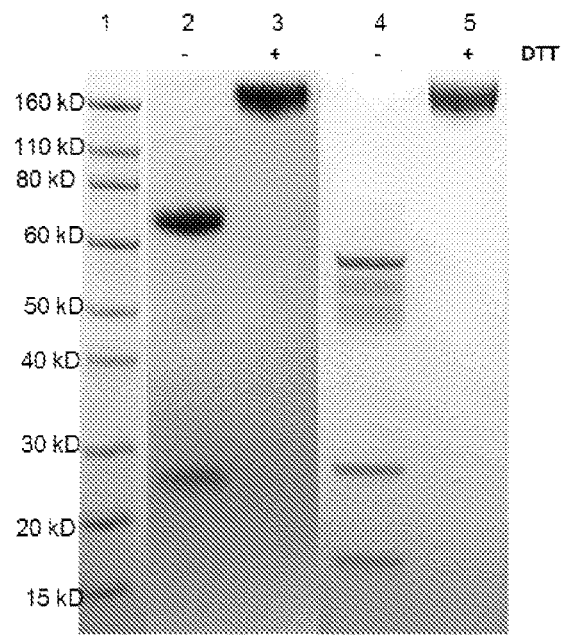

BLV1H12 hRelaxin2 based fusion proteins were expressed through transient transfections of free style HEK293 cells with vectors encoding BLV1H12 hRelaxin2 fusion protein heavy chain and the bovine antibody light chain. Expressed fusion proteins were secreted into the culture medium and harvested at 48 and 96 hours after transfection. The fusion proteins were purified by Protein A/G chromatography (Thermo Fisher Scientific, IL), and analyzed by SDS-PAGE gel (FIG. 8A). As shown in FIG. 8A, Lane 1 contains the protein ladder; Lane 2 contains BLV1H12 hRelaxin2 fusion processed with Factor Xa protein; Lane 3 contains BLV1H12 hRelaxin2 fusion protein processed with Factor Xa and treated with DTT; Lane 4 contains BLV1H12 hRelaxin2 fusion processed with Factor Xa protein and purified twice; and Lane 5 contains BLV1H12 hRelaxin2 fusion protein processed with Factor Xa, purified twice and treated with DTT.

Example 29

Figure 8B:
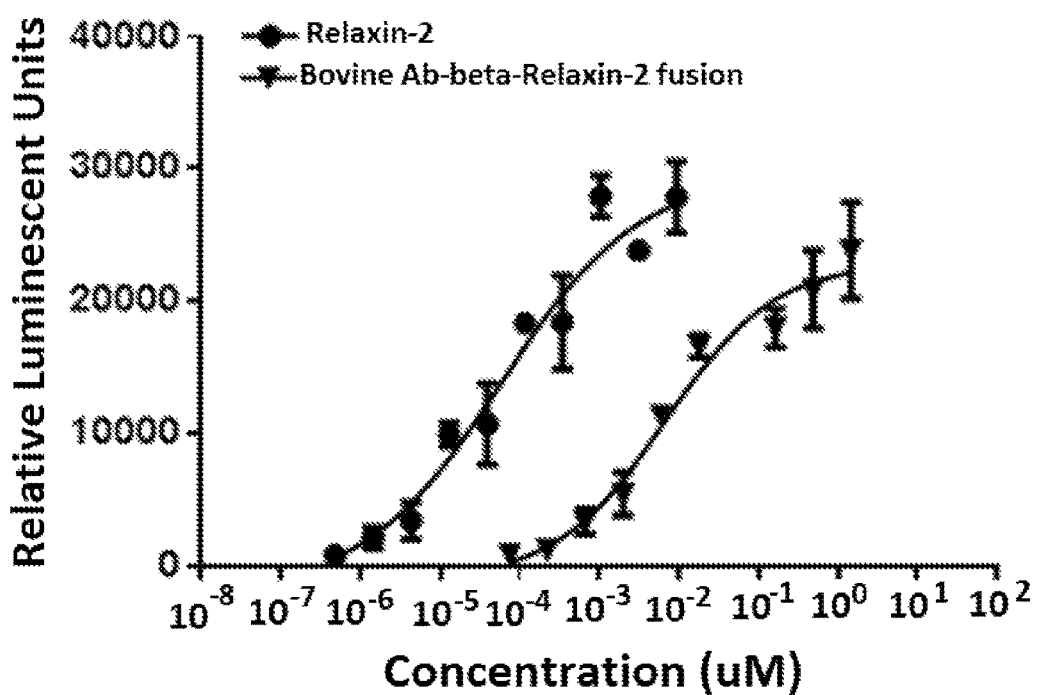

In Vitro Activity of BLV1H12 hRelaxin Fusion in Relaxin Receptor (LGR7) Overexpressing Cell Line 293 stable cells overexpressing relaxin receptor (LGR7) and CRE-responsive luciferase were seeded in a 384-well plate for 24 hours. Cells were subsequently treated with different doses of relaxin-2 or BLV1H12 hRelaxin2 fusion proteins for 24 hours. Luciferase assays were conducted and data were analyzed using GraphPad Prism 6. Results for the luciferase assays are shown in Table 12 and FIG. 8B. As shown in FIG. 8B, circles represent Relaxin2 and upside-down triangles represent BLV1H12 hRelaxin2 fusion proteins that have been cleaved by Factor Xa and purified.

TABLE 12

| Relaxin2 | | | | BLV1H12 hRelaxin 2 cleaved and purified | | | |
|---|---|---|---|---|---|---|---|
| Conc. (uM) | Fluorescence reading | | | Conc. (uM) | Fluorescence reading | | |
| 0.00946 | 30160 | 24880 | 28480 | 1.47 | 23520 | 27600 | 20320 |
| 0.003153 | 24480 | 23280 | 23680 | 0.49 | 23200 | 21840 | 17600 |
| 0.001051 | 29040 | 26800 | | 0.163333 | 16320 | 18480 | 19120 |
| 0.00035 | 21520 | 14560 | 19120 | 0.018148 | 17200 | | 16000 |
| 0.000117 | 18480 | | 18240 | 0.006049 | 11320 | 10800 | 11840 |
| 0.0000389 | 12080 | 7120 | 12800 | 0.002016 | 6720 | 5920 | 3600 |
| 0.000013 | 10800 | 8960 | 9840 | 0.000672 | 2640 | 4400 | 2960 |
| 0.00000433 | 4400 | 2400 | | 0.000224 | 1280 | 1200 | 1040 |
| 0.00000144 | 2880 | 2160 | 1280 | 0.0000747 | 320 | 1440 | 720 |
| 0.000000481 | 1440 | 480 | 560 | | | | |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All references cited herein are incorporated by reference in their entirety and for all purposes to the same extent as if "Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, single-chain Fvs (scFv), Fv, dsFv, diabody (e.g., (ds Fv)$_2$), Fd and Fd' fragments Fab fragments, Fd fragments, scFv fragments, linear antibodies, single-chain antibody molecules, minibodies, flex minibodies, bispecific fragments, and multispecific antibodies formed from antibody fragments (see, for example, Methods in Molecular Biology, Vol 207: Recombinant Antibodies for Cancer Therapy Methods and Protocols (2003); Chapter 1; p 3-25, Kipriyanov). Other known fragments include, but are not limited to, scFab fragments (Hust et al., BMC Biotechnology (2007), 7:14).

A "target protein" or "protein target" may refer to candidate proteins or peptides that are specifically recognized by an antibody or portion thereof and/or whose activity is modulated by an antibody or portion thereof. Modulating the activity can comprise increasing, decreasing, stimulating, or preventing the activity or expression of the target protein. A target protein includes any peptide or protein that contains an epitope for antibody recognition. Target proteins include proteins involved in the etiology of a disease or disorder by virtue of expression or activity. Exemplary target proteins are described herein. In some instances, the target protein is a transmembrane protein target. Transmembrane protein targets include, but are not limited to, GPCRs, ion channels, transporters, and cell surface receptors. Ion channels may be potassium ion channels, sodium ion channels, calcium ion channels, and voltage gated channels. In some instances, the antibodies disclosed herein modulate a Kv1.3 ion channel, Nav1.7 ion channel, or acid sensing ion channel (ASIC). The antibodies disclosed herein may modulate cell surface receptors such as GLP1R, GCGR, EPO receptor, FGFR, FGF21R, CSFR, GMCSFR, and GCSFR. Additional target proteins include, but are not limited to, cytokines, kinases, interferons, hormones, and growth factors. The target proteins can be from a mammal or non-mammal. The target proteins can be from a human. Alternatively, the target proteins are from a bovine.

TABLE 1

Immunoglobulin fusion proteins-Nucleic acid sequence

| Name | SEQ ID NO | Sequence |
|---|---|---|
| Light Chain | 1. | CAGGCCGTCCTGAACCAGCCAAGCAGCGTCTCCGGGTCTC<br>TGGGGCAGCGGGTCTCAATCACCTGTAGCGGGTCTTCCTC<br>CAATGTCGGCAACGGCTACGTGTCTTGGTATCAGCTGATC<br>CCTGGCAGTGCCCCACGAACCCTGATCTACGGCGACACAT<br>CCAGAGCTTCTGGGGTCCCCGATCGGTTCTCAGGGAGCAG<br>ATCCGGAAACACAGCTACTCTGACCATCAGCTCCCTGCAG<br>GCTGAGGACGAAGCAGATTATTTCTGCGCATCTGCCGAGG<br>ACTCTAGTTCAAATGCCGTGTTTGGAAGCGGCACCACACT<br>GACAGTCCTGGGGCAGCCCAAGAGTCCCCCTTCAGTGACT<br>CTGTTCCCACCCTCTACCGAGGAACTGAACGGAAACAAGG<br>CCACACTGGTGTGTCTGATCAGCGACTTTTACCCTGGATCC<br>GTCACTGTGGTCTGGAAGGCAGATGGCAGCACAATTACTA<br>GGAACGTGGAAACTACCCGCGCCTCCAAGCAGTCTAATAG<br>TAAATACGCCGCCAGCTCCTATCTGAGCCTGACCTCTAGT<br>GATTGGAAGTCCAAAGGGTCATATAGCTGCGAAGTGACCC<br>ATGAAGGCTCAACCGTGACTAAGACTGTGAAACCATCCGA<br>GTGCTCC |
| Heavy Chain | 2. | CAGGTCCAGCTGAGAGAGAGCGGCCCTTCACTGGTCA<br>AGCCATCCCAGACACTGAGCCTGACATGCACAGCAAGC<br>GGGTTTTCACTGAGCGACAAGGCAGTGGGATGGGTCC<br>GACAGGCACCAGGAAAAGCCCTGGAATGGCTGGGCAG<br>CATCGATACCGGCGGGAACACAGGGTACAATCCCGGA<br>CTGAAGAGCAGACTGTCCATTACCAAGGACAACTCTAA<br>AAGTCAGGTGTCACTGAGCGTGAGCTCCGTCACCACAG<br>AGGATAGTGCAACTTACTATTGCACCTCT<u>GTGCACCAG</u><br><u>GAAACTAAGAAATACCAGAGCTGTCCTGACGGCTATCG</u><br><u>GGAGAGATCTGATTGCAGTAATAGGCCAGCTTGTGGCA</u><br><u>CATCCGACTGCTGTCGCGTGTCTGTCTTCGGGAACTGC</u><br><u>CTGACTACCCTGCCTGTGTCCTACTCTTATACCTACAAT</u><br><u>TATGAATGGCATGTGGATGTCTGGGGACAGGGCCTGC</u><br>TGGTGACAGTCTCTAGT |
| 550 Fusion HC | 3. | CAGGTCCAGCTGAGAGAGAGCGGCCCTTCACTGGTCA<br>AGCCATCCCAGACACTGAGCCTGACATGCACAGCAAGC<br>GGGTTTTCACTGAGCGACAAGGCAGTGGGATGGGTCC<br>GACAGGCACCAGGAAAAGCCCTGGAATGGCTGGGCAG<br>CATCGATACCGGCGGGAACACAGGGTACAATCCCGGA<br>CTGAAGAGCAGACTGTCCATTACCAAGGACAACTCTAA<br>AAGTCAGGTGTCACTGAGCGTGAGCTCCGTCACCACAG<br>AGGATAGTGCAACTTACTATTGCACCTCT<u>GTGCACCAG</u><br><u>GAAACTAAGAAATACCAGAGC</u>GGGGGTGGCGGAAGCGAA<br><br>*TGCATCGGTATGTTCAAATCTTGCGACCCGGAAAACGACAAAT*<br>*GCTGCAAAGGTCGTACCTGCTCTCGTAAACACCGTTGGTGCAA*<br>*ATACAAACTGGGCGGAGGTGGGAGT*<u>TCTTATACCTACAATT</u><br><br><u>ATGAATGGCATGTGGATGTCTGGGGACAGGGCCTGCT</u> |

TABLE 1-continued

Immunoglobulin fusion proteins-Nucleic acid sequence

| Name | SEQ ID NO | Sequence |
|---|---|---|
| | | GGTGACAGTCTCTAGTGCTTCCACAACTGCACCAAAGG<br>TGTACCCCTGTCAAGCTGCTGTGGGACAAATCCTCT<br>AGTACCGTGACACTGGGATGCCTGGTCTCAAGCTATAT<br>GCCCGAGCCTGTGACTGTCACCTGGAACTCAGGAGCC<br>CTGAAAAGCGGAGTGCACACCTTCCCAGCTGTGCTGCA<br>GTCCTCTGGCCTGTATAGCCTGAGTTCAATGGTGACAG<br>TCCCCGGCAGTACTTCAGGGCAGACCTTCACCTGTAAT<br>GTGGCCCATCCTGCCAGCTCCACCAAAGTGGACAAAGC<br>AGTGGAACCCAAATCTTGCGACAAAACTCACACATGCCC<br>ACCGTGCCCAGCACCTGAACTCCTGGGGGACCGTCAGTC<br>TTCCTCTTCCCCCCAAAACCCAAGGACACCCTCATGATCTC<br>CCGGACCCCTGAGGTCACATGCGTGGTGGTGGACGTGAGC<br>CACGAAGACCCTGAGGTCAAGTTCAACTGGTACGTGGACG<br>GCGTGGAGGTGCATAATGCCAAGACAAAGCCGCGGGAGG<br>AGCAGTACAACAGCACGTACCGTGTGGTCAGCGTCCTCAC<br>CGTCCTGCACCAGGACTGGCTGAATGGCAAGGAGTACAAG<br>TGCAAGGTCTCCAACAAAGCCCTCCCAGCCCCCATCGAGA<br>AAACCATCTCCAAAGCCAAAGGGCAGCCCCGAGAACCAC<br>AGGTGTACACCCTGCCCCCATCCCGGGATGAGCTGACCAA<br>GAACCAGGTCAGCCTGACCTGCCTGGTCAAAGGCTTCTAT<br>CCCAGCGACATCGCCGTGGAGTGGGAGAGCAATGGGCAG<br>CCGGAGAACAACTACAAGACCACGCCTCCCGTGCTGGACT<br>CCGACGGCTCCTTCTTCCTCTACAGCAAGCTCACCGTGGAC<br>AAGAGCAGGTGGCAGCAGGGGAACGTCTTCTCATGCTCCG<br>TGATGCATGAGGCTCTGCACAACCACTACACGCAGAAGAG<br>CCTCTCCCTGTCTCCGGGTAAA |
| Amgen 1<br>Fusion HC | 4. | CAGGTCCAGCTGAGAGAGAGCGGCCCTTCACTGGTCA<br>AGCCATCCCAGACACTGAGCCTGACATGCACAGCAAGC<br>GGGTTTTCACTGAGCGACAAGGCAGTGGGATGGGTCC<br>GACAGGCACCAGGAAAAGCCCTGGAATGGCTGGGCAG<br>CATCGATACCGGCGGGAACACAGGGTACAATCCCGGA<br>CTGAAGAGCAGACTGTCCATTACCAAGGACAACTCTAA<br>AAGTCAGGTGTCACTGAGCGTGAGCTCCGTCACCACAG<br>AGGATAGTGCAACTTACTATTGCACCTCT<u>GTGCACCAG</u><br><u>GAAACTAAGAAATACCAGAGC</u>GGGGGTGGCGAAGCGAC<br>TGCCTGGGTTTCATGCGTAAATGCATCCCGGACAACGACAAAT<br>GCTGCCGTCCGAACCTGGTTTGCTCTCGTACCCACAAATGGTG<br>CAAATACGTTTTCGGCGGAGGTGGGAGT<u>TCTTATACCTACA</u><br><u>ATTATGAATGGCATGTGGATGTCTGGGGACAGGGCCT</u><br>GCTGGTGACAGTCTCTAGTGCTTCCACAACTGCACCAA<br>AGGTGTACCCCTGTCAAGCTGCTGTGGGACAAATCC<br>TCTAGTACCGTGACACTGGGATGCCTGGTCTCAAGCTA<br>TATGCCCGAGCCTGTGACTGTCACCTGGAACTCAGGAG<br>CCCTGAAAAGCGGAGTGCACACCTTCCCAGCTGTGCTG<br>CAGTCCTCTGGCCTGTATAGCCTGAGTTCAATGGTGAC<br>AGTCCCCGGCAGTACTTCAGGGCAGACCTTCACCTGTA<br>ATGTGGCCCATCCTGCCAGCTCCACCAAAGTGGACAAA<br>GCAGTGGAACCCAAATCTTGCGACAAAACTCACACATGC<br>CCACCGTGCCCAGCACCTGAACTCCTGGGGGACCGTCAG<br>TCTTCCTCTTCCCCCCAAAACCCAAGGACACCCTCATGATC<br>TCCCGGACCCCTGAGGTCACATGCGTGGTGGTGGACGTGA<br>GCCACGAAGACCCTGAGGTCAAGTTCAACTGGTACGTGGA<br>CGGCGTGGAGGTGCATAATGCCAAGACAAAGCCGCGGGA |

TABLE 1-continued

Immunoglobulin fusion proteins-Nucleic acid sequence

| Name | SEQ ID NO | Sequence |
|---|---|---|
| | | GGAGCAGTACAACAGCACGTACCGTGTGGTCAGCGTCCTC |
| | | ACCGTCCTGCACCAGGACTGGCTGAATGGCAAGGAGTACA |
| | | AGTGCAAGGTCTCCAACAAAGCCCTCCCAGCCCCCATCGA |
| | | GAAAACCATCTCCAAAGCCAAAGGGCAGCCCCGAGAACC |
| | | ACAGGTGTACACCCTGCCCCCATCCCGGGATGAGCTGACC |
| | | AAGAACCAGGTCAGCCTGACCTGCCTGGTCAAAGGCTTCT |
| | | ATCCCAGCGACATCGCCGTGGAGTGGGAGAGCAATGGGC |
| | | AGCCGGAGAACAACTACAAGACCACGCCTCCCGTGCTGGA |
| | | CTCCGACGGCTCCTTCTTCCTCTACAGCAAGCTCACCGTGG |
| | | ACAAGAGCAGGTGGCAGCAGGGGAACGTCTTCTCATGCTC |
| | | CGTGATGCATGAGGCTCTGCACAACCACTACACGCAGAAG |
| | | AGCCTCTCCCTGTCTCCGGGTAAA |
| Mamba 1 Fusion HC | 5. | CAGGTCCAGCTGAGAGAGAGCGGCCCCTTCACTGGTCA AGCCATCCCAGACACTGAGCCTGACATGCACAGCAAGC GGGTTTTCACTGAGCGACAAGGCAGTGGGATGGGTCC GACAGGCACCAGGAAAAGCCCTGGAATGGCTGGGCAG CATCGATACCGGCGGGAACACAGGGTACAATCCCGGA CTGAAGAGCAGACTGTCCATTACCAAGGACAACTCTAA AAGTCAGGTGTCACTGAGCGTGAGCTCCGTCACCACAG AGGATAGTGCAACTTACTATTGCACCTCTGTGCACCAG GAAACTAAGAAATACCAGAGCGGGGGTGGCGGAAGCCTG AAATGTTACCAACATGGTAAAGTTGTGACTTGTCATCGAGATAT GAAGTTTTGCTATCATAACACTGGCATGCCTTTTCGAAATCTCA AGCTCATCCTACAGGGATGTTCTTCTTCGTGCAGTGAAACAGA AAACAATAAGTGTTGCTCAACAGACAGATGCAACAAAGGCGGA GGTGGGAGTTCTTATACCTACAATTATGAATGGCATGTG GATGTCTGGGGACAGGGCCTGCTGGTGACAGTCTCTA GTGCTTCCACAACTGCACCAAAGGTGTACCCCCTGTCA AGCTGCTGTGGGGACAAATCCTCTAGTACCGTGACACT GGGATGCCTGGTCTCAAGCTATATGCCCGAGCCTGTGA CTGTCACCTGGAACTCAGGAGCCCTGAAAAGCGGAGT GCACACCTTCCCAGCTGTGCTGCAGTCCTCTGGCCTGT ATAGCCTGAGTTCAATGGTGACAGTCCCCGGCAGTACT TCAGGGCAGACCTTCACCTGTAATGTGGCCCATCCTGC CAGCTCCACCAAAGTGGACAAAGCAGTGGAACCCAAAT CTTGCGACAAAACTCACACATGCCCACCGTGCCCAGCACC |
| | | TGAACTCCTGGGGGACCGTCAGTCTTCCTCTTCCCCCCAA |
| | | AACCCAAGGACACCCTCATGATCTCCCGGACCCCTGAGGT |
| | | CACATGCGTGGTGGTGGACGTGAGCCACGAAGACCCTGAG |
| | | GTCAAGTTCAACTGGTACGTGGACGGCGTGGAGGTGCATA |
| | | ATGCCAAGACAAAGCCGCGGGAGGAGCAGTACAACAGCA |
| | | CGTACCGTGTGGTCAGCGTCCTCACCGTCCTGCACCAGGA |
| | | CTGGCTGAATGGCAAGGAGTACAAGTGCAAGGTCTCCAAC |
| | | AAAGCCCTCCCAGCCCCCATCGAGAAAACCATCTCCAAAG |
| | | CCAAAGGGCAGCCCCGAGAACCACAGGTGTACACCCTGCC |
| | | CCCATCCCGGGATGAGCTGACCAAGAACCAGGTCAGCCTG |
| | | ACCTGCCTGGTCAAAGGCTTCTATCCCAGCGACATCGCCG |
| | | TGGAGTGGGAGAGCAATGGGCAGCCGGAGAACAACTACA |
| | | AGACCACGCCTCCCGTGCTGGACTCCGACGGCTCCTTCTTC |
| | | CTCTACAGCAAGCTCACCGTGGACAAGAGCAGGTGGCAGC |

TABLE 1-continued

Immunoglobulin fusion proteins-Nucleic acid sequence

| Name | SEQ ID NO | Sequence |
|---|---|---|
| | | AGGGGAACGTCTTCTCATGCTCCGTGATGCATGAGGCTCT |
| | | GCACAACCACTACACGCAGAAGAGCCTCTCCCTGTCTCCG |
| | | GGTAAA |
| Oxyntomodulin Fusion HC | 6. | CAGGTCCAGCTGAGAGAGAGCGGCCCTTCACTGGTCA<br>AGCCATCCCAGACACTGAGCCTGACATGCACAGCAAGC<br>GGGTTTTCACTGAGCGACAAGGCAGTGGGATGGGTCC<br>GACAGGCACCAGGAAAAGCCCTGGAATGGCTGGGCAG<br>CATCGATACCGGCGGGAACACAGGGTACAATCCCGGA<br>CTGAAGAGCAGACTGTCCATTACCAAGGACAACTCTAA<br>AAGTCAGGTGTCACTGAGCGTGAGCTCCGTCACCACAG<br>AGGATAGTGCAACTTACTATTGCACCTCT<u>GTGCACCAG</u><br><u>GAAACTAAGAAATACCAGAGC</u>*GGGGGTGGCGGAAGCCAC*<br>*TCTCAGGGTACCTTCACCTCTGACTACTCTAAATACCTGGACTC*<br>*TCGTCGTGCTCAGGACTTCGTTCAGTGGCTGATGAACACCAAA*<br>*CGTAACCGTAACAACATCGCTGGCGGAGGTGGGAGT*TCTTAT<br>ACCTACAATTATGAATGGCATGTGGATGTCTGGGGACA<br>GGGCCTGCTGGTGACAGTCTCTAGTGCTTCCACAACTG<br>CACCAAAGGTGTACCCCCTGTCAAGCTGCTGTGGGGAC<br>AAATCCTCTAGTACCGTGACACTGGGATGCCTGGTCTC<br>AAGCTATATGCCCGAGCCTGTGACTGTCACCTGGAACT<br>CAGGAGCCCTGAAAAGCGGAGTGCACACCTTCCCAGC<br>TGTGCTGCAGTCCTCTGGCCTGTATAGCCTGAGTTCAA<br>TGGTGACAGTCCCCGGCAGTACTTCAGGGCAGACCTTC<br>ACCTGTAATGTGGCCCATCCTGCCAGCTCCACCAAAGT<br>GGACAAAGCAGTGGAACCCAAATCTTGCGACAAAACTC<br>ACACATGCCCACCGTGCCCAGCACCTGAACTCCTGGGGGG<br>ACCGTCAGTCTTCCTCTTCCCCCCAAAACCCAAGGACACC<br>CTCATGATCTCCCGGACCCCTGAGGTCACATGCGTGGTGG<br>TGGACGTGAGCCACGAAGACCCTGAGGTCAAGTTCAACTG<br>GTACGTGGACGGCGTGGAGGTGCATAATGCCAAGACAAA<br>GCCGCGGGAGGAGCAGTACAACAGCACGTACCGTGTGGT<br>CAGCGTCCTCACCGTCCTGCACCAGGACTGGCTGAATGGC<br>AAGGAGTACAAGTGCAAGGTCTCCAACAAAGCCCTCCCAG<br>CCCCCATCGAGAAAACCATCTCCAAAGCCAAAGGGCAGCC<br>CCGAGAACCACAGGTGTACACCCTGCCCCCATCCCGGGAT<br>GAGCTGACCAAGAACCAGGTCAGCCTGACCTGCCTGGTCA<br>AAGGCTTCTATCCCAGCGACATCGCCGTGGAGTGGGAGAG<br>CAATGGGCAGCCGGAGAACAACTACAAGACCACGCCTCC<br>CGTGCTGGACTCCGACGGCTCCTTCTTCCTCTACAGCAAGC<br>TCACCGTGGACAAGAGCAGGTGGCAGCAGGGGAACGTCT<br>TCTCATGCTCCGTGATGCATGAGGCTCTGCACAACCACTA<br>CACGCAGAAGAGCCTCTCCCTGTCTCCGGGTAAA |
| Parathyroid (PTH) Fusion HC | 7. | CAGGTCCAGCTGAGAGAGAGCGGCCCTTCACTGGTCA<br>AGCCATCCCAGACACTGAGCCTGACATGCACAGCAAGC<br>GGGTTTTCACTGAGCGACAAGGCAGTGGGATGGGTCC<br>GACAGGCACCAGGAAAAGCCCTGGAATGGCTGGGCAG<br>CATCGATACCGGCGGGAACACAGGGTACAATCCCGGA<br>CTGAAGAGCAGACTGTCCATTACCAAGGACAACTCTAA<br>AAGTCAGGTGTCACTGAGCGTGAGCTCCGTCACCACAG<br>AGGATAGTGCAACTTACTATTGCACCTCT<u>GTGCACCAG</u><br><u>GAAACTAAGAAATACCAGAGC</u>*GGGGGTGGCGGAAGCTCT*<br>*GTGAGTGAAATACAGCTTATGCATAACCTGGGAAAACATCTGA*<br>*ACTCGATGGAGAGAGTAGAATGGCTGCGTAAGAAGCTGCAGG* |

TABLE 1-continued

Immunoglobulin fusion proteins-Nucleic acid sequence

| Name | SEQ ID NO | Sequence |
|---|---|---|
| | | *ATGTGCACAATTTGTTGCCCTTGGAGCTCCTCTAGCTCCCAG* |
| | | *AGATGCTGGTTCCCAGAGGCCCCGAAAAAAGGAAGACAATGT* |
| | | *CTTGGTTGAGAGCCATGAAAAAAGTCTTGGAGAGGCAGACAAA* |
| | | *GCTGATGTGAATGTATTAACTAAAGCTAAATCCCAGGGCGGAG* |
| | | *GTGGGAGT*TCTTATACCTACAATTATGAATGGCATGTGG |
| | | ATGTCTGGGACAGGGCCTGCTGGTGACAGTCTCTAGT |
| | | GCTTCCACAACTGCACCAAAGGTGTACCCCCTGTCAAG |
| | | CTGCTGTGGGGACAAATCCTCTAGTACCGTGACACTGG |
| | | GATGCCTGGTCTCAAGCTATATGCCCGAGCCTGTGACT |
| | | GTCACCTGGAACTCAGGAGCCCTGAAAAGCGGAGTGC |
| | | ACACCTTCCCAGCTGTGCTGCAGTCCTCTGGCCTGTAT |
| | | AGCCTGAGTTCAATGGTGACAGTCCCCGGCAGTACTTC |
| | | AGGGCAGACCTTCACCTGTAATGTGGCCCATCCTGCCA |
| | | GCTCCACCAAAGTGGACAAAGCAGTGGAACCCAAATCT |
| | | TGCGACAAAACTCACACATGCCCACCGTGCCCAGCACCTG |
| | | AACTCCTGGGGGACCGTCAGTCTTCCTCTTCCCCCCAAA |
| | | ACCCAAGGACACCCTCATGATCTCCCGGACCCCTGAGGTC |
| | | ACATGCGTGGTGGTGGACGTGAGCCACGAAGACCCTGAG |
| | | GTCAAGTTCAACTGGTACGTGGACGGCGTGGAGGTGCATA |
| | | ATGCCAAGACAAAGCCGCGGGAGGAGCAGTACAACAGCA |
| | | CGTACCGTGTGGTCAGCGTCCTCACCGTCCTGCACCAGGA |
| | | CTGGCTGAATGGCAAGGAGTACAAGTGCAAGGTCTCCAAC |
| | | AAAGCCCTCCCAGCCCCCATCGAGAAAACCATCTCCAAAG |
| | | CCAAAGGGCAGCCCCGAGAACCACAGGTGTACACCCTGCC |
| | | CCCATCCCGGGATGAGCTGACCAAGAACCAGGTCAGCCTG |
| | | ACCTGCCTGGTCAAAGGCTTCTATCCCAGCGACATCGCCG |
| | | TGGAGTGGGAGAGCAATGGGCAGCCGGAGAACAACTACA |
| | | AGACCACGCCTCCCGTGCTGGACTCCGACGGCTCCTTCTTC |
| | | CTCTACAGCAAGCTCACCGTGGACAAGAGCAGGTGGCAGC |
| | | AGGGGAACGTCTTCTCATGCTCCGTGATGCATGAGGCTCT |
| | | GCACAACCACTACACGCAGAAGAGCCTCTCCCTGTCTCCG |
| | | GGTAAA |

For SEQ ID NOs: 2-7
bovine heavy chain sequence = bold
human heavy chain sequence = dashed underline
non-antibody sequence = *italic*
Stalk = bold, underline;
knob = bold, double underline;
linker = *italic, squiggly underline*

TABLE 2

Immunoglobulin fusion proteins-Amino acid sequence

| Name | SEQ ID NO | Sequence |
|---|---|---|
| Light Chain | 8. | QAVLNQPSSVSGSLGQRVSITCSGSSSNVGNGYVSWYQLIPG SAPRTLIYGDTSRASGVPDRFSGSRSGNTATLTISSLQAEDEA DYFCASAEDSSSNAVFGSGTTLTVLGQPKSPPSVTLFPPSTEE LNGNKATLVCLISDFYPGSVTVVWKADGSTITRNVETTRASK QSNSKYAASSYLSLTSSDWKSKGSYSCEVTHEGSTVTKTVKP SECS |
| Heavy Chain-no insert | 9. | QVQLRESGPSLVKPSQTLSLTCTASGFSLSDKAVGWVRQA PGKALEWLGSIDTGGNTGYNPGLKSRLSITKDNSKSQVSL SVSSVTTEDSATYYCTSVHQETKKYQ*SCPDGYRERSDCSNR PACGTSDCCRVSVFGNCLTTLPVSYS*YTYNYEWHVDVWGQ GLLVTVSS |

TABLE 2-continued

Immunoglobulin fusion proteins-Amino acid sequence

| Name | SEQ ID NO | Sequence |
|------|-----------|----------|
| 550 Fusion HC | 10. | QVQLRESGPSLVKPSQTLSLTCTASGFSLSDKAVGWVRQA PGKALEWLGSIDTGGNTGYNPGLKSRLSITKDNSKSQVSL SVSSVTTEDSATYYCT<u>SVHQETKKYQS</u>*GGGGS*<u>ECIGMFKSC DPENDKCCKGRTCSRKHRWCKYKL</u>*GGGGS*<u>SYTYNYEW</u>HVD VWGQGLLVTVSSASTTAPKVYPLSSCCGDKSSSTVTLGCL VSSYMPEPVTVTWNSGALKSGVHTFPAVLQSSGLYSLSSM VTVPGSTSGQTFTCNVAHPASSTKVDKAVEPKS<u>CDKTHTC PPCPAPELLGGPSVFLFPPKPKDTLMISRTPEVTCVVVDVSHE DPEVKFNWYVDGVEVHNAKTKPREEQYNSTYRVVSVLTVL HQDWLNGKEYKCKVSNKALPAPIEKTISKAKGQPREPQVYT LPPSRDELTKNQVSLTCLVKGFYPSDIAVEWESNGQPENNYK TTPPVLDSDGSFFLYSKLTVDKSRWQQGNVFSCSVMHEALH NHYTQKSLSLSPGK</u> |
| Amgen1 Fusion HC | 11. | QVQLRESGPSLVKPSQTLSLTCTASGFSLSDKAVGWVRQA PGKALEWLGSIDTGGNTGYNPGLKSRLSITKDNSKSQVSL SVSSVTTEDSATYYCT<u>SVHQETKKYQS</u>*GGGGS*<u>DCLGFMRK CIPDNDKCCRPNLVCSRTHKWCKYVF</u>*GGGGS*<u>SYTYNYEW</u>HV DVWGQGLLVTVSSASTTAPKVYPLSSCCGDKSSSTVTLGC LVSSYMPEPVTVTWNSGALKSGVHTFPAVLQSSGLYSLSS MVTVPGSTSGQTFTCNVAHPASSTKVDKAVEPKS<u>CDKTHT CPPCPAPELLGGPSVFLFPPKPKDTLMISRTPEVTCVVVDVSH EDPEVKFNWYVDGVEVHNAKTKPREEQYNSTYRVVSVLTV LHQDWLNGKEYKCKVSNKALPAPIEKTISKAKGQPREPQVY TLPPSRDELTKNQVSLTCLVKGFYPSDIAVEWESNGQPENNY KTTPPVLDSDGSFFLYSKLTVDKSRWQQGNVFSCSVMHEAL HNHYTQKSLSLSPGK</u> |
| Mamba1 Fusion HC | 12. | QVQLRESGPSLVKPSQTLSLTCTASGFSLSDKAVGWVRQA PGKALEWLGSIDTGGNTGYNPGLKSRLSITKDNSKSQVSL SVSSVTTEDSATYYCT<u>SVHQETKKYQS</u>*GGGGS*<u>LKCYQHGKV VTCHRDMKFCYHNTGMPFRNLKLILQGCSSSCSETENNKCCSTD RCNKG</u>*GGGGS*<u>SYTYNYEW</u>HVDVWGQGLLVTVSSASTTAPK VYPLSSCCGDKSSSTVTLGCLVSSYMPEPVTVTWNSGALK SGVHTFPAVLQSSGLYSLSSMVTVPGSTSGQTFTCNVAHP ASSTKVDKAVEPKS<u>CDKTHTCPPCPAPELLGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGK</u> |
| Oxyntomodulin Fusion HC | 13. | QVQLRESGPSLVKPSQTLSLTCTASGFSLSDKAVGWVRQA PGKALEWLGSIDTGGNTGYNPGLKSRLSITKDNSKSQVSL SVSSVTTEDSATYYCT<u>SVHQETKKYQS</u>*GGGGS*<u>HSQGTFTSD YSKYLDSRRAQDFVQWLMNTKRNRNNIA</u>*GGGGS*<u>SYTYNYEW</u>H VDVWGQGLLVTVSSASTTAPKVYPLSSCCGDKSSSTVTLG CLVSSYMPEPVTVTWNSGALKSGVHTFPAVLQSSGLYSLS SMVTVPGSTSGQTFTCNVAHPASSTKVDKAVEPKS<u>CDKTH TCPPCPAPELLGGPSVFLFPPKPKDTLMISRTPEVTCVVVDVS HEDPEVKFNWYVDGVEVHNAKTKPREEQYNSTYRVVSVLT VLHQDWLNGKEYKCKVSNKALPAPIEKTISKAKGQPREPQV YTLPPSRDELTKNQVSLTCLVKGFYPSDIAVEWESNGQPENN YKTTPPVLDSDGSFFLYSKLTVDKSRWQQGNVFSCSVMHEA LHNHYTQKSLSLSPGK</u> |
| Parathyroid (PTH) Fusion HC | 14. | QVQLRESGPSLVKPSQTLSLTCTASGFSLSDKAVGWVRQA PGKALEWLGSIDTGGNTGYNPGLKSRLSITKDNSKSQVSL SVSSVTTEDSATYYCT<u>SVHQETKKYQS</u>*GGGGS*<u>SVSEIQLMH NLGKHLNSMERVEWLRKKLQDVHNFVALGAPLAPRDAGSQRPR KKEDNVLVESHEKSLGEADKADVNVLTKAKSQ</u>*GGGGS*<u>SYTYNY EW</u>HVDVWGQGLLVTVSSASTTAPKVYPLSSCCGDKSSST VTLGCLVSSYMPEPVTVTWNSGALKSGVHTFPAVLQSSG LYSLSSMVTVPGSTSGQTFTCNVAHPASSTKVDKAVEPKS<u>CDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGNVFSCSV MHEALHNHYTQKSLSLSPGK</u> |

For SEQ ID NOs: 9-14
bovine heavy chain sequence = bold
human heavy chain sequence = <u>dashed underline</u>
non-antibody sequence = *italic*
Stalk = <u>bold, underline</u>; knob = <u>bold, double underline</u>;
linker = *italic, squiggly underline*

TABLE 3

| Name | SEQ ID NO | Sequence |
| --- | --- | --- |
| Linker1 | 15 | GGGSGGGGS |
| Linker2 | 16 | GGGGSGGGS |
| Linker3 | 17 | (GGGGS)n |

TABLE 4

| Description | SEQ ID NO | Sequence |
| --- | --- | --- |
| Stalk1A | 18 | TSVHQETKKYQ |
| Stalk1B | 19 | VHQETKKYQ |
| Stalk1C | 20 | TTVHQ |
| Stalk1D | 21 | TSVHQ |
| Stalk1E | 22 | VHQ |
| Stalk1F | 23 | KKQ |
| Stalk1G | 24 | VYQ |
| Stalk1H | 25 | CTTVHQXn |
| Stalk1I | 26 | CTSVHQXn |
| Stalk1J | 27 | $CX^1X^2X^3X^4Q$ |
| Stalk1K | 28 | $X^1X^2VHQ$ |
| Stalk1L | 29 | $CX^1X^2VHQ$ |
| Stalk1M | 30 | $X^1X^2VX^3Q$ |
| Stalk1N | 31 | $CX^1X^2VX^3Q$ |
| Stalk1O | 32 | $X^1X^2KKQ$ |
| Stalk1P | 33 | $CX^1X^2KKQ$ |
| Stalk2A | 34 | YTYNYEW |
| Stalk2B | 35 | YTYNYE |
| Stalk2C | 36 | YLYTYEH |
| Stalk2D | 37 | YLYTYE |
| Stalk2E | 38 | $YX^1YX^2$ |
| Stalk2F | 39 | $YX^1YX^2Y$ |
| Stalk2G | 40 | $YX^1YX^2YX^3$ |
| Stalk2H | 41 | $YX^1YX^2YX3X^4$ |
| Stalk2I | 42 | YEX |
| Stalk2J | 43 | YDX |
| Stalk2K | 44 | XYE |
| Stalk2L | 45 | XYD |
| Stalk2M | 46 | $Y(E/D)X^1 XnW$ |
| Stalk2N | 47 | $Y(E/D)X^1X^2X^3X^4X5W$ |

TABLE 5

| SEQ ID NO | SEQUENCE |
| --- | --- |
| 48 | $CX_{10}CX_5CX_5CXCX_7C$ |
| 49 | $CX_{10}CX_6CX_5CXCX_{15}C$ |
| 50 | $CX_{11}CXCX5C$ |
| 51 | $CX_{11}CX_5CX_5CXCX_7C$ |
| 52 | $CX_{10}CX_6CX_5CXCX_{13}C$ |
| 53 | $CX_{10}CX_5CXCX_4CX_8C$ |
| 54 | $CX_{10}CX_6CX_6CXCX_7C$ |
| 55 | $CX_{10}CX_4CX_7CXCX_8C$ |
| 56 | $CX_{10}CX_4CX_7CXCX_7C$ |
| 57 | $CX_{13}CX_8CX_8C$ |
| 58 | $CX_{10}CX_6CX_5CXCX_7C$ |
| 59 | $CX_{10}CX_5CX_5C$ |
| 60 | $CX_{10}CX_5CX_6CXCX_7C$ |
| 61 | $CX_{10}CX_6CX_5CX_7CX_9C$ |
| 62 | $CX_9CX_7CX_5CXCX_7C$ |
| 63 | $CX_{10}CX_6CX_5CXCX_9C$ |
| 64 | $CX_{10}CXCX_4CX_5CX_{11}C$ |
| 65 | $CX_7CX_3CX_6CX_5CXCX_5CX_{10}C$ |
| 66 | $CX_{10}CXCX_4CX_5CXCX_2CX_3C$ |
| 67 | $CX_{16}CX_5CXC$ |
| 68 | $CX_6CX_2CXCX_4CX_5C$ |
| 69 | $CX_{11}CX_4CX_5CX_6CX_3C$ |
| 70 | $CX_8CX_2CX_6CX_5C$ |
| 71 | $CX_{10}CX_5CX_5CXCX_{10}C$ |
| 72 | $CX_{10}CXCX_6CX_4CXC$ |
| 73 | $CX_{10}CX_5CX_5CXCX_2C$ |
| 74 | $CX_{14}CX_2CX_3CXCXC$ |
| 75 | $CX_{15}CX_5CXC$ |
| 76 | $CX_4CX_6CX_9CX_2CX_{11}C$ |
| 77 | $CX_6CX_4CX_5CX_5CX_{12}C$ |
| 78 | $CX_7CX_3CXCXCX_4CX_5CX_9C$ |
| 79 | $CX_{10}CX_6CX_5C$ |
| 80 | $CX_7CX_3CX_5CX_5CX_9C$ |
| 81 | $CX_7CX_5CXCX_2C$ |
| 82 | $CX_{10}CXCX_6C$ |
| 83 | $CX_{10}CX_3CX_3CX_5CX_7CXCX_6C$ |
| 84 | $CX_{10}CX_4CX_5CX_{12}CX_2C$ |
| 85 | $CX_{12}CX_4CX_5CXCXCX_9CX_3C$ |
| 86 | $CX_{12}CX_4CX_5CX_{12}CX_2C$ |

TABLE 5-continued

| SEQ ID NO | SEQUENCE |
|---|---|
| 87 | $CX_{10}CX_6CX_5CXCX_{11}C$ |
| 88 | $CX_{16}CX_5CXCXCX_{14}C$ |
| 89 | $CX_{10}CX_5CXCX_8CX_6C$ |
| 90 | $CX_{12}CX_4CX_5CX_8CX_2C$ |
| 91 | $CX_{12}CX_5CX_5CXCX_8C$ |
| 92 | $CX_{10}CX_6CX_5CXCX_4CXCX_9C$ |
| 93 | $CX_{11}CX_4CX_5CX_8CX_2C$ |
| 94 | $CX_{10}CX_6CX_5CX_8CX_2C$ |
| 95 | $CX_{10}CX_6CX_5CXCX_8C$ |
| 96 | $CX_{10}CX_6CX_5CXCX_3CX_8CX_2C$ |
| 97 | $CX_{10}CX_6CX_5CXCX_2CX_6CX_5C$ |
| 98 | $CX_{10}CX_6CX_5CX_3CX_8C$ |
| 99 | $CX_7CX_6CX_3CX_3CX_9C$ |
| 100 | $CX_9CX_8CX_5CX_6CX_5C$ |
| 101 | $CX_{10}CX_2CX_2CX_7CXCX_{11}CX_5C$ |
| 102 | $CX_{10}CX_6CX_5CXCX_2CX_8CX_4C$ |

TABLE 6

Immunoglobulin fusion protein-Nucleotide Sequence

| NAME | SEQ ID NO | SEQUENCE |
|---|---|---|
| Betatrophin L2 Fusion HC | 103 | CAGGTCCAGCTGAGAGAGAGCGGCCCTTCACTGGTCA AGCCATCCCAGACACTGAGCCTGACATGCACAGCAAG CGGGTTTTCACTGAGCGACAAGGCAGTGGGATGGGTC CGACAGGCACCAGGAAAAGCCCTGGAATGGCTGGGC AGCATCGATACCGGCGGGAACACAGGGTACAATCCCG GACTGAAGAGCAGACTGTCCATTACCAAGGACAACTC TAAAAGTCAGGTGTCACTGAGCGTGAGCTCCGTCACC ACAGAGGATAGTGCAACTTACTATTGCACCTCTGTGC ACCAGGAAACTAAGAAATACCAGAGC<u>GGGGGTGGCGG</u> <u>AAGCGGGGGTGGCGG</u>AAGCGCTCCTCTGGGCGGTCCTGAA CCAGCACAGTACGAGGAACTGACACTGTTGTTCCATGGAGCC TTGCAGCTGGGCCAGGCCCTCAACGGCGTGTACCGCGCCAC AGAGGCACGTTTGACCGAGGCCGGACACAGCCTGGGTTTGT ACGACAGAGCCCTGGAGTTTCTGGGTACCGAAGTGCGTCAG GGCCAGGACGCAACTCAGGAGCTGAGAACCTCCCTCTCTGA GATCCAGGTGGAGGAGGACGCCCCTGCACCTGCGCGCCGAG GCGACAGCACGCTCTTTGGGAGAAGTTGCTCGCGCTCAGCA GGGCCTGCGTGATACCGTGCGGAGACTCCAAGTTCAGCTCA GAGGCGCTTGGCTCGGACAGGCGCATCAGGAGTTCGAGACC CTGAAAGCTCGTGCCGACAAACAGTCCCACCTGCTGTGGGC GCTCACCGGTCACGTCCAGCGCCAGCAACGCGAAATGGCCG AGCAGCAGCAATGGCTGCGCCAAATCCAGCAGCGCCTGCAT ACCGCGGCCCTGCCAGCGTAAGGCGGAGGTGGGAGTGGCG GAGGTGGGAGT<u>TCTTATACCTACAATTATGAATGGCAT</u> GTGGATGTCTGGGGACAGGGCCTGCTGGTGACAGTCT CTAGTGCTTCCACAACTGCACCAAAGGTGTACCCCCT GTCAAGCTGCTGTGGGGACAAATCCTCTAGTACCGTG ACACTGGGATGCCTGGTCTCAAGCTATATGCCCGAGC CTGTGACTGTCACCTGGAACTCAGGAGCCCTGAAAAG CGGAGTGCACACCTTCCCAGCTGTGCTGCAGTCCTCT GGCCTGTATAGCCTGAGTTCAATGGTGACAGTCCCCG GCAGTACTTCAGGGCAGACCTTCACCTGTAATGTGGC CCATCCTGCCAGCTCCACCAAAGTGGACAAAGCAGTG GAACCCAAATCTTGC<u>GACAAAACTCACACATGCCCACC</u> <u>GTGCCCAGCACCTGAACTCCTGGGGGGACCGTCAGTCTT</u> <u>CCTCTTCCCCCCAAAACCCAAGGACACCCTCATGATCTCC</u> <u>CGGACCCCTGAGGTCACATGCGTGGTGGTGGACGTGAGC</u> <u>CACGAAGACCCTGAGGTCAAGTTCAACTGGTACGTGGAC</u> <u>GGCGTGGAGGTGCATAATGCCAAGACAAAGCCGCGGGA</u> <u>GGAGCAGTACAACAGCACGTACCGTGTGGTCAGCGTCCT</u> <u>CACCGTCCTGCACCAGGACTGGCTGAATGGCAAGGAGTA</u> <u>CAAGTGCAAGGTCTCCAACAAAGCCCTCCCAGCCCCCAT</u> <u>CGAGAAAACCATCTCCAAAGCCAAAGGGCAGCCCCGAG</u> <u>AACCACAGGTGTACACCCTGCCCCCATCCCGGGATGAGC</u> <u>TGACCAAGAACCAGGTCAGCCTGACCTGCCTGGTCAAAG</u> <u>GCTTCTATCCCAGCGACATCGCCGTGGAGTGGGAGAGCA</u> <u>ATGGGCAGCCGGAGAACAACTACAAGACCACGCCTCCCG</u> <u>TGCTGGACTCCGACGGCTCCTTCTTCCTCTACAGCAAGCT</u> <u>CACCGTGGACAAGAGCAGGTGGCAGCAGGGGAACGTCTT</u> <u>CTCATGCTCCGTGATGCATGAGGCTCTGCACAACCACTAC</u> <u>ACGCAGAAGAGCCTCTCCCTGTCTCCGGGTAAA</u> |

TABLE 6-continued

Immunoglobulin fusion protein-Nucleotide Sequence

| NAME | SEQ ID NO | SEQUENCE |
|---|---|---|
| Betatrophin L1 Fusion HC | 104 | CAGGTCCAGCTGAGAGAGAGCGGCCCTTCACTGGTCA<br>AGCCATCCCAGACACTGAGCCTGACATGCACAGCAAG<br>CGGGTTTTCACTGAGCGACAAGGCAGTGGGATGGGTC<br>CGACAGGCACCAGGAAAAGCCCTGGAATGGCTGGGC<br>AGCATCGATACCGGCGGGAACACAGGGTACAATCCCG<br>GACTGAAGAGCAGACTGTCCATTACCAAGGACAACTC<br>TAAAAGTCAGGTGTCACTGAGCGTGAGCTCCGTCACC<br>ACAGAGGATAGTGCAACTTACTATTGCACCTCTGTGC<br>ACCAGGAAACTAAGAAATACCAGAGC<u>GGGGGTGGCGG</u><br><u>AAGCGCTCCTCTGGGCGGTCCTGAACCAGCACAGTACGAGG</u><br>AACTGACACTGTTGTTCCATGGAGCCTTGCAGCTGGGCCAG<br>GCCCTCAACGGCGTGTACCGCGCCACAGAGGCACGTTTGAC<br>CGAGGCCGGACACAGCCTGGGTTTGTACGACAGAGCCCTGG<br><br>AGTTTCTGGGTACCGAAGTGCGTCAGGGCCAGGACGCAACT<br>CAGGAGCTGAGAACCTCCCTCTCTGAGATCCAGGTGGAGGA<br>GGACGCCCTGCACCTGCGCGCCGAGGCGACAGCACGCTCT<br>TTGGAGAAGTTGCTCGCGCTCAGCAGGCCCTGCGTGATAC<br>CGTGCGGAGACTCCAAGTTCAGCTCAGAGGCGCTTGGCTCG<br>GACAGGCGCATCAGGAGTTCGAGACCCTGAAAGCTCGTGCC<br>GACAAACAGTCCCACCTGCTGTGGGCGCTCACCGGTCACGT<br>CCAGCGCCAGCAACGCGAAATGGCCGAGCAGCAGCAATGG<br>CTGCGCCAAATCCAGCAGCGCCTGCATACCGCGGCCCTGCC<br>AGCGTAAGGCGGAGGTGGGAGT<u>TCT</u>TATACCTACAATTA<br>TGAATGGCATGTGGATGTCTGGGGACAGGGCCTGCTG<br>GTGACAGTCTCTAGTGCTTCCACAACTGCACCAAAGG<br>TGTACCCCCTGTCAAGCTGCTGTGGGGACAAATCCTC<br>TAGTACCGTGACACTGGGATGCCTGGTCTCAAGCTAT<br>ATGCCCGAGCCTGTGACTGTCACCTGGAACTCAGGAG<br>CCCTGAAAAGCGGAGTGCACACCTTCCCAGCTGTGCT<br>GCAGTCCTCTGGCCTGTATAGCCTGAGTTCAATGGTG<br>ACAGTCCCCGGCAGTACTTCAGGGCAGACCTTCACCT<br>GTAATGTGGCCCATCCTGCCAGCTCCACCAAAGTGGA<br><br>CAAAGCAGTGGAACCCAAATCTTGC<u>GACAAAACTCAC</u><br><u>ACATGCCCACCGTGCCCAGCACCTGAACTCCTGGGGGGA</u><br><u>CCGTCAGTCTTCCTCTTCCCCCCAAAACCCAAGGACACCC</u><br><u>TCATGATCTCCCGGACCCCTGAGGTCACATGCGTGGTGGT</u><br><u>GGACGTGAGCCACGAAGACCCTGAGGTCAAGTTCAACTG</u><br><u>GTACGTGGACGGCGTGGAGGTGCATAATGCCAAGACAAA</u><br><u>GCCGCGGGAGGAGCAGTACAACAGCACGTACCGTGTGGT</u><br><u>CAGCGTCCTCACCGTCCTGCACCAGGACTGGCTGAATGG</u><br><u>CAAGGAGTACAAGTGCAAGGTCTCCAACAAAGCCCTCCC</u><br><u>AGCCCCCATCGAGAAAACCATCTCCAAAGCCAAAGGGCA</u><br><u>GCCCCGAGAACCACAGGTGTACACCCTGCCCCCATCCCG</u><br><u>GGATGAGCTGACCAAGAACCAGGTCAGCCTGACCTGCCT</u><br><u>GGTCAAAGGCTTCTATCCCAGCGACATCGCCGTGGAGTG</u><br><u>GGAGAGCAATGGGCAGCCGGAGAACAACTACAAGACCA</u><br><u>CGCCTCCCGTGCTGGACTCCGACGGCTCCTTCTTCCTCTA</u><br><u>CAGCAAGCTCACCGTGGACAAGAGCAGGTGGCAGCAGG</u><br><u>GGAACGTCTTCTCATGCTCCGTGATGCATGAGGCTCTGCA</u><br><u>CAACCACTACACGCAGAAGAGCCTCTCCCTGTCTCCGGG</u><br>TAAA |
| hGH fusion HC | 105 | CAGGTCCAGCTGAGAGAGAGCGGCCCTTCACTGGTCA<br>AGCCATCCCAGACACTGAGCCTGACATGCACAGCAAG<br>CGGGTTTTCACTGAGCGACAAGGCAGTGGGATGGGTC<br>CGACAGGCACCAGGAAAAGCCCTGGAATGGCTGGGC<br>AGCATCGATACCGGCGGGAACACAGGGTACAATCCCG<br>GACTGAAGAGCAGACTGTCCATTACCAAGGACAACTC<br>TAAAAGTCAGGTGTCACTGAGCGTGAGCTCCGTCACC<br>ACAGAGGATAGTGCAACTTACTATTGCACCTCTGTGC<br>ACCAGGAAACTAAGAAATACCAGAGC<u>GGGGGTGGCGG</u><br><u>AAGCTTCCCAACCATTCCCTTATCCAGGCTTTTTGACAACGCT</u><br><br>ATGCTCCGCGCCCATCGTCTGCACCAGCTGGCCTTTGACAC<br>CTACCAGGAGTTTGAAGAAGCCTATATCCCAAAGGAACAGAA<br>GTATTCATTCCTGCAGAACCCCCAGACCTCCCTCTGTTTCTCA<br>GAGTCTATTCCGACACCCTCCAACAGGGAGGAAACACAACAG<br>AAATCCAACCTAGAGCTGCTCCGCATCTCCCTGCTGCTCATC<br>CAGTCGTGGCTGGAGCCCGTGCAGTTCCTCAGGAGTGTCTT<br>CGCCAACAGCCTGGTGTACGGCGCCTCTGACAGCAACGTCT<br>ATGACCTCCTAAAGGACCTAGAGGAAGGCATCCAAACGCTGA<br>TGGGGAGGCTGGAAGATGGCAGCCCCCGGACTGGGCAGAT<br>CTTCAAGCAGACCTACAGCAAGTTCGACACAAAACTCACACAA<br>CGATGACGCACTACTCAAGAACTACGGGCTGCTCTACTGCTT<br>CAGGAAGGACATGGACAAGGTCGAGACATTCCTGCGCATCG<br>TGCAGTGCCGCTCTGTGGAGGGCAGCTGTGGCTTCGGCGGA<br>GGTGGGAGT<u>TCT</u>TATACCTACAATTATGAATGGCATGT |

TABLE 6-continued

Immunoglobulin fusion protein-Nucleotide Sequence

| NAME | SEQ ID NO | SEQUENCE |
|---|---|---|
| | | GGATGTCTGGGGACAGGGCCTGCTGGTGACAGTCTCT<br>AGTGCTTCCACAACTGCACCAAAGGTGTACCCCCTGT<br>CAAGCTGCTGTGGGGACAAATCCTCTAGTACCGTGAC<br>ACTGGGATGCCTGGTCTCAAGCTATATGCCCGAGCCT<br>GTGACTGTCACCTGGAACTCAGGAGCCCTGAAAAGCG<br>GAGTGCACACCTTCCCAGCTGTGCTGCAGTCCTCTGG<br>CCTGTATAGCCTGAGTTCAATGGTGACAGTCCCCGGC<br>AGTACTTCAGGGCAGACCTTCACCTGTAATGTGGCCC<br>ATCCTGCCAGCTCCACCAAAGTGGACAAAGCAGTGGA<br>ACCCAAATCTTGC<u>GACAAAACTCACACATGCCCACCGT</u><br><u>GCCCAGCACCTGAACTCCTGGGGGGACCGTCAGTCTTCC</u><br><u>TCTTCCCCCCAAAACCCAAGGACACCCTCATGATCTCCCG</u><br><u>GACCCCTGAGGTCACATGCGTGGTGGTGGACGTGAGCCA</u><br><u>CGAAGACCCTGAGGTCAAGTTCAACTGGTACGTGGACGG</u><br><u>CGTGGAGGTGCATAATGCCAAGACAAAGCCGCGGGAGG</u><br><u>AGCAGTACAACAGCACGTACCGTGTGGTCAGCGTCCTCA</u><br><u>CCGTCCTGCACCAGGACTGGCTGAATGGCAAGGAGTACA</u><br><u>AGTGCAAGGTCTCCAACAAAGCCCTCCCAGCCCCCATCG</u><br><u>AGAAAACCATCTCCAAAGCCAAAGGGCAGCCCCGAGAA</u><br><u>CCACAGGTGTACACCCTGCCCCCATCCCGGGATGAGCTG</u><br><u>ACCAAGAACCAGGTCAGCCTGACCTGCCTGGTCAAAGGC</u><br><u>TTCTATCCCAGCGACATCGCCGTGGAGTGGGAGAGCAAT</u><br><u>GGGCAGCCGGAGAACAACTACAAGACCACGCCTCCCGTG</u><br><u>CTGGACTCCGACGGCTCCTTCTTCCTCTACAGCAAGCTCA</u><br><u>CCGTGGACAAGAGCAGGTGGCAGCAGGGGAACGTCTTCT</u><br><u>CATGCTCCGTGATGCATGAGGCTCTGCACAACCACTACA</u><br><u>CGCAGAAGAGCCTCTCCCTGTCTCCGGGTAAA</u> |
| IFN-B Fusion HC | 106 | CAGGTCCAGCTGAGAGAGAGCGGCCCTTCACTGGTCA<br>AGCCATCCCAGACACTGAGCCTGACATGCACAGCAAG<br>CGGGTTTTCACTGAGCGACAAGGCAGTGGGATGGGTC<br>CGACAGGCACCAGGAAAAGCCCTGGAATGGCTGGGC<br>AGCATCGATACCGGCGGGAACACAGGGTACAATCCCG<br>GACTGAAGAGCAGACTGTCCATTACCAAGGACAACTC<br>TAAAAGTCAGGTGTCACTGAGCGTGAGCTCCGTCACC<br>ACAGAGGATAGTGCAACTTACTATTGCACCTCTGTGC<br>ACCAGGAAACTAAGAAATACCAGAGC<u>GGGGGTGGCGG</u><br>==<br>*AAGCATGAGCTACAACTTGCTTGGATTCCTACAAAGAAGCAG*<br>*CAATTTTCAGTGTCAGAAGCTCCTGTGGCAATTGAATGGGAG*<br>*GCTTGAATACTGCCTCAAGGACAGGATGAACTTTGACATCCC*<br>*TGAGGAGATTAAGCAGCTGCAGCAGTTCCAGAAGGAGGACG*<br>*CCGCATTGACCATCTATGAGATGCTCCAGAACATCTTTGCTAT*<br>*TTTCAGACAAGATTCATCTAGCACTGGCTGGAATGAGACTATT*<br>*GTTGAGAACCTCCTGGCTAATGTCTATCATCAGATAAACCATC*<br>*TGAAGACAGTCCTGGAAGAAAAACTGGAGAAAGAAGATTTCA*<br>*CCAGGGGAAAACTCATGAGCAGTCTGCACCTGAAAAGATATT*<br>*ATGGGAGGATTCTGCATTACCTGAAGGCCAAGGAGTACAGTC*<br>*ACTGTGCCTGGACCATAGTCAGAGTGGAAATCCTAAGGAACT*<br>*TTTACTTCATTAACAGACTTACAGGTTACCTCCGAAACGGCGG*<br>*AGGTGGGAGT*<u>TCTTATACCTACAATTATGAATGGCATG</u><br>==<br>TGGATGTCTGGGGACAGGGCCTGCTGGTGACAGTCTC<br>TAGTGCTTCCACAACTGCACCAAAGGTGTACCCCCTG<br>TCAAGCTGCTGTGGGGACAAATCCTCTAGTACCGTGA<br>CACTGGGATGCCTGGTCTCAAGCTATATGCCCGAGCC<br>TGTGACTGTCACCTGGAACTCAGGAGCCCTGAAAAGC<br>GGAGTGCACACCTTCCCAGCTGTGCTGCAGTCCTCTG<br>GCCTGTATAGCCTGAGTTCAATGGTGACAGTCCCCGG<br>CAGTACTTCAGGGCAGACCTTCACCTGTAATGTGGCC<br>CATCCTGCCAGCTCCACCAAAGTGGACAAAGCAGTGG |

TABLE 6-continued

Immunoglobulin fusion protein-Nucleotide Sequence

| NAME | SEQ ID NO | SEQUENCE |
|---|---|---|
| | | AACCCAAATCTTGCGACAAAACTCACACATGCCCACCG<br>TGCCCAGCACCTGAACTCCTGGGGGGACCGTCAGTCTTC<br>CTCTTCCCCCCAAAACCCAAGGACACCCTCATGATCTCCC<br>GGACCCCTGAGGTCACATGCGTGGTGGTGGACGTGAGCC<br>ACGAAGACCCTGAGGTCAAGTTCAACTGGTACGTGGACG<br>GCGTGGAGGTGCATAATGCCAAGACAAAGCCGCGGGAG<br>GAGCAGTACAACAGCACGTACCGTGTGGTCAGCGTCCTC<br>ACCGTCCTGCACCAGGACTGGCTGAATGGCAAGGAGTAC<br>AAGTGCAAGGTCTCCAACAAAGCCCTCCCAGCCCCCATC<br>GAGAAAACCATCTCCAAAGCCAAAGGGCAGCCCCGAGA<br>ACCACAGGTGTACACCCTGCCCCCATCCCGGGATGAGCT<br>GACCAAGAACCAGGTCAGCCTGACCTGCCTGGTCAAAGG<br>CTTCTATCCCAGCGACATCGCCGTGGAGTGGGAGAGCAA<br>TGGGCAGCCGGAGAACAACTACAAGACCACGCCTCCCGT<br>GCTGGACTCCGACGGCTCCTTCTTCCTCTACAGCAAGCTC<br>ACCGTGGACAAGAGCAGGTGGCAGCAGGGGAACGTCTTC<br>TCATGCTCCGTGATGCATGAGGCTCTGCACAACCACTAC<br>ACGCAGAAGAGCCTCTCCCTGTCTCCGGGTAAA |
| hLeptin fusion HC | 107 | CAGGTCCAGCTGAGAGAGAGCGGCCCTTCACTGGTCA<br>AGCCATCCCAGACACTGAGCCTGACATGCACAGCAAG<br>CGGGTTTTCACTGAGCGACAAGGCAGTGGGATGGGTC<br>CGACAGGCACCAGGAAAAGCCCTGGAATGGCTGGGC<br>AGCATCGATACCGGCGGGAACACAGGGTACAATCCCG<br>GACTGAAGAGCAGACTGTCCATTACCAAGGACAACTC<br>TAAAAGTCAGGTGTCACTGAGCGTGAGCTCCGTCACC<br>ACAGAGGATAGTGCAACTTACTATTGCACCTCTGTGC<br>ACCAGGAAACTAAGAAATACCAGAGC_GGGGGTGGCGG_<br>_ATCTGTTCCAATTCAAAAGGTTCAAGATGATACCAAAACT_<br>CTGATTAAAACTATTGTCACGCGTATAAACGACATCAGC<br>CATACCCAGTCGGTTAGCTCAAAGCAAAAAGTTACCGGT<br>TTGGACTTTATTCCGGGACTGCACCCGATCCTGACCCTTA<br>GTAAAATGGACCAGACACTGGCCGTCTACCAGCAAATCC<br>TGACATCGATGCCATCCAGAAATGTGATACAAATTAGCA<br>ACGATTTGGAAAACCTTCGCGATCTGCTGCACGTGCTGG<br>CCTTCAGTAAGTCCTGTCATCTGCCGTGGGCGTCGGGACT<br>GGAGACTCTTGACTCGCTGGGTGGAGTGTTAGAGGCCTC<br>TGGCTATTCTACTGAAGTCGTTGCGCTGTCACGCCTCCAG<br>GGGAGCCTGCAGGACATGCTGTGGCAGCTGGACCTGTCA<br>CCTGGCTG_CGGAGGTGGTGGTTCA_TCTTATACCTACAATT<br>ATGAATGGCATGTGGATGTCTGGGGACAGGGCCTGCT<br>GGTGACAGTCTCTAGTGCTTCCACAACTGCACCAAAG<br>GTGTACCCCCTGTCAAGCTGCTGTGGGGGACAAATCCT<br>CTAGTACCGTGACACTGGGATGCCTGGTCTCAAGCTA<br>TATGCCCGAGCCTGTGACTGTCACCTGGAACTCAGGA<br>GCCCTGAAAAGCGGAGTGCACACCTTCCCAGCTGTGC<br>TGCAGTCCTCTGGCCTGTATAGCCTGAGTTCAATGGT<br><br>GACAGTCCCCGGCAGTACTTCAGGGCAGACCTTCACC<br>TGTAATGTGGCCCATCCTGCCAGCTCCACCAAAGTGG<br>ACAAAGCAGTGGAACCCAAATCTTGCGACAAAACTCA<br>CACATGCCCACCGTGCCCAGCACCTGAACTCCTGGGGGG<br>ACCGTCAGTCTTCCTCTTCCCCCCAAAACCCAAGGACACC<br>CTCATGATCTCCCGGACCCCTGAGGTCACATGCGTGGTG<br>GTGGACGTGAGCCACGAAGACCCTGAGGTCAAGTTCAAC<br>TGGTACGTGGACGGCGTGGAGGTGCATAATGCCAAGACA<br>AAGCCGCGGGAGGAGCAGTACAACAGCACGTACCGTGT<br>GGTCAGCGTCCTCACCGTCCTGCACCAGGACTGGCTGAA<br>TGGCAAGGAGTACAAGTGCAAGGTCTCCAACAAAGCCCT<br>CCCAGCCCCCATCGAGAAAACCATCTCCAAAGCCAAAGG<br>GCAGCCCCGAGAACCACAGGTGTACACCCTGCCCCCATC<br>CCGGGATGAGCTGACCAAGAACCAGGTCAGCCTGACCTG<br>CCTGGTCAAAGGCTTCTATCCCAGCGACATGCGCCGTGGA<br>GTGGGAGAGCAATGGGCAGCCGGAGAACAACTACAAGA<br>CCACGCCTCCCGTGCTGGACTCCGACGGCTCCTTCTTCCT<br>CTACAGCAAGCTCACCGTGGACAAGAGCAGGTGGCAGCA<br>GGGGAACGTCTTCTCATGCTCCGTGATGCATGAGGCTCTG<br>CACAACCACTACACGCAGAAGAGCCTCTCCCTGTCTCCG<br>GGTAAA |

For SEQ ID NOS: 103-107
bovine heavy chain sequence = bold
human heavy chain sequence = dashed underline
non-antibody sequence = *italic*
Stalk = bold, underline; knob = bold, double underline;
linker = *italic, squiggly underline*

TABLE 7

Immunoglobulin fusion protein-Amino Acid Sequence

| NAME | SEQ ID NO | SEQUENCE |
|---|---|---|
| Betatrophin L2 Fusion HC | 108 | QVQLRESGPSLVKPSQTLSLTCTASGFSLSDKAVGWVRQ APGKALEWLGSIDTGGNTGYNPGLKSRLSITKDNSKSQV SLSVSSVTTEDSATYYCTS<u>VHQETKKYQS</u>GGGGSGGGGSA PLGGPEPAQYEELTLLFHGALQLGQALNGVYRATEARLTEAGH SLGLYDRALEFLGTEVRQGQDATQELRTSLSEIQVEEDALHLRA EATARSLGEVARAQQALRDTVRRLQVQLRGAWLGQAHQEFETL KARADKQSHLLWALTGHVQRQQREMAEQQQWLRQIQQRLHT AALPAGGGGSGGGGS<u>=SYTYNYEW</u>HVDVWGQGLLVTVSSA STTAPKVYPLSSCCGDKSSSTVTLGCLVSSYMPEPVTVT WNSGALKSGVHTFPAVLQSSGLYSLSSMVTVPGSTSGQT FTCNVAHPASSTKVDKAVEPKSCDKTHTCPPCPAPELLGG PSVFLFPPKPKDTLMISRTPEVTCVVVDVSHEDPEVKFNWY VDGVEVHNAKTKPREEQYNSTYRVVSVLTVLHQDWLNGK EYKCKVSNKALPAPIEKTISKAKGQPREPQVYTLPPSRDELT KNQVSLTCLVKGFYPSDIAVEWESNGQPENNYKTTPPVLDS DGSFFLYSKLTVDKSRWQQGNVFSCSVMHEALHNHYTQKS LSLSPGK |
| Betatrophin L1 Fusion HC | 109 | QVQLRESGPSLVKPSQTLSLTCTASGFSLSDKAVGWVRQ APGKALEWLGSIDTGGNTGYNPGLKSRLSITKDNSKSQV SLSVSSVTTEDSATYYCTS<u>VHQETKKYQS</u>GGGGSAPLGGP EPAQYEELTLLFHGALQLGQALNGVYRATEARLTEAGHSLGLY DRALEFLGTEVRQGQDATQELRTSLSEIQVEEDALHLRAEATAR SLGEVARAQQALRDTVRRLQVQLRGAWLGQAHQEFETLKARA DKQSHLLWALTGHVQRQQREMAEQQQWLRQIQQRLHTAALP AGGGGS<u>=SYTYNYEW</u>HVDVWGQGLLVTVSSASTTAPKVY PLSSCCGDKSSSTVTLGCLVSSYMPEPVTVTWNSGALKS GVHTFPAVLQSSGLYSLSSMVTVPGSTSGQTFTCNVAHP ASSTKVDKAVEPKSCDKTHTCPPCPAPELLGGPSVFLFPPKP KDTLMISRTPEVTCVVVDVSHEDPEVKFNWYVDGVEVHNA KTKPREEQYNSTYRVVSVLTVLHQDWLNGKEYKCKVSNK ALPAPIEKTISKAKGQPREPQVYTLPPSRDELTKNQVSLTCL VKGFYPSDIAVEWESNGQPENNYKTTPPVLDSDGSFFLYSK LTVDKSRWQQGNVFSCSVMHEALHNHYTQKSLSLSPGK |
| hGH fusion HC | 110 | QVQLRESGPSLVKPSQTLSLTCTASGFSLSKDAVGWVRQ APGKALEWLGSIDTGGNTGYNPGLKSRLSITKDNSKSQV SLSVSSVTTEDSATYYCTS<u>VHQETKKYQS</u>GGGGSFPTIPLS RLFDNAMLRAHRLHQLAFDTYQEFEEAYIPKEQKYSFLQNPQT SLCFSESIPTPSNREETQQKSNLELLRISLLLIQSWLEPVQFLRSV FANSLVYGASDSNVYDLLKDLEEGIQTLMGRLEDGSPRTGQIFK QTYSKFDTNSHNDDALLKNYGLLYCFRKDMDKVETFLRIVQCR SVEGSCGFGGGGS<u>=SYTYNYEW</u>HVDVWGQGLLVTVSSAST TAPKVYPLSSCCGDKSSSTVTLGCLVSSYMPEPVTVTWN SGALKSGVHTFPAVLQSSGLYSLSSMVTVPGSTSGQTFT CNVAHPASSTKVDKAVEPKSCDKTHTCPPCPAPELLGGPS VFLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSRDELTKN QVSLTCLVKGFYPSDIAVEWESNGQPENNYKTTPPVLDSDG SFFLYSKLTVDKSRWQQGNVFSCSVMHEALHNHYTQKSLS LSPGK |
| IFN-B Fusion HC | 111 | QVQLRESGPSLVKPSQTLSLTCTASGFSLSDKAVGWVRQ APGKALEWLGSIDTGGNTGYNPGLSRLSITKDNSKSQV SLSVSSVTTEDSATYYCTS<u>VHQETKKYQS</u>GGGGSMSYNLL GFLQRSSNFQCQKLLWQLNGRLEYCLKDRMNFDIPEEIKQLQ QFQKEDAALTIYEMLQNIFAIFRQDSSSTGWNETIVENLLANVY HQINHLKTVLEEKLEKEDFTRGKLMSSLHLKRYYGRILHYLKAK EYSHCAWTIVRVEILRNFYFINRLTGYLRNGGGGS<u>SYTYNYEW</u> HVDVWGQGLLVTVSSASTTAPKVYPLSSCCGDKSSSTVT LGCLVSSYMPEPVTVTWNSGALKSGVHTFPAVLQSSGLY SLSSMVTVPGSTSGQTFTCNVAHPASSTKVDKAVEPKSC DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPSRDELTKNQVSLTCLVKGFYPSDIAVEWES NGQPENNYKTTPPVLDSDGSFFLYSKLTVDKSRWQQGNVF SCSVMHEALHNHYTQKSLSLSPGK |

TABLE 7-continued

Immunoglobulin fusion protein-Amino Acid Sequence

| NAME | SEQ ID NO | SEQUENCE |
|---|---|---|
| hRelaxin-2 Fusion HC | 112 | QVQLRESGPSLVKPSQTLSLTCTASGFSLSKDAVGWVRQ APGKALEWLGSIDTGGNTYNPGLKSRLSITKDNSKSQV SLSVSSVTTEDSATYYCTS<u>VHQETKKYQS</u>*GGGGSDSWMEE VIKLCGRELVRAQIAICGMSTWSIEGRSLSQEDAPQTPRPVAEIV PSFINKDTETINMMSEFVANLPQELKLTLSEMQPALPQLQQHV PVLKDSSLLFEEFKKLIRNRQSEAADSSPSELKYLGLDTHSIEGR QLYSALANKCCHVGCTKRSLARFCGGGGS***SYTYNYEWHVDV* WGQGLLVTVSSASTTAPKVYPLSSCCGDKSSSTVTLGCL VSSYMPEPVTVTWNSGALKSGVHTFPAVLQSSGLYSLSS MVTVPGSTSGQTFTCNVAHPASSTKVDKAVEPKS<span style="border-bottom: 1px dashed">CDKTH TCPPCPAPELLGGPSVFLFPPKPKDTLMISRTPEVTCVVVDV SHEDPEVKFNWYVDGVEVHNAKTKPREEQYNSTYRVVSVL TVLHQDWLNGKEYKCKVSNKALPAPIEKTISKAKGQPREPQ VYTLPPSRDELTKNQVSLTCLVKGFYPSDIAVEWESNGQPE NNYKTTPPVLDSDGSFFLYSKLTVDKSRWQQGNVFSCSVM HEALHNHYTQKSLSLSPGK</span> |
| hLeptin Fusion HC | 113 | QVQLRESGPSLVKPSQTLSLTCTASGFSLSKDAVGWVRQ APGKALEWLGSIDTGGNTYNPGLKSRLSITKDNSKSQV SLSVSSVTTEDSATYYCTS<u>VHQETKKYQS</u>*GGGGS*VPIQKV QDDTKTLIKTIVTRINDISHTQSVSSKQKVTGLDFIPGLHPILT LSKMDQTLAVYQQILTSMPSRNVIQISNDLENLRDLLHVLA FSKSCHLPWASGLETLDSLGGVLEASGYSTEVVALSRLQGS LQDMLWQLDLSPGC*GGGGS*SYTYNYEWHVDVWGQGLL VTVSSASTTAPKVYPLSSCCGDKSSSTVTLGCLVSSYMPE PVTVTWNSGALKSGVHTFPAVLQSSGLYSLSSMVTVPGS TSGQTFTCNVAHPASSTKVDKAVEPKS<span style="border-bottom: 1px dashed">CDKTHTCPPCPAP ELLGGPSVFLFPPKPKDTLMISRTPEVTCVVVDVSHEDPEVK FNWYVDGVEVHNAKTKPREEQYNSTYRVVSVLTVLHQDW LNGKEYKCKVSNKALPAPIEKTISKAKGQPREPQVYTLPPSR DELTKNQVSLTCLVKGFYPSDIAVEWESNGQPENNYKTTPP VLDSDGSFFLYSKLTVDKSRWQQGNVFSCSVMHEALHNHY TQKSLSLSPGK</span> |

For SEQ ID NOS: 108-113
bovine heavy chain sequence = bold
human heavy chain sequence = <span style="border-bottom: 1px dashed">dashed underline</span>
non-antibody sequence = *italic*
proteolytic cleavage site = *italic, single underline*
Stalk = bold, underline; knob = bold, double underline;
linker = *italic, squiggly underline*

TABLE 13

Non-antibody sequences-Nucleic acid sequence

| Name | SEQ ID NO | Sequence |
|---|---|---|
| GDF11 | 114 | AACCTGGGTCTGGACTGCGACGAACACTCTTCTGAATCTC GTTGCTGCCGTTACCCGCTGACCGTTGACTTCGAGGCGTT CGGTTGGGACTGGATCATCGCTCCGAAACGTTACAAAGCT AACTACTGCTCTGGTCAGTGCGAATACATGTTCATGCAGA AATACCCGCACACCCACCTGGTTCAGCAGGCTAACCCGCG TGGTTCTGCTGGTCCGTGCTGCACCCCGACCAAAATGTCT CCGATCAACATGCTGTACTTCAACGACAAACAGCAGATCA TCTACGGTAAAATCCCGGGTATGGTTGTTGACCGTTGCGG TTGCTCTTAA |
| ANGPTL3 | 115 | GGATCCGGTGGTTTCACCATCAAACTGCTGCTGTTCATCG TTCCGCTGGTTATCTCTTCTCGTATCGACCAGGACAACTCT TCTTTCGACTCTCTGTCTCCGGAACCGAAATCTCGTTTCGC TATGCTGGACGACGTTAAAATCCTGGCTAACGGTCTGCTG CAGCTGGGTCACGGTCTGAAAGACTTCGTTCACAAAACCA AAGGTCAGATCAACGACATCTTCCAGAAACTGAACATCTT CGACCAGTCTTTCTACGACCTGTCTCTGCAGACCTCTGAA ATCAAAGAAGAAGAAAAAGAACTGCGTCGTACCACCTAC AAACTGCAGGTTAAAAACGAAGAAGTTAAAAACATGTCT CTGGAACTGAACTCTAAACTGGAATCTCTGCTGGAAGAAA AAATCCTGCTGCAGCAGAAAGTTAAATACCTGGAAGAAC AGCTGACCAACCTGATCCAGAACCAGCCGGAAACCCCGG AACACCCGGAAGTTACCTCTCTGAAAACCTTCGTTGAAAA ACAGGACAACTCTATCAAAGACCTGCTGCAGACCGTTGAA GACCAGTACAAACAGCTGAACCAGCAGCACTCTCAGATC AAAGAAATCGAAAACCAGCTGCGTCGTACCTCTATCCAGG AACCGACCGAAATCTCTCTGTCTTCTAAACCGCGTGCTCC GCGTACCACCCCGTTCCTGCAGCTGAACGAAATCCGTAAC |

TABLE 13-continued

Non-antibody sequences-Nucleic acid sequence

| Name | SEQ ID NO | Sequence |
|---|---|---|
| | | GTTAAACACGACGGTATCCCGGCTGAATGCACCACCATCT<br>ACAACCGTGGTGAACACACCTCTGGTATGTACGCTATCCG<br>TCCGTCTAACTCTCAGGTTTTCCACGTTTACTGCGACGTTA<br>TCTCTGGTTCTCCGTGGACCCTGATCCAGCACCGTATCGA<br>CGGTTCTCAGAACTTCAACGAAACCTGGGAAAACTACAA<br>ATACGGTTTCGGTCGTCTGGACGGTGAATTCTGGCTGGGT<br>CTGGAAAAAATCTACTCTATCGTTAAACAGTCTAACTACG<br>TTCTGCGTATCGAACTGGAAGACTGGAAAGACAACAAAC<br>ACTACATCGAATACTCTTTCTACCTGGGTAACCACGAAAC<br>CAACTACACCCTGCACCTGGTTGCTATCACCGGTAACGTT<br>CCGAACGCTATCCCGAAGAAGAAGAAGAAAAAAAGAA<br>GAAGAAAT |
| hGH | 116 | TTCCCAACCATTCCCTTATCCAGGCTTTTTGACAACGCTAT<br>GCTCCGCGCCCATCGTCTGCACCAGCTGGCCTTTGACACC<br>TACCAGGAGTTTGAAGAAGCCTATATCCCAAAGGAACAG<br>AAGTATTCATTCCTGCAGAACCCCCAGACCTCCCTCTGTTT<br>CTCAGAGTCTATTCCGACACCCTCCAACAGGGAGGAAACA<br>CAACAGAAATCCAACCTAGAGCTGCTCCGCATCTCCCTGC<br>TGCTCATCCAGTCGTGGCTGGAGCCCGTGCAGTTCCTCAG<br>GAGTGTCTTCGCCAACAGCCTGGTGTACGGCGCCTCTGAC<br>AGCAACGTCTATGACCTCCTAAAGGACCTAGAGGAAGGC<br>ATCCAAACGCTGATGGGGAGGCTGGAAGATGGCAGCCCC<br>CGGACTGGGCAGATCTTCAAGCAGACCTACAGCAAGTTCG<br>ACACAAACTCACACAACGATGACGCACTACTCAAGAACT<br>ACGGGCTGCTCTACTGCTTCAGGAAGGACATGGACAAGGT<br>CGAGACATTCCTGCGCATCGTGCAGTGCCGCTCTGTGGAG<br>GGCAGCTGTGGCTTC |
| hIFN-alpha | 117 | TGTGATCTGCCTCAAACCCACAGCCTGGGTAGCAGGAGGA<br>CCTTGATGCTCCTGGCACAGATGAGGAGAATCTCTCTTTT<br>CTCCTGCTTGAAGGACAGACATGACTTTGGATTTCCCCAG<br>GAGGAGTTTGGCAACCAGTTCCAAAAGGCTGAAACCATC<br>CCTGTCCTCCATGAGATGATCCAGCAGATCTTCAATCTCTT<br>CAGCACAAAGGACTCATCTGCTGCTTGGGATGAGACCCTC<br>CTAGACAAATTCTACACTGAACTCTACCAGCAGCTGAATG<br>ACCTGGAAGCCTGTGTGATACAGGGGGTGGGGGTGACAG<br>AGACTCCCCTGATGAAGGAGGACTCCATTCTGGCTGTGAG<br>GAAATACTTCCAAAGAATCACTCTCTATCTGAAAGAGAAG<br>AAATACAGCCCTTGTGCCTGGGAGGTTGTCAGAGCAGAA<br>ATCATGAGATCTTTTTCTTTGTCAACAAACTTGCAAGAAA<br>GTTTAAGAAGTAAGGAA |
| Mamba | 118 | CTGAAATGTTACCAACATGGTAAAGTTGTGACTTGTCATC<br>GAGATATGAAGTTTTGCTATCATAACACTGGCATGCCTTT<br>TCGAAATCTCAAGCTCATCCTACAGGGATGTTCTTCTTCGT<br>GCAGTGAAACAGAAAACAATAAGTGTTGCTAACAGACA<br>GATGCAACAA |
| 550 peptide | 119 | CGAATGCATCGGTATGTTCAAATCTTGCGACCCGGAAAAC<br>GACAAATGCTGCAAAGGTCGTACCTGCTCTCGTAAACACC<br>GTTGGTGCAAATACAAACTG |
| Amgen1 | 120 | GACTGCCTGGGTTTCATGCGTAAATGCATCCCGGACAACG<br>ACAAATGCTGCCGTCCGAACCTGGTTTGCTCTCGTACCCA<br>CAAATGGTGCAAATACGTTTTC |
| Parathyroid hormone | 121 | TCTGTGAGTGAAATACAGCTTATGCATAACCTGGGAAAAC<br>ATCTGAACTCGATGGAGAGAGTAGAATGGCTGCGTAAGA<br>AGCTGCAGGATGTGCACAATTTTGTTGCCCTTGGAGCTCC<br>TCTAGCTCCCAGAGATGCTGGTTCCCAGAGGCCCCGAAAA<br>AAGGAAGACAATGTCTTGGTTGAGAGCCATGAAAAAAGT<br>CTTGGAGAGGCAGACAAAGCTGATGTGAATGTATTAACTA<br>AAGCTAAATCCCAG |
| IL-11 | 122 | ATGAACTGCGTGTGCCGCCTGGTGCTGGTGGTGCTGAGCC<br>TGTGGCCGGATACCGCGGTGGCGCCGGGCCCGCCGCCGG<br>GCCCGCCGCGCGTGAGCCCGGATCCGCGCGCGGAACTGG<br>ATAGCACCGTGCTGCTGACCCGCAGCCTGCTGGCGGATAC<br>CCGCCAGCTGGCGGCGCAGCTGCGCGATAAATTTCCGGCG<br>GATGGCGATCATAACCTGGATAGCCTGCCGACCCTGGCGA<br>TGAGCGCGGGCGCGCTGGGCGCGCTGCAGCTGCCGGGCG<br>TGCTGACCCGCCTGCGCGCGGATCTGCTGAGCTATCTGCG<br>CCATGTGCAGTGGCTGCGCCGCGCGGGCGGCAGCAGCCT<br>GAAAACCCTGGAACCGGAACTGGGCACCCTGCAGGCGCG<br>CCTGGATCGCCTGCTGCGCCGCCTGCAGCTGCTGATGAGC |

TABLE 13-continued

Non-antibody sequences-Nucleic acid sequence

| Name | SEQ ID NO | Sequence |
|---|---|---|
| | | CGCCTGGCGCTGCCGCAGCCGCCGCCGGATCCGCCGGCGC<br>CGCCGCTGGCGCCGCCGAGCAGCGCGTGGGGCGGCATTC<br>GCGCGGCGCTGGCGATTCTGGGCGGCCTGCATCTGACCCT<br>GGATTGGGCGGTGCGCGGCCTGCTGCTGCTGAAAACCCGC<br>CTG |
| Relaxin<br>FactorXa | 123 | GATAGCTGGATGGAAGAAGTGATTAAACTGTGCGGCCGC<br>GAACTGGTGCGCGCGCAGATTGCGATTTGCGGCATGAGCA<br>CCTGGAGCATTGAAGGCCGCAGCCTGAGCCAGGAAGATG<br>CGCCGCAGACCCCGCGCCCGGTGGCGGAAATTGTGCCGA<br>GCTTTATTAACAAAGATACCGAAACCATTAACATGATGAG<br>CGAATTTGTGGCGAACCTGCCGCAGGAACTGAAACTGACC<br>CTGAGCGAAATGCAGCCGGCGCTGCCGCAGCTGCAGCAG<br>CATGTGCCGGTGCTGAAAGATAGCAGCCTGCTGTTTGAAG<br>AATTTAAAAAACTGATTCGCAACCGCCAGAGCGAAGCGG<br>CGGATAGCAGCCCGAGCGAACTGAAATATCTGGGCCTGG<br>ATACCCATAGCATTGAAGGCCGCCAGCTGTATAGCGCGCT<br>GGCGAACAAATGCTGCCATGTGGGCTGCACCAAACGCAG<br>CCTGGCGCGCTTTTGC |
| Relaxin<br>fragment | 124 | AGCCTGAGCCAGGAAGATGCGCCGCAGACCCCGCGCCCG<br>GTGGCGGAAATTGTGCCGAGCTTTATTAACAAAGATACCG<br>AAACCATTAACATGATGAGCGAATTTGTGGCGAACCTGCC<br>GCAGGAACTGAAACTGACCCTGAGCGAAATGCAGCCGGC<br>GCTGCCGCAGCTGCAGCAGCATGTGCCGGTGCTGAAAGAT<br>AGCAGCCTGCTGTTTGAAGAATTTAAAAAACTGATTCGCA<br>ACCGCCAGAGCGAAGCGGCGGATAGCAGCCCGAGCGAAC<br>TGAAATATCTGGGCCTGGATACCCATAGC |
| IL8 | 125 | CCGCGCAGCGCGAAAGAACTGCGCTGCCAGTGCATTAAA<br>ACCTATAGCAAACCGTTTCATCCGAAATTTATTAAAGAAC<br>TGCGCGTGATTGAAAGCGGCCCGCATTGCGCGAACACCG<br>AAAATTATTGTGAAACTGAGCGATGGCCGCGAACTGTGCCT<br>GGATCCGAAAGAAAACTGGGTGCAGCGCGTGGTGGAAAA<br>ATTTCTGAAACGCGCGGAAAACAGC |
| ziconotide | 126 | TGCAAAGGCAAAGGCGCGAAATGCAGCCGCCTGATGTAT<br>GATTGCTGCACCGGCAGCTGCCGCAGCGGCAAATGC |
| somatostatin | 127 | GCGGGCTGCAAAAACTTTTTTTGGAAAACCTTTACCAGCT<br>GCGGC |
| chlorotoxin | 128 | ATGTGCATGCCGTGCTTTACCACCGATCATCAGATGGCGC<br>GCAAATGCGATGATTGCTGCGGCGGCAAAGGCCGCGGCA<br>AATGCTATGGCCCGCAGTGCCTG |
| SDF1(alpha) | 129 | AAACCGGTGAGCCTGAGCTATCGCTGCCCGTGCCGCTTTT<br>TTGAAAGCCATGTGGCGCGCGCGAACGTGAAACATCTGA<br>AAATTCTGAACACCCCGAACTGCGCGCTGCAGATTGTGGC<br>GCGCCTGAAAAACAACAACCGCCAGGTGTGCATTGATCC<br>GAAACTGAAATGGATTCAGGAATATCTGGAAAAAGCGCT<br>GAACAAA |
| IL21 | 130 | CAGGGCCAGGATCGCCATATGATTCGCATGCGCCAGCTGA<br>TTGATATTGTGGATCAGCTGAAAAACTATGTGAACGATCT<br>GGTGCCGGAATTTCTGCCGGCGCCGGAAGATGTGGAAAC<br>CAACTGCGAATGGAGCGCGTTTAGCTGCTTTCAGAAAGCG<br>CAGCTGAAAAGCGCGAACACCGGCAACAACGAACGCATT<br>ATTAACGTGAGCATTAAAAAACTGAAACGCAAACCGCCG<br>AGCACCAACGCGGGCCGCCGCCAGAAACATCGCCTGACC<br>TGCCCGAGCTGCGATAGCTATGAAAAAAAACCGCCGAAA<br>GAATTTCTGGAACGCTTTAAAAGCCTGCTGCAGAAAATGA<br>TTCATCAGCATCTGAGCAGCCGCACCCATGGCAGCGAAGA<br>TAGC |
| Elafin | 131 | GCGCAAGAGCCAGTCAAAGGTCCAGTCTCCACTAAGCCTG<br>GCTCCTGCCCCATTATCTTGATCCGGTGCGCCATGTTGAAT<br>CCCCCTAACCGCTGCTTGAAAGATACTGACTGCCCAGGAA<br>TCAAGAAGTGCTGTGAAGGCTCTTGCGGGATGGCCTGTTT<br>CGTTCCCCAG |
| BCCX2 | 132 | TATCGCAAATGTAGAGGAGGCCGAAGGTGGTGCTACCAA<br>AAG |

TABLE 14

| Name | SEQ ID NO | Sequence |
|---|---|---|
| GDF11 | 133 | NLGLDCDEHSSESRCCRYPLTVDFEAFGWDWIIAPKRY KANYCSGQCEYMFMQKYPHTHLVQQANPRGSAGPCCTP TKMSPINMLYFNDKQQIIYGKIPGMVVDRCGCS |
| ANGPTL3 | 134 | GSGGFTIKLLLFIVPLVISSRIDQDNSSFDSLSPEPKS RFAMLDDVKILANGLLQLGHGLKDFVHKTKGQINDIFQ KLNIFDQSFYDLSLQTSEIKEEEKELRRTTYKLQVKNE EVKNMSLELNSKLESLLEEKILLQQKVKYLEEQLTNLI QNQPETPEHPEVTSLKTFVEKQDNSIKDLLQTVEDQYK QLNQQHSQIKEIENQLRRTSIQEPTEISLSSKPRAPRT TPFLQLNEIRNVKHDGIPAECTTIYNRGEHTSGMYAIR PSNSQVFHVYCDVISGSPWTLIQHRIDGSQNFNETWEN YKYGFGRLDGEFWLGLEKIYSIVKQSNYVLRIELEDWK DNKHYIEYSFYLGNHETNYTLHLVAITGNVPNAIPKKK KKKKKKK |
| hGH | 135 | FPTIPLSRLFDNAMLRAHRLHQLAFDTYQEFEEAYIPK EQKYSFLQNPQTSLCFSESIPTPSNREETQQKSNLELL RISLLLIQSWLEPVQFLRSVFANSLVYGASDSNVYDLL KDLEEGIQTLMGRLEDGSPRTGQIFKQTYSKFDTNSHN DDALLKNYGLLYCFRKDMDKVETFLRIVQCRSVEGSCG F |
| hIFN-alpha | 136 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE |
| Mamba | 137 | LKCYQHGKVVTCHRDMKFCYHNTGMPFRNLKLILQGCS SSCSETENNKCCSTDRCN |
| 550 peptide | 138 | ECIGMFKSCDPENDKCCKGRTCSRKHRWCKYKL |
| Amgen1 | 139 | DCLGFMRKCIPDNDKCCRPNLVCSRTHKWCKYVF |
| Parathyroid Hormond | 140 | SVSEIQLMHNLGKHLNSMERVEWLRKKLQDVHNFVALG APLAPRDAGSQRPRKKEDNVLVESHEKSLGEADKADVN VLTKAKSQ |
| IL-11 | 141 | MNCVCRLVLVVLSLWPDTAVAPGPPPGPPRVSPDPRAE LDSTVLLTRSLLADTRQLAAQLRDKFPADGDHNLDSLP TLAMSAGALGALQLPGVLTRLRADLLSYLRHVQWLRRA GGSSLKTLEPELGTLQARLDRLLRRLQLLMSRLALPQP PPDPPAPPLAPPSSAWGGIRAALAILGGLHLTLDWAVR GLLLLKTRL |
| Relaxin FactorXa | 142 | DSWMEEVIKLCGRELVRAQIAICGMSTWS<u>IEGR</u>SLSQE DAPQTPRPVAEIVPSFINKDTETINMMSEFVANLPQEL KLTLSEMQPALPQLQQHVPVLKDSSLLFEEFKKLIRNR QSEAADSSPSELKYLGLDTHS<u>IEGR</u>QLYSALANKCCHV GCTKRSLARFC |
| Relaxin fragment | 143 | SLSQEDAPQTPRPVAEIVPSFINKDTETINMMSEFVAN LPQELKLTLSEMQPALPQLQQHVPVLKDSSLLFEEFKK LIRNRQSEAADSSPSELKYLGLDTHS |
| IL8 | 144 | PRSAKELRCQCIKTYSKPFHPKFIKELRVIESGPHCAN TEIIVKLSDGRELCLDPKENWVQRVVEKFLKRAENS |
| ziconotide | 145 | CKGKGAKCSRLMYDCCTGSCRSGKC |
| somatostatin | 146 | AGCKNFFWKTFTSCG |
| chlorotoxin | 147 | MCMPCFTTDHQMARKCDDCCGGKGRGKCYGPQCL |
| SDF1(alpha) | 148 | KPVSLSYRCPCRFFESHVARANVKHLKILNTPNCALQI VARLKNNNRQVCIDPKLKWIQEYLEKALNK |
| IL21 | 149 | QGQDRHMIRMRQLIDIVDQLKNYVNDLVPEFLPAPEDV ETNCEWSAFSCFQKAQLKSANTGNNERIINVSIKKLKR KPPSTNAGRRQKHRLTCPSCDSYEKKPPKEFLERFKSL LQKMIHQHLSSRTHGSEDS |

TABLE 14-continued

Non-antibody Sequences-Amino acid sequences

| Name | SEQ ID NO | Sequence |
| --- | --- | --- |
| Elafin | 150 | AQEPVKGPVSTKPGSCPIILIRCAMLNPPNRCLKDTDC PGIKKCCEGSCGMACFVPQ |
| BCCX2 | 151 | YRKCRGGRRWCYQK |

What is claimed is:

1. A fusion protein comprising:
   a. a non-antibody region comprising a polypeptide selected from a group consisting of relaxin, betatrophin, elafin, and BCCX2;
   b. an antibody variable domain;
   c. a stalk domain of an ultralong complementarity determining region 3 (CDR3) comprising at least one of SEQ ID NOs: 18-21, 25, 26, and 34-37; and
   d. one or more serine residues from a knob domain of an ultralonq CDR3; wherein the non-antibody region is inserted into or replaces at least a portion of a complementarity-determining region (CDR) of the antibody variable domain;
   wherein the non-antibody sequence is connected to the antibody variable domain by the stalk domain and knob domain; and
   wherein the polypeptide within the antibody variable domain is functional to treat or ameliorate a disease, disorder or condition when the fusion protein is administered to a subject in need thereof.

2. The fusion protein of claim 1, wherein the polypeptide is relaxin.

3. The fusion protein of claim 2, wherein the relaxin is human relaxin 2.

4. The fusion protein of claim 1, wherein the polypeptide is betatrophin.

5. The fusion protein of claim 1, wherein the polypeptide is elafin.

6. The fusion protein of claim 1, wherein the polypeptide is BCCX2.

7. The fusion protein of claim 1, wherein the antibody is selected from a human antibody, a humanized antibody, a human engineered antibody, a chimeric antibody, a bovine antibody, and fragments thereof.

8. A pharmaceutical composition comprising a therapeutically effective amount of the fusion protein of claim 1, and a pharmaceutically acceptable carrier.

9. The fusion protein of claim 1, wherein the non-antibody region contains a polypeptide encoded by a polynucleotide sequence selected from SEQ ID NOS: 123, 124, 131, and 132, or an amino acid sequence selected from SEQ ID NOs: 142, 143, 150, and 151.

10. The fusion protein of claim 1, wherein the non-antibody region is inserted into or replaces at least a portion of a CDR3 of the antibody variable domain.

11. A method of treating a disease or condition in a subject in need thereof comprising administering to the subject a therapeutically effective amount of the fusion protein of claim 1.

12. The method of claim 11, wherein the disease or condition is selected from a group consisting of autoimmune disease, heteroimmune disease or condition, inflammatory disease, pathogenic infection, thromboembolic disorder, respiratory disease or condition, metabolic disease, central nervous system (CNS) disorder, bone disease, cancer, blood disorder, obesity, diabetes, osteoporosis, anemia, and pain.

* * * * *

UNITED STATES PATENT AND TRADEMARK OFFICE
CERTIFICATE OF CORRECTION

PATENT NO. : 10,259,863 B2
APPLICATION NO. : 14/760115
DATED : April 16, 2019
INVENTOR(S) : Wang et al.

Page 1 of 1

It is certified that error appears in the above-identified patent and that said Letters Patent is hereby corrected as shown below:

In the Specification

Column 1, Line 20, insert the paragraph below:
-- STATEMENT OF GOVERNMENT LICENSE RIGHTS
This invention was made with government support under grant number GM062159 awarded by The National Institutes of Health. The government has certain rights in the invention. --

Signed and Sealed this
Eighth Day of June, 2021

Drew Hirshfeld
*Performing the Functions and Duties of the
Under Secretary of Commerce for Intellectual Property and
Director of the United States Patent and Trademark Office*